US012781289B2

(12) United States Patent
Elling et al.

(10) Patent No.: US 12,781,289 B2
(45) Date of Patent: Nov. 3, 2026

(54) METHOD FOR PARALLEL NUCLEIC ACID ANALYSIS

(71) Applicant: IMBA—INSTITUT FÜR MOLEKULARE BIOTECHNOLOGIE GMBH, Vienna (AT)

(72) Inventors: Ulrich Elling, Perchtoldsdorf (AT); Ramesh Yelagandula, Vienna (AT); Alexander Stark, Vienna (AT); Maria Luisa Cochella, Baltimore, MD (US)

(73) Assignee: IMBA—INSTITUT FÜR MOLEKULARE BIOTECHNOLOGIE GMBH, Vienna (AT)

( * ) Notice: Subject to any disclaimer, the term of this patent is extended or adjusted under 35 U.S.C. 154(b) by 763 days.

(21) Appl. No.: 18/245,795

(22) PCT Filed: Oct. 19, 2021

(86) PCT No.: PCT/EP2021/078911
§ 371 (c)(1),
(2) Date: Mar. 17, 2023

(87) PCT Pub. No.: WO2022/084295
PCT Pub. Date: Apr. 8, 2022

(65) Prior Publication Data

US 2024/0026473 A1 Jan. 25, 2024

(30) Foreign Application Priority Data

Oct. 19, 2020 (EP) .................................... 20202627
Mar. 5, 2021 (EP) .................................... 21161020

(51) Int. Cl.
*C12Q 1/68* (2018.01)
*C12Q 1/70* (2006.01)

(52) U.S. Cl.
CPC ......... *C12Q 1/701* (2013.01); *C12Q 2600/16* (2013.01)

(58) Field of Classification Search
CPC ........................................................ C12Q 1/68
See application file for complete search history.

(56) References Cited

U.S. PATENT DOCUMENTS

2006/0105380 A1* 5/2006 Slepnev ............... C12Q 1/6809 435/6.14
2015/0259734 A1 9/2015 Asbury et al.
(Continued)

FOREIGN PATENT DOCUMENTS

CN 110029147 A 7/2019
CN 111593141 A 8/2020

OTHER PUBLICATIONS

First Office Action received in Chinese Application No. 202180012016.2, dated Jun. 19, 2025.
(Continued)

*Primary Examiner* — Aaron A Priest
(74) *Attorney, Agent, or Firm* — Greer, Burns & Crain, Ltd

(57) ABSTRACT

A method for detecting a nucleic acid in a plurality of samples, including a) providing analyte nucleic acids from samples in separate containers, the containers are in a subset array; b) amplifying acids by reaction using primers hybridized to the acids, forward and reverse primers of the primer pair both include an adaptor sequence, a sample identifier sequence and a binding sequence; c) combining the acids of step b) of containers of subsets to a container array; d) amplifying acids by a primer extension reaction using a pair of further primers hybridized to the acids of containers of step c), the further primers include a further forward and a further reverse primer, both including an identifier sequence and a hybridization sequence; e) determining the sequences
(Continued)

Figure 2:
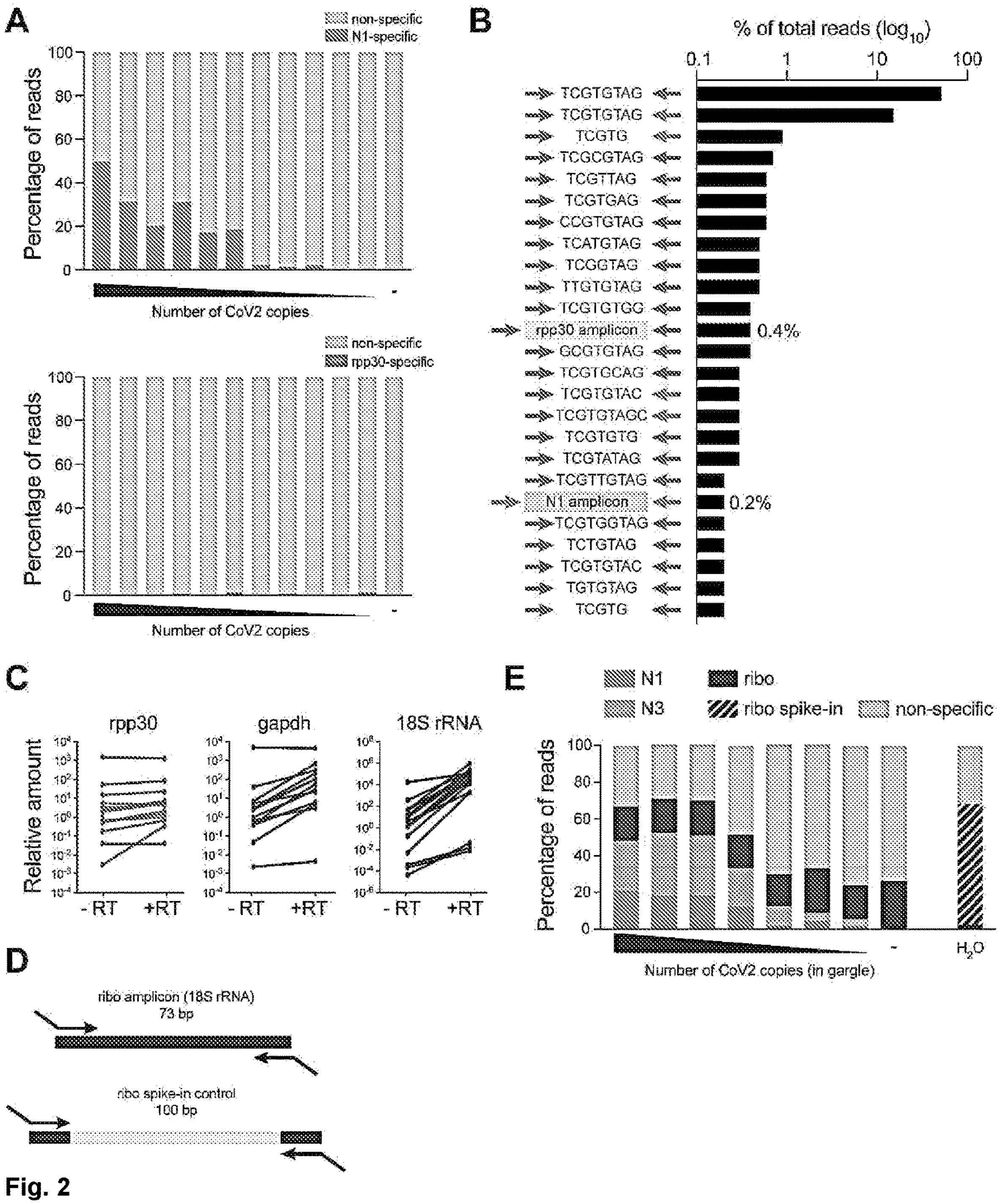

of the acids of step d); f) assigning a determined sequence of a nucleic acid of interest of step e) to a sample.

25 Claims, 23 Drawing Sheets

Specification includes a Sequence Listing.

(56) References Cited

U.S. PATENT DOCUMENTS

2016/0208322 A1* 7/2016 Anderson .............. C12Q 1/686
2024/0240267 A1* 7/2024 Santos ................. C12Q 1/6844

OTHER PUBLICATIONS

Chen, Y., et al., “Establishment of Multiplex RT-PCR for Detecting Five Kinds of Main Respiratory Viruses,” Progress in Modern Biomedicine, vol. 12, No. 7, Mar. 2012, 2 pages. English Summary.
International Search Report and Written Opinion received for PCT/EP2021/078911, mailed Jan. 25, 2022.
European Search Report received for Application No. 20202627.4, dated Mar. 19, 2021.
Ben-Ami, R., et al., “Large-scale implementation of pooled RNA extraction and RT-PCR for SARS-CoV-2 detection,” Clinical Microbiology and Infection 26, 2020, pp. 1248-1253.
Bloom, J., et al., “Swab-Seq: A high-throughput platform for massively scaled up SARS-CoV-2 testing,” published on medRxiv on Aug. 6, 2020, 45 pages.
Bose, M., et al., “Rapid Semiautomated Subtyping of Influenza Virus Species during the 2009 Swine Origin Influenza A H1N1 Virus Epidemic in Milwaukee, Wisconsin,” Journal of Clinical Microbiology, Sep. 2009, pp. 2779-2786.
Dao Thi, V., “A colorimetric RT-LAMP assay and LAMP-sequencing for detecting SARS-CoV-2 RNA in clinical samples,” Science Translational Medicine 12 , Research Article, Aug. 12, 2020, 13 pages.
Do, D., et al., “A One-Step, Real-Time PCR Assay for Rapid Detection of Rhinovirus,” Journal of Molecular Diagnostics, vol. 12, No. 1, Jan. 2010, pp. 102-108.
Jayamohan, H., et al., “SARS-CoV-2 pandemic: a review of molecular diagnostic tools including sample collection and commercial response with associated advantages and limitations,” Analytical and Bioanalytical Chemistry 413, 2021, pp. 49-71.
Ladha, A., et al., “A 5-min RNA preparation method for COVID-19 detection with RT-qPCR,” published on medRxiv on May 8, 2020, 3 pages.
Lalli, M., et al., “Rapid and extraction-free detection of SARS-CoV-2 from saliva with colorimetric LAMP,” published on medRxiv on May 11, 2020, 25 pages.
Picelli, S., et al., “Tn5 transposase and tagmentation procedures for massively scaled sequencing objects,” Genome Research 24, 2014, pp. 2033-2040.
Visseaux, B., et al., “Evaluation of the QIAstat-Dx Respiratory SARS-CoV-2 Panel, the First Rapid Multiplex PCR Commercial Assay for SARS-CoV-2 Detection,” J Clin Micr 58, vol. 8, Aug. 2020, e00630-20, 5 pages.
Vogels, C., et al., “SalivaDirect: Simple and sensitive molecular diagnostic test for SARS-CoV-2 surveillance,” published on medRxiv on Aug. 4, 2020, 26 pages.
Chinese Office Action dated Apr. 15, 2026 for Chinese Application No. 2021800120162.
Tremblay, J., et al., “Primer and platform effects on 16S rRNA tag sequencing”, Frontiers in Microbiology, Aug. 4, 2025, pp. 1-15, vol. 6, No. 771.
Macconaill, L., et al., “Unique, dual-indexed sequencing adapters with UMIs effectively eliminate index crosstalk and significantly improve sensitivity of massively parallel sequencing”, BMC Genomics, (2018), pp. 1-10, vol. 19 No. 30.

* cited by examiner

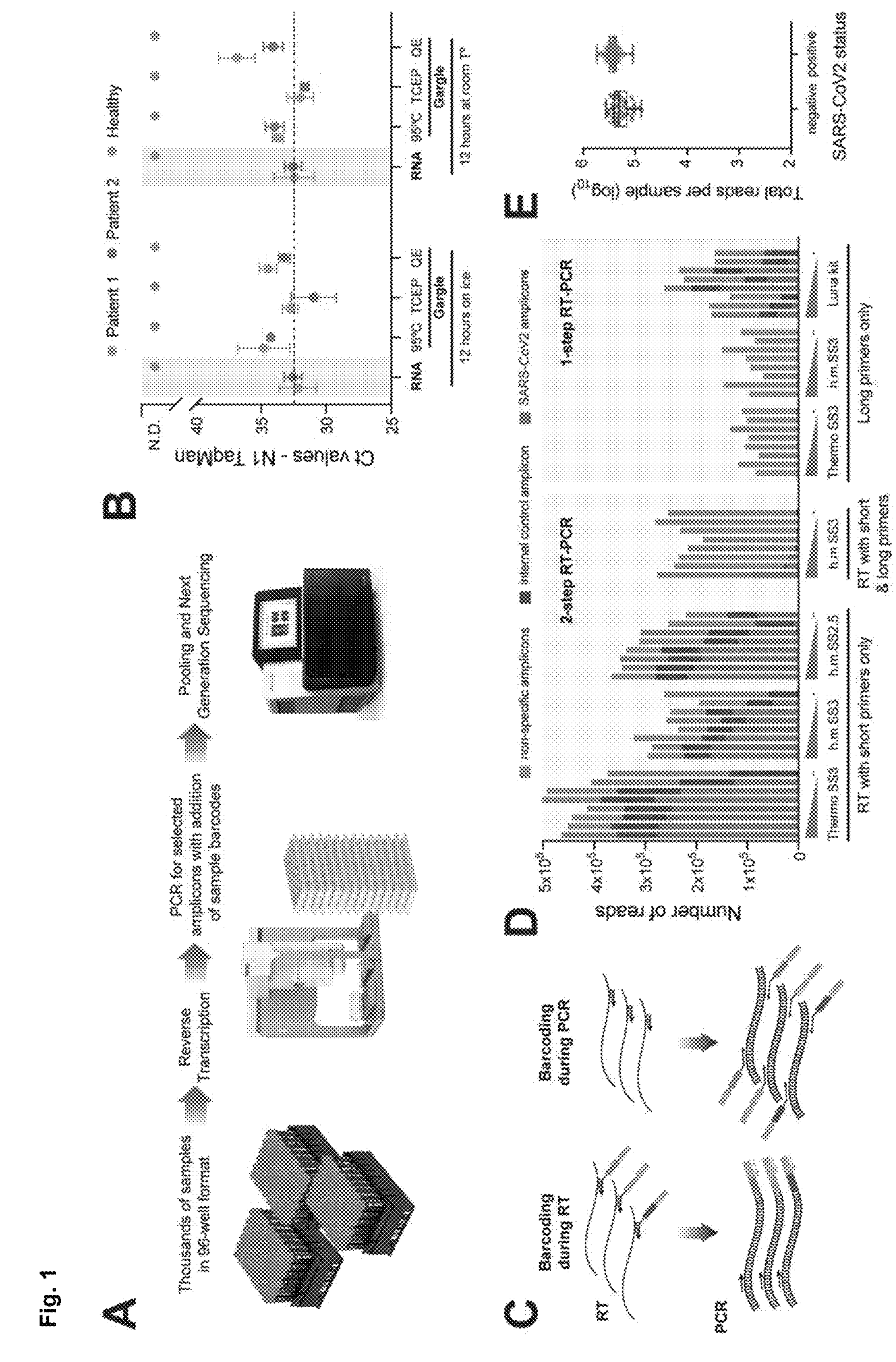
Fig. 1
A
Thousands of samples in 96-well format
Reverse Transcription
PCR for selected amplicons with addition of sample barcodes
Pooling and Next Generation Sequencing
B
Patient 1
Patient 2
Healthy
Ct values - N1 TaqMan
N.D.
40
35
30
25
RNA
95°C
TCEP
QE
Gargle
12 hours on ice
12 hours at room T°
C
RT
PCR
Barcoding during RT
Barcoding during PCR
D
Number of reads
non-specific amplicons
internal control amplicon
SARS-CoV2 amplicons
2-step RT-PCR
1-step RT-PCR
Thermo SS3
h.m.SS3
h.m.SS2.5
Luna kit
RT with short primers only
RT with short & long primers
Long primers only
E
Total reads per sample (log10)
negative
positive
SARS-CoV2 status

A

Test primer ID

| | | | | | | | | | | | | |
|---|---|---|---|---|---|---|---|---|---|---|---|---|
| NGS4 | 1 | 2 | 3 | 4 | 5 | 6 | 7 | 8 | 9 | 10 | 11 | 12 |
| | 13 | 14 | 15 | 16 | 17 | 18 | 19 | 20 | 21 | 22 | 23 | 24 |
| | 25 | 26 | 27 | 28 | 29 | 30 | n.d. | n.d. | n.d. | n.d. | n.d. | n.d. |
| NGS5 | 31 | 32 | 33 | 34 | 35 | 36 | 37 | 38 | 39 | 40 | 41 | 42 |
| | 43 | 44 | 45 | 46 | 47 | 48 | 49 | 50 | 51 | 52 | 53 | 54 |
| | 55 | 56 | 57 | 58 | 59 | 60 | 61 | 62 | 63 | 64 | 65 | 66 |
| | 67 | 68 | 69 | 70 | 71 | 72 | 73 | 74 | 75 | 76 | 77 | 78 |
| | 79 | 80 | 81 | 82 | 83 | 84 | 85 | 86 | 87 | 88 | 89 | 90 |
| | 91 | 92 | 93 | 94 | 95 | 96 | 97 | 98 | 99 | 100 | 101 | 102 |
| | 103 | 104 | 105 | 106 | 107 | 108 | 109 | 110 | H2O | H2O | H2O | H2O |

Tested 110 barcoded primer pairs for each amplicon over two NGS runs

Fig. 7

N1

1000 copies SARS-CoV2

| | | | | | | | | | | | |
|---|---|---|---|---|---|---|---|---|---|---|---|
| 6246 | 6368 | 6654 | 6747 | 5878 | 5711 | 5349 | 4664 | 4629 | 6674 | 6248 | 4431 |
| 6861 | 5659 | 6061 | 6693 | 6920 | 4410 | 5216 | 4349 | 7584 | 7344 | 6472 | 7181 |
| 6684 | 7037 | 7608 | 6265 | 5701 | 6536 | | | | | | |

| | | | | | | | | | | | |
|---|---|---|---|---|---|---|---|---|---|---|---|
| 54472 | 58029 | 50982 | 42623 | 56932 | 31353 | 51726 | 50708 | 72944 | 87883 | 80499 | 52241 |
| 60248 | 55258 | 59631 | 47359 | 72534 | 65345 | 59106 | 55439 | 65672 | 70841 | 73572 | 68784 |
| 28922 | 47372 | 82558 | 85199 | 61022 | 44832 | 70892 | 74436 | 35657 | 57987 | 78030 | 72730 |
| 50934 | 47798 | 73808 | 56824 | 81253 | 47073 | 72578 | 56271 | 85843 | 87984 | 64239 | 81031 |
| 48432 | 44394 | 49296 | 43136 | 60298 | 58333 | 44363 | 48402 | 59592 | 57971 | 51109 | 54773 |
| 51523 | 55585 | 51042 | 43492 | 57204 | 58278 | 61803 | 60448 | 55363 | 50781 | 73472 | 63352 |
| 46540 | 48758 | 53918 | 48750 | 53279 | 43210 | 47375 | 44357 | | | | |

100 copies SARS-CoV2

| | | | | | | | | | | | |
|---|---|---|---|---|---|---|---|---|---|---|---|
| 5313 | 5690 | 5537 | 6470 | 4909 | 4046 | 4729 | 3075 | 2283 | 4618 | 5118 | 3006 |
| 5552 | 4441 | 4356 | 5175 | 5206 | 1801 | 3189 | 2578 | 6241 | 4665 | 4663 | 6160 |
| 6353 | 6975 | 6178 | 3988 | 3142 | 5335 | | | | | | |

| | | | | | | | | | | | |
|---|---|---|---|---|---|---|---|---|---|---|---|
| 52735 | 53949 | 46930 | 39441 | 45068 | 23556 | 34909 | 38835 | 58853 | 58478 | 56834 | 38554 |
| 57888 | 48961 | 59681 | 49212 | 64370 | 51249 | 43701 | 43808 | 53604 | 56622 | 66888 | 59681 |
| 29427 | 45855 | 81630 | 73885 | 58313 | 45141 | 58587 | 71220 | 31899 | 52628 | 78394 | 68403 |
| 52180 | 48839 | 74935 | 86448 | 45198 | 31038 | 47240 | 66173 | 84852 | 88149 | 80541 | 58487 |
| 48883 | 45816 | 48675 | 46399 | 58451 | 58148 | 35386 | 45200 | 59808 | 58432 | 48861 | 50410 |
| 51156 | 50188 | 48769 | 40214 | 56312 | 60068 | 82324 | 68956 | 45926 | 42755 | 68697 | 64315 |
| 48916 | 47690 | 54946 | 49647 | 53649 | 40347 | 38288 | 40903 | | | | |

0 copies SARS-CoV2

| | | | | | | | | | | | |
|---|---|---|---|---|---|---|---|---|---|---|---|
| 6650 | 0 | 0 | 0 | 0 | 0 | 0 | 0 | 409 | 0 | 0 | 0 |
| 0 | 0 | 0 | 0 | 0 | 0 | 0 | 0 | 0 | 0 | 0 | 0 |
| 0 | 0 | 0 | 0 | 0 | 0 | | | | | | |

| | | | | | | | | | | | |
|---|---|---|---|---|---|---|---|---|---|---|---|
| 0 | 0 | 0 | 0 | 0 | 0 | 0 | 0 | 0 | 0 | 0 | 0 |
| 0 | 0 | 0 | 0 | 0 | 0 | 1 | 0 | 0 | 0 | 0 | 0 |
| 0 | 0 | 0 | 0 | 0 | 0 | 0 | 0 | 0 | 0 | 0 | 0 |
| 0 | 1 | 0 | 0 | 0 | 0 | 0 | 0 | 0 | 0 | 0 | 0 |
| 0 | 0 | 0 | 0 | 0 | 0 | 0 | 0 | 0 | 0 | 0 | 0 |
| 0 | 0 | 0 | 0 | 0 | 0 | 0 | 0 | 0 | 24 | 0 | 1 |
| 0 | 0 | 0 | 0 | 0 | 0 | 0 | 0 | | | | |

Fig 7 (continued)

N3

| | | | | | | | | | | | |
|---|---|---|---|---|---|---|---|---|---|---|---|
| 9843 | 11502 | 11202 | 6106 | 10002 | 10535 | 10333 | 10029 | 10362 | 10521 | 10075 | 8796 |
| 7120 | 8786 | 10673 | 10723 | 11146 | 6652 | 6525 | 7802 | 9135 | 9135 | 11779 | 11675 |
| 10169 | 11420 | 10363 | 10283 | 7862 | 10530 | | | | | | |

| | | | | | | | | | | | |
|---|---|---|---|---|---|---|---|---|---|---|---|
| 53295 | 59819 | 46390 | 44471 | 59034 | 53698 | 55153 | 60508 | 77579 | 79789 | 69139 | 74014 |
| 68391 | 69961 | 74004 | 70807 | 82713 | 76203 | 66062 | 78443 | 69602 | 61650 | 84037 | 63318 |
| 63668 | 70628 | 77086 | 74348 | 66032 | 62138 | 61215 | 76921 | 53018 | 77263 | 79932 | 62717 |
| 54419 | 60497 | 62365 | 57753 | 75517 | 73848 | 57887 | 21826 | 65032 | 55629 | 56430 | 41204 |
| 51663 | 55285 | 43592 | 50688 | 72257 | 60345 | 51040 | 62093 | 41783 | 50863 | 58215 | 72126 |
| 59711 | 56458 | 54053 | 38691 | 52080 | 44035 | 63178 | 58653 | 50371 | 57413 | 54933 | 51046 |
| 61965 | 64671 | 66375 | 48032 | 65836 | 57924 | 50604 | 61590 | | | | |

| | | | | | | | | | | | |
|---|---|---|---|---|---|---|---|---|---|---|---|
| 4914 | 12063 | 11777 | 5644 | 11241 | 12096 | 11886 | 11372 | 11554 | 11291 | 9621 | 11040 |
| 7102 | 7584 | 10712 | 10701 | 11379 | 3110 | 7197 | 7732 | 9266 | 8797 | 10601 | 11638 |
| 11730 | 12785 | 12298 | 6315 | 4403 | 7589 | | | | | | |

| | | | | | | | | | | | |
|---|---|---|---|---|---|---|---|---|---|---|---|
| 51023 | 59815 | 43858 | 43351 | 45180 | 39916 | 36146 | 47142 | 82263 | 87367 | 66473 | 60928 |
| 69695 | 68378 | 79453 | 74536 | 79466 | 61244 | 52861 | 67534 | 80875 | 52923 | 76210 | 73148 |
| 63697 | 74629 | 79583 | 86322 | 61462 | 64817 | 53455 | 74540 | 49519 | 74838 | 79837 | 60798 |
| 60724 | 65822 | 86541 | 67914 | 57247 | 50486 | 36159 | 19814 | 63595 | 50573 | 50942 | 38419 |
| 55978 | 59874 | 45407 | 54799 | 74151 | 61036 | 44818 | 61912 | 38291 | 49766 | 56135 | 69275 |
| 58347 | 55717 | 56277 | 36315 | 51310 | 41067 | 53883 | 60321 | 47782 | 53758 | 44672 | 46795 |
| 64489 | 64288 | 66617 | 46471 | 66012 | 56809 | 40558 | 59510 | | | | |

| | | | | | | | | | | | |
|---|---|---|---|---|---|---|---|---|---|---|---|
| 0 | 0 | 0 | 0 | 0 | 0 | 0 | 0 | 0 | 0 | 0 | 0 |
| 0 | 0 | 0 | 0 | 0 | 0 | 0 | 0 | 0 | 0 | 0 | 0 |
| 0 | 0 | 0 | 0 | 0 | 0 | | | | | | |

| | | | | | | | | | | | |
|---|---|---|---|---|---|---|---|---|---|---|---|
| 0 | 1 | 0 | 0 | 0 | 0 | 0 | 0 | 0 | 0 | 0 | 0 |
| 0 | 0 | 0 | 0 | 0 | 0 | 0 | 0 | 0 | 0 | 0 | 0 |
| 0 | 0 | 0 | 0 | 0 | 0 | 0 | 0 | 0 | 0 | 0 | 0 |
| 0 | 0 | 0 | 1 | 0 | 0 | 0 | 0 | 0 | 0 | 0 | 0 |
| 0 | 0 | 0 | 1 | 0 | 1 | 0 | 1 | 0 | 0 | 0 | 0 |
| 0 | 0 | 0 | 0 | 0 | 0 | 0 | 0 | 0 | 0 | 0 | 0 |
| 0 | 0 | 0 | 0 | 0 | 0 | 0 | 0 | | | | |

Fig 7 (continued)

# ribosome

| | | | | | | | | | | | |
|---|---|---|---|---|---|---|---|---|---|---|---|
| 4344 | 4931 | 4977 | 4191 | 5089 | 5149 | 4553 | 3659 | 5061 | 5158 | 4255 | 4609 |
| 4067 | 4632 | 5315 | 3297 | 5465 | 20675 | 19176 | 23056 | 20532 | 15958 | 5536 | 5445 |
| 4781 | 5242 | 4912 | 4433 | 461 | 5253 | | | | | | |

| | | | | | | | | | | | |
|---|---|---|---|---|---|---|---|---|---|---|---|
| 30147 | 27514 | 26194 | 35061 | 29048 | 36248 | 31318 | 33297 | 39589 | 42918 | 43110 | 35765 |
| 32936 | 30214 | 39309 | 39557 | 28532 | 28728 | 39912 | 36407 | 27235 | 24039 | 33519 | 39121 |
| 37858 | 33808 | 34800 | 33768 | 33493 | 28217 | 28902 | 32537 | 25424 | 30361 | 28625 | 33661 |
| 31964 | 25259 | 35035 | 26157 | 32389 | 25425 | 34422 | 25095 | 24758 | 23169 | 35687 | 28731 |
| 30833 | 27039 | 26811 | 27014 | 28726 | 35043 | 23454 | 24778 | 23929 | 27435 | 18398 | 31026 |
| 26836 | 24453 | 24854 | 30845 | 26094 | 22935 | 29617 | 19846 | 20537 | 27754 | 31098 | 29832 |
| 30929 | 34342 | 35715 | 14119 | 39201 | 32129 | 23530 | 28303 | | | | |

| | | | | | | | | | | | |
|---|---|---|---|---|---|---|---|---|---|---|---|
| 4515 | 5124 | 5017 | 4634 | 5745 | 5614 | 5409 | 4387 | 5861 | 5806 | 5387 | 5741 |
| 3968 | 4779 | 5019 | 4505 | 4876 | 16458 | 16517 | 20669 | 15791 | 16801 | 6573 | 6158 |
| 5277 | 6212 | 5501 | 5339 | 292 | 4658 | | | | | | |

| | | | | | | | | | | | |
|---|---|---|---|---|---|---|---|---|---|---|---|
| 31581 | 29559 | 27075 | 35934 | 24627 | 28960 | 21727 | 28358 | 33241 | 40002 | 43421 | 30089 |
| 33914 | 31950 | 43229 | 43589 | 25707 | 24378 | 30350 | 33175 | 34778 | 21754 | 32291 | 35937 |
| 41314 | 37872 | 36759 | 39892 | 34161 | 29355 | 26692 | 33385 | 25708 | 31574 | 29106 | 34619 |
| 37174 | 30216 | 40541 | 31559 | 25277 | 18669 | 23573 | 29592 | 26409 | 23418 | 37196 | 28771 |
| 34391 | 32129 | 29832 | 31511 | 29595 | 39161 | 21798 | 28590 | 23848 | 28358 | 19510 | 31808 |
| 28906 | 26106 | 26939 | 33625 | 27394 | 24383 | 27209 | 21344 | 20307 | 28327 | 31813 | 31312 |
| 32994 | 36983 | 37919 | 16987 | 41367 | 33195 | 20976 | 28767 | | | | |

| | | | | | | | | | | | |
|---|---|---|---|---|---|---|---|---|---|---|---|
| 896 | 12649 | 6868 | 5435 | 9524 | 5489 | 8931 | 4627 | 22670 | 7825 | 14976 | 9017 |
| 2074 | 8780 | 8980 | 1675 | 4858 | 53059 | 66163 | 23734 | 22331 | 49916 | 11371 | 9819 |
| 16582 | 21561 | 6001 | 10128 | 0 | 8561 | | | | | | |

| | | | | | | | | | | | |
|---|---|---|---|---|---|---|---|---|---|---|---|
| 2745 | 1318 | 5589 | 6050 | 4215 | 4536 | 5579 | 4146 | 8076 | 6432 | 17577 | 9455 |
| 6538 | 6820 | 13411 | 7567 | 4714 | 1038 | 8098 | 4405 | 2712 | 2045 | 4928 | 7457 |
| 3907 | 3726 | 4158 | 7595 | 8530 | 5212 | 8040 | 9404 | 12365 | 1278 | 285 | 3309 |
| 9422 | 1442 | 4645 | 6144 | 5902 | 13606 | 1905 | 11060 | 1398 | 14989 | 11406 | 6641 |
| 4405 | 5041 | 1147 | 8783 | 1900 | 304 | 6121 | 6504 | 4891 | 7418 | 655 | 2008 |
| 3747 | 3065 | 5475 | 15619 | 3439 | 3506 | 14336 | 8259 | 2142 | 5286 | 7176 | 5786 |
| 2071 | 3307 | 10136 | 370 | 8465 | 4633 | 4358 | 11646 | | | | |

Fig 7 (continued)

Selected a set of 96 pairs of indices
that work well for all amplicons

Final primer plate

| | | | | | | | | | | | |
|---|---|---|---|---|---|---|---|---|---|---|---|
| 5 | 6 | 7 | 8 | 9 | 10 | 11 | 12 | 13 | 14 | 15 | 16 |
| 17 | 18 | 19 | 20 | 21 | 22 | 23 | 24 | 25 | 26 | 27 | 28 |
| 31 | 32 | 33 | 34 | 35 | 36 | 37 | 38 | 39 | 40 | 41 | 42 |
| 43 | 44 | 45 | 46 | 47 | 48 | 49 | 50 | 51 | 52 | 53 | 54 |
| 55 | 56 | 57 | 58 | 59 | 60 | 61 | 62 | 63 | 64 | 65 | 66 |
| 67 | 68 | 69 | 70 | 71 | 72 | 73 | 103 | 75 | 76 | 77 | 78 |
| 79 | 80 | 81 | 82 | 83 | 84 | 85 | 86 | 87 | 88 | 89 | 90 |
| 91 | 92 | 93 | 94 | 95 | 96 | 97 | 98 | 99 | 100 | 101 | 102 |

104 105 106 107 108 109 110

Fig. 7 (Continued)

A

| 18aa | 52aa | 67aa | 69aa | 70aa | 80aa | 98aa | 138aa | 143aa | 144aa | 189aa | 215aa | 242aa | 417aa | 439aa | 477aa | 478aa | 484aa | 501aa | 477aa | 478aa | 484aa | 501aa | 522aa | 570aa | 614aa | 675aa | 677aa | 681aa | 701aa | 716aa | 772aa | Variant |
|---|---|---|---|---|---|---|---|---|---|---|---|---|---|---|---|---|---|---|---|---|---|---|---|---|---|---|---|---|---|---|---|---|
| + | + | + | + | + | + | + | + | + | + | + | + | + | + | + | + | + | + | + | + | + | + | + | + | + | G | + | + | + | + | + | + | norm. |
| + | + | + | + | + | A | + | + | + | + | + | G | - | N | + | + | + | K | Y | + | + | K | Y | + | + | G | + | + | + | V | + | + | B.1.351 + K417N |
| + | R | V | - | - | + | + | + | + | - | + | + | + | + | + | + | + | K | + | + | + | K | + | + | + | G | + | H | + | + | + | + | Delta69-70; delta144; E484K; Q677H |
| + | + | + | - | - | + | + | + | + | - | + | + | + | + | + | + | + | + | Y | + | + | + | Y | + | D | G | + | + | H | + | I | + | B.1.1.7 |
| + | + | + | - | - | + | + | + | + | - | + | + | + | + | + | + | + | + | Y | + | + | + | Y | + | D | G | + | + | H | + | V | + | B.1.1.7 (T716V) |
| + | + | + | - | - | + | + | + | + | + | F | + | + | + | K | + | + | + | + | + | + | + | + | + | + | G | + | + | + | + | + | I | delta 69-70; L189F; N439K |
| + | + | + | - | - | + | + | + | + | + | + | + | + | + | K | + | + | + | + | + | + | + | + | + | + | G | + | + | + | + | + | + | delta 69-70; N439K |
| + | + | + | + | + | + | + | + | + | + | + | + | + | + | + | N | + | + | + | N | + | + | + | + | + | G | + | + | + | + | + | + | S477N |
| + | + | + | + | + | + | + | + | + | + | + | + | + | + | + | N | + | + | + | N | + | + | + | + | + | G | + | + | + | + | + | + | S477N |
| + | + | + | + | + | + | + | Y | + | + | + | + | + | + | + | N | + | + | + | N | + | + | + | S | + | G | R | + | + | + | + | + | S477N |
| + | + | + | + | + | + | + | + | + | + | + | + | + | + | + | + | K | + | + | + | K | + | + | + | + | G | + | + | + | + | + | + | T478K |
| F | + | + | + | + | + | + | + | + | + | + | + | + | + | + | + | + | + | + | + | + | + | + | + | + | G | R | + | + | + | + | + | L18F |
| + | + | + | + | + | + | F | + | + | + | + | + | + | + | + | + | + | + | + | + | + | + | + | + | + | G | + | + | + | + | + | + | S98F |

8

9

Fig. 11

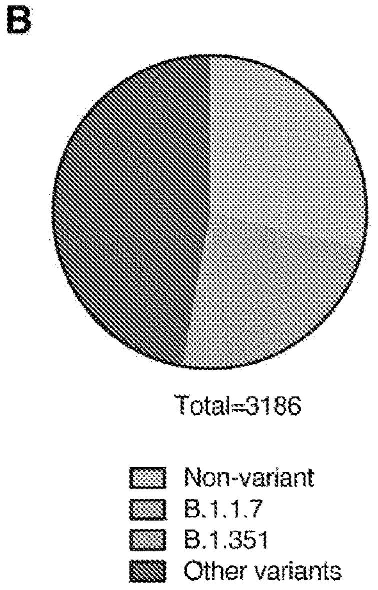
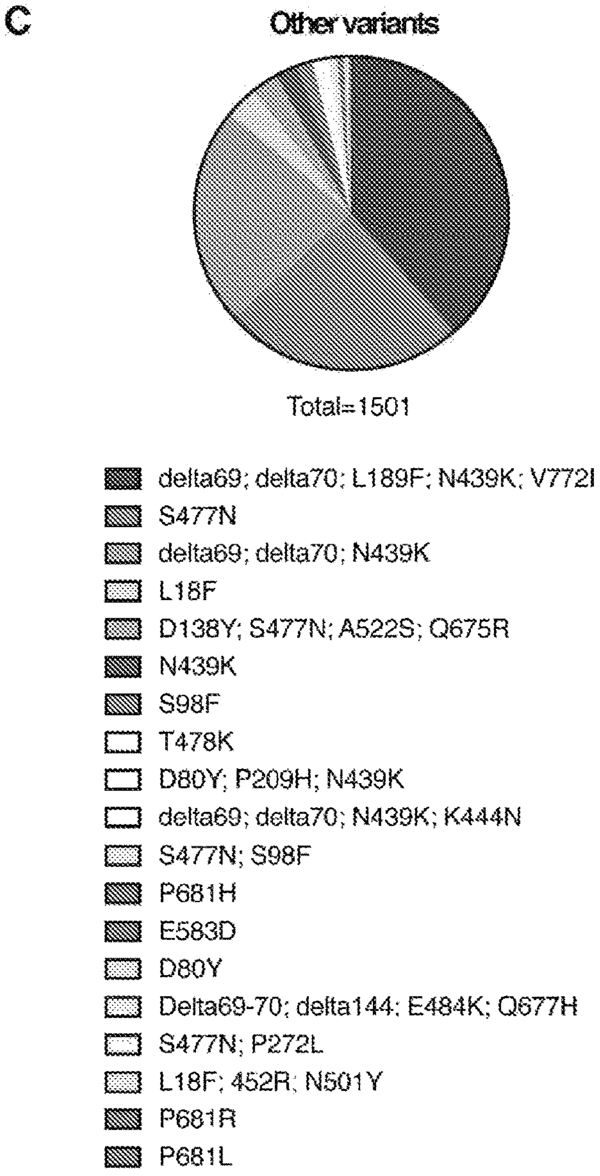
Fig. 11 (Continued)

METHOD FOR PARALLEL NUCLEIC ACID ANALYSIS

REFERENCE TO AN ELECTRONIC SEQUENCE LISTING

The contents of the electronic sequence listing (Sequence Listing.txt; Size: (271,954 bytes) was created on Feb. 23, 2023 herein incorporated by reference in its entirety.

The present invention relates to the field of parallel nucleic acid analytics.

BACKGROUND

Within just a few months the newly emerged coronavirus Sars-CoV2 caused the worldwide pandemic of Covid-19. While the world is awaiting an effective and scalable vaccination and an antiviral therapy, Covid-19 must be contained as good as possible. To this end two measures are available, namely social distancing e.g. via lockdown measures and molecular testing for contact tracing and random surveillance. However, the molecular method to detect active disease, i.e. the presence of viral RNA from swab, gargle, sputum, or saliva, is currently costly and hindered by shortage of equipment and supply of reagents. Large scale testing can be implemented by PCR detection in pooled RNA extracts (Ben-Ami et al., Clinical Microbiology and Infection 2020, 26: 1248-1253). However, such pooling approaches may need retesting to identify the individual positive sample in a positively tested pool. In order to identify individual samples in a multiplex approach, sample-derived DNA is barcoded by a specific nucleotide sequence (Dao Thi et al., Sci. Transl. Med. 2020; 12: eabc7075). The barcode sequence is determined together with the viral sequence, thereby creating the connection of viral presence within the respective sample. In general, however, multiplexing reduces the sensitivity of the assay and/or increases the limit of detection for viral genetic material (Visseaux et al., J Clin Micr 2020, 58(8): e00630-20).

Yet there still remains the need to further increase testing capacity while at the same time reducing testing costs and preferably also maintain or increase test sensitivity. A goal of the present invention is to improve large scale testing capacities to address these needs.

SUMMARY

The present invention provides a method for detecting a nucleic acid of interest in a plurality of samples, comprising the steps of a) providing analyte nucleic acids from a plurality of samples in separate containers for each sample, wherein the containers are arranged into an array of subsets, wherein the array comprises two or more subsets; b) amplifying nucleic acids by a primer extension reaction using at least one pair of primers hybridized to the analyte nucleic acids, wherein a pair of primers comprises a forward and a reverse primer, wherein the forward and reverse primers both comprise an adaptor sequence, an sample identifier sequence and a binding sequence for hybridization to the analyte nucleic acids, respectively; c) combining the amplified nucleic acids of step b) of containers of two or more subsets to an array of combined containers, wherein containers of one subset, but not of another subset, are combined to a combined container; d) amplifying nucleic acids by a primer extension reaction using at least one pair of further primers hybridized to the amplified nucleic acids of combined containers of step c), wherein a pair of further primers comprises a further forward and a further reverse primer, wherein the further forward and further reverse primers both comprise a subset identifier sequence and a sequence for hybridization to the adaptor sequence; e) determining the sequences of the amplified nucleic acids of step d); f) assigning a determined sequence of a nucleic acid of interest of step e) to a sample through association to a subset and container with the subset identifier sequences and the sample identifier sequences.

The invention further provides a set of primers suitable for a method of the invention. Such a set may comprise at least 10 different primers A which comprise the sequence, from 5' to 3': an adaptor A sequence, an identifier sequence of at least 4 nt in length and a target binding sequence, wherein the identifier sequence is different within the at least 10 different primers A, optionally with a sequence distance of a Hamming distance of at least 1 or a Levenshtein distance of at least 1; at least 10 different primers B which comprise the sequence, from 5' to 3': an adaptor B sequence, an identifier sequence of at least 4 nt in length and a target binding sequence, wherein the identifier sequence is different within the at least 10 different primers B, optionally with a sequence distance of a Hamming distance of at least 1 or a Levenshtein distance of at least 1; at least 10 different primers C which comprise the sequence, from 5' to 3': an adaptor C sequence, an identifier sequence of at least 4 nt in length and a binding sequence that binds to the adaptor A sequence, wherein the identifier sequence is different within the at least 10 different primers C, optionally with a sequence distance of a Hamming distance of at least 1 or a Levenshtein distance of at least 1; and at least 10 different primers D which comprise the sequence, from 5' to 3': an adaptor D sequence, an identifier sequence of at least 4 nt in length and a binding sequence that binds to the adaptor B sequence, wherein the identifier sequence is different within the at least 10 different primers D, optionally with a sequence distance of a Hamming distance of at least 1 or a Levenshtein distance of at least 1.

In preferred embodiments the nucleic acid of interest is RNA, such as from an RNA virus. The method includes a conversion of the RNA to cDNA in step a). As such the inventive method can also be written as a method for detecting a nucleic acid of interest, including ribonucleic acid (RNA), in a plurality of samples, comprising the steps of a) providing analyte nucleic acids from a plurality of samples in separate containers for each sample, wherein the containers are arranged into an array of subsets, wherein the array comprises two or more subsets; comprising reverse transcribing RNA, thereby generating a complementary DNA of the RNA as analyte nucleic acids; b) amplifying nucleic acids, in particular DNA, by a primer extension reaction using at least one pair of primers hybridized to the analyte nucleic acids, wherein a pair of primers comprises a forward and a reverse primer, wherein the forward and reverse primers both comprise an adaptor sequence, a sample identifier sequence and a binding sequence for hybridization to the analyte nucleic acids, respectively; wherein the amplification is preferably DNA specific and/or with a DNA polymerase; c) combining the amplified nucleic acids of step b) of containers of two or more subsets to an array of combined containers, wherein containers of one subset, but not of another subset, are combined to a combined container; d) amplifying nucleic acids by a primer extension reaction using at least one pair of further primers hybridized to the amplified nucleic acids of combined containers of step c), wherein a pair of further primers comprises a further forward and a further reverse primer, wherein the further forward and further reverse primers both comprise a subset identifier sequence and a sequence for hybridization to the adaptor sequence; e) determining the sequences of the amplified nucleic acids of step d); f) assigning a determined sequence of a nucleic acid of interest of step e) to a sample through association to a subset and container with the subset identifier sequences and the sample identifier sequences.

The disclosure of the invention relates to all aspects of the invention likewise, e.g. descriptions of the method also relate to the set as a suitability or a use of the set; likewise, descriptions of the set also relate to its components that can be used in the method. In particular, primers A and B may be used as forward and as reverse primer; primers C and D may be used as further forward and as further reverse primers.

DETAILED DESCRIPTION

The present invention provides a method for detecting a nucleic acid of interest in a plurality of samples. Such a nucleic acid of interest can e.g. be from a pathogen, such as a virus, bacteria or fungi, and thus be used to detected said pathogen via its nucleic acid. This allows the method to be used in the diagnosis of diseases that are associated with the presence of the pathogen.

Usually, the nucleic acid of interest is preselected, i.e. by using primers that bind to the nucleic acid of intertest. As such, the inventive method can be used to detect the presence of specific pathogens of interest.

The inventive method is usually performed in vitro, i.e. a sample is analysed according to the invention ex vivo and/or outside of a subject from whom the sample has been previously obtained.

The subject from whom the sample is obtained can e.g. be a human or a non-human animal, e.g. a mammal, a bird or reptile. Preferably the subject is a mammal, in particular a human.

The sample can be from or contain a biological sample such as a body fluid, such as a sputum, saliva, nasal mucus, bronchoalveolar lavage, urine, a serum or blood sample. Such a sample containing sputum, saliva, or nasal mucus may be obtained from a nasopharyngeal swab, an oropharyngeal swab, a nasal swab, a gargle solution, or providing sputum into a container. More generally the sample may be a solid sample, liquid sample, or aerosols carried in gaseous exhale.

The nucleic acid of interest can be released from the biological sample, cell or encapsulation (e.g. viral encapsulation) so that it is accessible in solution for further treatment. Such a release may include a removal from the pathogenic source, e.g. by the disassembly of the pathogen, which may include virus disassembly or lysis or porosis of bacteria or fungi. Optionally the nucleic acid of interest is stabilized by e.g. removing and/or inactivating any enzymes that would degrade or digest the nucleic acid of interest. E.g. a DNase inhibitor can be added if the nucleic acid of interest is or comprises DNA or a RNase inhibitor can be added if the nucleic acid of interest is or comprises RNA. In combination or as an alternative, the sample may be treated by elevated temperature or chemicals, such as e.g. at an intensity and for a time sufficient to inactivate such unwanted enzymes like DNases and/or RNases.

As said, the nucleic acid of interest can be DNA or RNA, preferably it comprises or consists of RNA.

The nucleic acids of interest, e.g. as released from a biological sample, cell or encapsulation as described above, may be used as the analyte nucleic acids in the inventive methods. In further embodiments, the nucleic acids may be further treated, copied or converted into another type of nucleic acid, such as for example creating a cDNA from an RNA of a biological sample. The cDNA may be generated by reverse transcription. The cDNA may then be used as analyte nucleic acid in the inventive method. A further modification may be fragmentation of a nucleic acid from a sample.

In preferred embodiments of the invention viral RNA is a nucleic acid of interest. Such viral RNA is released from virus capsules, such as capsids or envelopes, and converted into cDNA by performing a reverse transcription. In particular, the invention can comprise in step a) providing RNA from a sample and generating a cDNA of said RNA by reverse transcription, wherein the nucleic acids that are amplified in step b) comprise said cDNA. Reverse transcription can be performed by reverse transcriptase, such as a M-MLV reverse transcriptase, wild type or modified, such as a SuperScript™ reverse transcriptase, e.g. SuperScript™ III reverse transcriptase or SuperScript™ IV reverse transcriptase. Such modified M-MLV reverse transcriptase preferably has reduced RNase H activity and/or increased thermal stability as compared to wild type M-MLV reverse transcriptase under operative conditions (ambient pressure at 1 bar, 50° C.). Example primers for reverse transcription can be e.g. random primers, such as random hexamers, which is a collection of various primers with variable sequences at a given length. Example lengths of primers are 5, 6, 7, 8, 9, 10, 11, 12, 13, 14 or more nucleotides in length, preferably 6 (hexamers) or preferably 8-12 for target specific primers. If performed, preferably no barcodes or "identifier sequences" are added during reverse transcription. It is preferred to add such "identifier sequence" in the inventive method later during step b) and d), especially when treating DNA (e.g. cDNA) as analyte nucleic acids. Such barcodes or "identifier sequences" may be later used downstream to connect a determined nucleic acid sequence to a subject from whom the sample originated (and who may thus have an infection with a pathogen).

A container to hold the nucleic acid of a sample may be any holding means suitable for the inventive method. Example containers may be selected from a flask, vial, bag, syringe, or a well, including a microwell on a well-plate, or a droplet. In particular, wells on well-plates are preferred as they allow easy organisation, parallel pipetting, easy handling and automation during the inventive method. Before being put into the preferred container to be used in the inventive method, a sample may have been handled, transported and/or treated in another container, e.g. to facilitate transportation from the patient to the facility performing the inventive method.

Each sample that is distinguished according to the plurality of samples is at least initially in a separate container. Of course, the invention does include using pooled biological samples (e.g. from more than one subject) to be treated as one sample but it is preferred that each sample is associated to only one subject for individual association with the nucleic acid of interest.

The plurality of samples may include 10 or more samples, e.g. 20, 50, 75, 100, 150, 200, 250, 300, 400, 500, 600, 700, 800, 900, 1000, 1200, 1400, 1600, 1800, 2000, 2500, 3000, 4000, 5000, 6000, 7000, 8000, 9000, 9500, 10000, 12000, or more samples and any range in between these values. For example, the plurality of samples is 20 to 1000000 samples, e.g. 40 to 500000 samples or 90 to 100000 samples.

In step a) of the inventive method, analyte nucleic acids from a plurality of samples are provided in separate containers for each sample. The analyte nucleic acids may be RNA or DNA; DNA is preferred, as such the analyte nucleic acids may comprises or consists of DNA. If the nucleic acid of interest, e.g. from a pathogen, is RNA, it is preferred to generate a cDNA therefrom to be used as the analyte nucleic acid, as discussed above. The generation of cDNA may be done in the same containers that are later used during the inventive method. Enzymes, like a reverse transcriptase may be inactivated, such as by elevated temperature (e.g. 70° C. or more for a SuperScript™ reverse transcriptase), before continuing with step b).

The containers are arranged into an array of subsets, wherein the array comprises two or more subsets. "array of subsets" means that the containers (with the analyte nucleic acids) are grouped in at least two groups ("array comprises two or more subsets"). This arrangement can be an information available to the user who performs the inventive method and/or a special grouping from which the subset arrangement is apparent and/or a labelling or marking of the containers. For example, the containers may be arranged into an array of subsets and the subsets comprise the containers at a coordinate. That coordinate may be noted and information of its container may be stored by the user. Coordinates may be of a 2D or 3D arrangement, e.g. rows, columns and/or stacks of one or more carrier(s) with the containers. Such a carrier may be a plate, e.g. with depressions as containers, such as a well plate. Of course, any other form of coordinate may be used to identify a container of a subset and/or of a sample from a particular subject, including water-based droplets in oil. Containers may have walls or not, such as in the case of droplets. In a preferred embodiment, the containers are arranged into an array of subsets and the subsets comprise the containers at a coordinate. The containers with a corresponding coordinate for each subset are combined in step c).

An example is using two or more well-plates. All wells (containers) in one well-plate are a subset with each well-plate forming a subset of its wells (containers). According to this example, a plurality of two or more well-plates would thus contain an array of two or more subsets with the subset amount being the number of well-plates and each subset (individual well-plate) consisting of the number of wells (containers) per plate or less, if not all wells contain an analyte nucleic acid. In fact, in preferred embodiments such a well-plate (subset) may use 1-10 of its wells (containers) for controls, so that in case of 96-well plates fewer than 96 wells may be used for analyte nucleic acids. Irrespective of this example, in any embodiment of the invention, each subset may comprise one or more control nucleic acids or empty controls without nucleic acids in a container, that are treated similarly throughout the inventive method as containers with analyte nucleic acids.

In preferred embodiments of the invention, the two or more subsets are 8 or more subsets, 10 or more subsets, such as 20 or more subsets, e.g. 30 or more subsets, 40 or more subsets, 50 or more subsets, 60 or more subsets, 70 or more subsets, 80 or more subsets, or 90 or more subsets. An example for 8 subsets are 8 well plates of PCR strips.

In equally preferred embodiments, a subset comprises 10 or more containers, preferably 20 or more containers, or 30 or more containers, or 40 or more containers, or 50 or more containers, or 60 or more containers, or 70 or more containers, or 80 or more containers, or 90 or more containers.

Examples of such number for subset or container arrays are well plates such as 96-, 384- or 1536-well plates. Any such number as mentioned above (at least 2, 10, 20, etc.) of wells can be used as containers or members of subsets of the present invention. Remaining wells on a plate may or may not be used, e.g. as controls. With the subset representing plates or in general any such array, the number of subsets represents the number of plates or arrays. When subsets are combined in step c), their combined nucleic acids may also be stored in a container, with each combined nucleic acids of a subset being in a separate container. Again, in some examples, well plates may be used, with e.g. one or more wells containing the combined nucleic acids of a subset. In preferred embodiments, the method uses 96 containers (subset size) and 96 subsets; in further options the method uses 384 containers (subset size) and 96 or 384 subsets. This would make full use of 96- or 384 well plates. Also 1536 well plates can be used for the containers or the subsets. In any of these embodiments, the number of containers to accommodate samples or subsets (when combined in the step d) can be lower to accommodate controls as mentioned above.

In step b) of the inventive method, nucleic acids are amplified by a primer extension reaction using at least one pair of primers hybridized to the analyte nucleic acids, wherein a pair of primers comprises a forward and a reverse primer, wherein the forward and reverse primers both comprise an adaptor sequence, a sample identifier sequence ("sample index") and a binding sequence for hybridization to the analyte nucleic acids, respectively.

As mentioned above, the analyte nucleic acids are preferably DNA—either because DNA has been provided by the sample or after conversion of RNA into cDNA with the cDNA being used as analyte nucleic acids in step b). Primer extension reactions are conventional in the art and include binding the primers to the analyte nucleic acids and extending the primers with further nucleotides in a template specific fashion, with the template being the analyte nucleic acid. Accordingly, a complementary strand is generated if the sample contains the appropriate template. Such a reaction is preferably performed with a DNA polymerase. A second strand can be generated likewise with another primer. Both primers are referred to as forward and reverse primers for first and second strand generation as is common in the art. An example of a primer extension reaction is PCR.

Alternatively, the analyte nucleic acid is RNA. With RNA as template, it is preferred to generate a complementary DNA strand (also termed copy DNA or cDNA). As such the (forward) primer preferably is DNA with the extended nucleotides also being DNA. Such a reaction is for example a reverse transcription, which can be facilitated by a reverse transcriptase. Second strand generation with the reverse primer is then a DNA templated DNA polymerisation, preferably with a DNA polymerase as described above. Further rounds or cycles of amplification can then be entirely DNA-based, including primer extension reactions using the forward primer, which in a further round or cycle may use the generated complementary strand of the reverse primers' amplification product as template. The difference with the previous paragraph—according to this embodiment—would be that in the previous paragraph, both forward and reverse primers add their sample identifier in entirely DNA-based amplification procedures, whereas the second alternative adds primers with the sample identifier already in a reverse transcription reaction (or generally in an RNA-based amplification reaction). It is preferred according to the invention to add the sample identifier only using DNA templates since DNA-based primer extension reactions are more robust with fewer side reactions but of course using RNA templates is also a possibility, in particular given that the invention uses two sample identifiers (on both, the forward and reverse primers) to compensate and even add further reliability to the method, thereby increasing specificity.

As said, according to the invention, the forward and reverse primers both comprise an adaptor sequence, a sample identifier sequence and a binding sequence for hybridization to the analyte nucleic acids, respectively.

The binding sequence for hybridization to the analyte nucleic acids comprises a complementary sequence to the analyte nucleic acid (or its complementary sequence in case of the reverse primer) so that the primer specifically binds to the analyte nucleic acid (or its complementary sequence in case of the reverse primer) by hybridisation under reaction conditions. Reaction conditions for hybridization may vary according to the enzymes and/or buffers used and may e.g. comprise heating to 58° C. in a PCR buffer comprising 750 mM Tris-HCl pH 8.3, 200 mM $(NH_4)_2SO_4$, 1% Triton X-100, which is a preferred embodiment of the invention. Also variations of the buffers can be used. E.g. a buffer may comprise a pH of 7 to 9, preferably about 8.3. Preferably sulphate ions are present; also preferred a crowding agent such as Triton X-100 is used; preferably in a concentration of 0.3 to 3%, e.g. about 1%, (all w/w-%). Preferably the complementary sequence to the analyte nucleic acid comprises 8 or more, e.g. 9, 10, 11, 12, 13, 14, 15, 16, 17, 18, 19, 20, 21, 22 or even more nucleotides, e.g. 8-30 nucleotides that are complementary with the analyte nucleic acid (or its complementary sequence in case of the reverse primer). The number of complementary nucleotides of the forward and reverse primer can be selected independently. Through the binding sequence, the primers are specific to an analyte nucleic acid sequence of interest. These analyte sequences can e.g. be from a pathogen as will be elaborated in more detail below.

The adaptor sequences on the forward and reverse primers are sequences that are used downstream of the inventive method to bind further forward and reverse primers in step d) to the amplified nucleic acids given that the adaptor sequences are preserved in the amplification products. Such adaptor sequences are usually artificial and usually do not bind to expected nucleic acids in the sample. Suitable adaptor sequences are known in the art and have e.g. been deposited in databases (e.g. the Illumina Adapter Sequences 1000000002694 v14 of July 2020). Any such adaptors can be used according to the invention. Generally, almost any sequence is possible, but of course complementary sequences are used in the further forward and reverse primers of step d), which thus form interrelated primers with the forward and reverse primers of step b). Of course, only one primer sequence in the amplified nucleic acids is bound by each sequence for hybridization to the adaptor sequence in the further forward and reverse primers. For example, the sequence for hybridization to the adaptor sequence in the further forward primer binds to the adaptor sequence of the forward primer but not of the reverse primer; the sequence for hybridization to the adaptor sequence of the further reverse primer binds to the adaptor sequence of the reverse primer but not of the forward primer; or both vice-versa. The adaptor sequence of the forward and reverse primer, selected independently, can be 8 or more, e.g. 9, 10, 11, 12, 13, 14, 15, 16, 17, 18, 19, 20, 21, 22 or even more nucleotides, e.g. 8-30 nucleotides in length.

The sample identifier sequence is a label or barcode that identifies the amplification product of a sample and is introduced in said amplification product via the primers. The sample identifier sequences are usually selected to identify a sample within a subset. Since further identifier sequences are introduced in step d), it is not needed to uniquely label each sample of the entire array. The sample identifier sequences can be shared between different types of analyte nucleic acids/binding sequence for hybridization to the analyte nucleic acids. Nucleic acids of different subsets may be labelled with sample identifier sequences that are selected from the same pool of sample identifier sequences and/or may comprise nucleic acids that are labelled by the same sample identifier sequences. Since both the forward and reverse primers comprise sample identifier sequences—selected independently—the inventive method introduces high specificity. In a preferred embodiment, the sample identifier sequences of the forward and reverse primers of a given container/sample should not be identical or at least not selected to be the same with identities being only random occurrences that should be below 5% or below 1% of the containers or samples. The inventors have noticed with this method that the incidence of false positive results can be significantly reduced, which otherwise occurs when high numbers of amplification cycles are used. Unwanted amplification reactions may lead to a product despite the absence of the nucleic acid of interest in a sample, thus leading to a false positive result—if no further control steps are incurred.

Preferably in step b) each sample identifier sequence of the forward primers is different from the sample identifier sequences of other forward primers for a given binding sequence for hybridization to the analyte nucleic acids. In other words, the sample identifier sequences are each unique for a given analyte nucleic acid or binding sequence for hybridization to the analyte nucleic acid—or in the final amplification product—unique for a given amplicon. For different binding sequences for hybridization to the analyte nucleic acid/amplicons the same sample identifier sequences may be used. In similar preferred embodiments, in step b) each sample identifier sequence of the reverse primers is different from the sample identifier sequences of other reverse primers for a given binding sequence for hybridization to the analyte nucleic acids. These two preferred embodiments can of course be combined; i.e. the sample identifier sequences of the forward and reverse primers are unique for a given binding sequences for hybridization to the analyte nucleic acid/amplicons. In other embodiments, the sample identifier sequences may also be unique among the combined group of forward and reverse primers, but this is not required but of course optional—optionally only for a given binding sequences for hybridization to the analyte nucleic acid/amplicon or not only for a given binding sequences for hybridization to the analyte nucleic acid/amplicon.

The inventive method is based on repeated amplifications of analyte nucleic acids and then of complementary nucleic acids ("amplification cycles"). Each amplification initiated by at least either a forward or reverse primer is considered an amplification cycle. Thus, for illustration, an amplification reaction of both the forward and reverse primer but no further amplification reaction is considered as a reaction with 2 amplification cycles. 2 amplification cycles are thus the minimum for both the forward and reverse primer to get incorporated into the amplification product, for labelling with the sample identifiers. If both forward and reverse primers are present as well as templates for both the forward and the reverse primer, then both primers will result in an amplification product in one amplification cycle. This is usually the case for amplification cycle number 2 onwards. In experimental practice, an amplification cycle is one round of heating and cooling. High numbers of amplification cycles increase the number of erroneous results. However, large numbers of amplification cycles may be needed to detect a nucleic acid of interest or analyte nucleic acid that is present in low amounts. Standardized conditions for all samples/containers are usually used, i.e. the same number of amplification cycles for all containers/samples. In some containers, high numbers of analyte nucleic acids may be present, whereas in other containers low numbers are present. Prior to the invention, this caused sub-optimal conditions for some samples leading to false positive or false negative results. The present invention has improved on such methods to allow sufficient sensitivity and selectivity to detect various samples in one multiplexed reaction, as e.g. shown in the examples. The invention works with various amplification cycles for step b), such as 280 amplification cycles, preferably 5 to 75, 10 to 70, 20 to 65, 25 to 60, 30 to 55, 35 to 50, or 40 to 45 amplification cycles, or any ranges between these values. In preferred embodiments the amplification of step b) is an endpoint amplification. According to this embodiment that is preferred in all aspects of the invention as it strives towards equalizing the number of amplified nucleic acids in each container regardless of initial nucleic acid amount. This greatly helps in detecting nucleic acids of interest at various concentration and amount ranges in the inventive parallel detection method. Endpoint amplification means that the amplification reaction is carried out until no further amplification can occur (in each container). This can be caused by the fact that the required nucleotides for a further amplification cycle are consumed and/or the primers for another amplification cycle have been consumed. A container with fewer nucleis acids that are amplified will take more amplification cycles than a container with a higher number of nucleic acids that are amplified. Accordingly, since all containers are treated similarly, i.e. with the same number of amplification cycles, a number of amplification cycles is selected that will amplify a container with a minimum amount of nucleic acids of interest that are to be detected. Of course, an empty container will not produce any amplification products regardless of the number of amplification cycles and amounts of nucleotides and/or primers. Primer and/or nucleotide consumption during amplification can be due to analyte nucleic acids (if present), controls and/or spike-ins. If no controls and spike-ins are present, then a detection limit may be chosen for a minimum number of analyte nucleic acids that lead in a given number of cycles to the endpoint (no further complete amplification possible). Such a minimum number of analyte nucleic acids can be e.g. 10 or 100 or 500 or 1000 analyte nucleic acids. The selected number of amplification cycles shall take into account the amounts of nucleotides and primers that are added, which determine the cycle number until they are consumed (amplification to saturation). Accordingly, in preferred embodiments of the invention, the number of amplification cycles in step b) is selected so that no further amplification of an analyte nucleic acid occurs in the containers. Under normal circumstances 40 or more, e.g. 45 or more cycles are sufficient for an endpoint amplification. A skilled practitioner can choose a suitable amplification cycle number for the sample at hand. In general, if low amounts of nucleic acids of interest are expected to be in a sample, then higher numbers of amplification cycles will be selected. With the present invention, it was possible to detect nucleic acids of interest that had high differences in sample abundance, with samples differing by a factor of up to $\times 10^7$ copies of nucleic acids of interest per sample. It was quite surprising that such differing samples could be processed in one multiplexed reaction at the same conditions for all samples.

In a preferred structure of the forward and/or the reverse primer the binding sequence for hybridization to the analyte nucleic acids is preferably on the 3' end of the forward and/or reverse primer. This allows an efficient extension reaction in 5' to 3' direction. Preferably the sample identifier sequence is between the binding sequence and the adaptor sequence. The adaptor sequence may be at or near the 5' end of the forward and/or reverse primer. Accordingly, a preferred primer structure for the forward and/or reverse primer comprises in 5' to 3' direction: [adaptor sequence]—[sample identifier sequence]—[binding sequence].

Step c) comprises combining the amplified nucleic acids of step b) of containers of two or more subsets to an array of combined containers, wherein containers of one subset, but not of another subset, are combined to a combined container. Accordingly, the containers of one subset are combined to the combined container. This is done for more than two subsets, thereby creating two or more combined containers, each corresponding to one subset. Given that the analyte nucleic acids have been amplified to create amplification products that are labelled by the sample identifier in step b), each amplified nucleic acid carries the sample/original container information despite the combination into one pool of multiple different amplification products of different analyte nucleic acids in the combined container.

In preferred embodiments of the invention, the two or more subsets that are combined (for each subset separately of course) are preferably 10 or more subsets, such as 20 or more subsets, e.g. 30 or more subsets, 40 or more subsets, 50 or more subsets, 60 or more subsets, 70 or more subsets, 80 or more subsets, or 90 or more subsets. In preferred embodiments 96 subsets, 384 or 1536 subsets are combined to fully use 96-, 384-, or 1536-well plates with each well containing a combined subset. The number of containers to accommodate subsets can be lower to accommodate controls as mentioned above.

The combined containers may be physically similar to the containers described above, but of course contain various amplified nucleic acids. Example combined containers may be selected from a flask, vial, bag, syringe, or a well, including a microwell on a well-plate. In particular, a well-plate is preferred with different wells being or containing different combined containers.

Step d) comprises amplifying nucleic acids by a primer extension reaction using at least one pair of further primers hybridized to the amplified nucleic acids of combined containers of step c), wherein a pair of further primers comprises a further forward and a further reverse primer, wherein the further forward and further reverse primers both comprise a subset identifier sequence ("subset index") and a sequence for hybridization to the adaptor sequence. Step d) is similar to step b), wherein now amplification products are amplified instead of analyte nucleic acids, the primers are referred to as "further primers", and the label is now used to identify the subset (or combined container) instead of the analyte. Adaptors for a further amplification reaction or other uses, such as a sequencing adaptor sequence, are now optional and may or may not be present. The further primers bind to the adaptor sequences that have been incorporated into the amplification products through the primers of step b) as described above.

In a preferred structure of the further forward and/or the reverse primer the sequence for hybridization to the adaptor sequence is preferably on the 3' end of the forward and/or reverse primer. This allows an efficient extension reaction in 5' to 3' direction. Preferably the subset identifier sequence is in 5' direction from the sequence for hybridization to the adaptor sequence.

In preferred embodiments, in step d) each subset identifier sequence of the further forward primers is different from subset identifier sequence of other further forward primers; and/or in step d) each subset identifier sequence of the further reverse primers is different from subset identifier sequence of other further reverse primers. As said above with regard to the uniqueness of the forward and reverse primers in step b), also the further forward and/or reverse primers are unique among each group, i.e. subset identifier sequences of further forward primers differ from other subset identifier sequences of other further forward primers. The same applies for the subset identifier sequence of further reverse primers. Accordingly, in this preferred embodiment the subset identifier sequences are unique within the respective groups of further forward primers and the further reverse primers. In other embodiments, subset identifier sequences may also be unique among the combined group of further forward and further reverse primers, but this is not required but of course optional.

In preferred embodiments, the further forward and/or the reverse primer may comprise a further adaptor sequence. Such a further adapter sequence may allow further primer binding reaction or binding to probes during a sequencing reaction, as such the further primer is also referred to as a "sequencing adaptor sequence". When such a further adaptor is present, it is preferred that the subset identifier sequence is between the sequence for hybridization to the adaptor sequence and the sequencing or further adaptor sequence. The further or sequencing adaptor sequence may be at or near the 5' end of the further forward and/or reverse primer. Accordingly, a preferred primer structure for the further forward and/or reverse primer comprises in 5' to 3' direction: [sequencing adaptor sequence]—[subset identifier sequence]—[sequence for hybridization to the adaptor sequence].

In preferred embodiments, the main amplification leading to a substantial increase in amplification products is in step b). Further amplification can be achieved in step d). However, it is preferred to leave the amplification focus on step b). Accordingly, in this preferred embodiment, only few amplification cycles are done in step d). At least two amplification cycles should be done to have a reaction of both the further forward primer and of the further reverse primer. The invention works with few but also several amplification cycles for step d), such as up to 35 amplification cycles or up to 20 amplification cycles. In preferred embodiments 2 to 14 amplification cycles, preferably 3 to 13, 4 to 12, 5 to 11, 6 to 10, 7 to 9, or 8 amplification cycles, or any ranges between these values are used. In preferred embodiments, amplifying nucleic acids in step d) is restricted to at most 12 amplification cycles, preferably at most 10 amplification cycles.

In preferred embodiments, the amplification product as obtained in step b) is DNA. Also in step d), preferably DNA amplification products are obtained. A DNA polymerase can be used as described above for step b). Likewise, also a PCR reaction is preferred for step d).

In further preferred embodiments, in step d) staggered primers are used to amplify nucleic acids. "Staggered primers" means that multiple primers are used, wherein the primers have 0 to 10, such as 1, 2, 3, 4, 5, 6, 7, 8, 9, or 10, preferably 1 to 4, inserted nucleotides as distancing nucleotides between the "further adaptor sequence" (e.g. "sequencing adaptor") and the subset identifier sequence. This embodiment applies to both or one of the further forward and/or further reverse primers. Usually only one of the further primers, either the further forward or further reverse primer, has these distancing nucleotides to have their benefits, when sequencing of amplification products is from one end of the amplification products. Preferably the further forward primers comprise the distancing nucleotides. The distancing nucleotides cause an offset during sequencing of different amplified nucleic acids in step e) so that a specific nucleotide of the subset identifier sequence is at a different distance to the further adaptor sequence and is thus read at a different time-point or instance of the sequencing reaction. The distancing nucleates are preferably random, i.e. mixtures of A, G, C, T at a given position in the primer. Having various distances reduces competitive reactions and/or optimizes the gain of the sequencer when sequencing the same nucleotide position, which without the staggering would be the same nucleotide type (e.g. G, A, C, T) at the same time or instance. A distancing nucleotide can be any nucleotide type, preferably at a given position (distance from further adaptor sequence) different distancing nucleotides are used in different primers to avoid creating such competitive reactions with the distancing nucleotides. Such staggered primers (mixtures of primers with different distancing nucleotides) are used per container/subset. A particular container may have a constant number of distancing nucleotides, whereas other containers have other numbers of distancing nucleotides.

Step e) comprises determining the sequences of the amplified nucleic acids of step d). Sequence determination can be done in the way as known in the art, e.g. by Sanger sequencing or next generation sequencing. Preferably, for sequencing, the amplified nucleic acids of step d) are immobilized on a solid phase, such as on a column or on beads. An example is flow cell sequencing. For such immobilization binding to probes on the solid phase is possible, e.g. by the sequencing adaptors mentioned above. Sequencing adaptors may be Illumina P5 and/or P7 adaptors. Either only one end of the amplified nucleic acids of step d) is immobilized or both ends of the amplified nucleic acids of step d) are immobilized, thereby forming a loop with the solid phase. For one end immobilization only one of the further forward primer and further reverse primers may have a sequencing adaptor; for both end immobilization both of the further forward primer and further reverse primers may have a sequencing adaptor.

The sequences that are determined in step e) are the subset identifier sequences as introduced by the further forward and further reverse primers into the amplified nucleic acids, the sample identifier sequences as introduced by the forward and reverse primers into the amplified nucleic acids and the analyte sequence that corresponds to the sequence between the region that is hybridized in the analyte nucleic acid by the binding sequences for hybridization to the analyte nucleic acids of the forward and reverse primers. The analyte sequence corresponds to and identifies the nucleic acid of interest and the sample identifier sequences and the subset identifier sequences correspond to and identify a sample.

Preferably the binding sequences for hybridization to the analyte nucleic acids in the forward and reverse primers are selected so that costs for sequencing are limited, i.e. the region between these corresponding regions on the analyte molecule—leading to the analyte sequence (amplicon)—has a length of at least 10 and/or up to 400 nucleotides, preferably 20 to 300 nucleotides, even more preferred 30 to 200 nucleotides, such as 40 to 150 nucleotides, even more preferred 45 to 100 nucleotides, or about 70 nucleotides.

In preferred embodiments, any amplicons for analyte nucleic acids, spike-ins, internal and added controls are all within these ranges, in particular preferred are approximately the same, such as within 30% of their length (+/−30% of the longest amplicon length in nucleotides). Having similar lengths minimized competitive reactions.

As a data processing step that follows from the information generated in step e), in step f) a determined sequence of a nucleic acid of interest of step e) is assigned to a sample through association to a subset and container with the subset identifier sequences and the sample identifier sequences. In other embodiments, step f) can be performed with technical means, such as on a computer. The computer may receive sample identification information, such as the location of its container, e.g. in the array, the subset identifier sequences and the sample identifier sequences and the determined sequences and present the information of a detected nucleic acid of interest, via its analyte sequence, in a sample. Preferably the information given in step f) includes a yes or no information of the nucleotide acid of interest being or not being in a sample. The computer, or the inventive set or kit, may comprise a computer readable data memory device, such as a flash memory or a hard disk, to store instructions for performing such a method. In some embodiments of the invention, step f) may be omitted or outsourced to another service provider, who is not performing the method of steps a) to e).

In preferred embodiments of the inventive method, at least one of the forward and reverse primers of step b) is depleted during and/or after step b) but before step c). Alternatively or in combination, preferably in combination also free nucleotides (substrate in an amplification reaction) are depleted. Such a depletion reduces the risk of adverse reaction based on priming by the forward and reverse primers during step d). Such a depletion can e.g. be a physical removal, such as by binding to a solid phase, such as beads and removing the beads with the primers. The solid phase may comprise complementary sequences that bind single stranded primers but not double stranded amplified products. Preferably the primers and/or nucleotides are enzymatically depleted, e.g. by a nuclease or phosphatase, which removes phosphates from primers and/or nucleotides 3' end so that they are unsuitable for further extension reactions. An example is the enzyme mixture ExoStar™. Preferably, exonuclease 1 and/or alkaline phosphatase are used for enzymatic depletion of primers and/or nucleotides.

In preferred embodiments of the invention with a reverse transcription of RNA nucleic acids of interest in step a) as mentioned above, it is also preferred to deplete primers (RT primers) and/or nucleotides before step b) in order to avoid adverse reactions. Said depletion can be performed mechanically or enzymatically as described above, e.g. by purification, absorption, e.g. on a solid phase, or enzymatic activity, such as by a phosphatase or nuclease.

Another method of depletion would be amplification of a spike-in nucleic acid with the forward and/or reverse primer. In this embodiment, the forward and reverse primers bind to the spike-in nucleic acid (or just "spike-in"), that has a complementary nucleic acid sequence to the binding sequence for hybridization to the analyte nucleic acids of the primers but a different sequence than the analyte nucleic acids between said complementary sequences so as to not confuse the spike-ins with nucleic acids of interest. The spike-in nucleic acids thus create a competitive amplification reaction to the analyte nucleic acids and thereby deplete the primers. Since such a competitive reaction may reduce sensitivity of analyte nucleic acids, it is preferred to deplete the primers, e.g. physically or enzymatically. However, it was surprisingly found that in most instances of the inventive method such a competitive reaction does not hinder the detection of analyte nucleic acids—see examples.

An enzymatic removal can e.g. be with a single strand specific nuclease. This is one of the preferred embodiments. Thus, the inventive method may comprise a depletion of the forward and reverse primers, comprising treatment with a single strand specific nuclease.

Spike-ins or any other added control nucleic acids, that is/are added to a container and are amplified and labelled like an analyte nucleic acid in the inventive method, are used in preferred embodiments for all containers. Such spike-ins and controls can be used to identify problems in the inventive detection method, e.g. if an inhibitor of any reaction was present. Spike-ins and added control nucleic acids should produce a detectable product at step e) regardless of sample quality.

The inventive method may further comprise amplifying and processing through steps a) to d), preferably also steps e) and or f), an internal control of the sample, which is a nucleic acid or gene or its coding region that is expected to exist in a sample regardless of the nucleic acid of interest. Such internal controls may e.g. be from constitutively expressed genes of a subject, e.g. a human. In preferred embodiments, the internal control may be a ribosomal gene or coding sequence. A primer pair that binds to a ribosomal gene or coding sequence or any other internal control of a nucleic acid that is expected to exist in a sample may be used in step a) (in case of RNA) or step b) (in particular in case of DNA). RNA internal controls are preferred. A ribosomal gene or coding region or other internal control may be amplified in parallel to the analyte nucleic acids and its amplification products in step b) and d) as a control. The control reaction may be contained in a separate container without analyte nucleic acids or in a container with analyte nucleic acids.

In particular the comparison of spike-ins' and added controls' products of step d) can be compared with step d)'s products of internal controls of a sample. This comparison can be an indicator of problems in the inventive method (when the added controls do not produce an expected product or amount thereof) or provide an indicator if the sample was not isolated or processed properly (if the added control or spike-in produces an expected product in step d) but not the internal control). Such problems can e.g. be improper gargling and other improper sample procurement methods.

The nucleic acid of interest can be a pathogen nucleic acid. Such a pathogen nucleic acid may be characteristic of a particular pathogen. By identifying the pathogen nucleic acid, the presence of at least parts of a pathogen in the sample can be inferred. Preferably the pathogen nucleic acid is a viral nucleic acid.

In general, the nucleic acid of interest or analyte sequence can be from any organism, including a virus, a bacterium, or fungi. An example are gut bacteria. A characteristic sequence in any organism can be detected, in particular identified, with the inventive method.

In a particular preferred embodiment of the invention, the nucleic acid of interest is selected from a SARS-CoV-2 nucleic acid, an influenza nucleic acid, a parainfluenza nucleic acid, a respiratory syncytial virus nucleic acid, a rhinovirus nucleic acid, or a combination thereof. When referring to combinations of the nucleic acid of interest two or more nucleic acids of interest are detected in parallel in the inventive method. Accordingly, more primer pairs are included in step b) that are specific for the analyte nucleic acids corresponding to the two or more nucleic acids of interest, via their binding sequence for hybridization to the analyte nucleic acids. Also, pathogen specific primers may optionally be used in step a), in a reverse transcription, or in step b) to increase sensitivity of the method.

In preferred embodiments of the invention two or more nucleic acids of interest are selected for detection in the inventive method, preferably wherein the two or more nucleic acids of interest are from a virus. The virus can be the same virus or a different virus for two or more nucleic acids of interest. In preferred embodiments in step b) forward and reverse primers with binding sequences for hybridization to the two or more analyte nucleic acids are used. The two or more nucleic acids of interest can be searched for in step f) and assigned to a sample.

In preferred embodiments, 1, 2, 3, 4, 5, 6, 7, 8 or more nucleic acids of interest, preferably two or more nucleic acids of interest, are detected in parallel. In preferred embodiments the two or more nucleic acids of interest are detected from 1, 2, 3, 4, 5, 6, 7, 8 or more organisms, such as pathogens. E.g. it is possible to detect two or more different nucleic acids of interest from the same organism, such as a pathogen, or from differing organisms, e.g. pathogens. In preferred embodiments, the choice of amplicons also includes an internal control directed towards host RNA as sample quality control.

The pathogen may be a virus, a bacterium, or a fungal pathogen.

Example viruses include enterovirus, metapneumovirus, adenovirus, influenza A, B, C, D virus, respiratory syncytial virus (RSV), SARS-associated coronavirus, including SARS-CoV-1, SARS-CoV-2, MERS-CoV, rubeola virus, varicella zoster virus, norovirus, rotavirus, enterovirus, among others. Preferably the virus is an RNA virus.

In preferred embodiments, the present invention can be employed to detect variants of one or more pathogens or variants of one or more marker proteins, e.g. those variants that are indicative for a pathogen's pathogenicity and/or its reactivity to a hosts immune system, or the progression, severability and/or treatability of a disease (e.g. infection, or tumour).

In preferred embodiments, the one or more pathogens are viruses. In particular preferred embodiments the virus to be detected includes a particular variant or strain of SARS-CoV-2, such as for example 20A.EU1, 20A.EU2, B.1.1.7 (also known as 201/501Y.V1 or Alpha), B.1.351 (also known as 20H/501Y.V2 or Beta), P.1 (also known as 20J/501Y.V3 or Gamma), B.1.617.2 and AY lineages (also known as Delta), B.1.525 (also known as Eta), B.1.526 (also known as Iota), B.1.617.1 (also known as Kappa), B.1.617.3, P.2 (also known as Zeta), B.1.621 (also known as Mu), 20B/S.484K, as well as variants or strains with mutations or deletions in the Spike protein, including S:S13I, S:L18F, S:D80Y, S:S98Y, S:D138Y, S:W152C, S:L189F, S:P209H, S:A222V, S:P272L, S:K417N, S:N439K, S:K444N, S:452R, S:S477N, S:T478K, S:N501Y, S:D614G, S:Q677H, S:A222V, S:S477N, S:N501, especially S:N501Y, S:N501T, S:N501S, S:E484, especially S:E484K, S:N453F, S:S98F, S:L452R, S:D80Y, S:A522S, S:E583D, S:A626S, S:Q675R, S:P681, especially S:P681H, S:P681R, S:P681L, S:I692V, S:V772I, S:V1122L, S:M1229I, S:A570D, S:D614G, S:P681H, S:T716I, S:S982A, S:D1118H, and deletion variant with deletion S:H69-, S:V70-, S:69/70-, S:144-, or variants with mutations at other loci, such as ORF10:V30L, N: S186Y, N: D377Y, N:P199L, N:A220V, N:M234I, N:A376T, ORF1b:A176S, ORF1b:V767L, ORF1b:K1141R, ORF1b:E1184D, ORF1a:I2501T, ORF3a:Q38R, ORF3a:G172R, ORF3a:V202L, ORF1a:14205V, ORF1b:D1183Y, ORF1a:T945I, ORF1a:T1567I, ORF1a:Q3346K, ORF1a:V3475F, ORF1a:M3862I, ORF1b:P255T, ORF7a:R80I, or combinations thereof, such as in B.1.1.7, e.g. a combination of S:deletion 69-70, S:deletion 144, S:N501Y, S:A570D, S:D614G, S:P681H, S:T716I, S:S982A, S:D1118H.

The nucleic acid of interest to be detected may comprise a nucleic acid of the SARS-CoV-2 spike protein. The spike protein is highly indicative of SARS-CoV-2 infections and the virus' virality or reactivity to a host's immune system as well as its capability to dock to its cellular receptor, ACE2.

Example variants of the spike protein that may be detected with the inventive method may comprise any one of the following mutations: any one or more mutations selected from E484Q E484G K417N F456V T478I E484A S494Q N439K F490S S477R S477I S477N N501T K417T T478R L455F N501Y G446S E484K Y449N T478K S494P (in GH Glade (B.l.*); any one or more mutations selected from E484Q T478I N439K Y449H G446V F490S Y495H F490L S477N Y489H N501T G476S K417T G496S L455F N501Y V445I E484K T478K G485R S494P (in GR & GRY Glade, e.g. B.1.1.1 & B.1.1.7); any one or more mutations selected from E484Q T478I A475T S494T F490I G504S S477N G476S S494A N501Y G446L G447V V503A P499R E484K E484V Q493L K458N T500S Y453H Y505W E484G G504D V503F Y453F T500N E484A Q493E K417E V5031 G485V Q506K P499L K417T G485D R403K G504N G485S G446S G502K N501S K458R V445F V445A P499H G485F S494L Y449H G446V F456L N439D Y495H F490L F486L N501T T478R G496S G446A T478K G485R S494P Q498R Q493R K417N N5011 A475S N439K S477G A475V F490S S477R G502N S477I Y489L F490V L455F V445I E484D G446R G446D N501K (in G, GK & GV Glade (B.l, B.1.617.2, AY.* & B.1.177); any one or more mutations selected from K417N E484Q Y453F S477G S494L G446V F490L S477I K417T G496S N501Y L455F E484K P499R T478K K458N S494P (in nonG Glade (A, B & B.2).

The inventive detection method comprises the step of determining the sequences of the amplified nucleic acids, which stem from the analytes nucleic acids that are processed in the method by amplification steps and wherein the nucleic acid of interest is selected by the primers. The determination of the nucleic acids automatically leads to the identification of the sequence that is amplified. Accordingly, the inventive method can be used to identify known and yet unknown or new variants or strains of a pathogen, such as of SARS-CoV-2. Accordingly, the inventive method in all aspects of the invention may comprise the step of identifying a variant or strain of a pathogen in the samples or analyte nucleic acids. Preferably the variant or strain is of SARS-CoV-2.

In case of SARS-CoV-2 it is particularly preferred when nucleic acid sequences corresponding to amino acids 1-722 and 767-839 of the SARS-CoV-2 spike protein are detected, since in this region many mutations occur that are relevant to the virus' infectivity. In also preferred embodiments, the nucleic acid of interest comprises any of the above-mentioned mutations of variants or strains of SARS-CoV-2 or their location in the SARS-CoV-2 genome, which—as said in the preceding paragraph—allows to identify new variants or strains with new mutations at these genetic positions with the inventive detection method.

Bacterial pathogens may be selected from *Neisseria meningitidis, Mycoplasma pneumoniae, Bordetella pertussis, Streptococcus* spp., e.g. *Streptococcus pneumoniae*, a group A *Streptococcus, Staphylococcus aureus*, e.g. Methicillin-resistant *Staphylococcus aureus, Mycobacterium tuberculosis*, among others.

A fungal pathogen is e.g. selected from *Aspergillus* spp. (in particular spores thereof).

The pathogen may be a respiratory pathogen, which e.g. can be found in sputum, saliva, nasal mucus, bronchoalveolar lavage. Such body fluids could be collected as samples and pathogens therein could be detected.

Furthermore, the inventive method could be used to detect DNA with a biomarker of a disease as nucleic acid of interest, such as a KrasG12D mutation in DNA shed from lung cancer nodules.

The inventive method can be used to detect any such pathogen or biomarker. The inventive set may comprise primers with a binding sequence for hybridization to the analyte nucleic acids comprising such pathogen nucleic acids or nucleic acids with the biomarker.

In preferments, the sample identifier sequences of the forward primers comprise a sequence distance, preferably a Hamming distance or a Levenshtein distance, to other sample identifier sequences of forward primers of at least 1, preferably of at least 2 or at least 3.

In further preferments, the sample identifier sequences of the reverse primers comprise a sequence distance, preferably a Hamming distance or a Levenshtein distance, to other sample identifier sequences of reverse primers of at least 1, preferably of at least 2 or at least 3.

In preferments, the subset identifier sequences of the further forward primers comprise a sequence distance, preferably a Hamming distance or a Levenshtein distance, to other subset identifier sequences of further forward primers of at least 1, preferably of at least 2 or at least 3.

In further preferments, the subset identifier sequences of the further reverse primers comprise a sequence distance, preferably a Hamming distance or a Levenshtein distance, to other subset identifier sequences of further reverse primers of at least 1, preferably of at least 2 or at least 3.

As mentioned above, the identifier's sequences can be independently selected from the same sequence pools. The nature of being an identifier sequence in the amplified products of step d) being related to the forward, reverse, further forward, or further reverse primer is apparent on the position of the identifier sequence within the amplified products. Amplified products will usually have the structure: [subset identifier from the further forward primer]—[sample identifier sequence from the forward primer]—[analyte sequence]—[sample identifier sequence from the reverse primer]—[subset identifier sequence from the further reverse primer], or any complementary sequence to any part or the entirety of this structure. In dependence of alternate adaptor use, the structure may have the inner part from analyte to sample identifier sequence reversed, such as: [subset identifier from the further forward primer]—[sample identifier sequence from the reverse primer]—[analyte sequence]—[sample identifier sequence from the forward primer]—[subset identifier sequence from the further reverse primer], or any complementary sequence to any part or the entirety of this structure. As such, the position of the identifier sequences can be known and thus using the same pool of sequences for selecting any one of the identifier sequences is non-problematic. Of course, within a group of identifier sequences, no double sequences should occur that would label two different samples identically, or similarly, such as by requiring a sequence distance as mentioned above within a group of identifier sequences. A sequence distance within a group of identifier sequences reduces misassigning in step f), e.g. due to sequencing errors.

In further preferred embodiments, selected independently any or all of the identifier sequences have a length of at least 4, preferably 5, more preferred at least 6 nucleotides, or at least 7 or at least 8, nucleotides. In particular, the sample identifier sequences of the forward primers may have a length of at least 4, preferably at least 5, even more preferred at least 6 nucleotides (nt), preferably at least 7 nucleotides or at least 8 nucleotides, such as 4-16 nucleotides in length; the sample identifier sequences of the reverse primers may have a length of at least 4, preferably at least 5, even more preferred at least 6 nucleotides, preferably at least 7 nucleotides or at least 8 nucleotides, such as 4-16 nucleotides in length; the subset identifier sequences of the further forward primers may have a length of at least 4, preferably at least 5, even more preferred at least 6 nucleotides, preferably at least 7 nucleotides or at least 8 nucleotides, such as 4-16 nucleotides in length; the subset identifier sequences of the further reverse primers may have a length of at least 4, preferably at least 5, even more preferred at least 6 nucleotides, preferably at least 7 nucleotides or at least 8 nucleotides, such as 4-16 nucleotides in length. The length can be scaled according to the numbers of sample processed in parallel in the inventive method in order to maintain distinguishability between the samples and subsets.

The present invention further comprises a set of primers suitable for a method of the invention. The set may comprise or consist of at least 10 different primers A which comprise the sequence, from 5' to 3': an adaptor A sequence, an identifier sequence of at least 4, preferably at least 5, even more preferred at least 6, nt in length and a target binding sequence, wherein the identifier sequence is different within the at least 10 different primers A, preferably with a sequence distance of a Hamming distance of at least 1 or a Levenshtein distance of at least 1, preferably of at least 2 or at least 3. Everything disclosed above regarding to forward primers applies to primers A of the set.

The set may further comprise at least 10 different primers B which comprise the sequence, from 5' to 3': an adaptor B sequence, an identifier sequence of at least 4 nt in length, preferably at least 5, even more preferred at least 6, nt in length, and a target binding sequence, wherein the identifier sequence is different within the at least 10 different primers B, preferably with a sequence distance of a Hamming distance of at least 1, preferably of at least 2 or at least 3, or a Levenshtein distance of at least 1, preferably of at least 2 or at least 3. Everything disclosed above regarding reverse primers applies to primers B of the set.

The set may further comprise at least 10 different primers C which comprise the sequence, from 5' to 3': an adaptor C sequence, an identifier sequence of at least 4 nt in length, preferably at least 5, even more preferred at least 6, nt in length, and a binding sequence that binds to the adaptor A sequence, wherein the identifier sequence is different within the at least 10 different primers C, preferably with a sequence distance of a Hamming distance of at least 1, preferably of at least 2 or at least 3, or a Levenshtein distance of at least 1, preferably of at least 2 or at least 3. Everything disclosed above regarding further forward primers applies to primers C of the set.

The set may further comprise at least 10 different primers D which comprise the sequence, from 5' to 3': an adaptor D sequence, an identifier sequence of at least 4 nt in length, preferably at least 5, even more preferred at least 6, nt in length, and a binding sequence that binds to the adaptor B sequence, wherein the identifier sequence is different within the at least 10 different primers D, preferably with a sequence distance of a Hamming distance of at least 1, preferably of at least 2 or at least 3, or a Levenshtein distance of at least 1, preferably of at least 2 or at least 3. Everything disclosed above regarding further reverse primers applies to primers D of the set.

Primers A may be used as forward primers in the inventive method; primers B may be used as reverse primers in the inventive method; primers C may be used as further forward primers in the inventive method; primers D may be used as further reverse primers in the inventive method.

In preferred embodiments, the target binding sequences of the primers A (or of the forward primers) and primers B (or of the reverse primers) comprise a sequence or antisense-sequence, respectively, of a viral gene. Both primers have a target binding sequence that allows binding of primers to a target nucleotide comprising the target sequence or a complementary sequence thereto (depending if the sense or anti-sense strand is bound). The target binding sequence is also referred to as binding sequence for hybridization to the analyte nucleic acids herein. In the inventive methods, the analyte nucleic acids comprise the target binding sequence or a complementary sequence thereto.

The viral gene preferably is of a SARS-CoV-2 N, M, E or S gene or coding sequence thereof, influenza PA, PB1, PB2, PA, HA, NP, NA, M1, M2, NS1 or NEP gene or coding sequence thereof, a parainfluenza HN, F, M, NP, P or L gene or coding sequence thereof, a rhinovirus VP1, VP2, VP3, VP4, 2A, 2B, 2C, 3A, 3B, 3C or 3D gene or coding sequence; a human respiratory syncytial virus A (HRSV-A) GA1, GA2, GA3, GA4, GA5, GA6, GA7, SAA1, NA1, or NA2 gene or coding sequence; a human respiratory syncytial virus B (HRSV-B) GB1, GA2, GA3, GB4, SAB1, SAB2, SAB3, BA1, BA2, BA3, BA4, BA5, or BA6 gene or coding sequence. These genes or coding regions are also preferred nucleic acids of interest and can be hybridized in step b) of the inventive method with the forward and reverse primers. In particular preferred embodiments of all aspects of the invention, the nucleic acids of interest or viral genes targeted by the primers, are the N gene of SARS-CoV-2, preferably bound or targeted by two different primer pairs, and the influenza M1 or M2 genes. In especially preferred embodiments of all aspects of the invention, the nucleic acids of interest or viral genes targeted by the primers, are the S gene of SARS-CoV-2, preferably bound or targeted by 1, 2, 3, 4, 5, 6, 7, 8, 9, 10, 11, 12, 13 or more, different primer pairs.

The set may further comprise a primer pair that binds to a ribosomal gene or coding sequence or any other internal control of a nucleic acid that is expected to exist in a sample. Such a ribosomal gene or coding region or other internal control may be amplified as a control in parallel to the analyte nucleic acids and its amplification products in step b) and d). The control reaction may be contained in a separate container without analyte nucleic acids or in a container with analyte nucleic acids.

The inventive set may be provided in a kit. Such a kit may be provided in a packaging container comprising the contents of the kit. The kit may also comprise instruction for performing the inventive method.

Furthermore, the kit may comprise any components needed in the inventive method, such as a polymerase, optionally a reverse transcriptase, buffers, nucleotides, a single strand specific nuclease such as a single strand specific RNA nuclease and/or a single strand specific DNA nuclease.

Throughout the present disclosure, the articles "a," "an," and "the" are used herein to refer to one or to more than one (i.e., to at least one) of the grammatical object of the article.

As used herein, words of approximation such as, without limitation, "about", "substantial" or "substantially" refer to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by e.g. ±10%.

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. The "comprising" expressions when used on an element in combination with a numerical range of a certain value of that element means that the element is limited to that range and "comprising" relates to the optional presence of other elements. E.g. the element with a range may be subject to an implicit proviso excluding the presence of that element in an amount outside of that range. As used herein, the phrase "consisting essentially of" requires the specified integer(s) or steps as well as those that do not materially affect the character or function of the claimed invention. As used herein, the closed term "consisting" is used to indicate the presence of the recited elements only.

The present invention will be further described by the figures and examples, without being necessarily limited to these embodiments of the invention.

FIGURES

FIG. 1: Setup of a next generation sequencing (NGS) based pipeline for the detection of Sars-CoV2 from crude respiratory samples. A. Overview scheme to illustrate the envisioned analysis pipeline. B. Comparative analysis of SARS-CoV2 detection following different RNA extraction treatments by TaqMan qRT-PCR on the N1 amplicon. Gargle samples from two SARS-CoV2 positive and one negative person were collected in HBSS. RNA was purified (without concentrating) or crude lysates were produced using either heat inactivation for 30 min (REF), TCEP/EDTA (HUDSON buffer), or QuickExtract. C. Illustration of amplicon indexing either during RT or PCR. Colored boxes symbolize different indexes to be used in individual samples for detection during NGS. Arrows illustrate oligonucleotides hybridizing to RNA during RT or DNA in PCR. D. Comparison of amplicons obtained upon indexing in RT or PCR. Long primers containing indexes and complementary sequences of >20 bp and thus compatible with PCR were either included as RT primers already, or RT was performed with short primers, i.e., random hexamers and two N gene-specific primers binding the 3' of the SARS-CoV2 amplicon. In 1-step PCR, hot start Taq polymerase was already present during RT, while in 2-step PCR hot start Taq polymerase was added subsequent to RT. Grey triangle symbolizes a dilution series of synthetic template of 3645, 1215, 405, 135, 45, 15, 5, or 0 molecules. Thermo SS3: Superscript III enzyme provided by Thermofisher; h.m. SS3: homemade superscript III like enzyme; h.m. SS2.5: homemade advanced superscript II like enzyme; E. Comparison of total read counts obtained from a total of 192 samples either negative or positive for SARS-CoV2 at various concentrations.

FIG. 2: A control primer pair targeting 18S rRNA provides better specificity than the widely used RPP30 primers. A. NGS read counts obtained with the SARS-CoV2 N gene-specific primer pair N1 as well as the human RNAse P (RPP30)-specific primer pair designed by the CDC. RT-PCR was performed on inactivated gargle-QE samples spiked with 5120, 2560, 1280, . . . , 5 molecules of synthetic template in a twofold dilution series as well as 0 molecules. Non-specific amplicons are defined as amplicons generated by the respective matched primer pairs but with incorrect sequence in between. B. Analysis of all amplicons generated in the pool of conditions shown in A. Unspecific amplicons typically incorporated a short stretch of sequence complementary to primer sequence and were almost exclusively generated by at least one RPP30-specific primer. Specific amplicons add up to <1% of reads in this condition. C. SYBR Green qPCR analysis of RPP30 primers and two alternative internal control primer pairs in the presence and absence of RT on RNA purified from gargle of 16 individuals. Ct values are transformed to arbitrary units. D.,E. Illustration of an RT control (RTC) spike-in; An amplicon with identical primer binding sites to the ribosomal internal control yet different and longer intermediate sequence was synthesized, cloned, and T7 transcribed. It was added to the reverse transcription at 1000 molecules/reaction. The ratio of ribosomal versus RTC reads serves as a sample quality measurement, reads for neither the ribosome nor the spike-in point towards an inhibited/failed PCR reaction for the specific sample.

Figure 3:
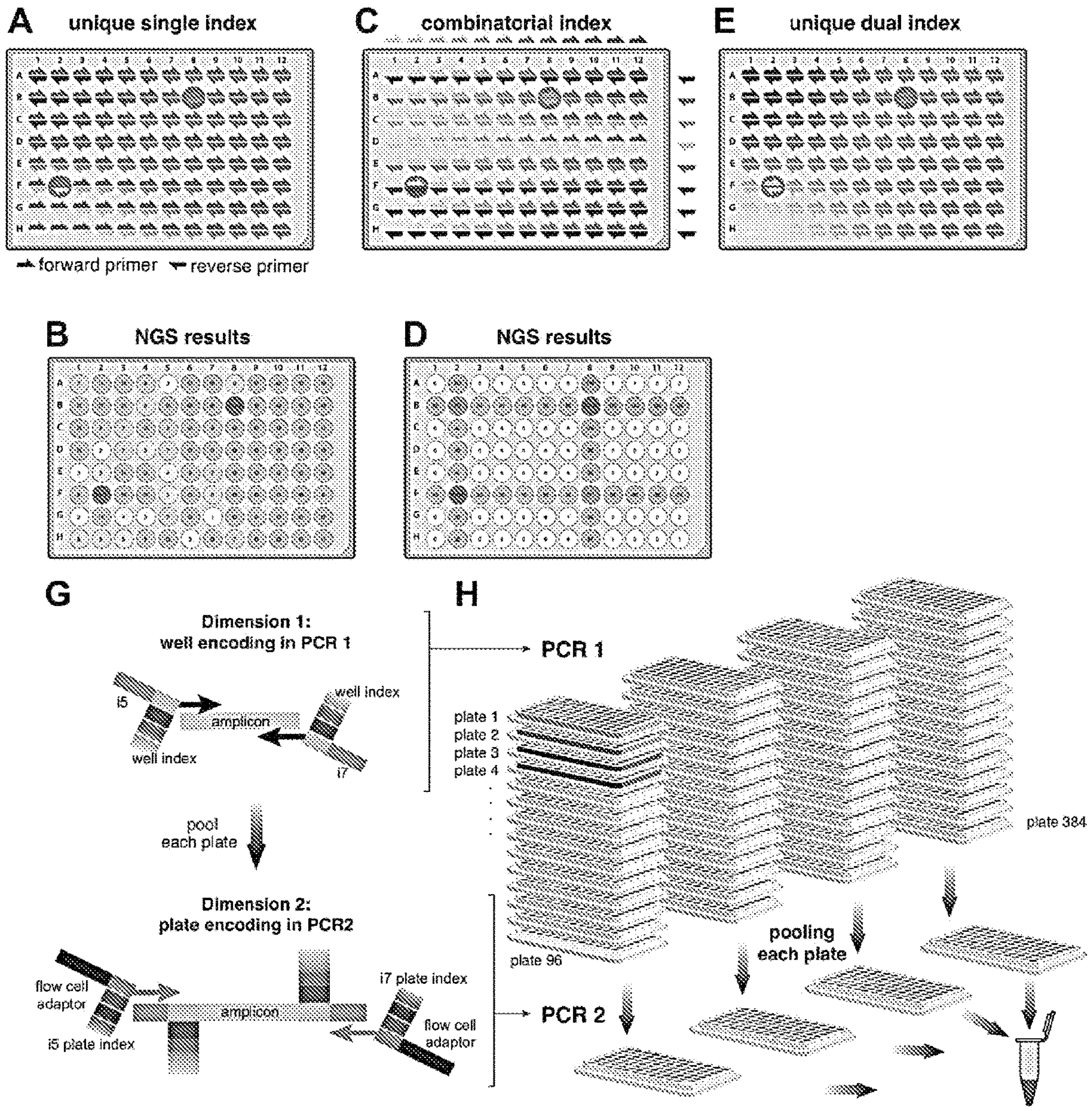
Figure 3:
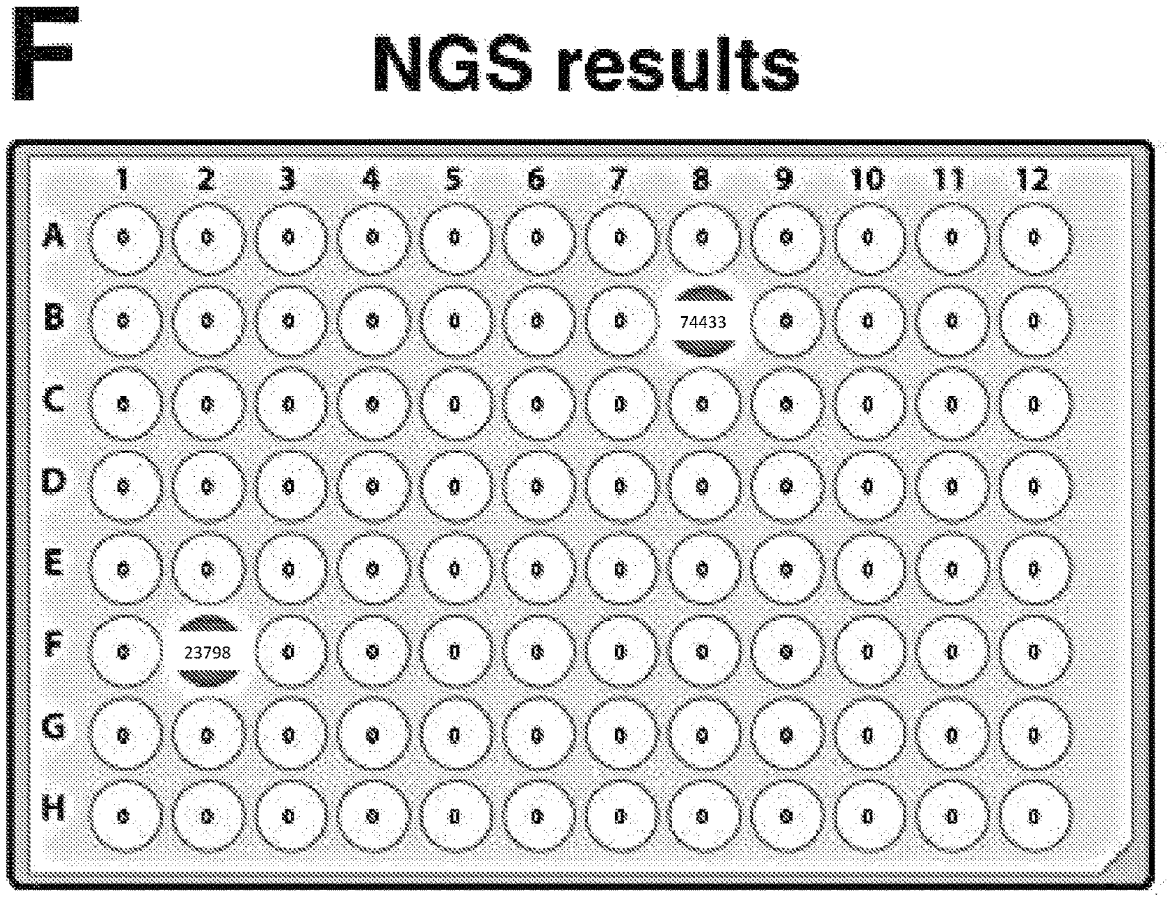

FIG. 3: Two-dimensional redundant dual indexing allows scaling to population-level testing. A. Scheme depicting 96 well-based indices. These can be incorporated by forward primers or reverse primers. For the latter they can be incorporated during RT or PCR. Red circles highlight the positions into which synthetic template was loaded to test performance of the indexing strategy. B. N3 amplicon reads obtained from next generation sequencing mapped to wells based on indices incorporated by reverse primers during PCR as in A. Forward primer indices were disregarded in this analysis. Note the frequent mis-assignment to incorrect positions. C. Scheme depicting combinatorial indexing. Each well is identified as a unique combination of forward and reverse index. D. N3 NGS reads mapped to wells based on combinatorial indexing as in C. To simulate combinatorial indexing the identical dataset as in B and F was used and primers were treated in pools pointing to columns or rows. E. Unique dual indexing is a redundant indexing method that encodes e.g. wells both by forward and reverse primers. Thus, illegitimate recombination products of reads can be bioinformatically rejected. F. NGS result for the same dataset as in B and D analyzed with dual indices as in E successfully filtered away all misassigned reads. G. Two-step PCR strategy to integrate redundant dual indices pointing to wells and subsequently plates. Colored boxes represent indices. H. Illustration of the PCR workflow. RT and PCR 1 are performed on all samples individually. Subsequently each plate is pooled to one well position, the amplicon is treated with Exostar to remove excess primers, and a second PCR is done. Our currently used and validated barcode set allows pooling of up to 36,864 samples. All PCR 2 amplicons are pooled, gel purified, and sequenced on any Illumina platform.

Figure 4:
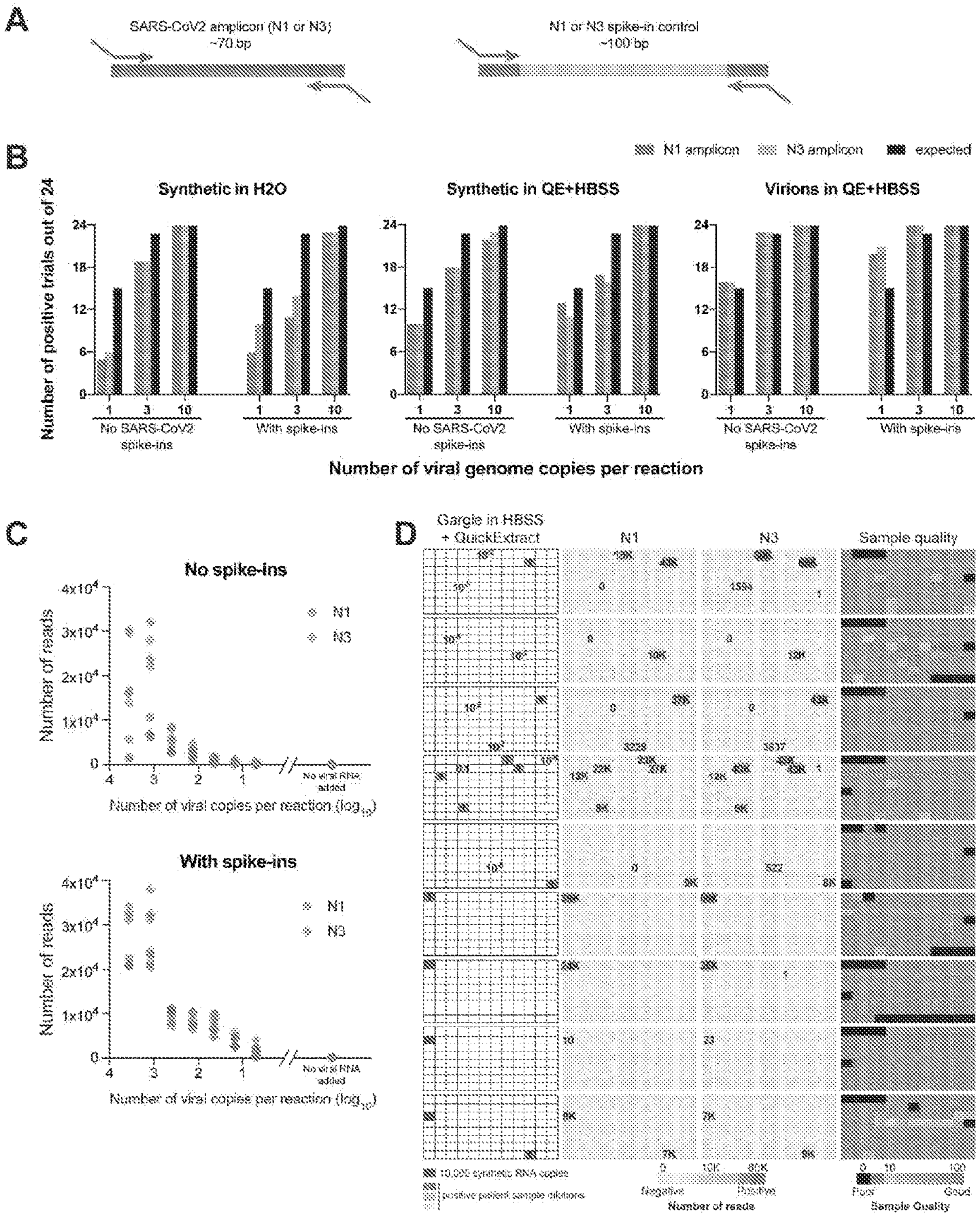

FIG. 4: SARSeq is specific and sensitive when tested on a large set of gargle samples. A. Schematic illustration of RNA spike-ins to scavenge N1 and N3 primers during PCR 1 in SARS-CoV2 negative samples. Analogous to the RTC, primer binding sites are identical to N1/3 amplicons, but intermediate sequence is distinct and longer so as not to compete with virus-derived amplicons. B. Frequency of detection of SARS-CoV2 at minimal template concentration. Number of detected cases of 24 is depicted. Note that the expected frequency of detection is only 63% and 95% for one and three molecules assuming a Poisson distribution of molecules in wells. C. Read counts of quadruplicates in dependency of synthetic SARS-CoV2 template. Note the reduced variability in the presence of N1/3 spike-ins. D. SARSeq performance on a test pool of 864 samples. Gargle samples collected in HBSS for our in-house testing pipeline of personnel were spiked with synthetic RNA or a dilution series generated from a positive sample presenting undiluted with a Ct of 30. All missed samples were 1:100,000 dilutions of that probe and thus presumably negative for SARS-CoV2. No negative positions presented with >1 read. Sample quality is assessed by the ratio or ribosomal reads to ribosomal spike-in.

Figure 5:
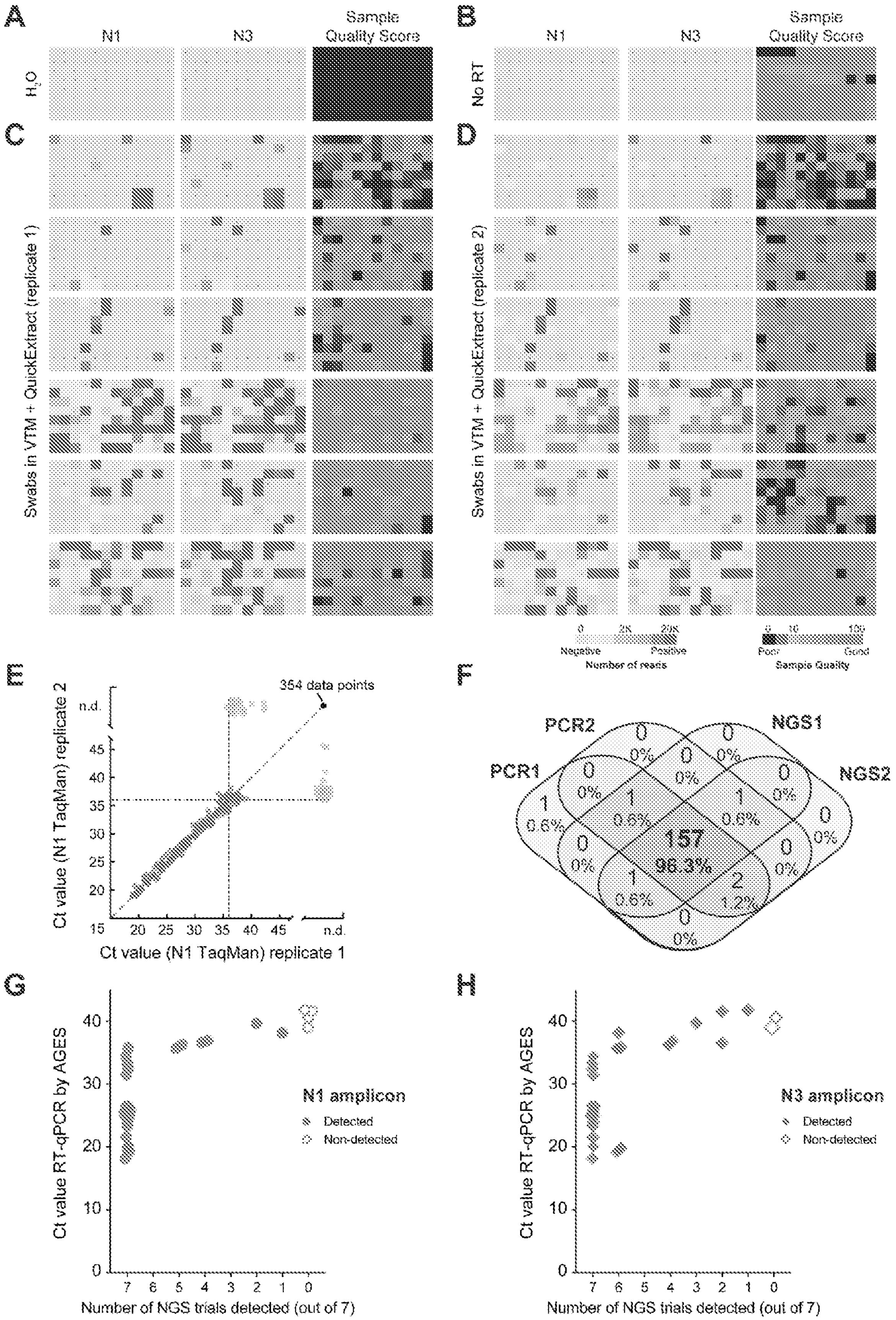

FIG. 5: Validation of SARSeq on patient samples. A. $H_2O$ control plate of SARSeq with three primer pairs, namely N1, N3, and ribosome in the presence of RTC as well as N1 and N3 scavenger spike-ins. B. SARSeq on a gargle-QuickExtract plate in the absence of reverse transcriptase. No false positive wells were detected. Sample QC scores high due to the absence of RTC reads while DNA templated ribosomal amplicon is observed. C. Analysis of 576 samples obtained by swab and collected in VTM. D. Independent replicate of C based on the same inactivated patient swab. Color codes depict read counts and sample quality score for C and D. E. Two independent N1 TaqMan qPCR runs on samples as in C and D. Ct values of both runs are plotted against each other. Color code: red: sample scoring positive in both qPCR replicates, orange: sample scoring once, black: sample scoring negative. Stochastic and latest detection of SARS-CoV2 at cycle 36. F. Venn diagram of reproducibility for all samples scoring positive with Ct 36 or less for at least one qPCR replicate. G, H. Comparison of NGS results by SARSeq to Ct values obtained by diagnostic qPCR. A set of 90 samples (including swabs and gargle in different buffers) was used for RNA extraction and qPCR measurements and in parallel aliquots of these samples were mixed either with QuickExtract or TCEP/EDTA and measured by SARSeq in triplicates and quadruplicates, respectively. We report the number of replicates in which we called a sample positive by NGS (with the N1 or N3 amplicon) relative to the qPCR Ct values. Not shown are 63 samples that were negative by qPCR and NGS.

Figure 6:
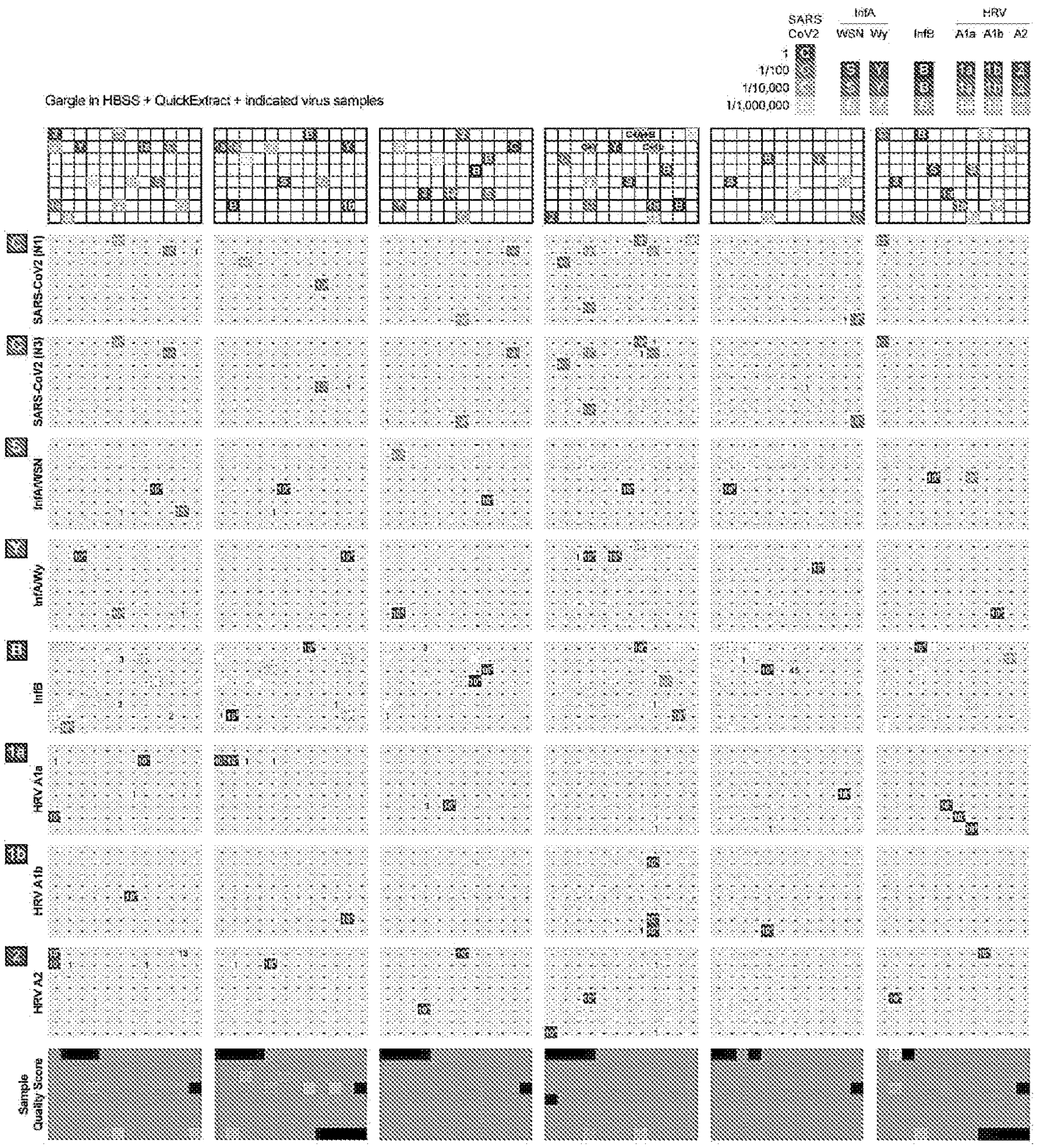
Figure 6:
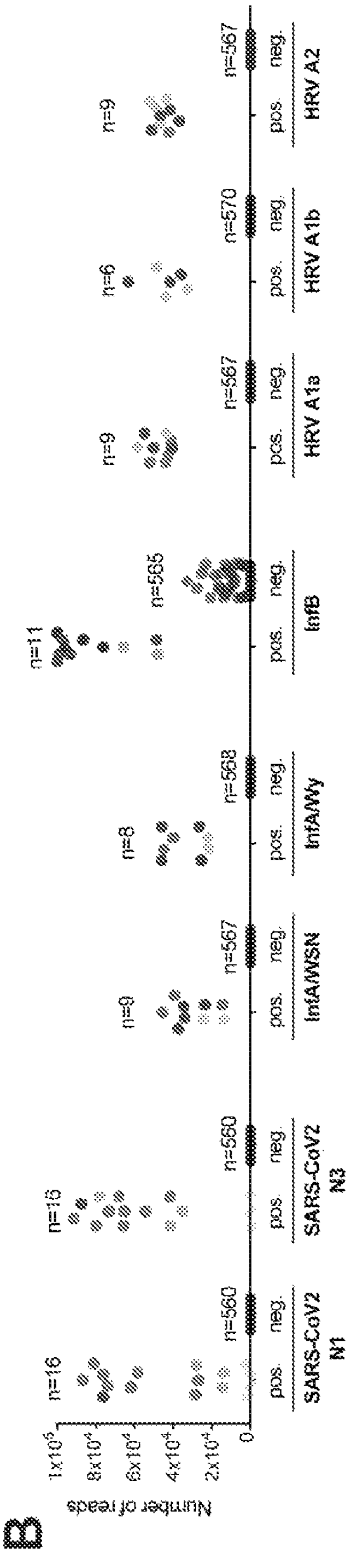

FIG. 6: Multiplexed analysis of several respiratory viruses. A. Six 96 well plates filled with gargle in HBSS and inactivated in QuickExtract from our in-house pipeline were spiked with RNA from various respiratory viruses. For SARS-CoV2, a positive gargle sample with Ct value of 30 was diluted as indicated. RNA for all other viruses was obtained from HEK cells 48 h after infection with the virus. Dilution indicated by volumetric ratio. SARSeq was performed with six primer pairs in one reaction, namely N1 and N3 for SARS-CoV2, Influenza A virus, Influenza B virus, human rhinovirus (HRV), and the ribosome. Influenza A substrains and HRV substrains were distinguished based on amplicon sequence variants. B. Analysis of false positive and false negative rate of the experiment in panel A. As expected, 1:100,000 dilutions of the SARS-CoV2 sample with a Ct of 30 were missed. All other positive samples were detected for all viral spike-ins. False positive samples were detected for Influenza B virus presumably due to sporadic contamination of reagents or equipment with purified RNA also in the $H_2O$ control plate (not shown). False positive read counts did not reach numbers observed in truly positive samples. No false positive samples above threshold were detected for any other virus.

FIG. 7: Testing of primer pairs for three amplicons (SARS-CoV2 N1 and N3, and human ribosome) carrying extensions with 110 unique dual indexes. Primer pairs with indices #29 were excluded as they did not efficiently produce the ribosome amplicon; primer pairs with indices #74 were excluded as they did not efficiently produce the N3 amplicon. Primer pairs 1-4 can be used efficiently but were not included in the final set because these indices were frequently used in the lab during initial setup of the method and we wanted to eliminate all possible sources of cross contamination.

Figure 8:
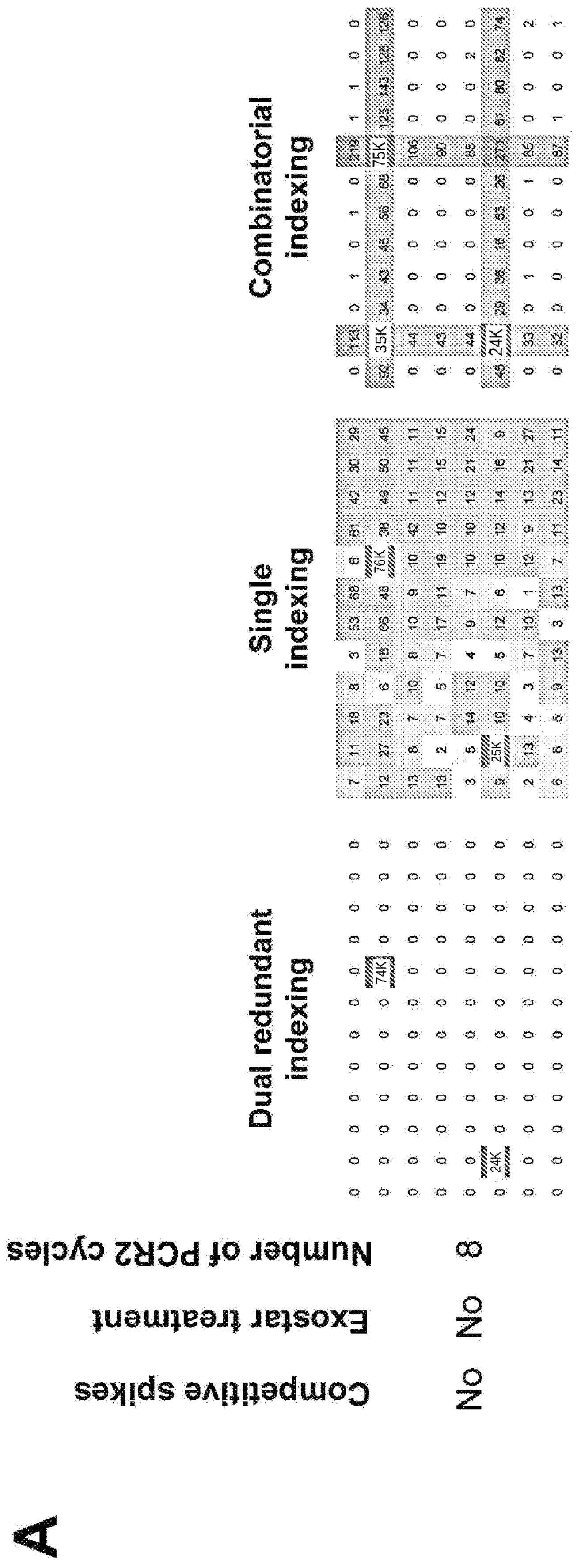
Figure 8:
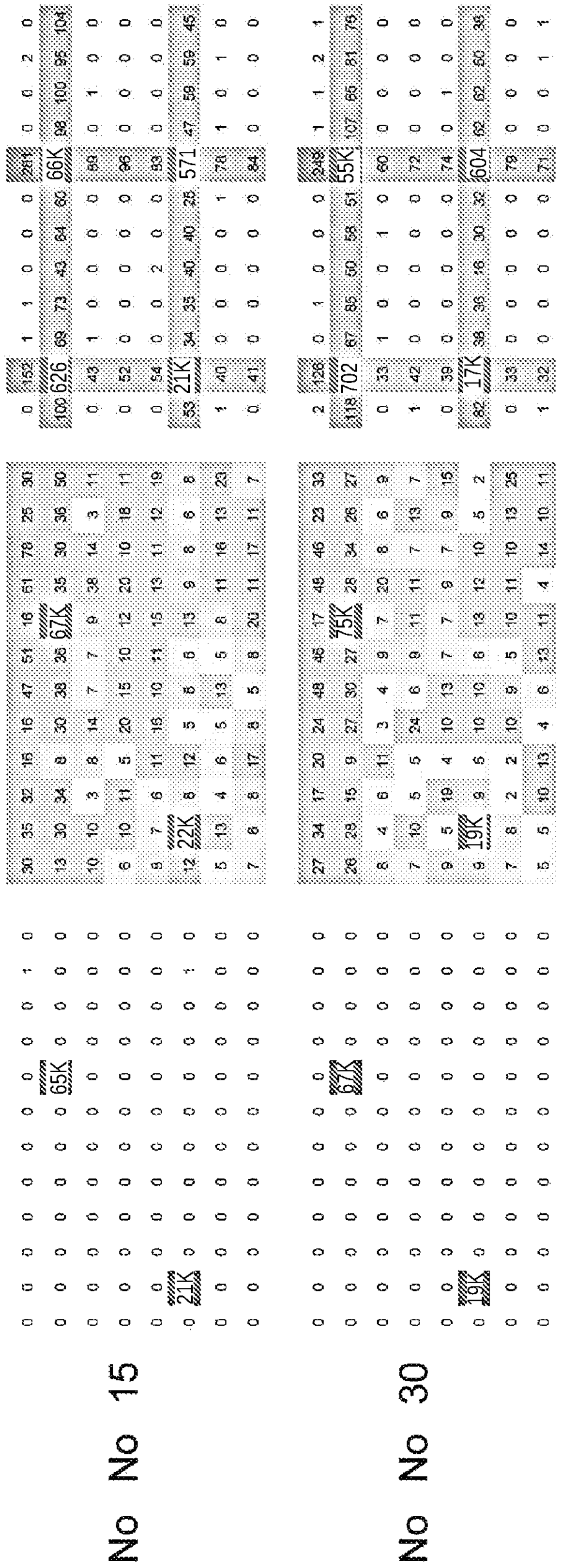
Figure 8:
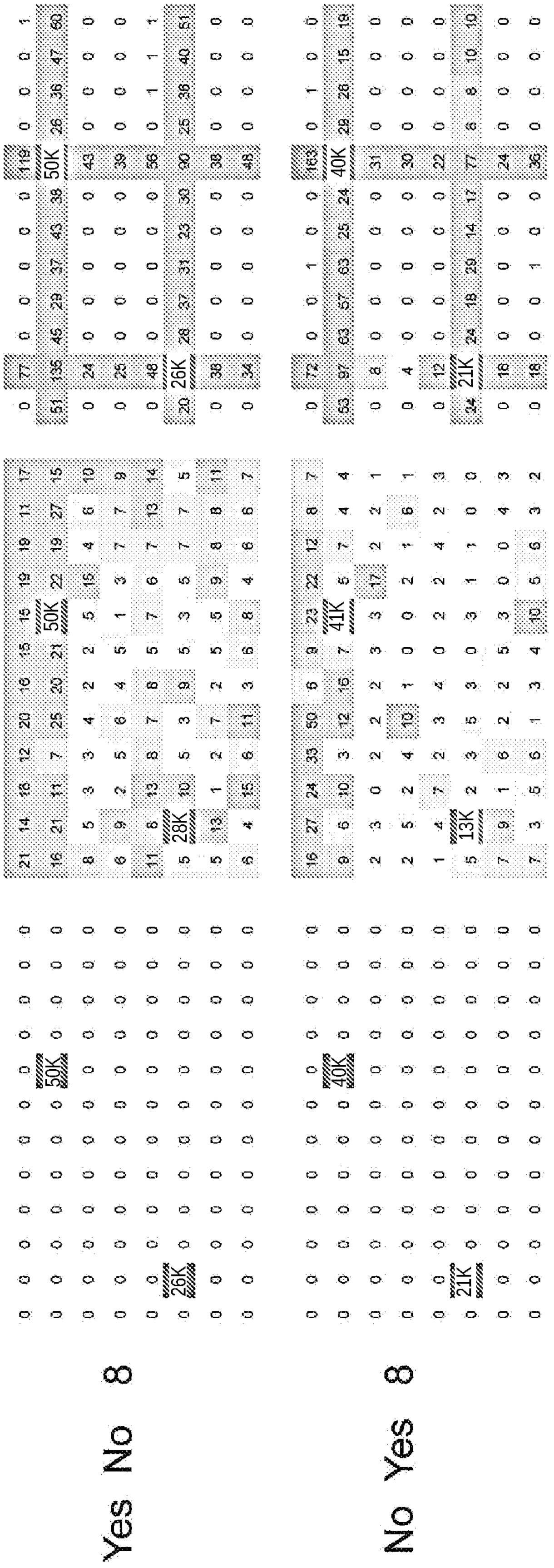
Figure 8:
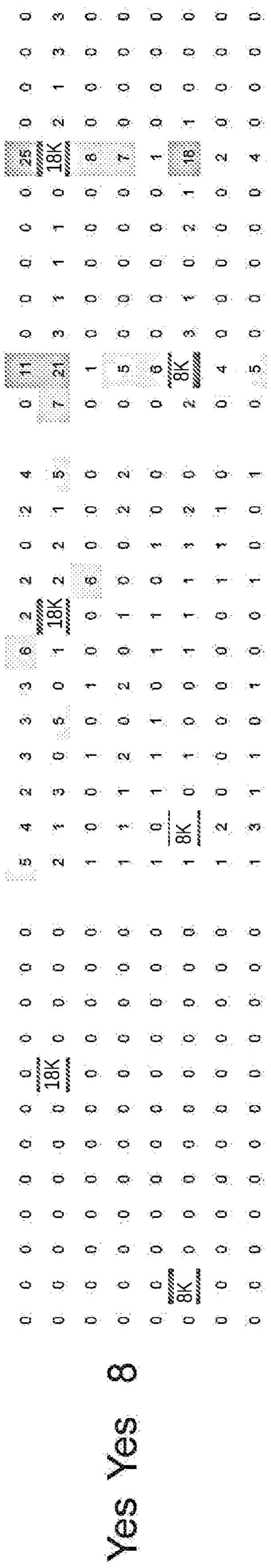
Figure 8:
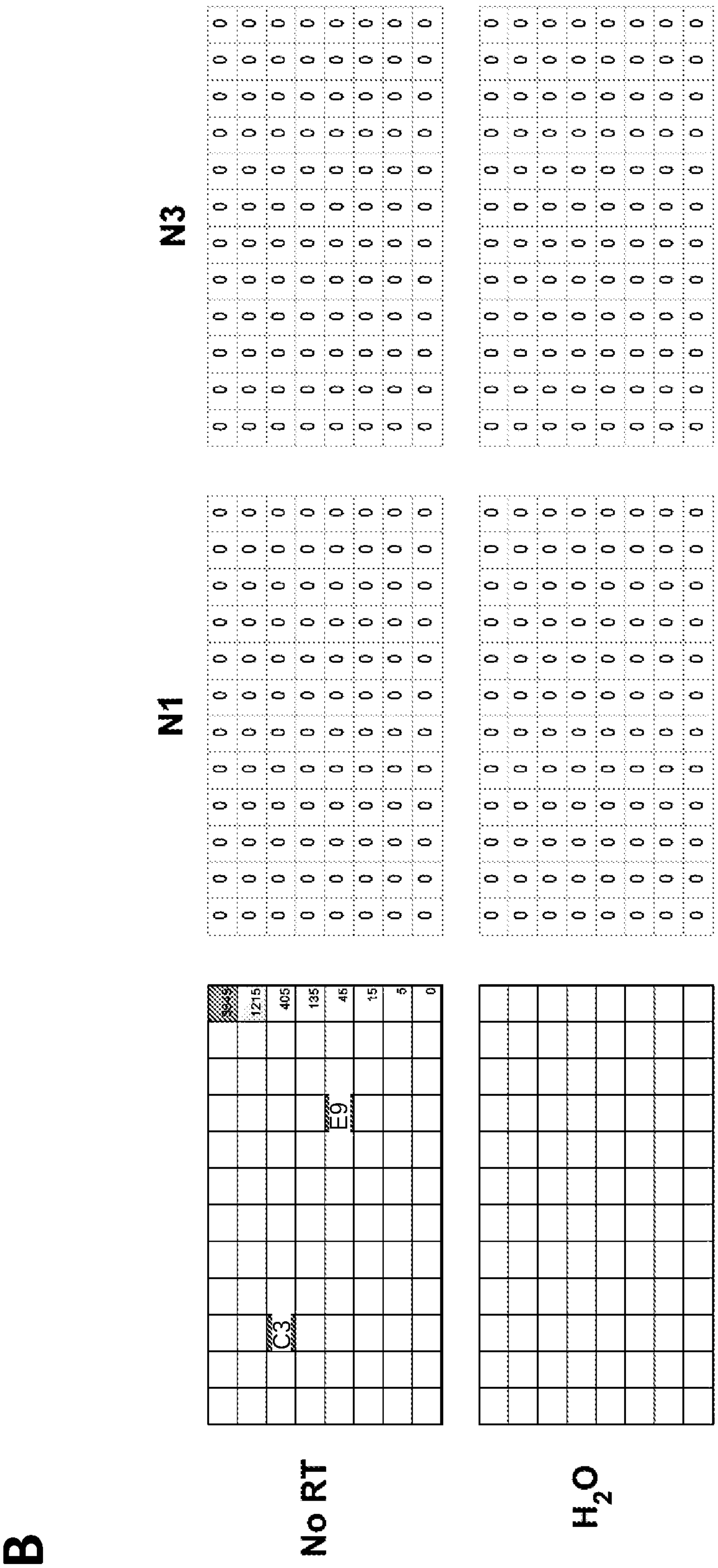

FIG. 8: A. Contribution of the different measures taken to completely suppress mis-assignment of indices to incorrect samples (and in that way avoid false positives). SARS-CoV2 synthetic RNA was added to positions B8 and F2. Assigning sample identities based on single indices or combinatorial indices produces a substantial amount of misassignments. These can be reduced with three independent measures: addition of a competitive spike-in and treatment with Exostar to remove any left-over primers after PCR1, and limiting the number of cycles in PCR2 to prevent recombination between amplicons and their indices. Whereas all these measures help reduce misassignments, adding dual redundant indices (or unique dual indices) completely suppresses this. B. Shown are N1 and N3 reads for two negative control plates (–RT and $H_2O$) that were run together with numerous other positive plates in the same run. The fact that we detect 0 reads shows that there is no misassignment of well identities across plates either. This is because each plate is also encoded by redundant/unique dual indices.

Figure 9:
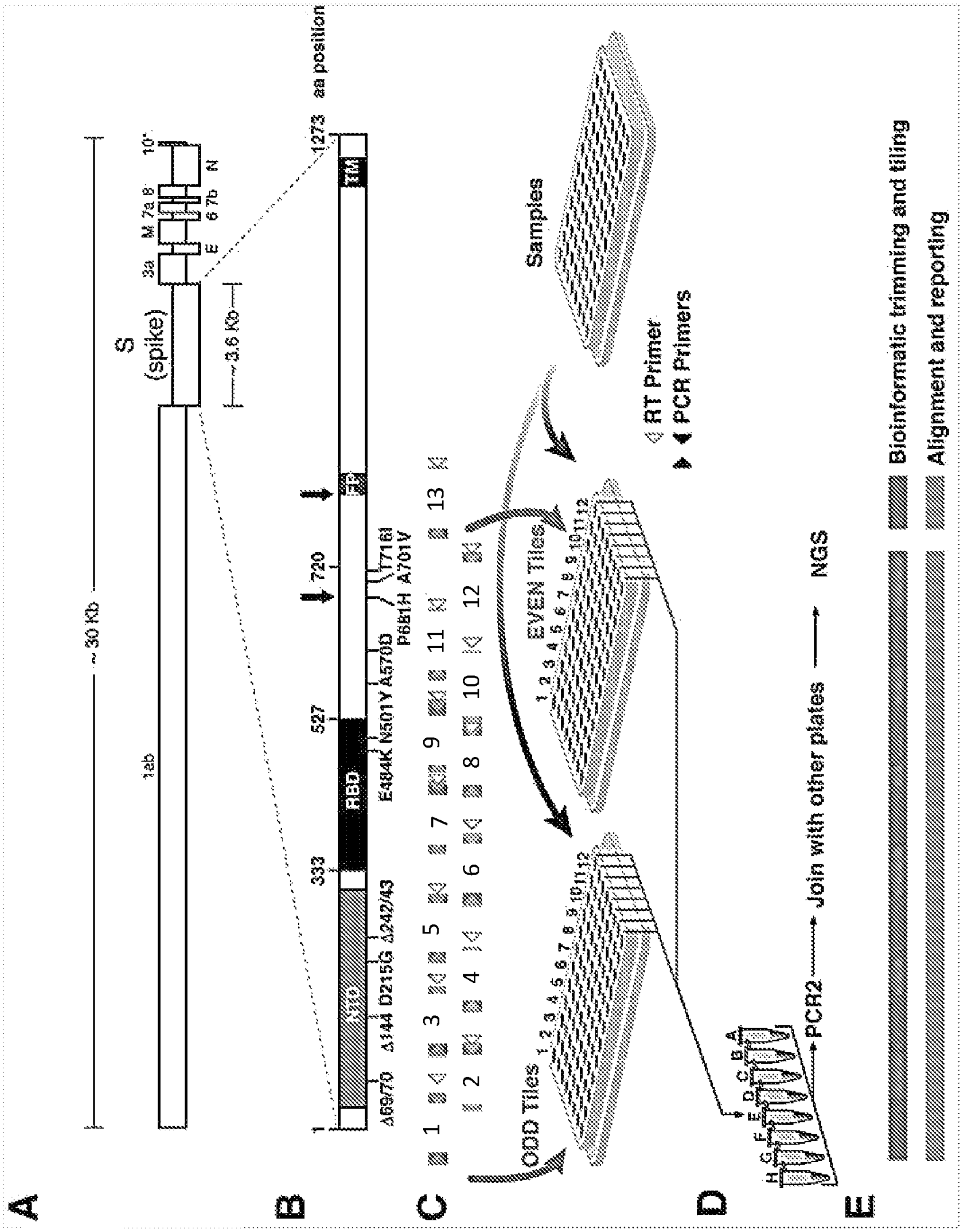

FIG. 9: SARSeq spike protein variant detection. Viral genomic RNA is reverse transcribed with 13 primer pairs that are specific to the S gene and the resulting cDNA is amplified in 13 partially overlapping fragments or "tiles" that together cover about two thirds of the S-gene (Fig. A and B). Specifically, the part of the S-gene encoding the extracellular part of the Spike protein is covered, where interaction with the ACE2 receptor and the majority of the known neutralizing antibodies occurs. This is also the part where all current mutations of concern have been identified (Fig. B). The critical region from amino acids (aa) 470-502 is covered twice (by tiles 8 and 9) to ensure robust detection of variants of particular interest. Because overlapping fragments cannot be amplified together in the same reaction tube (as primers would then preferentially amplify the overlap), the RT and PCR are practically conducted in two separate reactions (Fig. C) which are referred to as "odd" and "even" referring to the numbers of the tiles included. After RT and PCR1, samples are pooled, subjected to PCR2 to add the second set of barcodes and eventually pooled with samples from other plates to be sequenced (Fig. C and D). The tiles are bioinformatically aligned to extract a consensus sequence that can be compared to the reference S-gene sequence to identify variants.

Figure 10:
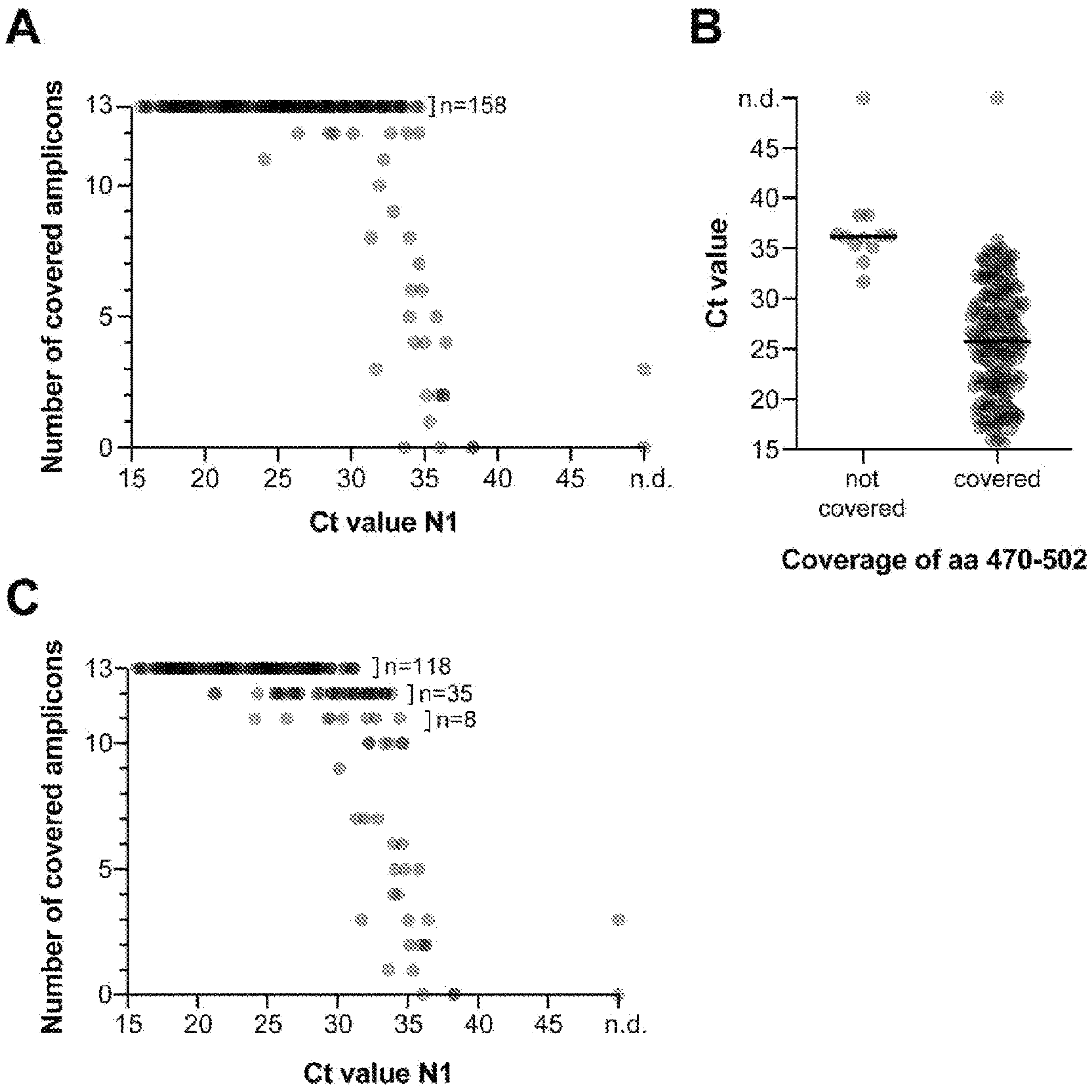

FIG. 10: SARSeq sequence recovery efficiency; For 192 positive samples qPCR Ct values using a commercial one-step kit (LUNA) were compared to amplicon coverage by SARSeq. Cutoff for recovery is 2% of median number of reads for that amplicon or a minimum of 10 reads. Sequencing data are obtained as a pool of 2255 on one NovaSeq lane. (A) Recovery of up to 13 amplicons per sample in dependence of Ct value. Sequence recovery is almost complete until a Ct of 33. (B) Sequence coverage at the most variable domain (amino acid positions 470-502) of the S-gene by at least amplicon 8 or 9. Almost all samples <Ct35 can be analyzed for the relevant mutations S477N, E484K, N501Y and other mutations in the region. (C) Due to the efficient and specific sequence retrieval and the focus on the S-gene as well as a robust barcoding strategy, SARSeq enables multiplexing of >20k samples into a single NovaSeq lane for sequence analysis. The plot estimates sequencing efficiency of >20000 samples together by setting the cutoff 10× higher, namely to 100 reads.

FIG. 11: SARSeq output exemplified on one analysis batch; (A) Example of a tabular output of the analysis pipeline highlighting a few relevant amino acids. The total analysis window covers amino acids 1-722 and 767-839, see primers in example 23. (B) Pie chart of variant distribution highlighting the two variants of concern B.1.1.7 and B.1.351 versus strains with minor or other mutations. (C) Breakdown of other variants with annotation of observed amino acid changes.

Figure 12:
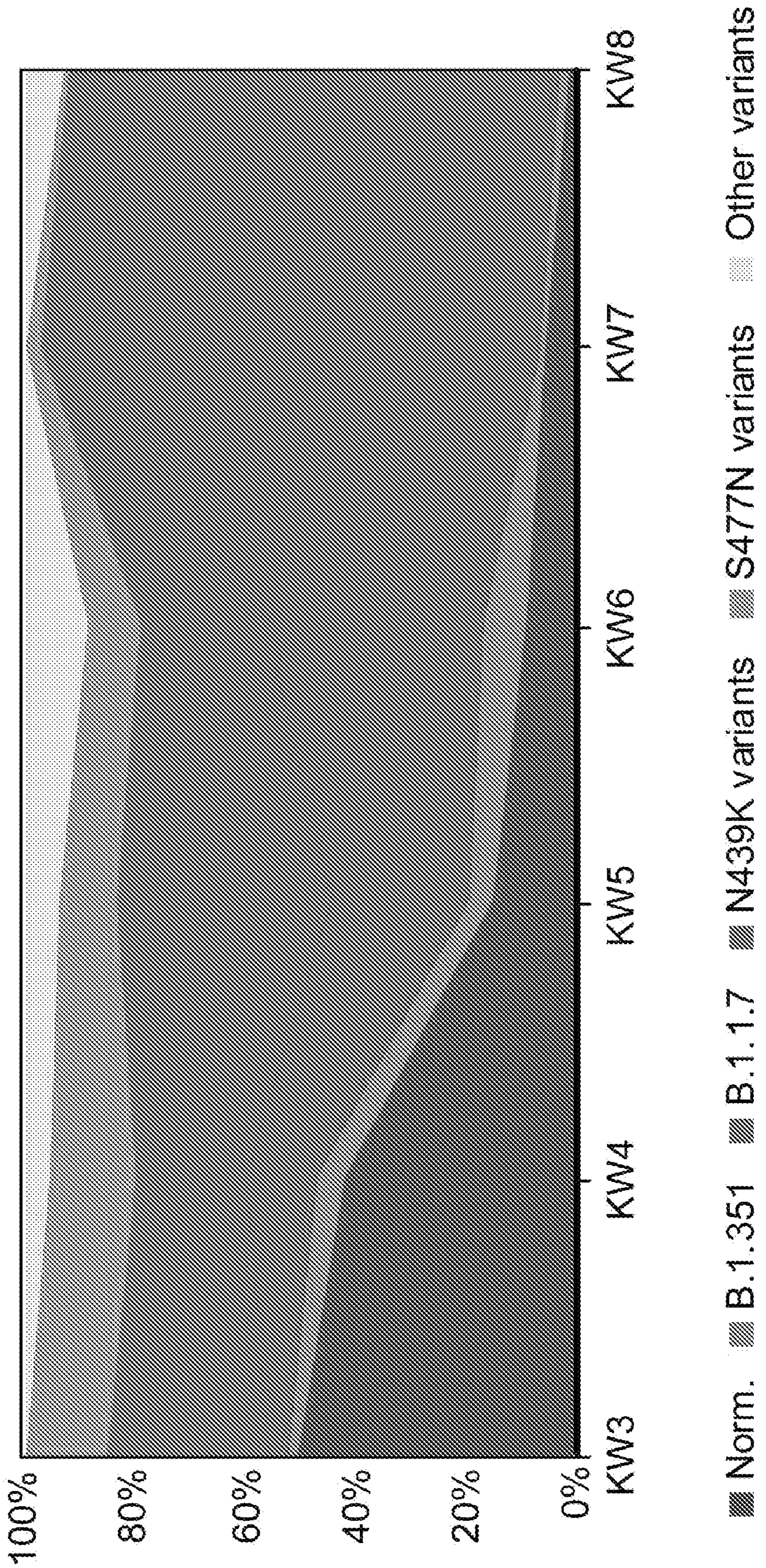

FIG. 12: Timeline of variant distribution observed in SARSeq analysis runs; Mutation frequency within analyzed samples per week (calendar week of 2021, KW) is plotted. Each time point consists of 2200-2500 analyzed samples.

EXAMPLES

The invention provides a sensitive and specific method to detect SARS-CoV2 RNAs and other nucleic acids that could be scaled to tens of thousands of parallel tests. The gold standard to detect SARS-CoV2 are RT-qPCR-based assays, which measure the abundance of short RNA fragments characteristic of SARS-CoV2 by means of DNA amplification. As PCR reactions can amplify incorrect fragments (unspecific amplicons), despite the use of specific primer pairs, RT-qPCR assays typically increase specificity by the use of fluorescently labeled TaqMan probes. This typically means that only a few different amplicons can be detected per reaction, which—together with the need for specific qPCR machines—severely limits the scalability and throughput of these assays (especially if sample-pooling is not desirable).

Next-Generation-Sequencing (NGS) can in principle allow the detection of specific amplicons by sequencing and computational analyses and is not limited in the number of different amplicons it can detect: as the amplicon identity is revealed during sequencing, multiple different fragments (viral and cellular controls) can be amplified in the same reaction if the primer pair used for the different amplicons are compatible. In addition to detecting multiple different amplicons per sample in parallel, individual samples can be uniquely labeled with characteristic sequence-barcodes, allowing the subsequent pooling and pooled sequencing. The advantages of detecting multiple amplicons per sample and processing tens of thousands of samples in parallel mean that NGS-protocols offer huge cost-saving potential and are thus highly attractive for large-scale testing.

However, while NGS-protocols are conceptually simple and indeed several different protocols have been proposed, their efficient implementation is challenged at various steps and these challenges directly impact general feasibility, costs and potential cost savings.

Here, we describe a robust high-throughput protocol based on a redundant, dual and two-dimensional barcoding strategy that achieves perfect sample-recall by redundant dual indexing while scaling to tens-of-thousands of samples by combinatorial indexing along two dimensions, termed SARSeq (Saliva Analysis by RNA Sequencing, according to one of its preferred uses). Example protocols further use a 2-step endpoint RT-PCR and using NGS-compatible amplicons and primer pairs. The protocols were validated on samples with synthetic RNAs and on patient samples, demonstrating that the protocols' utility extends to the simultaneous detection of SARS-CoV2, influenza and HRV viruses from the same sample in a single experiment. Overall, the pipeline can be efficiently combined with high-throughput sample collection in e.g. 96- or 384-well formats, robotics and NGS to detect SARS-CoV2 and other viruses in tens of thousands of samples per experiment with a turn-around time of about 1 day (FIG. 1A).

Example 1: Input Sample Preparation

The pipeline we describe can start from a variety of different input samples. The types of tested samples:

- Purified RNA from gargle samples
- Gargle samples mixed with QuickExtract solution form Lucigen (1:1 ratio)
- Swabs in VTM mixed with QuickExtract (1:1 ratio) Samples mixed directly with QuickExtract were incubated for 5 min at 95° C. for inactivation and used directly or stored frozen at −80° C. We did not observe a decline in positive signals upon freezing and thawing (even after two cycles of freeze-thaw).

The samples were arrayed in 96-well plates. The described reaction setup uses up to 5 μL of any of the above described samples.

Example 2: Reverse Transcription

Reverse transcription was performed with Superscript III reverse transcriptase and a primer mix containing random hexamers as well as two 12-mer oligonucleotides that prime on the SARS-CoV2 N gene.

A master mix containing all components listed below was prepared and distributed to 96-well plates (20 μL per well). Using a liquid-handling robot (or multi-channel pipettes), 5 μL of each sample were transferred to individual wells containing the RT reaction mix. RT reactions were set up at room temperature. Plates were sealed with aluminum sealing foil (It facilitates easy removal after RT reaction that reduces vibrations in wells avoiding generation of aerosols which may cause cross contamination between samples) and incubated in a thermocycler following conditions listed below.

Master Mix Composition per Reaction/Well (Volumes in μL):

| | |
|---|---|
| 10x RT Buffer$^{A}$ | 2.5 |
| 25 mM each dNTPs | 0.5 |
| 1M DTT | 0.1 |
| RT primer mix$^{B}$ | 2 |
| RNAse Inhibitor | 0.5 |
| Superscript III | 0.5 |
| Water | 13.8 |

Wherever mentioned, for each reaction 1000 copies of Ribosome synthetic RNA spike-in and 50 copies of each N1 and N3 RNA synthetic spike-in is included in the RT master mix. Also, wherever mentioned Thermofisher/Invitrogen™ SuperScript™ III or Luna Universal One-Step RT-qPCR Kit (NEB) or Superscript 2.5 is used for reverse transcription. In all other experiments Superscript III is used for reverse transcription.

Thermocycler Program:

- 5 min at 25° C. (primer annealing)
- 15 min at 55° C. (reverse transcription)
- 3 min at 95° C. (RT inactivation)
- Cool down to 12° C. (removing the plate while it's still hot will cause bending of the plastic, making further pipetting and sealing more difficult)

$^{A}$10× RT Buffer Composition:

- 200 mM Tris-HCl pH 8.3
- 500 mM KCl
- 50 mM $MgCl_2$
- 200 mM $(NH_4)_2SO_4$
- 1% Triton X-100

$^{B}$RT primer mix composition: 12.5 mM of each random hexamers, N-gene specific 12-mer #1 and N-gene specific 12-mer #2 (final concentration in the complete 25 μL RT reaction is 1 mM each)

Example 3: In Vitro Transcription of Spike-In Synthetic RNA Templates

Ribo, N1 and N3 spike-in DNA fragments with unique identification sequences in the middle and away from primer binding sites are ordered from IDT or Microsynth. Spike-in templates are cloned into pCR2.1 plasmid by topo cloning. Spike-in template containing plasmid clones are confirmed with Sanger sequencing. For efficient in vitro transcription, plasmids are linearized downstream of the T7 promoter and spike-in template by cutting with a unique restriction enzyme. In vitro transcription is carried out using NEB HiScribe™ kit according to manufacturer's instructions. Transcribed reaction was treated with Turbo DNAse/Thermofisher for 1 hr and RNA is purified using Zymo RNA clean and concentrator spin columns. RNA is aliquoted and stored at −80 C.

Example 4: First PCR

A first PCR was performed for amplification of cDNA with addition of sample indexes as dual barcodes.

A master mix containing all components listed below, including HotStart Taq Polymerase and Uracil DNA glycosylase (Antarctic Thermolabile UDG from NEB/M0372L) was prepared and distributed to a deep-well 96-well plate. The 96 primer pair combinations$^{C}$ containing dual well barcodes were also arrayed in 96-well plates (multiple primer plates can be prepared simultaneously and stored frozen at −20° C.). Using a liquid-handling robot, the 96 sets of barcoded primers were added to the PCR master mix and mixed thoroughly. 25 μL of this complete 2×PCR mix were added to the 25 μL RT reactions prepared as above. Plates were sealed with aluminum sealing foil and incubated in a thermocycler following conditions listed below.

All components were kept at room temperature during reaction set up; together with the first step in the thermocycler, a 10 min incubation at 30° C., this provides the right conditions for UDG to act on Uracil-containing amplification products of previous PCR reactions, thereby removing spurious carry over contaminants. After UDG heat inactivation, the subsequent PCR reaction was again carried out in the presence of UTP to prevent carry over contamination in following runs.

Forward Primers:

- 1st set for the SarsCoV2 N gene (N1): SEQ ID NO: 1 to 96
- 2nd set for the SarsCoV2 N gene (N3): SEQ ID NO: 97 to 192
- Set for rRNA: SEQ ID NO: 193 to 288
- Set for influenza A: SEQ ID NO 289 to 384
- Set for influenza B: SEQ ID NO: 385 to 480
- Set for human rhino virus: SEQ ID NO: 481 to 495

All forward primers contain the same 5' part containing the adaptor sequence (CTACACGACGCTCTTCCGATCT (SEQ ID NO: 991)—nt 1 to 22 of any of SEQ ID NO: 1 to 495) followed be the staggering nucleotides, i.e. 1 to 4 N, which are randomly selected from A, C, G, or T, followed by the sample identifier sequence, which is different for all primers within a given amplicon-specific set, here a 8-mer for all of SEQ ID NO: 1 to 495 (e.g. CCAATACT (SEQ ID NO: 992), nt 24-31 of SEQ ID NO: 1), followed by a binding sequence for hybridization to the analyte nucleic acids; e.g. for N1: gaccccaaaatcagcgaaat (SEQ ID NO: 993) (nt 32 to 51 of SEQ ID NO: 1); for N3: gggagccttgaatacaccaaaa (SEQ ID NO: 994) (nt 32 to 53 of SEQ ID NO: 97); for rRNA: ggcattcgtattgcgccgcta (SEQ ID NO: 995) (nt 32 to 52 of SEQ ID NO: 193); for influenza A: CTCATGGARTGGCTAAAG (SEQ ID NO: 996) (nt 32 to 49 of SEQ ID NO: 289); for influenza B: GCCTTCTCCATCTTCTG (SEQ ID NO: 997) (nt 32 to 48 of SEQ ID NO: 385); for human rhino virus: TCCTCCGGCCCCTGAAT (SEQ ID NO: 998) (nt 32 to 48 of SEQ ID NO: 481).

Reverse Primers:

- 1st set for the SarsCoV2 N gene (N1): SEQ ID NO: 496 to 591
- 2nd set for the SarsCoV2 N gene (N3): SEQ ID NO: 592 to 687
- Set for rRNA: SEQ ID NO: 688 to 783
- Set for influenza A: SEQ ID NO 784 to 879
- Set for influenza B: SEQ ID NO: 880 to 975
- Set for human rhino virus: SEQ ID NO: 976 to 990

All reverse primers contain the same 5' part containing the adaptor sequence (GTGACTGGAGTTCAGACGTGTGCTCTTCCGATCT (SEQ ID NO: 999)—nt 1 to 34 of any of SEQ ID NO: 496 to 990); followed by the sample identifier sequence, which is different for all primers within a given amplicon-specific set, here a 8-mer for all of SEQ ID NO: 1 to 495 (e.g. AGCTTGGT (SEQ ID NO: 1000), nt 35-42 of SEQ ID NOs: 496 to 990), followed by the binding sequence for hybridization to the analyte nucleic acids; e.g. for N1: TCTGGTTACTGCCAGTTGAATCTG (SEQ ID NO: 1001) (nt 43 to 66 of SEQ ID NO: 496); for N3: tgtagcacgattgcagcattg (SEQ ID NO: 1002) (nt 43 to 63 of SEQ ID NO: 592); for rRNA: GGCAAATGCTTTCGCTCTGGTC (SEQ ID NO: 1003) (nt 43 to 64 of SEQ ID NO: 688); for influenza A; TGGACAAANCGTCTACGCTGCAG (SEQ ID NO: 1004) (nt 43 to 65 of SEQ ID NO: 784); for influenza B: GTCGCTGTTTGGAGACAC (SEQ ID NO: 1005) (nt 43 to 60 of SEQ ID NO: 880); for human rhino virus: GAAACACGGACACCCAAAGTAGT (SEQ ID NO: 1006) (nt 43 to 65 of SEQ ID NO: 976).

Staggering distancing nucleotides are only used for the forward but not the reverse primer since their effect is only needed on one side of the amplifications products to have their effects during sequencing.

Master Mix Composition per Reaction/Well (volumes in μL)

| | |
|---|---|
| 10x PCR top up Buffer$^{D}$ | 2.5 |
| 100 mM dUTP (NEB) | 0.07 |
| HotStart Taq Polymerase | 0.5 |
| Antarctic thermolabile UDG | 0.5 |
| Water | 16.43 |

Thermocycler Program:

- 10 min at 30° C. (for high UDG activity)
- 3 min at 95° C. (UDG inactivation and HotStart Taq activation)
- 45 cycles of: 20 sec at 95° C., 30 sec at 58° C., 20 sec at 72° C.
- 2 min at 72° C.
- Cool down to 12° C. (removing the plate while it's still hot will cause bending of the plastic, making further pipetting and sealing more difficult)

$^{C}$PCR primer mix composition: 2 mM of each forward and reverse primer, for all viral amplicons and 1 mM of each forward and reverse primer for the rRNA amplicon (final concentration of each primer pair in the complete 50 μL reaction is 200 and 100 nM, respectively)

$^{D}$10×PCR Top Up Buffer Composition:

- 750 mM Tris-HCl pH 8.3
- 200 mM $(NH_4)_2SO_4$
- 1% Triton X-100

Example 5: Plate Pooling

All well-barcoded PCR products from a single 96-well plate were pooled, typically 20 μL of each reaction was combined in a plastic reservoir using a multi-channel pipette, and after mixing thoroughly 1 mL was transferred to an Eppendorf tube. This was repeated for every PCR plate. 5 μL from each plate pool were re-arrayed in a new 96-well plate and treated with 2 μL of illustra ExoProStar 1-step for 30 min at 37° C. followed by 15 min at 80° C. to remove any left-over primer.

Example 6: Second PCR

Subset indices are added (plate barcodes) with sequencing adaptors. A master mix with all components listed below was distributed across a 96-well plate (37.5 μL/well). To each we added 10 μL of unique dual-indexed i5/i7 primer pairs (Custom synthesized index primers with Nextflex barcodes, arrayed in 96-well plates) and 2.5 μL of Exostar-treated PCR1 pool. The reactions were run for 8 cycles to add sequencing adaptors with plate barcodes.

Master Mix Composition per Reaction/Well (Volumes in μL)

| | |
|---|---|
| 10x Sequencing-ready PCR Buffer$^{E}$ | 5 |
| 25 mM each dNTPs | 0.5 |
| 100 mM dUTP | 0.07 |
| Hot start Taq Polymerase | 0.5 |
| Water | 31.43 |

Thermocycler Program:

3 min at 95° C.

8 cycles of: 15 sec at 95° C., 30 sec at 65° C., 30 sec at 72° C.

2 min at 72° C.

Cool down to 12° C.

$^{E}$10× Sequencing-Ready PCR Buffer Composition:

750 mM Tris-HCl pH 8.3

200 mM $(NH_4)_2SO_4$ 20 mM $MgCl_2$ 0.1% Tween 20

Example 7: Pooling and Preparation for Sequencing

All samples from a 96-well plate (20 μL from each well) were pooled and 250 μL of pooled sample is resolved on 2% agarose gel and 220 bp to 260 bp size amplicons are excised and gel purified using Qiagen gel extraction kit.

In order to ensure fast turnaround, the preparation of libraries for Illumina sequencing was optimized empirically. In the first four sequencing runs, standard quality control of the library, including Qubit measurement, a size analysis and qPCR, was performed. A correlation between the concentration measurement by Qubit and the qPCR was detected. In every case the molarity determined by qPCR was 10× higher than the concentration measured by Qubit. Thus, we can omit the size analysis and the qPCR, which are both time consuming. Eventually the library concentration is determined by 3 independent Qubit measurements, the obtained value in ng/μL is multiplied by 10 and used as the molarity of the sample in nanomolar. This procedure enables us to start the sequencer within a 15 min time-frame after receiving the sequencing library. Final preparation of the sequencing run happens according to Illumina's guidelines, including denaturation of the sample, neutralization and final dilution for sequencing.

Example 8: Sequencing

Depending on the sequencer type, the following concentrations were used for sequencing: 10 pM for MiSeq V2 chemistry, 15 pM for MiSeq V3 chemistry, 2.2 pM for NextSeq550 high output and 1.3 pM for NextSeq550 medium output. In every sequencing run 10% of PhiX library were spiked-in to increase complexity. To avoid contaminations with barcodes from previous sequencing runs, the sequencers were washed with bleach according to Illumina's guidelines before every run.

Example 9: Data Analysis

The NGS data (fastq.gz files) were mapped in a single pass to sets of expected amplicon sequences and to sets of expected well- and plate indices. While any standard NGS workflow and read-mapping software (e.g. bowtie or similar) would be suitable, we used dedicated shell and awk scripts based on string-hashing that allows for 0 or 1 mismatch per amplicon and index. The i5 and i7 indices signified the plate-indices (subset index) and parts of the forward read (and the reverse read in the case of paired-end sequencing) signified the well-indices (sample index); we required the correct redundant encoding of plate and well. As the well-index on the forward read started at random offsets, we first determined the amplicon identity and position, then inferred the position of the well index, and finally compared the well index to the intended well indices.

Example 10: Direct Sample Processing Without RNA Extraction

Many current pipelines for detection of viral RNA begin with purification of RNA from biological material (swabs, saliva, gargle, etc). However, to lower costs and match the throughput of an NGS-based pipeline, RNA extraction was bypassed. Typically, samples are collected in viral transport medium (VTM). Additionally, saliva represents an ideal viral transport medium and is now frequently used as input for SARS-CoV2 testing pipelines. We found that gargling of 10 ml HBSS is compatible with self-sampling. Gargle samples enable similar sensitivity to swabs collected by medical staff and are preferred to pure saliva as samples become more uniform in viscosity and are thus easier to pipette, making the samples better suited for automation (FIG. 1A). Several approaches to stabilize viral RNA from respiratory specimens, circumventing RNA purification and enabling the required scalability are known (swab-seq (Bloom et al., doi.org/10.1101/2020.08.04.20167874), Salivadirect (Vogels et al., doi.org/10.1101/2020.08.03.20167791), Quick extract (Ladha et al., doi.org/10.1101/2020.05.07.20055947), HUDSON buffer (Lalli et al., doi.org/10.1101/2020.05.07.20093542)). To compare these methods, we mixed retroviral particles packaged in cell culture into gargle samples and then treated the samples according to the different protocols: i) 30 min at 95° C. (swab-seq), ii) 5 min at 95 after addition of Proteinase K (Saliva-direct), iii) 1:1 mixture with QuickExtract and 5 min at 95° C., and iv) lysis and RNA extraction. We then assessed efficiency of RNA unmasking and its stability before and after treatment, by performing quantitative RT-PCR of a virus specific amplicon. We confirmed that all these methods generate stable RNA that are compatible with RT-PCR. DNA QuickExtract, however, showed the least precipitation of VTM upon boiling and was thus used for most experiments unless otherwise stated (FIG. 1B).

Example 11: 2-Step RT-PCR has Increased Specificity Compared to 1-Step RT-PCR

The amplification of viral genome fragments for sequencing consists of RT and PCR steps. Indexes pointing towards individual samples can be incorporated during the reverse transcription (RT) step as well as during PCR (FIG. 1C). However, we found that introduction of sample barcodes in the RT step resulted in an increased fraction of non-specific PCR products as compared to their introduction at the PCR step, presumably because the higher temperature of PCRs constitute more restrictive and thus specific conditions (FIG. 1D). Given the large but limited sequence space on NGS flow cells, such lack of specificity means that many unspecific amplicons would be sequence, which interferes with upscaling to very large sample numbers. We therefore settled on integration of positional indexes during PCR only. Specifically, individual samples are arrayed in individual wells of 96-well plates in which the RNA from each sample is first subjected to reverse transcription (RT) and then to amplification by PCR to produce diverse desired viral and control amplicons. Priming in the RT step is performed with random hexamers as well as two gene specific twelve-mers that increase sensitivity for Sars-CoV2.

Example 12: Compression of Dynamic Range by 45-Cycle End-Point-PCR Enables Sensitive Detection of Samples with Low Viral Titers One of the hurdles towards establishing a pooled NGS-based assay for samples from virus-infected individuals derives from the fact that viral loads can differ by many orders of magnitude such that high-titer samples would dominate NGS. TaqMan RT-qPCR reports differences in Ct values of 20-25 cycles, which translate into $2^{25}$=33.5 million-fold differences in viral titers. Therefore, if samples with low virus titer are to be robustly identified as positives, e.g. with >100 virus-derived amplicon reads, the samples with high virus titers required $3.3\times10^{9}$ reads, which is prohibitive. Therefore, the dynamic range needs to be compressed, in order to dampen the signal from a highly positive sample at the expense of providing sufficient sensitivity to detect samples with lower titers. In order to achieve this compression of signal, we run the first PCR reaction for 45 cycles until each individual sample reaches saturation. This results in the generation of similar numbers of amplicons per well independent of the initial viral titer (FIG. 1D,E). In summary, using crude respiratory specimens as input, a 2-step RT-PCR generates high specificity and even representation of characteristic amplicons across samples to enable pooling of many samples for analysis by NGS.

Example 13: Selection of Viral and Human Control Amplicons

In addition to the very large dynamic range of viral titers between patients, nonspecific PCR amplicons can severely impact the detection of viral amplicons by NGS, because the number of NGS reads is inherently limited (and directly proportional to the total costs). For example, the parallel analysis of approximately 40K (96×384) samples means that each sample can receive a total of only ~500 reads on a MiSeq, ~2K on a HiSeq, and ~10K on a NextSeq platform. If a substantial fraction of these reads were spent on sequencing nonspecific amplicons, assay sensitivity would be severely impacted. It is thus pivotal to select amplicons and primer pairs that i) show high sensitivity ii) generate amplicons of comparable short size iii) generate few nonspecific amplicons alone or in combination with any other primer pairs present in the same reaction, which is of particular importance when using primers with long extensions (here: sample-identifying barcode sequences and primer-binding sites for a 2nd PCR as discussed below).

Example 14: 18S-rRNA-Specific Primer Pair to Control for Sample Presence and Quality We tested several published Sars-CoV2 specific primer pairs for the performance with our DNA overhangs. The Sars-CoV2 N-gene-specific primers N1 and N3 proposed by the Center for Disease Control (CDC), both being specific for the SARS-CoV2 N gene, performed best in SYBR-Green qPCR (which does not control for amplicon identity) as well as in initial sequencing runs, and had an ideal amplicon length of ~70. We also tested the N1 amplicon together with the widely used internal control primer pair targeting RPP30 (RNAse P). While the N1 primers showed a fair amount of correct amplicons in dependence of the amount of synthetically spiked in template, the fraction of specific amplicons for RPP30 was only 0.06-1.5% (FIG. 2A). When analyzing all observed amplicons across conditions, we detected various short sequences that together used up >99% of all NGS reads. The vast majority was generated by the RPP30 specific primers (FIG. 2B), suggesting that these primers are not compatible with multiplexed PCR and NGS. We therefore set out to establish a new control primer pair that would produce much fewer nonspecific amplicons. We tested several primer sets on gargle samples obtained from 16 individuals, yet only a single primer pair, specific for 18S ribosomal RNA, was detected in all samples and showed a strong dependency on the presence of reverse transcriptase (FIG. 2C). We therefore chose this 18S ribosomal RNA specific primer pair to control for sample quality. Of note, ribosomal amplicons were detected at Ct values of 15-45 and therefore in a comparable range as viral amplicons in patients. We therefore tested ribosomal RNA as host control in the SARSeq panel. Indeed, the ribosomal primer pair/amplicon selection performed well and neither generated abundant unspecific amplicons alone, nor in combination with N1 or N3 primer pairs (FIG. 2E).

Example 15: Synthetic Spike-In RNA Controls for RT-PCR Performance

Since the 18S amplicon—like the RPP30 amplicon—does not span an intron it cannot discriminate against genomic DNA templates abundant in respiratory samples. In particular, QuickExtract processed gargle did not show a dominant RNA based signal even with ribosomal primers (FIG. 2C). This is maybe expected since very few living cells will shed during the gargle procedure and released RNA will also not survive for extended periods of sample storage. In contrast, viral particles with genomic RNA are shed efficiently and maintained well in particular in buffered isotonic conditions such as viral transport medium (VTM), saliva, and gargle in HBSS to protect viral RNA from very abundant RNAse activity in respiratory specimen REF. To integrate an additional internal RNA control to assess successful reverse transcription in all probes, we therefore included RNA with identical primer binding sites as the ribosomal amplicon, yet unrelated sequence in between. This in vitro transcribed RNA was spiked into the reverse transcription mix at a concentration of 1000 molecules/reaction (FIG. 2D). Using the RT- and PCR buffers (Examples 2, 3 and 6) SARSeq reached a very good amplicon specificity with the majority of amplicons (FIG. 2E). The ratio of reads for the ribosomal amplicon and spike in serves as a very good assessment of sample quality. The high specificity of amplicons set the stage to develop a high throughput indexing strategy that allows to analyze tens of thousands of samples in parallel.

Example 16—Comparative Example: Simple Sample Indexing Strategies Don't Retain Sample Identity To exploit the high-throughput nature of NGS, we designed a sample barcoding strategy that allows multiplexing of tens of thousands of samples for a single sequencing run while retaining perfect sample specificity, i.e. suppressing misassignment of reads to incorrect samples. Retaining perfect sample specificity is crucial in the context of samples from healthy individuals (no viruses) and from patients with the abovementioned very wide range of virus titers. Several strategies for sample indexing are currently available that make use of the possibility that NGS can not only determine the amplicon identity but any other information on the amplicon, including sample-specific barcode sequences or indices. First, samples can be individually indexed by a sample-specific barcode in one of the two primers, i.e. in the forward or in the reverse primer (FIG. 3A). In such a setup, sample-specific primers incorporate sample-indexes into the amplicons of each sample that can be detected in NGS (REF e.g. the 19000RT barcodes and swab seq 2.0). This strategy however does not scale well as it requires distinct primer pairs for each amplicon and sample (linear/additive scaling).

More importantly, it cannot retain perfect sample identity due to template-switching PCR artifacts and index-hopping on flow cells, which can lead to random associations between amplicon- and index sequences. This problem is of particular relevance when high-titer samples are analyzed in parallel with samples from healthy individuals as we demonstrated by spiking synthetic Sars-CoV2 template into two wells of a 96 well plate (wells B8 and F2) in which all other wells are negative (FIG. 3B). Simple combinatorial indexing with a column barcode on one primer and a row barcode on the other primer can overcome the scalability problem (swab seq 1.0) (combinatorial/multiplicative scaling; FIG. 3C), but suffers from the same inability to retain perfect sample identity, which in this case leads to a characteristic cross-shaped pattern along the rows and columns of the positive samples (FIG. 3D).

Example 17: Two-Dimensional Redundant Dual Indexing is Scalable and Retains Sample Identity We implemented redundant, dual indexing (also referred to as "unique dual") that retains perfect sample identity by redundantly encoding sample identity on both ends of the amplicon, thereby eliminating illegitimate index combinations (FIG. 3E,F,G). We achieve this by two indices introduced through forward and reverse primers that both point to the same sample/position (FIG. 3E, G). Such an approach requires two indices (=unique primers) per sample (FIG. 3E) and therefore does not scale well when a single PCR is used (1 dimension). We therefore use a two-dimensional indexing strategy by adding a second PCR step that again uses redundant, dual indexing, yet allows fully combinatorial indexing between dimension 1 and 2 (combinatorial/multiplicative; FIG. 3G). This strategy of two-dimensional redundant dual indexing has only a modest requirement to increase indexing primer numbers for very large panels of parallel samples and allows the encoding of 96×96 or 96×384 samples with 2×96 amplicon-specific primers (2 per amplicon; 1st dimension) plus 2×96 or 2×384 global primers (irrespective of amplicon; 2nd dimension), respectively, when using standard 96- and 384-well plates, for example. Greater number of indexes/primers are easily scalable due to the multiplicity of the 2-step index strategy, which presents a robust and scalable indexing strategy.

Example 18: A Set of 96 Validated Primer Pairs Per Amplicon for the 1st Dimension In practice, we extended the amplicon-specific primers for the 1st PCR (1st dimension—sample indexing) at their 5' ends to include a sample-specific barcode and i5/i7 sequences as primer-binding sites for the 2nd PCR. To ensure sufficiently complex sequences of the NGS forward reads for cluster identification and stable sequencing, we staggered the sample-barcode and the amplicon-specific sequence by a random offset of 1-4 base pairs in the forward primers—see "n" nucleotides in SEQ ID NO: 1 to 495 (see FIG. 3G and Example 4). We tested a total of 110 primer pairs per amplicon to establish a set of 96 primer pairs that show good amplification behavior for all amplicons (FIG. 7). Importantly, all amplicons within one well obtain the identical stagger and index to also prevent recombination between amplicons during PCR. Pre-prepared primer-plates and robotic pipetting pipelines allow us to process thousands of samples in parallel.

Example 19: Perfectly Retaining Sample Identity Across the Two Dimensions

After the indexing of individual samples (=wells of a 96 well plate; 1st dimension), all samples of one plate are pooled to one position in a new 96-well plate, and in a second PCR, a plate specific index is added (2nd dimension). We implemented four measures to ensure that sample identity is perfectly retained between the 1st and 2nd PCR. i) To avoid that primers from the 1st PCR are present during the 2nd PCR, we included an RNA template with N1 and N3 primer binding sites similar to our RT control and the denominator used in the Swab-Seq pipeline to suppress stochastic contaminations. In addition, we ii) treated the pools with DNA exonuclease to enzymatically degrade all single-stranded DNA and thus all remaining primers especially from Sars-CoV2 negative wells. iii) We keep the cycle number for PCR 2 at a minimum to avoid amplicon recombination during PCR and use a PCR protocol that prevents premature termination of an extension step. Indeed, the measures synergistically contributed to the robustness of read assignment (FIG. 8A). iv) In each dimension we use dual and redundant indices with a Lowenstein distance of at least three mismatches. This pipeline also suppressed read misassignment across plates, such that the positions of FIG. 3A, C, E were not detected on other plates run in the same experiment (FIG. 8B).

We thus established a scalable and robust indexing for Sars-CoV2 by setting up a PCR-based indexing-strategy, that incorporates two sets of redundant indices and we bioinformatically filter to only allow legitimate combinations of those four indices. The ability to encode 96 well barcodes and 384 plate barcodes means this can be used to investigate 36,864 individual samples simultaneously. To illustrate scalability of the approach, a 4-fold increase in each dimension for example by using 384-well plates would enable multiplexing of >145,000 samples. Sequencing capacity is thus no longer a bottleneck to frequent population wide testing for many countries and the sequencing price is negligible. This indexing systems allows to filter against any DNA remnants in sequencing flow cells, that can result in read misassignment between independent analysis runs. In summary, dual redundant indexing introduced during PCR 1 ensures sample identity specificity and two-dimensional indexing allows scalability while preventing any spill of reads from positive to negative samples even across multiple orders of magnitude in signal intensity. We termed this direct analysis of respiratory samples using next generation sequencing SARSeq for "Saliva Analysis by RNA Sequencing".

Example 20: Specificity and Sensitivity of SARSeq

To test sensitivity, specificity, and scalability of SARSeq we set out to run large sample cohorts. To assay under close to real-life conditions we prepared samples plates and processed them in parallel using a robotic pipetting platform. We also tested the effect of spike-ins with identical primer binding sites to the N1/N3 amplicons but different sequences in between, as introduced previously.

Initially we tested sensitivity of the SARSeq pipeline by diluting viral templates to 1, 3, or 10 copies per 5 ul probe volume (2-0.2 copies/ul). To account for the contribution of Quick Extract as input buffer to the pipeline as well as to test RNA extraction with this method we tested above dilutions with synthetic RNA in $H_2O$ as well as Quick Extract mixed to HBSS and also assayed viral particles in Quick extract.

Using $H_2O$ for dilution we were able to detect Sars-CoV2 in 5 and 6 of 24 tested cases for N1 and N3 respectively at a dilution of in average 1 amplicon per well (FIG. 4A). At such dilution 63% of wells are expected to contain one or more viral templates assuming a Poisson distribution pointing towards a detection efficiency of 0.3-0.4 per molecule. Quick Extract increased that efficiency to 0.7 while detection straight from viral particles was at 1.1 per molecule (FIG. 4B). Presence of N1 and N3 denominator spike-ins even showed slightly better detection efficiencies. It is assumed that infectious Covid-19 patients show with detectable viral titers of $>10^3/\mu L$. Our detection limit is thus at least 100 times more sensitive than required for mitigation of the current Sars-CoV2 pandemic. Next, we tested the effect of spike-ins on the quantitative behavior of SARSeq (FIG. 4C). Due to the endpoint PCR we perform, SARSeq intentionally only returns semi-quantitative results. However, when testing a dilution series of synthetic spikes in quadruplicate we noticed an improved reproducibility in presence of these spike-ins and therefore included them in the final setup.

To challenge SARSeq with hundreds of real samples omitting RNA purification, we next generated sample plates from gargle samples collected in HBSS. Such crude samples may contain reagents inhibitory to the RT or PCR step. To this end, we generated a dilution series of synthetic template and also spiked a dilution series of a subject or patient sample presenting with Ct=30 in a taqman Q-PCR assay into several positions. Indeed, when testing six 96-well plates, we were able to detect all patients previously detected with an RNA purification followed by a Taqman-based qPCR. In addition, we saw all patients and synthetic spike-ins that we had added prior to running the pipeline. Overlap between N1 and N3 amplicon-based results was 100% (FIG. 4D).

Another critical parameter when testing very large numbers of patients is the false positive rate. We were therefore extremely pleased to see that our indexing strategy and pipeline delivered typically zero and very rarely 1 read indicative of SARS-CoV2 for gargle of persons previously tested negative by Q-PCR as well as all $H_2O$ controls. This binary result showcased an unambiguous assessment of infection status by SARSeq. Due to the absence of false positive results we did not need to use our denominator amplicons to set a threshold for signal strength for positive results. However, we envision that they could be a powerful method to reduce stochastic reads if incorporated at sufficiently high concentration to reduce sensitivity.

Example 21: Performance of SARSeq on Large Panels of Patient Samples

To test if SARSeq would robustly detect real SARS-CoV2 virus in VTM samples collected in clinical diagnostic pipelines of many independent patients, we tested a set of 564 samples with SARSeq in duplicate. While we did not detect N1 or N3 amplicons in $H_2O$ or −RT conditions (FIG. 5A, B) we frequently obtained SarsCoV2 reads across all plates with good correspondence between amplicons and replicates. (FIG. 5C, D). To assay correspondence to the standard test, we also measured the samples in a Taqman Q-PCR assay in duplicates. Expectedly we found a very good correspondence of both replicates for Ct values below 36 (FIG. 5E, red dots) and a stochastic behavior at the detection border (FIG. 5E, orange dots) with either one or two replicates scoring positive. No Sars-CoV2 was detected in an additional 354 samples. We analyzed the overlap between detection in qPCR- and NGS-based assays and found that 157 or 96.3% of samples that scored with a Ct value of <36 in at least one qPCR in fact scored positive in all four assays while six samples were detected with one or two assays only (FIG. 5F). We hypothesized that the stochastic behavior at detection border is due to presence or absence of a single viral genome in the reaction. If that was true, then correspondence between amplicons of a single replicate is expected to be better than correspondence per amplicon between replicates even though N1 and N3 might show different sensitivities. Indeed, of the samples detected with 1-3 assays, 48 and 43 samples show detection of Sars-CoV2 with both amplicons within one replicate while only 18 and 25 samples are detected twice independently with N1 or N3, respectively. We thus conclude that SARSeq is sensitive down to single viral genomes. We plotted read counts of both SARSeq replicates against each other to visualize read count reproducibility (FIG. 5G, H). As anticipated, we see a lower correlation than with qPCR, some samples undetected in NGS but present in one qPCR run at any Ct, as well as the detection of some samples missed by one or both Q-PCRs. We also observe a distinct upper end of N1/N3 read counts attributed to the intentional blunting of reads in end point PCR to distribute sequencing space evenly across samples (see also FIG. 1E). Taken together, SARSeq was able to reproducibly identify Sars-CoV2 across a patient cohort of 564 samples with high reproducibility and a sensitivity to single molecule level.

Example 22: Broader Applicability to Detection of Respiratory Infectious Agents Multiple infectious agents cause disease with overlapping clinical symptoms, foremost Influenza A and B. Moreover, it is expected that particularly in the winter season, various respiratory symptoms will cause concerns for patients (even if clinical symptoms are not strictly overlapping) and thereby dramatically increase the demand for reliable/sensitive Sars-CoV2 tests. Most prominently, we anticipate that rhinoviral infections will remain frequent even in measures of social distancing as a typical winter season brings several episodes of rhinoviral infection per person. For SARSeq additional amplicons come at no extra cost if it doesn't increase sequencing depth requirements. Therefore, we can further multiplex SARSeq to detect in addition other common respiratory viruses found in the same type of sample as SARS-CoV2.

To accommodate for the aforementioned RNA viruses, we sought to optimize primers for influenza A, B, and rhinovirus to be combined with our Sars-CoV2 specific SARSeq pipeline. To this end we selected primers based on qPCR performance, amplicon length, and an NGS pilot. For a pan-influenza A amplicon we settled on combining a degenerated forward primer from Bose et al. (J Clin Microbiol 47(9), 2009: 2779-2786) with a degenerate WHO reverse primer, both targeting the M gene. For pan-influenza B we selected a primers (see example 4) of SEQ ID NO: SEQ ID NO: 385 to 480 (forward primers) and SEQ ID NO: 880 to 975 (reverse primers) to the M gene. Rhinovirus is detected using a primer pair of Do et al. (J Mol Diagn. 2010; 12(1): 102-108).

To test performance across a large number of specimen we took gargle-Quick extract samples and spiked in purified RNA obtained from HEK293T cells infected with respective virus strains 48 h prior purification at a voluminometric ratio of 1:100 or dilutions thereof. Samples were processed using the robotic pipeline. We performed PCR1 in the presence of six primer pairs, two against Sars-CoV2, and one each for ribosomal control, influenza A, influenza B, and rhinovirus.

Upon pooling and PCR2, samples were sequenced by paired end sequencing to account for the presence of longer amplicons, and reads were mapped to wells/samples (FIG. 6B). Of note, by pipetting spike-in RNA prior to setting up the RT reaction we apparently generated an RNA contamination of influenza B that was stochastically distributed across all reactions (including $H_2O$ controls but not –RT controls) and obtained reproducibly lower read counts than spike in samples. This event emphasizes the importance of a local separation of reaction mix preparation and sample handling. All post-PCR steps were always performed in a different lab from the beginning and thus DNA amplicons did not generate detectable contamination of our pipeline. Nevertheless, we implemented incorporation of UTP and a UDG digestion step prior to PCR in our protocol to protect against contamination risk with amplicons. Importantly, however, our multiplexes pipeline to detect RNA of various viral respiratory diseases in parallel performed robustly across six 96-well plates. We obtained no false negative samples besides expectedly the 1/1 mio dilutions of a Sars-CoV2 sample with Ct30. Aside from the apparent influenza B sample contamination, we did also not see any other false positive events. Moreover, the amplicon sequence of influenza A allowed us to distinguish between the two spike-in strains we had used, namely A/WSN and A/Wy. This is of particular interest since A/Wy like B/Lee used as an Influenza B spike-in is contained in the current vaccination as it is anticipated to circulate in the northern hemisphere 2020/21 flu season. Similarly, we were able to distinguish between the three rhinoviral strains used as spike-in, namely HRV A1a, A1b and A2, by polymorphism in respective amplicons. Taken together our pipeline in its current setup thus differentially detects seven different viral respiratory agents in a single reaction, contains various internal controls, a sample quality control, and by design has a particular sensitivity for Sars-CoV2. SARSeq thus represents a multiplexed, massively parallelized assay for the detection of respiratory infections by means of RT-PCR and next generation sequencing.

Example 23: Sars-CoV2 Spike Variant Detection

A variation of the method described in examples 2-9 allows sensitive detection of commonly known and new variants of the spike protein of Sars-CoV2 on a large scale. This method is employed to routinely analyze 2400 per day in high throughput.

The method basically follows example 2-9 with minor modifications in the methodology, using different primers, however, to analyze different parts of the spike protein. In particular, 13 different amplicons for the spike protein are generated. These cover the nucleic acid sequences corresponding to amino acids 1-722 and 767-839 of the spike protein, which is where the immunologically relevant mutations are found.

Briefly, the method contains the steps:

1. RNA extraction: For illustration purposes, the method is exemplified using purified RNA. However, it also works with other sample types, such as gargle or saliva, as described in example 1.
2. Reverse transcription: RT is done as described as in example 2 with modified primers. Two separate parallel reactions are performed per sample, each with distinct sets of RT primers ("odd" and "even"). The method and spike gene coverage by the primer sets are illustrated in FIG. 9. Briefly, 5 μl of sample are added to each an "odd" and an "even" complete RT mix (20 μl per reaction). Plates are sealed and incubated at 55° C. for 30 min and inactivated 3 min at 95° C. The primers have been selected for specificity of different parts of the S gene (see FIG. 9C) and for having a melting temperature of about 58° C. Selecting a melting temperature slightly above the working temperature of the reverse transcriptase (55° C.) avoids efficiency loss due to secondary structure of the virus genome.

The RT primer sequences are:

```
1:
                                     (SEQ ID NO: 1007)
CATGTATAGCATGGAACCAAGTAACA

2:
                                     (SEQ ID NO: 1008)
CGTTATTAACAATAAGTAGGGACTGGGT

3:
                                     (SEQ ID NO: 1009)
CCATCAATATTCTTAAACACAAATTCCCTAAG

4:
                                     (SEQ ID NO: 1010)
CCCACATAATAAGCTGCAGCA

5:
                                     (SEQ ID NO: 1011)
CTACAGTGAAGGATTTCAACGTACA

6:
                                     (SEQ ID NO: 1012)
GCATAGACATTAGTAAAGCAGAGATCA

7:
                                     (SEQ ID NO: 1013)
CAGGTAATTATAATTACCACCAACCTT

8:
                                     (SEQ ID NO: 1014)
AGTTCAAAAGAAAGTACTACTACTCTGT

9:
                                     (SEQ ID NO: 1015)
CCAAATTGTTGGAAAGGCAGAAAC

10:
                                     (SEQ ID NO: 1016)
GCATGAATAGCAACAGGGACT

11:
                                     (SEQ ID NO: 1017)
GTCTGATAACTAGCGCATATACCTG

12:
                                     (SEQ ID NO: 1018)
GTACAATCTACTGATGTCTTGGTCA

13:
                                     (SEQ ID NO: 1019)
GTGCACAAATGAGGTCTCTAGCA

7 (alternative version):
                                     (SEQ ID NO: 1020)
GAGATTAGACTTCCTAAACAATCTATACAGGT
```

3. PCR1: A first PCR reaction is performed similar to example 4. cDNA plates are opened and 25 μl of complete PCR top up mix (including primers) is added. An "even" PCR mix is added to the even numbered RT plates and an "odd" PCR mix is added to the odd numbered RT plates. The PCR primers in addition to being specific for the 13 different S gene fragments ("tiles") (Fig. C) have the same structure as the primers described in example 4, i.e. they have unique dual index combinations in the forward and the reverse primer that point to a specific well in a plate (see FIG.

3). While in example 4 a 96 distinct dual index combination was used, here 12 or 24 indices are used for cost considerations, but conceptually the same principles as described in example 4 are adhered to, the only difference is that in the next step not a complete plate is pooled, but only 12 (or 24) samples that carry different indices are pooled together.

As described in example 4, the forward primers again contain a 5' part containing the adaptor sequence, followed by the staggering nucleotides, i.e. 1 to 4 nucleotides, which are randomly selected from A, C, G, or T, followed by the sample identifier sequence, which is different for all primers within a given amplicon-specific set, e.g. an 8-mer, followed by a binding sequence for hybridization to the analyte nucleic acids.

Also as described in example 4, all reverse primers contain the same 5' part containing the adaptor sequence, followed by the sample identifier sequence, which is different for all primers within a given amplicon-specific set, e.g. an 8-mer, followed by the binding sequence for hybridization to the analyte nucleic acids.

The binding sequence for hybridization to the analyte nucleic acids for the spike gene fragments are:

```
1-forward:
                              (SEQ ID NO: 1021)
GGGGTACTGCTGTTATGTCTTTAAAAGA

1-reverse:
                              (SEQ ID NO: 1022)
CTGAGGATCTGAAAACTTTGTCAGGGT

2-forward:
                              (SEQ ID NO: 1023)
CCCCTGCATACACTAATTCTTTCACAC

2-reverse:
                              (SEQ ID NO: 1024)
CTGGGTCTTCGAATCTAAAGTAGTACCA

3-forward:
                              (SEQ ID NO: 1025)
GCTTCCACTGAGAAGTCTAACATAATAAGAGG

3-reverse:
                              (SEQ ID NO: 1026)
CCCTGTTTTCCTTCAAGGTCCA

4-forward:
                              (SEQ ID NO: 1027)
GTTGGATGGAAAGTGAGTTCAGAGT

4-reverse:
                              (SEQ ID NO: 1028)
ACCTATTGGCAAATCTACCAATGGTTC

5-forward:
                              (SEQ ID NO: 1029)
GCGTGATCTCCCTCAGGGTTT

5-reverse:
                              (SEQ ID NO: 1030)
CGTACACTTTGTTTCTGAGAGAGGGT

6-forward:
                              (SEQ ID NO: 1031)
CAGATGCTGTAGACTGTGCACTT

6-reverse:
                              (SEQ ID NO: 1032)
CACTTAAAAGTGGAAAATGATGCGGAA

7-forward:
                              (SEQ ID NO: 1033)
GGAAGAGAATCAGCAACTGTGTTGC
```

-continued

```
7-reverse:
                              (SEQ ID NO: 1034)
CACCAACCTTAGAATCAAGATTGTTAGAATTCC

8-forward:
                              (SEQ ID NO: 1035)
CCAGATGATTTTACAGGCTGCGT

8-reverse:
                              (SEQ ID NO: 1036)
GTACTACTACTCTGTATGGTTGGTAACCAAC

9-forward:
                              (SEQ ID NO: 1037)
GTCTAATCTCAAACCTTTTGAGAGAGAT

9-reverse:
                              (SEQ ID NO: 1038)
GAACACCTGTGCCTGTTAAACCAT

10-forward:
                              (SEQ ID NO: 1039)
GCACCAGCAACTGTTTGTGGAC

10-reverse:
                              (SEQ ID NO: 1040)
CAGCAACCTGGTTAGAAGTATTTGTTCC

11-forward:
                              (SEQ ID NO: 1041)
CGTGATCCACAGACACTTGAGATTCT

11-reverse:
                              (SEQ ID NO: 1042)
CCTGCACCAATGGGTATGTCACA

12-forward:
                              (SEQ ID NO: 1043)
GCAGGCTGTTTAATAGGGGCTG

12-reverse:
                              (SEQ ID NO: 1044)
GGTCATAGACACTGGTAGAATTTCTGTGG

13-forward:
                              (SEQ ID NO: 1045)
GGCAGTTTTTGTACACAATTAAACCGTG

13-reverse:
                              (SEQ ID NO: 1046)
TCTAGCAGCAATATCACCAAGGCA
```

In this example 24 different primers for each group with different sample identifier sequences, which are different for all primers within a given amplicon-specific set, e.g. 24 “1-forward”, 24 “1-reverse”, etc., primers, are used for different wells as described for example 4.

4. PCR2: Samples are pooled by plate (if using 96 indices) or by row (if using 12 indices only) and each pool is first treated with Exostar to degrade left-over primers and nucleotides, and subsequently subjected to a second PCR as described in example 7, adding a “plate” or “row” index that allows combinatorial encoding of samples and therefore higher throughput. PCR2 primers also include the Illumina flow-cell adaptors as described in example 7.
5. Library clean-up: PCR2 produces sequencing-ready products that simply need to be pooled and cleaned up by gel purification to remove primer dimers and unspecific smaller amplicons.
6. Sequencing: Illumina sequencing according to manufacturer instructions is performed. More sequencing depth is used than in example 2-9 because longer regions are covered.

Data analysis shows a high coverage of all amplicons (FIG. 10). In a practical application, 2200-2500 samples from Covid19 patients were analyzed each week. FIG. 11 shows the detected SARS-CoV2 variants with amino acids (aa) changes as compared to the normal variant. FIG. 12 shows the changes in SARS-CoV2 variants detected per week (calendar weeks 3-8 of the year 2021 are shown).

Summary

The global pandemic caused by Sars-CoV2 has majorly impacted on our societies and economies worldwide. It has demonstrated that most countries are not prepared to fight such challenges despite our progress in modern medicine as well as our conceptual understanding of infection cascades. Social distancing measures to interfere with further spread of Sars-CoV2 are likewise affecting almost all aspects of human life. To minimize such measures, it is required to implement them as directed as possible, for which data of infection events are needed. Importantly, such screening efforts serve a different goal than testing symptomatic individuals for Sars-CoV2. While the latter requires gold-standard methods to advise on the optimal treatment, screening for mitigation does allow for some ambiguity especially if the alternative is not to test. However, mass testing for mitigation comes with major practical challenges: i) Sample collection requires major investment into logistics. Amongst them are supply chain issues, personnel, the need for digital data management, and often legal hurdles. Also, communication to improve compliance has been identified as an increasing challenge. ii) Tests must be highly specific for Sars-CoV2 and almost devoid of false positives to prevent isolation of people based on erroneous results to build trust. NGS based detection of Sars-CoV2 can supply such results by detecting genome fragments at a precision even more specific than Taqman probes can be. In addition, the detection of two fragments in parallel represents an independent detection. iii) Costs for mass testing must be as low as possible to reasonably enable scaling. SARSeq as presented here relies on enzymes that can be purchased at scale and produced in-house. Buffers are made from standard salts. iv) Mass testing must not interfere or be confused with the tests performed in medical/diagnostic facilities. It should thus neither be carried out at the same facilities nor compete for supply required to diagnose symptomatic patients. SARSeq relies exclusively on equipment available in sufficient quantity in classical molecular biology facilities such as universities, institutes, biotech, and pharma. v) Tests must scale massively. We have set up SARSeq for a maximum analysis of 36K samples in parallel and tested up to 20K samples in a single sequencing run. Therefore, NGS capacities do not represent a practical limitation of this method. SARSeq is limited by sample supply as well as the throughput of PCRs that can be implemented.

Beyond Sars-CoV2, the pipeline can be rapidly adapted to additional amplicons for the detection of other infectious agents such as newly emerging viruses. We already implemented parallelized screening for Sars-CoV2, Influenza A and B, as well as HRV and aim to extend it to further respiratory infections with overlapping clinical manifestations such as RSV. Moreover, any newly emerging virus can be added to the panel. Also, SARSeq is not limited to respiratory specimen but the pipeline can be extended to other human samples or even monitoring pipelines such as waste-water monitoring.

A limitation of SARSeq is the time requirement of the assay. Two PCR reactions must be performed followed by sequencing (NGS) and analysis, so the theoretical time requirement is around 15 h. Therefore, SARSeq is not ideally suited for situations where immediate results are required. In such cases, antigen tests or RT-LAMP are superior methods. Rather, it is ideally implemented for regular (e.g. weekly) surveillance of infections at very large scale. Also, SARSeq is currently only semiquantitative. If exact viral titers are required e.g. to terminate quarantine it might be preferable to use non-multiplexed qPCR.

The invention claimed is:

1. A method for detecting a nucleic acid of interest in a plurality of samples, comprising the steps of:

a) providing analyte nucleic acids from a plurality of samples in separate containers for each sample, wherein the containers are arranged into an array of subsets, wherein the array comprises two or more subsets;

b) amplifying nucleic acids by a primer extension reaction using at least one pair of primers hybridized to the analyte nucleic acids, wherein a pair of primers comprises a forward and a reverse primer, wherein the forward and reverse primers both comprise an adaptor sequence, a sample identifier sequence and a binding sequence for hybridization to the analyte nucleic acids, respectively, and wherein in the forward primer the sample identifier sequence and the binding sequence for hybridization to the analyte nucleic acids are staggered by a random offset of 1-4 bases;

c) combining the amplified nucleic acids of step b) of containers of two or more subsets to an array of combined containers, wherein containers of one subset, but not of another subset, are combined to a combined container;

d) amplifying nucleic acids by a primer extension reaction using at least one pair of further primers hybridized to the amplified nucleic acids of combined containers of step c), wherein a pair of further primers comprises a further forward and a further reverse primer, wherein the further forward and further reverse primers both comprise a subset identifier sequence and a sequence for hybridization to the adaptor sequence;

e) determining the sequences of the amplified nucleic acids of step d); and f) assigning a determined sequence of a nucleic acid of interest of step e) to a sample through association to a subset and container with the subset identifier sequences and the sample identifier sequences.

2. The method of claim 1, wherein i) in step b) each sample identifier sequence of the forward primers is different from sample identifier sequence of other forward primers for a given binding sequence for hybridization to the analyte nucleic acids;

and/or ii) in step b) each sample identifier sequence of the reverse primers is different from sample identifier sequence of other reverse primers for a given binding sequence for hybridization to the analyte nucleic acids;

and/or iii) in step d) each subset identifier sequence of the further forward primers is different from subset identifier sequence of other further forward primers;

and/or iv) in step d) each subset identifier sequence of the further reverse primers is different from subset identifier sequence of other further reverse primers.

3. The method of claim 1, wherein the further primers of step d) comprise a sequencing adaptor sequence.

4. The method of claim 1, wherein the step a) comprises providing a RNA from a sample and generating a cDNA of said RNA by reverse transcription, wherein the nucleic acids that are amplified in step b) comprise said cDNA.

5. The method of claim 1, wherein the at least one of the forward and reverse primers of step b) is depleted during and/or after step b) but before step c).

6. The method of claim 1, wherein amplifying nucleic acids in step d) is restricted to at most 35 amplification cycles.

7. The method of claim 1, wherein the plurality of samples comprises 4000 or more samples and/or the two or more subsets are 40 or more subsets and/or wherein a subset comprises 40 or more containers.

8. The method of claim 1, wherein the nucleic acid of interest is a pathogen nucleic acid.

9. The method of claim 8, wherein the nucleic acid of interest is selected from a coronavirus nucleic acid, an influenza nucleic acid, a parainfluenza nucleic acid, a rhinovirus nucleic acid, or a combination thereof.

10. The method of claim 1, wherein two or more nucleic acids of interest are selected.

11. The method of claim 1, wherein the sample identifier sequence of the forward primers, the sample identifier sequence of the reverse primers, the subset identifier sequence of the further forward primers, and the subset identifier sequence of the further reverse primers, respectively, comprise a sequence distance to other sample identifier sequences of forward primers, sample identifier sequences of the reverse primers, subset identifier sequences of further forward primers, and subset identifier sequences of further reverse primers, respectively, of at least 2.

12. The method of claim 1, wherein the sample identifier sequence of the forward primers, the sample identifier sequence of the reverse primers, the subset identifier sequence of the further forward primers, and the subset identifier sequence of the further reverse primers, respectively, each selected independently, have a length of at least 4 nucleotides.

13. The method of claim 2, wherein i) in step b) each sample identifier sequence of the forward primers is different from sample identifier sequence of other forward primers for a given binding sequence for hybridization to the analyte nucleic acids;

and ii) in step b) each sample identifier sequence of the reverse primers is different from sample identifier sequence of other reverse primers for a given binding sequence for hybridization to the analyte nucleic acids;

and iii) in step d) each subset identifier sequence of the further forward primers is different from subset identifier sequence of other further forward primers;

and iv) in step d) each subset identifier sequence of the further reverse primers is different from subset identifier sequence of other further reverse primers.

14. The method of claim 5, wherein the depletion is during step b) and comprises amplification of a spike-in nucleic acid with the forward and/or reverse primer.

15. The method of claim 5, wherein the depletion of the forward and reverse primers comprises treatment with a single-strand specific nuclease.

16. The method of claim 6, wherein amplifying nucleic acids in step d) is restricted to at most 20 amplification cycles.

17. The method of claim 8, wherein the nucleic acid of interest is a viral nucleic acid.

18. The method of claim 9, wherein the coronavirus nucleic acid is a SARS-COV-2 nucleic acid.

19. The method of claim 10, wherein the two or more nucleic acids of interest are from a virus, which is the same virus or a different virus for two or more nucleic acids of interest.

20. The method of claim 10, wherein in step b) forward and reverse primers with binding sequences for hybridization to the two or more analyte nucleic acids are used.

21. The method of claim 11, wherein the sequence distance is a Hamming distance or a Levenshtein distance.

22. The method of claim 11, wherein the sequence distance is at least 3.

23. A set of primers suitable for a method of claim 1, at least 10 different primers A which comprise the sequence, from 5' to 3': an adaptor A sequence, an identifier sequence of at least 4 nt in length and a target binding sequence, wherein the identifier sequence is different within the at least 10 different primers A, and wherein in the forward primer the sample identifier sequence and the binding sequence for hybridization to the analyte nucleic acids are staggered by a random offset of 1-4 bases, optionally with a sequence distance of a Hamming distance of at least 1 or a Levenshtein distance of at least 1;

at least 10 different primers B which comprise the sequence, from 5' to 3': an adaptor B sequence, an identifier sequence of at least 4 nt in length and a target binding sequence, wherein the identifier sequence is different within the at least 10 different primers B, optionally with a sequence distance of a Hamming distance of at least 1 or a Levenshtein distance of at least 1;

at least 10 different primers C which comprise the sequence, from 5' to 3': an adaptor C sequence, an identifier sequence of at least 4 nt in length and a binding sequence that binds to the adaptor A sequence, wherein the identifier sequence is different within the at least 10 different primers C, optionally with a sequence distance of a Hamming distance of at least 1 or a Levenshtein distance of at least 1; and at least 10 different primers D which comprise the sequence, from 5' to 3': an adaptor D sequence, an identifier sequence of at least 4 nt in length and a binding sequence that binds to the adaptor B sequence, wherein the identifier sequence is different within the at least 10 different primers D, optionally with a sequence distance of a Hamming distance of at least 1 or a Levenshtein distance of at least 1.

24. The set of primers according to claim 23, wherein the target binding sequences of the primers A and primers B comprise a sequence or antisense-sequence, respectively, of a viral gene, preferably of a SARS-COV-2 N, M, E or S gene or coding sequence thereof, Influenza PA, PB1, PB2, PA, HA, NP, NA, M1, M2, NS1 or NEP gene or coding sequence thereof, a parainfluenza HN, F, M, NP, P or L gene or coding sequence thereof, a rhinovirus VP1, VP2, VP3, VP4, 2A, 2B, 2C, 3A, 3B, 3C or 3D gene or coding sequence; a human respiratory syncytial virus A (HRSV-A) GA1, GA2, GA3, GA4, GA5, GA6, GA7, SAA1, NA1, or NA2 gene or coding sequence; a human respiratory syncytial virus B (HRSV-B) GB1, GA2, GA3, GB4, SAB 1, SAB2, SAB3, BA1, BA2, BA3, BA4, BA5, or BA6 gene or coding sequence.

25. The set of primers according to claim 23, further comprising a primer pair that binds to a ribosomal gene or coding sequence.

* * * * *

SEQUENCE LISTING

<160> NUMBER OF SEQ ID NOS: 1046

<210> SEQ ID NO 1
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 1
ctacacgacg ctcttccgat ctnccaatac tgaccccaaa atcagcgaaa t 51

<210> SEQ ID NO 2
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 2
ctacacgacg ctcttccgat ctnntcgcgc atgaccccaa aatcagcgaa at 52

<210> SEQ ID NO 3
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 3
ctacacgacg ctcttccgat ctnnngtgtg aacgacccca aaatcagcga aat 53

<210> SEQ ID NO 4
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 4
ctacacgacg ctcttccgat ctnnnnggtg gcacgacccc aaaatcagcg aaat 54

<210> SEQ ID NO 5
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 5
ctacacgacg ctcttccgat ctntaggtgc tgaccccaaa atcagcgaaa t 51

<210> SEQ ID NO 6
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 6
ctacacgacg ctcttccgat ctnngagcgg ttgaccccaa aatcagcgaa at 52

<210> SEQ ID NO 7
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 7
ctacacgacg ctcttccgat ctnnnaggat taggacccca aaatcagcga aat 53

<210> SEQ ID NO 8
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 8
ctacacgacg ctcttccgat ctnnnngtga gccagacccc aaaatcagcg aaat 54

<210> SEQ ID NO 9
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 9
ctacacgacg ctcttccgat ctnaattatg cgaccccaaa atcagcgaaa t 51

<210> SEQ ID NO 10
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 10
ctacacgacg ctcttccgat ctnnttacgc cggaccccaa aatcagcgaa at 52

<210> SEQ ID NO 11
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 11
ctacacgacg ctcttccgat ctnnngtagt gatgacccca aaatcagcga aat 53

<210> SEQ ID NO 12
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 12
ctacacgacg ctcttccgat ctnnnntggt tgcagacccc aaaatcagcg aaat 54

<210> SEQ ID NO 13
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 13
ctacacgacg ctcttccgat ctngtccgac cgaccccaaa atcagcgaaa t 51

<210> SEQ ID NO 14
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 14
ctacacgacg ctcttccgat ctnngccagc cggaccccaa aatcagcgaa at 52

<210> SEQ ID NO 15
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 15
ctacacgacg ctcttccgat ctnnnctcgt gtcgacccca aaatcagcga aat 53

<210> SEQ ID NO 16
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 16
ctacacgacg ctcttccgat ctnnnngccg tggcgacccc aaaatcagcg aaat 54

<210> SEQ ID NO 17
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 17
ctacacgacg ctcttccgat ctngtagcca cgaccccaaa atcagcgaaa t 51

<210> SEQ ID NO 18
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 18
ctacacgacg ctcttccgat ctnngactta tagaccccaa aatcagcgaa at 52

<210> SEQ ID NO 19
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 19
ctacacgacg ctcttccgat ctnnngaacg tcggacccca aaatcagcga aat 53

<210> SEQ ID NO 20
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 20
ctacacgacg ctcttccgat ctnnnnatgc gtaggacccc aaaatcagcg aaat 54

<210> SEQ ID NO 21
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 21
ctacacgacg ctcttccgat ctnaattaga tgaccccaaa atcagcgaaa t 51

<210> SEQ ID NO 22
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 22
ctacacgacg ctcttccgat ctnnttacga tagaccccaa aatcagcgaa at 52

<210> SEQ ID NO 23
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 23
ctacacgacg ctcttccgat ctnnnctgta caagacccca aaatcagcga aat 53

<210> SEQ ID NO 24
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 24
ctacacgacg ctcttccgat ctnnnncgtg gttggacccc aaaatcagcg aaat 54

<210> SEQ ID NO 25
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 25
ctacacgacg ctcttccgat ctnaataacg tgaccccaaa atcagcgaaa t 51

<210> SEQ ID NO 26
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 26
ctacacgacg ctcttccgat ctnnttcttg aagaccccaa aatcagcgaa at 52

<210> SEQ ID NO 27
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)

<223> OTHER INFORMATION: n is a, c, g, or t

<400> SEQUENCE: 27
ctacacgacg ctcttccgat ctnnnggcag atcgacccca aaatcagcga aat 53

<210> SEQ ID NO 28
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 28
ctacacgacg ctcttccgat ctnnnnctat gttagacccc aaaatcagcg aaat 54

<210> SEQ ID NO 29
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 29
ctacacgacg ctcttccgat ctngttgacg cgaccccaaa atcagcgaaa t 51

<210> SEQ ID NO 30
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 30
ctacacgacg ctcttccgat ctnnatctac gagaccccaa aatcagcgaa at 52

<210> SEQ ID NO 31
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 31
ctacacgacg ctcttccgat ctnnnctcga caggacccca aaatcagcga aat 53

<210> SEQ ID NO 32
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 32
ctacacgacg ctcttccgat ctnnnngagg ctgcgacccc aaaatcagcg aaat 54

<210> SEQ ID NO 33
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 33
ctacacgacg ctcttccgat ctncctcgta ggaccccaaa atcagcgaaa t 51

<210> SEQ ID NO 34
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 34
ctacacgacg ctcttccgat ctnncatagg cagaccccaa aatcagcgaa at 52

<210> SEQ ID NO 35
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 35
ctacacgacg ctcttccgat ctnnnagatg aacgacccca aaatcagcga aat 53

<210> SEQ ID NO 36
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 36
ctacacgacg ctcttccgat ctnnnnccga gtatgacccc aaaatcagcg aaat 54

<210> SEQ ID NO 37
<211> LENGTH: 51
<212> TYPE: DNA
<213> ORGANISM: Artificial Sequence
<220> FEATURE:
<223> OTHER INFORMATION: primer
<220> FEATURE:

<221> NAME/KEY: misc_feature
<222> LOCATION: 23
<223> OTHER INFORMATION: n is a, c, g, or t

<400> SEQUENCE: 37
ctacacgacg ctcttccgat ctnaatattg agaccccaaa atcagcgaaa t 51

<210> SEQ ID NO 38
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 38
ctacacgacg ctcttccgat ctnngtatac cggaccccaa aatcagcgaa at 52

<210> SEQ ID NO 39
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 39
ctacacgacg ctcttccgat ctnnngatcc aacgacccca aaatcagcga aat 53

<210> SEQ ID NO 40
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 40
ctacacgacg ctcttccgat ctnnnnagat acgcgacccc aaaatcagcg aaat 54

<210> SEQ ID NO 41
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 41
ctacacgacg ctcttccgat ctnggtatct tgaccccaaa atcagcgaaa t 51

<210> SEQ ID NO 42
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 42
ctacacgacg ctcttccgat ctnncctctg gcgaccccaa aatcagcgaa at 52

<210> SEQ ID NO 43
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 43
ctacacgacg ctcttccgat ctnccattgt ggaccccaaa atcagcgaaa t 51

<210> SEQ ID NO 44
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 44
ctacacgacg ctcttccgat ctnnactacg gtgaccccaa aatcagcgaa at 52

<210> SEQ ID NO 45
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 45
ctacacgacg ctcttccgat ctnnnaagtg ctagacccca aaatcagcga aat 53

<210> SEQ ID NO 46
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 46
ctacacgacg ctcttccgat ctnnnngccg aacggacccc aaaatcagcg aaat 54

<210> SEQ ID NO 47
<211> LENGTH: 51
<212> TYPE: DNA
<213> ORGANISM: Artificial Sequence
<220> FEATURE:

<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 47
ctacacgacg ctcttccgat ctntgtccac ggaccccaaa atcagcgaaa t 51

<210> SEQ ID NO 48
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 48
ctacacgacg ctcttccgat ctnngacaca ctgaccccaa aatcagcgaa at 52

<210> SEQ ID NO 49
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 49
ctacacgacg ctcttccgat ctnnnaatat gctgacccca aaatcagcga aat 53

<210> SEQ ID NO 50
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 50
ctacacgacg ctcttccgat ctnnnnttct catagacccc aaaatcagcg aaat 54

<210> SEQ ID NO 51
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 51
ctacacgacg ctcttccgat ctntctgtga tgaccccaaa atcagcgaaa t 51

<210> SEQ ID NO 52
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 52
ctacacgacg ctcttccgat ctnnccgaac ttgaccccaa aatcagcgaa at 52

<210> SEQ ID NO 53
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 53
ctacacgacg ctcttccgat ctnnngtcta acagacccca aaatcagcga aat 53

<210> SEQ ID NO 54
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 54
ctacacgacg ctcttccgat ctnnnngacg ccatgacccc aaaatcagcg aaat 54

<210> SEQ ID NO 55
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 55
ctacacgacg ctcttccgat ctngccaatg tgaccccaaa atcagcgaaa t 51

<210> SEQ ID NO 56
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 56
ctacacgacg ctcttccgat ctnnccaacg tcgaccccaa aatcagcgaa at 52

<210> SEQ ID NO 57
<211> LENGTH: 53
<212> TYPE: DNA

<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 57
ctacacgacg ctcttccgat ctnnngtaga taagacccca aaatcagcga aat 53

<210> SEQ ID NO 58
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 58
ctacacgacg ctcttccgat ctnnnnctta cggcgacccc aaaatcagcg aaat 54

<210> SEQ ID NO 59
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 59
ctacacgacg ctcttccgat ctnccaagtg cgaccccaaa atcagcgaaa t 51

<210> SEQ ID NO 60
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 60
ctacacgacg ctcttccgat ctnnctaact cagaccccaa aatcagcgaa at 52

<210> SEQ ID NO 61
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 61
ctacacgacg ctcttccgat ctnnnaatat ctggacccca aaatcagcga aat 53

<210> SEQ ID NO 62
<211> LENGTH: 54

<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 62
ctacacgacg ctcttccgat ctnnnnttat atcagacccc aaaatcagcg aaat 54

<210> SEQ ID NO 63
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 63
ctacacgacg ctcttccgat ctnctgcgga tgaccccaaa atcagcgaaa t 51

<210> SEQ ID NO 64
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 64
ctacacgacg ctcttccgat ctnngcggct tggaccccaa aatcagcgaa at 52

<210> SEQ ID NO 65
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 65
ctacacgacg ctcttccgat ctnnngagtt gatgacccca aaatcagcga aat 53

<210> SEQ ID NO 66
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 66
ctacacgacg ctcttccgat ctnnnngcac tgaggacccc aaaatcagcg aaat 54

<210> SEQ ID NO 67

<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 67
ctacacgacg ctcttccgat ctngaccacc tgaccccaaa atcagcgaaa t 51

<210> SEQ ID NO 68
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 68
ctacacgacg ctcttccgat ctnaatagca agaccccaaa atcagcgaaa t 51

<210> SEQ ID NO 69
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 69
ctacacgacg ctcttccgat ctncctaccg ggaccccaaa atcagcgaaa t 51

<210> SEQ ID NO 70
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 70
ctacacgacg ctcttccgat ctnnggagga tggaccccaa aatcagcgaa at 52

<210> SEQ ID NO 71
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 71
ctacacgacg ctcttccgat ctnnncgctg aatgacccca aaatcagcga aat 53

<210> SEQ ID NO 72
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 72
ctacacgacg ctcttccgat ctnnnntgtg acgagacccc aaaatcagcg aaat 54

<210> SEQ ID NO 73
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 73
ctacacgacg ctcttccgat ctnaatagat tgaccccaaa atcagcgaaa t 51

<210> SEQ ID NO 74
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 74
ctacacgacg ctcttccgat ctnnttagcg cagaccccaa aatcagcgaa at 52

<210> SEQ ID NO 75
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 75
ctacacgacg ctcttccgat ctnnngcggc cgtgacccca aaatcagcga aat 53

<210> SEQ ID NO 76
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 76
ctacacgacg ctcttccgat ctnnnncagt aaccgacccc aaaatcagcg aaat 54

<210> SEQ ID NO 77
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 77
ctacacgacg ctcttccgat ctngcctagt agaccccaaa atcagcgaaa t 51

<210> SEQ ID NO 78
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 78
ctacacgacg ctcttccgat ctnncacggc gcgaccccaa aatcagcgaa at 52

<210> SEQ ID NO 79
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 79
ctacacgacg ctcttccgat ctnnnggtgc agagacccca aaatcagcga aat 53

<210> SEQ ID NO 80
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 80
ctacacgacg ctcttccgat ctnnnntcgc tgacgacccc aaaatcagcg aaat 54

<210> SEQ ID NO 81
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 81
ctacacgacg ctcttccgat ctncagccag tgaccccaaa atcagcgaaa t 51

<210> SEQ ID NO 82
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 82
ctacacgacg ctcttccgat ctnncgtcaa ccgaccccaa aatcagcgaa at 52

<210> SEQ ID NO 83
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 83
ctacacgacg ctcttccgat ctngccggcg agaccccaaa atcagcgaaa t 51

<210> SEQ ID NO 84
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 84
ctacacgacg ctcttccgat ctnngcctcc gggaccccaa aatcagcgaa at 52

<210> SEQ ID NO 85
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 85
ctacacgacg ctcttccgat ctnnnaatag tccgacccca aaatcagcga aat 53

<210> SEQ ID NO 86
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 86
ctacacgacg ctcttccgat ctnnnnttag acgtgacccc aaaatcagcg aaat 54

<210> SEQ ID NO 87
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 87
ctacacgacg ctcttccgat ctngtggact agaccccaaa atcagcgaaa t 51

<210> SEQ ID NO 88
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 88
ctacacgacg ctcttccgat ctnncacgga cggaccccaa aatcagcgaa at 52

<210> SEQ ID NO 89
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 89
ctacacgacg ctcttccgat ctnnncacta gaggacccca aaatcagcga aat 53

<210> SEQ ID NO 90
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 90
ctacacgacg ctcttccgat ctnnnngcag atgggacccc aaaatcagcg aaat 54

<210> SEQ ID NO 91
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 91
ctacacgacg ctcttccgat ctnctctcac ggaccccaaa atcagcgaaa t 51

<210> SEQ ID NO 92
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 92
ctacacgacg ctcttccgat ctnnggaatc acgaccccaa aatcagcgaa at 52

<210> SEQ ID NO 93
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 93
ctacacgacg ctcttccgat ctnnncgttg acggacccca aaatcagcga aat 53

<210> SEQ ID NO 94
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 94
ctacacgacg ctcttccgat ctnnnncatc aggtgacccc aaaatcagcg aaat 54

<210> SEQ ID NO 95
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 95
ctacacgacg ctcttccgat ctncgttgta agaccccaaa atcagcgaaa t 51

<210> SEQ ID NO 96
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 96
ctacacgacg ctcttccgat ctnnggcacg gtgaccccaa aatcagcgaa at 52

<210> SEQ ID NO 97
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 97
ctacacgacg ctcttccgat ctnccaatac tgggagcctt gaatacacca aaa 53

<210> SEQ ID NO 98
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 98
ctacacgacg ctcttccgat ctnntcgcgc atgggagcct tgaatacacc aaaa 54

<210> SEQ ID NO 99
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 99
ctacacgacg ctcttccgat ctnnngtgtg aacgggagcc ttgaatacac caaaa 55

<210> SEQ ID NO 100
<211> LENGTH: 56
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 100
ctacacgacg ctcttccgat ctnnnnggtg gcacgggagc cttgaataca ccaaaa 56

<210> SEQ ID NO 101
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 101
ctacacgacg ctcttccgat ctntaggtgc tgggagcctt gaatacacca aaa 53

<210> SEQ ID NO 102
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 102
ctacacgacg ctcttccgat ctnngagcgg ttgggagcct tgaatacacc aaaa 54

<210> SEQ ID NO 103
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 103
ctacacgacg ctcttccgat ctnnnaggat taggggagcc ttgaatacac caaaa 55

<210> SEQ ID NO 104
<211> LENGTH: 56
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 104
ctacacgacg ctcttccgat ctnnnngtga gccagggagc cttgaataca ccaaaa 56

<210> SEQ ID NO 105
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 105
ctacacgacg ctcttccgat ctnaattatg cgggagcctt gaatacacca aaa 53

<210> SEQ ID NO 106
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)

<223> OTHER INFORMATION: n is a, c, g, or t

<400> SEQUENCE: 106
ctacacgacg ctcttccgat ctnnttacgc cggggagcct tgaatacacc aaaa 54

<210> SEQ ID NO 107
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 107
ctacacgacg ctcttccgat ctnnngtagt gatgggagcc ttgaatacac caaaa 55

<210> SEQ ID NO 108
<211> LENGTH: 56
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 108
ctacacgacg ctcttccgat ctnnnntggt tgcagggagc cttgaataca ccaaaa 56

<210> SEQ ID NO 109
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 109
ctacacgacg ctcttccgat ctngtccgac cgggagcctt gaatacacca aaa 53

<210> SEQ ID NO 110
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 110
ctacacgacg ctcttccgat ctnngccagc cggggagcct tgaatacacc aaaa 54

<210> SEQ ID NO 111
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 111
ctacacgacg ctcttccgat ctnnnctcgt gtcgggagcc ttgaatacac caaaa 55

<210> SEQ ID NO 112
<211> LENGTH: 56
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 112
ctacacgacg ctcttccgat ctnnnngccg tggcgggagc cttgaataca ccaaaa 56

<210> SEQ ID NO 113
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 113
ctacacgacg ctcttccgat ctngtagcca cgggagcctt gaatacacca aaa 53

<210> SEQ ID NO 114
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 114
ctacacgacg ctcttccgat ctnngactta tagggagcct tgaatacacc aaaa 54

<210> SEQ ID NO 115
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 115
ctacacgacg ctcttccgat ctnnngaacg tcggggagcc ttgaatacac caaaa 55

<210> SEQ ID NO 116
<211> LENGTH: 56
<212> TYPE: DNA
<213> ORGANISM: Artificial Sequence
<220> FEATURE:
<223> OTHER INFORMATION: primer
<220> FEATURE:

<221> NAME/KEY: misc_feature
<222> LOCATION: (23)..(26)
<223> OTHER INFORMATION: n is a, c, g, or t

<400> SEQUENCE: 116
ctacacgacg ctcttccgat ctnnnnatgc gtaggggagc cttgaataca ccaaaa 56

<210> SEQ ID NO 117
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 117
ctacacgacg ctcttccgat ctnaattaga tgggagcctt gaatacacca aaa 53

<210> SEQ ID NO 118
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 118
ctacacgacg ctcttccgat ctnnttacga tagggagcct tgaatacacc aaaa 54

<210> SEQ ID NO 119
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 119
ctacacgacg ctcttccgat ctnnnctgta caagggagcc ttgaatacac caaaa 55

<210> SEQ ID NO 120
<211> LENGTH: 56
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 120
ctacacgacg ctcttccgat ctnnnncgtg gttggggagc cttgaataca ccaaaa 56

<210> SEQ ID NO 121
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 121
ctacacgacg ctcttccgat ctnaataacg tgggagcctt gaatacacca aaa 53

<210> SEQ ID NO 122
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 122
ctacacgacg ctcttccgat ctnnttcttg aagggagcct tgaatacacc aaaa 54

<210> SEQ ID NO 123
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 123
ctacacgacg ctcttccgat ctnnnggcag atcgggagcc ttgaatacac caaaa 55

<210> SEQ ID NO 124
<211> LENGTH: 56
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 124
ctacacgacg ctcttccgat ctnnnnctat gttagggagc cttgaataca ccaaaa 56

<210> SEQ ID NO 125
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 125
ctacacgacg ctcttccgat ctngttgacg cgggagcctt gaatacacca aaa 53

<210> SEQ ID NO 126
<211> LENGTH: 54
<212> TYPE: DNA
<213> ORGANISM: Artificial Sequence
<220> FEATURE:

<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 126
ctacacgacg ctcttccgat ctnnatctac gagggagcct tgaatacacc aaaa 54

<210> SEQ ID NO 127
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 127
ctacacgacg ctcttccgat ctnnnctcga caggggagcc ttgaatacac caaaa 55

<210> SEQ ID NO 128
<211> LENGTH: 56
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 128
ctacacgacg ctcttccgat ctnnnngagg ctgcgggagc cttgaataca ccaaaa 56

<210> SEQ ID NO 129
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 129
ctacacgacg ctcttccgat ctncctcgta ggggagcctt gaatacacca aaa 53

<210> SEQ ID NO 130
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 130
ctacacgacg ctcttccgat ctnncatagg cagggagcct tgaatacacc aaaa 54

<210> SEQ ID NO 131
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 131
ctacacgacg ctcttccgat ctnnnagatg aacgggagcc ttgaatacac caaaa 55

<210> SEQ ID NO 132
<211> LENGTH: 56
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 132
ctacacgacg ctcttccgat ctnnnnccga gtatgggagc cttgaataca ccaaaa 56

<210> SEQ ID NO 133
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 133
ctacacgacg ctcttccgat ctnaatattg agggagcctt gaatacacca aaa 53

<210> SEQ ID NO 134
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 134
ctacacgacg ctcttccgat ctnngtatac cggggagcct tgaatacacc aaaa 54

<210> SEQ ID NO 135
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 135
ctacacgacg ctcttccgat ctnnngatcc aacgggagcc ttgaatacac caaaa 55

<210> SEQ ID NO 136
<211> LENGTH: 56
<212> TYPE: DNA

<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 136
ctacacgacg ctcttccgat ctnnnnagat acgcgggagc cttgaataca ccaaaa 56

<210> SEQ ID NO 137
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 137
ctacacgacg ctcttccgat ctnggtatct tgggagcctt gaatacacca aaa 53

<210> SEQ ID NO 138
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 138
ctacacgacg ctcttccgat ctnncctctg gcgggagcct tgaatacacc aaaa 54

<210> SEQ ID NO 139
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 139
ctacacgacg ctcttccgat ctnccattgt ggggagcctt gaatacacca aaa 53

<210> SEQ ID NO 140
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 140
ctacacgacg ctcttccgat ctnnactacg gtgggagcct tgaatacacc aaaa 54

<210> SEQ ID NO 141
<211> LENGTH: 55

<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 141
ctacacgacg ctcttccgat ctnnnaagtg ctagggagcc ttgaatacac caaaa 55

<210> SEQ ID NO 142
<211> LENGTH: 56
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 142
ctacacgacg ctcttccgat ctnnnngccg aacggggagc cttgaataca ccaaaa 56

<210> SEQ ID NO 143
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 143
ctacacgacg ctcttccgat ctntgtccac ggggagcctt gaatacacca aaa 53

<210> SEQ ID NO 144
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 144
ctacacgacg ctcttccgat ctnngacaca ctgggagcct tgaatacacc aaaa 54

<210> SEQ ID NO 145
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 145
ctacacgacg ctcttccgat ctnnnaatat gctgggagcc ttgaatacac caaaa 55

<210> SEQ ID NO 146

<211> LENGTH: 56
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 146
ctacacgacg ctcttccgat ctnnnnttct catagggagc cttgaataca ccaaaa 56

<210> SEQ ID NO 147
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 147
ctacacgacg ctcttccgat ctntctgtga tgggagcctt gaatacacca aaa 53

<210> SEQ ID NO 148
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 148
ctacacgacg ctcttccgat ctnnccgaac ttgggagcct tgaatacacc aaaa 54

<210> SEQ ID NO 149
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 149
ctacacgacg ctcttccgat ctnnngtcta acagggagcc ttgaatacac caaaa 55

<210> SEQ ID NO 150
<211> LENGTH: 56
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 150
ctacacgacg ctcttccgat ctnnnngacg ccatgggagc cttgaataca ccaaaa 56

<210> SEQ ID NO 151
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 151
ctacacgacg ctcttccgat ctngccaatg tgggagcctt gaatacacca aaa 53

<210> SEQ ID NO 152
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 152
ctacacgacg ctcttccgat ctnnccaacg tcgggagcct tgaatacacc aaaa 54

<210> SEQ ID NO 153
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 153
ctacacgacg ctcttccgat ctnnngtaga taagggagcc ttgaatacac caaaa 55

<210> SEQ ID NO 154
<211> LENGTH: 56
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 154
ctacacgacg ctcttccgat ctnnnnctta cggcgggagc cttgaataca ccaaaa 56

<210> SEQ ID NO 155
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 155
ctacacgacg ctcttccgat ctnccaagtg cgggagcctt gaatacacca aaa 53

<210> SEQ ID NO 156
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 156
ctacacgacg ctcttccgat ctnnctaact cagggagcct tgaatacacc aaaa 54

<210> SEQ ID NO 157
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 157
ctacacgacg ctcttccgat ctnnnaatat ctggggagcc ttgaatacac caaaa 55

<210> SEQ ID NO 158
<211> LENGTH: 56
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 158
ctacacgacg ctcttccgat ctnnnnttat atcagggagc cttgaataca ccaaaa 56

<210> SEQ ID NO 159
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 159
ctacacgacg ctcttccgat ctnctgcgga tgggagcctt gaatacacca aaa 53

<210> SEQ ID NO 160
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 160
ctacacgacg ctcttccgat ctnngcggct tggggagcct tgaatacacc aaaa 54

<210> SEQ ID NO 161
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 161
ctacacgacg ctcttccgat ctnnngagtt gatgggagcc ttgaatacac caaaa 55

<210> SEQ ID NO 162
<211> LENGTH: 56
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 162
ctacacgacg ctcttccgat ctnnnngcac tgaggggagc cttgaataca ccaaaa 56

<210> SEQ ID NO 163
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 163
ctacacgacg ctcttccgat ctngaccacc tgggagcctt gaatacacca aaa 53

<210> SEQ ID NO 164
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 164
ctacacgacg ctcttccgat ctnaatagca agggagcctt gaatacacca aaa 53

<210> SEQ ID NO 165
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 165
ctacacgacg ctcttccgat ctncctaccg ggggagcctt gaatacacca aaa 53

<210> SEQ ID NO 166
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 166
ctacacgacg ctcttccgat ctnnggagga tggggagcct tgaatacacc aaaa 54

<210> SEQ ID NO 167
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 167
ctacacgacg ctcttccgat ctnnncgctg aatgggagcc ttgaatacac caaaa 55

<210> SEQ ID NO 168
<211> LENGTH: 56
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 168
ctacacgacg ctcttccgat ctnnnntgtg acgagggagc cttgaataca ccaaaa 56

<210> SEQ ID NO 169
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 169
ctacacgacg ctcttccgat ctnaatagat tgggagcctt gaatacacca aaa 53

<210> SEQ ID NO 170
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 170
ctacacgacg ctcttccgat ctnnttagcg cagggagcct tgaatacacc aaaa 54

<210> SEQ ID NO 171
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 171
ctacacgacg ctcttccgat ctnnngcggc cgtgggagcc ttgaatacac caaaa 55

<210> SEQ ID NO 172
<211> LENGTH: 56
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 172
ctacacgacg ctcttccgat ctnnnncagt aaccgggagc cttgaataca ccaaaa 56

<210> SEQ ID NO 173
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 173
ctacacgacg ctcttccgat ctngcctagt agggagcctt gaatacacca aaa 53

<210> SEQ ID NO 174
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 174
ctacacgacg ctcttccgat ctnncacggc gcgggagcct tgaatacacc aaaa 54

<210> SEQ ID NO 175
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 175
ctacacgacg ctcttccgat ctnnnggtgc agagggagcc ttgaatacac caaaa 55

<210> SEQ ID NO 176
<211> LENGTH: 56
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 176
ctacacgacg ctcttccgat ctnnnntcgc tgacgggagc cttgaataca ccaaaa 56

<210> SEQ ID NO 177
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 177
ctacacgacg ctcttccgat ctncagccag tgggagcctt gaatacacca aaa 53

<210> SEQ ID NO 178
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 178
ctacacgacg ctcttccgat ctnncgtcaa ccgggagcct tgaatacacc aaaa 54

<210> SEQ ID NO 179
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 179
ctacacgacg ctcttccgat ctngccggcg agggagcctt gaatacacca aaa 53

<210> SEQ ID NO 180
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 180
ctacacgacg ctcttccgat ctnngcctcc gggggagcct tgaatacacc aaaa 54

<210> SEQ ID NO 181
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 181
ctacacgacg ctcttccgat ctnnnaatag tccgggagcc ttgaatacac caaaa 55

<210> SEQ ID NO 182
<211> LENGTH: 56
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 182
ctacacgacg ctcttccgat ctnnnnttag acgtgggagc cttgaataca ccaaaa 56

<210> SEQ ID NO 183
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 183
ctacacgacg ctcttccgat ctngtggact agggagcctt gaatacacca aaa 53

<210> SEQ ID NO 184
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 184
ctacacgacg ctcttccgat ctnncacgga cggggagcct tgaatacacc aaaa 54

<210> SEQ ID NO 185
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)

<223> OTHER INFORMATION: n is a, c, g, or t

<400> SEQUENCE: 185
ctacacgacg ctcttccgat ctnnncacta gaggggagcc ttgaatacac caaaa 55

<210> SEQ ID NO 186
<211> LENGTH: 56
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 186
ctacacgacg ctcttccgat ctnnnngcag atgggggagc cttgaataca ccaaaa 56

<210> SEQ ID NO 187
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 187
ctacacgacg ctcttccgat ctnctctcac ggggagcctt gaatacacca aaa 53

<210> SEQ ID NO 188
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 188
ctacacgacg ctcttccgat ctnnggaatc acgggagcct tgaatacacc aaaa 54

<210> SEQ ID NO 189
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 189
ctacacgacg ctcttccgat ctnnncgttg acggggagcc ttgaatacac caaaa 55

<210> SEQ ID NO 190
<211> LENGTH: 56
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 190
ctacacgacg ctcttccgat ctnnnncatc aggtgggagc cttgaataca ccaaaa 56

<210> SEQ ID NO 191
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 191
ctacacgacg ctcttccgat ctncgttgta agggagcctt gaatacacca aaa 53

<210> SEQ ID NO 192
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 192
ctacacgacg ctcttccgat ctnnggcacg gtgggagcct tgaatacacc aaaa 54

<210> SEQ ID NO 193
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 193
ctacacgacg ctcttccgat ctnccaatac tggcattcgt attgcgccgc ta 52

<210> SEQ ID NO 194
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 194
ctacacgacg ctcttccgat ctnntcgcgc atggcattcg tattgcgccg cta 53

<210> SEQ ID NO 195
<211> LENGTH: 54
<212> TYPE: DNA
<213> ORGANISM: Artificial Sequence
<220> FEATURE:
<223> OTHER INFORMATION: primer
<220> FEATURE:

<221> NAME/KEY: misc_feature
<222> LOCATION: (23)..(25)
<223> OTHER INFORMATION: n is a, c, g, or t

<400> SEQUENCE: 195
ctacacgacg ctcttccgat ctnnngtgtg aacggcattc gtattgcgcc gcta 54

<210> SEQ ID NO 196
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 196
ctacacgacg ctcttccgat ctnnnnggtg gcacggcatt cgtattgcgc cgcta 55

<210> SEQ ID NO 197
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 197
ctacacgacg ctcttccgat ctntaggtgc tggcattcgt attgcgccgc ta 52

<210> SEQ ID NO 198
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 198
ctacacgacg ctcttccgat ctnngagcgg ttggcattcg tattgcgccg cta 53

<210> SEQ ID NO 199
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 199
ctacacgacg ctcttccgat ctnnnaggat tagggcattc gtattgcgcc gcta 54

<210> SEQ ID NO 200
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 200
ctacacgacg ctcttccgat ctnnnngtga gccaggcatt cgtattgcgc cgcta 55

<210> SEQ ID NO 201
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 201
ctacacgacg ctcttccgat ctnaattatg cggcattcgt attgcgccgc ta 52

<210> SEQ ID NO 202
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 202
ctacacgacg ctcttccgat ctnnttacgc cgggcattcg tattgcgccg cta 53

<210> SEQ ID NO 203
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 203
ctacacgacg ctcttccgat ctnnngtagt gatggcattc gtattgcgcc gcta 54

<210> SEQ ID NO 204
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 204
ctacacgacg ctcttccgat ctnnnntggt tgcaggcatt cgtattgcgc cgcta 55

<210> SEQ ID NO 205
<211> LENGTH: 52
<212> TYPE: DNA
<213> ORGANISM: Artificial Sequence
<220> FEATURE:

<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 205
ctacacgacg ctcttccgat ctngtccgac cggcattcgt attgcgccgc ta 52

<210> SEQ ID NO 206
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 206
ctacacgacg ctcttccgat ctnngccagc cgggcattcg tattgcgccg cta 53

<210> SEQ ID NO 207
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 207
ctacacgacg ctcttccgat ctnnnctcgt gtcggcattc gtattgcgcc gcta 54

<210> SEQ ID NO 208
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 208
ctacacgacg ctcttccgat ctnnnngccg tggcggcatt cgtattgcgc cgcta 55

<210> SEQ ID NO 209
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 209
ctacacgacg ctcttccgat ctngtagcca cggcattcgt attgcgccgc ta 52

<210> SEQ ID NO 210
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 210
ctacacgacg ctcttccgat ctnngactta taggcattcg tattgcgccg cta 53

<210> SEQ ID NO 211
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 211
ctacacgacg ctcttccgat ctnnngaacg tcgggcattc gtattgcgcc gcta 54

<210> SEQ ID NO 212
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 212
ctacacgacg ctcttccgat ctnnnnatgc gtagggcatt cgtattgcgc cgcta 55

<210> SEQ ID NO 213
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 213
ctacacgacg ctcttccgat ctnaattaga tggcattcgt attgcgccgc ta 52

<210> SEQ ID NO 214
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 214
ctacacgacg ctcttccgat ctnnttacga taggcattcg tattgcgccg cta 53

<210> SEQ ID NO 215
<211> LENGTH: 54
<212> TYPE: DNA

<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 215
ctacacgacg ctcttccgat ctnnnctgta caaggcattc gtattgcgcc gcta 54

<210> SEQ ID NO 216
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 216
ctacacgacg ctcttccgat ctnnnncgtg gttgggcatt cgtattgcgc cgcta 55

<210> SEQ ID NO 217
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 217
ctacacgacg ctcttccgat ctnaataacg tggcattcgt attgcgccgc ta 52

<210> SEQ ID NO 218
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 218
ctacacgacg ctcttccgat ctnnttcttg aaggcattcg tattgcgccg cta 53

<210> SEQ ID NO 219
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 219
ctacacgacg ctcttccgat ctnnnggcag atcggcattc gtattgcgcc gcta 54

<210> SEQ ID NO 220
<211> LENGTH: 55

<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 220
ctacacgacg ctcttccgat ctnnnnctat gttaggcatt cgtattgcgc cgcta 55

<210> SEQ ID NO 221
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 221
ctacacgacg ctcttccgat ctngttgacg cggcattcgt attgcgccgc ta 52

<210> SEQ ID NO 222
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 222
ctacacgacg ctcttccgat ctnnatctac gaggcattcg tattgcgccg cta 53

<210> SEQ ID NO 223
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 223
ctacacgacg ctcttccgat ctnnnctcga cagggcattc gtattgcgcc gcta 54

<210> SEQ ID NO 224
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 224
ctacacgacg ctcttccgat ctnnnngagg ctgcggcatt cgtattgcgc cgcta 55

<210> SEQ ID NO 225

<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 225
ctacacgacg ctcttccgat ctncctcgta gggcattcgt attgcgccgc ta 52

<210> SEQ ID NO 226
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 226
ctacacgacg ctcttccgat ctnncatagg caggcattcg tattgcgccg cta 53

<210> SEQ ID NO 227
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 227
ctacacgacg ctcttccgat ctnnnagatg aacggcattc gtattgcgcc gcta 54

<210> SEQ ID NO 228
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 228
ctacacgacg ctcttccgat ctnnnnccga gtatggcatt cgtattgcgc cgcta 55

<210> SEQ ID NO 229
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 229
ctacacgacg ctcttccgat ctnaatattg aggcattcgt attgcgccgc ta 52

<210> SEQ ID NO 230
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 230
ctacacgacg ctcttccgat ctnngtatac cgggcattcg tattgcgccg cta 53

<210> SEQ ID NO 231
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 231
ctacacgacg ctcttccgat ctnnngatcc aacggcattc gtattgcgcc gcta 54

<210> SEQ ID NO 232
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 232
ctacacgacg ctcttccgat ctnnnnagat acgcggcatt cgtattgcgc cgcta 55

<210> SEQ ID NO 233
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 233
ctacacgacg ctcttccgat ctnggtatct tggcattcgt attgcgccgc ta 52

<210> SEQ ID NO 234
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 234
ctacacgacg ctcttccgat ctnncctctg gcggcattcg tattgcgccg cta 53

<210> SEQ ID NO 235
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 235
ctacacgacg ctcttccgat ctnccattgt gggcattcgt attgcgccgc ta 52

<210> SEQ ID NO 236
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 236
ctacacgacg ctcttccgat ctnnactacg gtggcattcg tattgcgccg cta 53

<210> SEQ ID NO 237
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 237
ctacacgacg ctcttccgat ctnnnaagtg ctaggcattc gtattgcgcc gcta 54

<210> SEQ ID NO 238
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 238
ctacacgacg ctcttccgat ctnnnngccg aacgggcatt cgtattgcgc cgcta 55

<210> SEQ ID NO 239
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 239
ctacacgacg ctcttccgat ctntgtccac gggcattcgt attgcgccgc ta 52

<210> SEQ ID NO 240
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 240
ctacacgacg ctcttccgat ctnngacaca ctggcattcg tattgcgccg cta 53

<210> SEQ ID NO 241
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 241
ctacacgacg ctcttccgat ctnnnaatat gctggcattc gtattgcgcc gcta 54

<210> SEQ ID NO 242
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 242
ctacacgacg ctcttccgat ctnnnnttct cataggcatt cgtattgcgc cgcta 55

<210> SEQ ID NO 243
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 243
ctacacgacg ctcttccgat ctntctgtga tggcattcgt attgcgccgc ta 52

<210> SEQ ID NO 244
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 244
ctacacgacg ctcttccgat ctnnccgaac ttggcattcg tattgcgccg cta 53

<210> SEQ ID NO 245
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 245
ctacacgacg ctcttccgat ctnnngtcta acaggcattc gtattgcgcc gcta 54

<210> SEQ ID NO 246
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 246
ctacacgacg ctcttccgat ctnnnngacg ccatggcatt cgtattgcgc cgcta 55

<210> SEQ ID NO 247
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 247
ctacacgacg ctcttccgat ctngccaatg tggcattcgt attgcgccgc ta 52

<210> SEQ ID NO 248
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 248
ctacacgacg ctcttccgat ctnnccaacg tcggcattcg tattgcgccg cta 53

<210> SEQ ID NO 249
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 249
ctacacgacg ctcttccgat ctnnngtaga taaggcattc gtattgcgcc gcta 54

<210> SEQ ID NO 250
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 250
ctacacgacg ctcttccgat ctnnnnctta cggcggcatt cgtattgcgc cgcta 55

<210> SEQ ID NO 251
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 251
ctacacgacg ctcttccgat ctnccaagtg cggcattcgt attgcgccgc ta 52

<210> SEQ ID NO 252
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 252
ctacacgacg ctcttccgat ctnnctaact caggcattcg tattgcgccg cta 53

<210> SEQ ID NO 253
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 253
ctacacgacg ctcttccgat ctnnnaatat ctgggcattc gtattgcgcc gcta 54

<210> SEQ ID NO 254
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 254
ctacacgacg ctcttccgat ctnnnnttat atcaggcatt cgtattgcgc cgcta 55

<210> SEQ ID NO 255
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 255
ctacacgacg ctcttccgat ctnctgcgga tggcattcgt attgcgccgc ta 52

<210> SEQ ID NO 256
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 256
ctacacgacg ctcttccgat ctnngcggct tgggcattcg tattgcgccg cta 53

<210> SEQ ID NO 257
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 257
ctacacgacg ctcttccgat ctnnngagtt gatggcattc gtattgcgcc gcta 54

<210> SEQ ID NO 258
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 258
ctacacgacg ctcttccgat ctnnnngcac tgagggcatt cgtattgcgc cgcta 55

<210> SEQ ID NO 259
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 259
ctacacgacg ctcttccgat ctngaccacc tggcattcgt attgcgccgc ta 52

<210> SEQ ID NO 260
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 260
ctacacgacg ctcttccgat ctnaatagca aggcattcgt attgcgccgc ta 52

<210> SEQ ID NO 261
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 261
ctacacgacg ctcttccgat ctncctaccg gggcattcgt attgcgccgc ta 52

<210> SEQ ID NO 262
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 262
ctacacgacg ctcttccgat ctnnggagga tgggcattcg tattgcgccg cta 53

<210> SEQ ID NO 263
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 263
ctacacgacg ctcttccgat ctnnncgctg aatggcattc gtattgcgcc gcta 54

<210> SEQ ID NO 264
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)

<223> OTHER INFORMATION: n is a, c, g, or t

<400> SEQUENCE: 264
ctacacgacg ctcttccgat ctnnnntgtg acgaggcatt cgtattgcgc cgcta 55

<210> SEQ ID NO 265
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 265
ctacacgacg ctcttccgat ctnaatagat tggcattcgt attgcgccgc ta 52

<210> SEQ ID NO 266
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 266
ctacacgacg ctcttccgat ctnnttagcg caggcattcg tattgcgccg cta 53

<210> SEQ ID NO 267
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 267
ctacacgacg ctcttccgat ctnnngcggc cgtggcattc gtattgcgcc gcta 54

<210> SEQ ID NO 268
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 268
ctacacgacg ctcttccgat ctnnnncagt aaccggcatt cgtattgcgc cgcta 55

<210> SEQ ID NO 269
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 269
ctacacgacg ctcttccgat ctngcctagt aggcattcgt attgcgccgc ta 52

<210> SEQ ID NO 270
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 270
ctacacgacg ctcttccgat ctnncacggc gcggcattcg tattgcgccg cta 53

<210> SEQ ID NO 271
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 271
ctacacgacg ctcttccgat ctnnnggtgc agaggcattc gtattgcgcc gcta 54

<210> SEQ ID NO 272
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 272
ctacacgacg ctcttccgat ctnnnntcgc tgacggcatt cgtattgcgc cgcta 55

<210> SEQ ID NO 273
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 273
ctacacgacg ctcttccgat ctncagccag tggcattcgt attgcgccgc ta 52

<210> SEQ ID NO 274
<211> LENGTH: 53
<212> TYPE: DNA
<213> ORGANISM: Artificial Sequence
<220> FEATURE:
<223> OTHER INFORMATION: primer
<220> FEATURE:

<221> NAME/KEY: misc_feature
<222> LOCATION: (23)..(24)
<223> OTHER INFORMATION: n is a, c, g, or t

<400> SEQUENCE: 274
ctacacgacg ctcttccgat ctnncgtcaa ccggcattcg tattgcgccg cta 53

<210> SEQ ID NO 275
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 275
ctacacgacg ctcttccgat ctngccggcg aggcattcgt attgcgccgc ta 52

<210> SEQ ID NO 276
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 276
ctacacgacg ctcttccgat ctnngcctcc ggggcattcg tattgcgccg cta 53

<210> SEQ ID NO 277
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 277
ctacacgacg ctcttccgat ctnnnaatag tccggcattc gtattgcgcc gcta 54

<210> SEQ ID NO 278
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 278
ctacacgacg ctcttccgat ctnnnnttag acgtggcatt cgtattgcgc cgcta 55

<210> SEQ ID NO 279
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 279
ctacacgacg ctcttccgat ctngtggact aggcattcgt attgcgccgc ta 52

<210> SEQ ID NO 280
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 280
ctacacgacg ctcttccgat ctnncacgga cgggcattcg tattgcgccg cta 53

<210> SEQ ID NO 281
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 281
ctacacgacg ctcttccgat ctnnncacta gagggcattc gtattgcgcc gcta 54

<210> SEQ ID NO 282
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 282
ctacacgacg ctcttccgat ctnnnngcag atggggcatt cgtattgcgc cgcta 55

<210> SEQ ID NO 283
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 283
ctacacgacg ctcttccgat ctnctctcac gggcattcgt attgcgccgc ta 52

<210> SEQ ID NO 284
<211> LENGTH: 53
<212> TYPE: DNA
<213> ORGANISM: Artificial Sequence
<220> FEATURE:

<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 284
ctacacgacg ctcttccgat ctnnggaatc acggcattcg tattgcgccg cta 53

<210> SEQ ID NO 285
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 285
ctacacgacg ctcttccgat ctnnncgttg acgggcattc gtattgcgcc gcta 54

<210> SEQ ID NO 286
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 286
ctacacgacg ctcttccgat ctnnnncatc aggtggcatt cgtattgcgc cgcta 55

<210> SEQ ID NO 287
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 287
ctacacgacg ctcttccgat ctncgttgta aggcattcgt attgcgccgc ta 52

<210> SEQ ID NO 288
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 288
ctacacgacg ctcttccgat ctnnggcacg gtggcattcg tattgcgccg cta 53

<210> SEQ ID NO 289
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 289
ctacacgacg ctcttccgat ctnccaatac tctcatggar tggctaaag 49

<210> SEQ ID NO 290
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 290
ctacacgacg ctcttccgat ctnntcgcgc atctcatgga rtggctaaag 50

<210> SEQ ID NO 291
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 291
ctacacgacg ctcttccgat ctnnngtgtg aacctcatgg artggctaaa g 51

<210> SEQ ID NO 292
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 292
ctacacgacg ctcttccgat ctnnnnggtg gcacctcatg gartggctaa ag 52

<210> SEQ ID NO 293
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 293
ctacacgacg ctcttccgat ctntaggtgc tctcatggar tggctaaag 49

<210> SEQ ID NO 294
<211> LENGTH: 50
<212> TYPE: DNA

<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 294
ctacacgacg ctcttccgat ctnngagcgg ttctcatgga rtggctaaag 50

<210> SEQ ID NO 295
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 295
ctacacgacg ctcttccgat ctnnnaggat tagctcatgg artggctaaa g 51

<210> SEQ ID NO 296
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 296
ctacacgacg ctcttccgat ctnnnngtga gccactcatg gartggctaa ag 52

<210> SEQ ID NO 297
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 297
ctacacgacg ctcttccgat ctnaattatg cctcatggar tggctaaag 49

<210> SEQ ID NO 298
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 298
ctacacgacg ctcttccgat ctnnttacgc cgctcatgga rtggctaaag 50

<210> SEQ ID NO 299
<211> LENGTH: 51

<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 299
ctacacgacg ctcttccgat ctnnngtagt gatctcatgg artggctaaa g 51

<210> SEQ ID NO 300
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 300
ctacacgacg ctcttccgat ctnnnntggt tgcactcatg gartggctaa ag 52

<210> SEQ ID NO 301
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 301
ctacacgacg ctcttccgat ctngtccgac cctcatggar tggctaaag 49

<210> SEQ ID NO 302
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 302
ctacacgacg ctcttccgat ctnngccagc cgctcatgga rtggctaaag 50

<210> SEQ ID NO 303
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 303
ctacacgacg ctcttccgat ctnnnctcgt gtcctcatgg artggctaaa g 51

<210> SEQ ID NO 304

<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 304
ctacacgacg ctcttccgat ctnnnngccg tggcctcatg gartggctaa ag 52

<210> SEQ ID NO 305
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 305
ctacacgacg ctcttccgat ctngtagcca cctcatggar tggctaaag 49

<210> SEQ ID NO 306
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 306
ctacacgacg ctcttccgat ctnngactta tactcatgga rtggctaaag 50

<210> SEQ ID NO 307
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 307
ctacacgacg ctcttccgat ctnnngaacg tcgctcatgg artggctaaa g 51

<210> SEQ ID NO 308
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 308
ctacacgacg ctcttccgat ctnnnnatgc gtagctcatg gartggctaa ag 52

<210> SEQ ID NO 309
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 309
ctacacgacg ctcttccgat ctnaattaga tctcatggar tggctaaag 49

<210> SEQ ID NO 310
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 310
ctacacgacg ctcttccgat ctnnttacga tactcatgga rtggctaaag 50

<210> SEQ ID NO 311
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 311
ctacacgacg ctcttccgat ctnnnctgta caactcatgg artggctaaa g 51

<210> SEQ ID NO 312
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 312
ctacacgacg ctcttccgat ctnnnncgtg gttgctcatg gartggctaa ag 52

<210> SEQ ID NO 313
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 313
ctacacgacg ctcttccgat ctnaataacg tctcatggar tggctaaag 49

<210> SEQ ID NO 314
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 314
ctacacgacg ctcttccgat ctnnttcttg aactcatgga rtggctaaag 50

<210> SEQ ID NO 315
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 315
ctacacgacg ctcttccgat ctnnnggcag atcctcatgg artggctaaa g 51

<210> SEQ ID NO 316
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 316
ctacacgacg ctcttccgat ctnnnnctat gttactcatg gartggctaa ag 52

<210> SEQ ID NO 317
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 317
ctacacgacg ctcttccgat ctngttgacg cctcatggar tggctaaag 49

<210> SEQ ID NO 318
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 318
ctacacgacg ctcttccgat ctnnatctac gactcatgga rtggctaaag 50

<210> SEQ ID NO 319
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 319
ctacacgacg ctcttccgat ctnnnctcga cagctcatgg artggctaaa g 51

<210> SEQ ID NO 320
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 320
ctacacgacg ctcttccgat ctnnnngagg ctgcctcatg gartggctaa ag 52

<210> SEQ ID NO 321
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 321
ctacacgacg ctcttccgat ctncctcgta gctcatggar tggctaaag 49

<210> SEQ ID NO 322
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 322
ctacacgacg ctcttccgat ctnncatagg cactcatgga rtggctaaag 50

<210> SEQ ID NO 323
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 323
ctacacgacg ctcttccgat ctnnnagatg aacctcatgg artggctaaa g 51

<210> SEQ ID NO 324
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 324
ctacacgacg ctcttccgat ctnnnnccga gtatctcatg gartggctaa ag 52

<210> SEQ ID NO 325
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 325
ctacacgacg ctcttccgat ctnaatattg actcatggar tggctaaag 49

<210> SEQ ID NO 326
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 326
ctacacgacg ctcttccgat ctnngtatac cgctcatgga rtggctaaag 50

<210> SEQ ID NO 327
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 327
ctacacgacg ctcttccgat ctnnngatcc aacctcatgg artggctaaa g 51

<210> SEQ ID NO 328
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 328
ctacacgacg ctcttccgat ctnnnnagat acgcctcatg gartggctaa ag 52

<210> SEQ ID NO 329
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 329
ctacacgacg ctcttccgat ctnggtatct tctcatggar tggctaaag 49

<210> SEQ ID NO 330
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 330
ctacacgacg ctcttccgat ctnncctctg gcctcatgga rtggctaaag 50

<210> SEQ ID NO 331
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 331
ctacacgacg ctcttccgat ctnccattgt gctcatggar tggctaaag 49

<210> SEQ ID NO 332
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 332
ctacacgacg ctcttccgat ctnnactacg gtctcatgga rtggctaaag 50

<210> SEQ ID NO 333
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 333
ctacacgacg ctcttccgat ctnnnaagtg ctactcatgg artggctaaa g 51

<210> SEQ ID NO 334
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 334
ctacacgacg ctcttccgat ctnnnngccg aacgctcatg gartggctaa ag 52

<210> SEQ ID NO 335
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 335
ctacacgacg ctcttccgat ctntgtccac gctcatggar tggctaaag 49

<210> SEQ ID NO 336
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 336
ctacacgacg ctcttccgat ctnngacaca ctctcatgga rtggctaaag 50

<210> SEQ ID NO 337
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 337
ctacacgacg ctcttccgat ctnnnaatat gctctcatgg artggctaaa g 51

<210> SEQ ID NO 338
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 338
ctacacgacg ctcttccgat ctnnnnttct catactcatg gartggctaa ag 52

<210> SEQ ID NO 339
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 339
ctacacgacg ctcttccgat ctntctgtga tctcatggar tggctaaag 49

<210> SEQ ID NO 340
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 340
ctacacgacg ctcttccgat ctnnccgaac ttctcatgga rtggctaaag 50

<210> SEQ ID NO 341
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 341
ctacacgacg ctcttccgat ctnnngtcta acactcatgg artggctaaa g 51

<210> SEQ ID NO 342
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 342
ctacacgacg ctcttccgat ctnnnngacg ccatctcatg gartggctaa ag 52

<210> SEQ ID NO 343
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23

<223> OTHER INFORMATION: n is a, c, g, or t

<400> SEQUENCE: 343
ctacacgacg ctcttccgat ctngccaatg tctcatggar tggctaaag 49

<210> SEQ ID NO 344
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 344
ctacacgacg ctcttccgat ctnnccaacg tcctcatgga rtggctaaag 50

<210> SEQ ID NO 345
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 345
ctacacgacg ctcttccgat ctnnngtaga taactcatgg artggctaaa g 51

<210> SEQ ID NO 346
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 346
ctacacgacg ctcttccgat ctnnnnctta cggcctcatg gartggctaa ag 52

<210> SEQ ID NO 347
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 347
ctacacgacg ctcttccgat ctnccaagtg cctcatggar tggctaaag 49

<210> SEQ ID NO 348
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 348
ctacacgacg ctcttccgat ctnnctaact cactcatgga rtggctaaag 50

<210> SEQ ID NO 349
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 349
ctacacgacg ctcttccgat ctnnnaatat ctgctcatgg artggctaaa g 51

<210> SEQ ID NO 350
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 350
ctacacgacg ctcttccgat ctnnnnttat atcactcatg gartggctaa ag 52

<210> SEQ ID NO 351
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 351
ctacacgacg ctcttccgat ctnctgcgga tctcatggar tggctaaag 49

<210> SEQ ID NO 352
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 352
ctacacgacg ctcttccgat ctnngcggct tgctcatgga rtggctaaag 50

<210> SEQ ID NO 353
<211> LENGTH: 51
<212> TYPE: DNA
<213> ORGANISM: Artificial Sequence
<220> FEATURE:
<223> OTHER INFORMATION: primer
<220> FEATURE:

<221> NAME/KEY: misc_feature
<222> LOCATION: (23)..(25)
<223> OTHER INFORMATION: n is a, c, g, or t

<400> SEQUENCE: 353
ctacacgacg ctcttccgat ctnnngagtt gatctcatgg artggctaaa g 51

<210> SEQ ID NO 354
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 354
ctacacgacg ctcttccgat ctnnnngcac tgagctcatg gartggctaa ag 52

<210> SEQ ID NO 355
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 355
ctacacgacg ctcttccgat ctngaccacc tctcatggar tggctaaag 49

<210> SEQ ID NO 356
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 356
ctacacgacg ctcttccgat ctnaatagca actcatggar tggctaaag 49

<210> SEQ ID NO 357
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 357
ctacacgacg ctcttccgat ctncctaccg gctcatggar tggctaaag 49

<210> SEQ ID NO 358
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 358
ctacacgacg ctcttccgat ctnnggagga tgctcatgga rtggctaaag 50

<210> SEQ ID NO 359
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 359
ctacacgacg ctcttccgat ctnnncgctg aatctcatgg artggctaaa g 51

<210> SEQ ID NO 360
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 360
ctacacgacg ctcttccgat ctnnnntgtg acgactcatg gartggctaa ag 52

<210> SEQ ID NO 361
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 361
ctacacgacg ctcttccgat ctnaatagat tctcatggar tggctaaag 49

<210> SEQ ID NO 362
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 362
ctacacgacg ctcttccgat ctnnttagcg cactcatgga rtggctaaag 50

<210> SEQ ID NO 363
<211> LENGTH: 51
<212> TYPE: DNA
<213> ORGANISM: Artificial Sequence
<220> FEATURE:

<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 363
ctacacgacg ctcttccgat ctnnngcggc cgtctcatgg artggctaaa g 51

<210> SEQ ID NO 364
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 364
ctacacgacg ctcttccgat ctnnnncagt aaccctcatg gartggctaa ag 52

<210> SEQ ID NO 365
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 365
ctacacgacg ctcttccgat ctngcctagt actcatggar tggctaaag 49

<210> SEQ ID NO 366
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 366
ctacacgacg ctcttccgat ctnncacggc gcctcatgga rtggctaaag 50

<210> SEQ ID NO 367
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 367
ctacacgacg ctcttccgat ctnnnggtgc agactcatgg artggctaaa g 51

<210> SEQ ID NO 368
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 368
ctacacgacg ctcttccgat ctnnnntcgc tgacctcatg gartggctaa ag 52

<210> SEQ ID NO 369
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 369
ctacacgacg ctcttccgat ctncagccag tctcatggar tggctaaag 49

<210> SEQ ID NO 370
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 370
ctacacgacg ctcttccgat ctnncgtcaa ccctcatgga rtggctaaag 50

<210> SEQ ID NO 371
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 371
ctacacgacg ctcttccgat ctngccggcg actcatggar tggctaaag 49

<210> SEQ ID NO 372
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 372
ctacacgacg ctcttccgat ctnngcctcc ggctcatgga rtggctaaag 50

<210> SEQ ID NO 373
<211> LENGTH: 51
<212> TYPE: DNA

<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 373
ctacacgacg ctcttccgat ctnnnaatag tccctcatgg artggctaaa g 51

<210> SEQ ID NO 374
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 374
ctacacgacg ctcttccgat ctnnnnttag acgtctcatg gartggctaa ag 52

<210> SEQ ID NO 375
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 375
ctacacgacg ctcttccgat ctngtggact actcatggar tggctaaag 49

<210> SEQ ID NO 376
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 376
ctacacgacg ctcttccgat ctnncacgga cgctcatgga rtggctaaag 50

<210> SEQ ID NO 377
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 377
ctacacgacg ctcttccgat ctnnncacta gagctcatgg artggctaaa g 51

<210> SEQ ID NO 378
<211> LENGTH: 52

<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 378
ctacacgacg ctcttccgat ctnnnngcag atggctcatg gartggctaa ag 52

<210> SEQ ID NO 379
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 379
ctacacgacg ctcttccgat ctnctctcac gctcatggar tggctaaag 49

<210> SEQ ID NO 380
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 380
ctacacgacg ctcttccgat ctnnggaatc acctcatgga rtggctaaag 50

<210> SEQ ID NO 381
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 381
ctacacgacg ctcttccgat ctnnncgttg acgctcatgg artggctaaa g 51

<210> SEQ ID NO 382
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 382
ctacacgacg ctcttccgat ctnnnncatc aggtctcatg gartggctaa ag 52

<210> SEQ ID NO 383

<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 383
ctacacgacg ctcttccgat ctncgttgta actcatggar tggctaaag 49

<210> SEQ ID NO 384
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 384
ctacacgacg ctcttccgat ctnnggcacg gtctcatgga rtggctaaag 50

<210> SEQ ID NO 385
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 385
ctacacgacg ctcttccgat ctnccaatac tgccttctcc atcttctg 48

<210> SEQ ID NO 386
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 386
ctacacgacg ctcttccgat ctnntcgcgc atgccttctc catcttctg 49

<210> SEQ ID NO 387
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 387
ctacacgacg ctcttccgat ctnnngtgtg aacgccttct ccatcttctg 50

<210> SEQ ID NO 388
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 388
ctacacgacg ctcttccgat ctnnnnggtg gcacgccttc tccatcttct g 51

<210> SEQ ID NO 389
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 389
ctacacgacg ctcttccgat ctntaggtgc tgccttctcc atcttctg 48

<210> SEQ ID NO 390
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 390
ctacacgacg ctcttccgat ctnngagcgg ttgccttctc catcttctg 49

<210> SEQ ID NO 391
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 391
ctacacgacg ctcttccgat ctnnnaggat taggccttct ccatcttctg 50

<210> SEQ ID NO 392
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 392
ctacacgacg ctcttccgat ctnnnngtga gccagccttc tccatcttct g 51

<210> SEQ ID NO 393
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 393
ctacacgacg ctcttccgat ctnaattatg cgccttctcc atcttctg 48

<210> SEQ ID NO 394
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 394
ctacacgacg ctcttccgat ctnnttacgc cggccttctc catcttctg 49

<210> SEQ ID NO 395
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 395
ctacacgacg ctcttccgat ctnnngtagt gatgccttct ccatcttctg 50

<210> SEQ ID NO 396
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 396
ctacacgacg ctcttccgat ctnnnntggt tgcagccttc tccatcttct g 51

<210> SEQ ID NO 397
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 397
ctacacgacg ctcttccgat ctngtccgac cgccttctcc atcttctg 48

<210> SEQ ID NO 398
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 398
ctacacgacg ctcttccgat ctnngccagc cggccttctc catcttctg 49

<210> SEQ ID NO 399
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 399
ctacacgacg ctcttccgat ctnnnctcgt gtcgccttct ccatcttctg 50

<210> SEQ ID NO 400
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 400
ctacacgacg ctcttccgat ctnnnngccg tggcgccttc tccatcttct g 51

<210> SEQ ID NO 401
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 401
ctacacgacg ctcttccgat ctngtagcca cgccttctcc atcttctg 48

<210> SEQ ID NO 402
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 402
ctacacgacg ctcttccgat ctnngactta tagccttctc catcttctg 49

<210> SEQ ID NO 403
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 403
ctacacgacg ctcttccgat ctnnngaacg tcggccttct ccatcttctg 50

<210> SEQ ID NO 404
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 404
ctacacgacg ctcttccgat ctnnnnatgc gtaggccttc tccatcttct g 51

<210> SEQ ID NO 405
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 405
ctacacgacg ctcttccgat ctnaattaga tgccttctcc atcttctg 48

<210> SEQ ID NO 406
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 406
ctacacgacg ctcttccgat ctnnttacga tagccttctc catcttctg 49

<210> SEQ ID NO 407
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 407
ctacacgacg ctcttccgat ctnnnctgta caagccttct ccatcttctg 50

<210> SEQ ID NO 408
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 408
ctacacgacg ctcttccgat ctnnnncgtg gttggccttc tccatcttct g 51

<210> SEQ ID NO 409
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 409
ctacacgacg ctcttccgat ctnaataacg tgccttctcc atcttctg 48

<210> SEQ ID NO 410
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 410
ctacacgacg ctcttccgat ctnnttcttg aagccttctc catcttctg 49

<210> SEQ ID NO 411
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 411
ctacacgacg ctcttccgat ctnnnggcag atcgccttct ccatcttctg 50

<210> SEQ ID NO 412
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 412
ctacacgacg ctcttccgat ctnnnnctat gttagccttc tccatcttct g 51

<210> SEQ ID NO 413
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 413
ctacacgacg ctcttccgat ctngttgacg cgccttctcc atcttctg 48

<210> SEQ ID NO 414
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 414
ctacacgacg ctcttccgat ctnnatctac gagccttctc catcttctg 49

<210> SEQ ID NO 415
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 415
ctacacgacg ctcttccgat ctnnnctcga caggccttct ccatcttctg 50

<210> SEQ ID NO 416
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 416
ctacacgacg ctcttccgat ctnnnngagg ctgcgccttc tccatcttct g 51

<210> SEQ ID NO 417
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 417
ctacacgacg ctcttccgat ctncctcgta ggccttctcc atcttctg 48

<210> SEQ ID NO 418
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 418
ctacacgacg ctcttccgat ctnncatagg cagccttctc catcttctg 49

<210> SEQ ID NO 419
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 419
ctacacgacg ctcttccgat ctnnnagatg aacgccttct ccatcttctg 50

<210> SEQ ID NO 420
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 420
ctacacgacg ctcttccgat ctnnnnccga gtatgccttc tccatcttct g 51

<210> SEQ ID NO 421
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 421
ctacacgacg ctcttccgat ctnaatattg agccttctcc atcttctg 48

<210> SEQ ID NO 422
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)

<223> OTHER INFORMATION: n is a, c, g, or t

<400> SEQUENCE: 422
ctacacgacg ctcttccgat ctnngtatac cggccttctc catcttctg 49

<210> SEQ ID NO 423
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 423
ctacacgacg ctcttccgat ctnnngatcc aacgccttct ccatcttctg 50

<210> SEQ ID NO 424
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 424
ctacacgacg ctcttccgat ctnnnnagat acgcgccttc tccatcttct g 51

<210> SEQ ID NO 425
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 425
ctacacgacg ctcttccgat ctnggtatct tgccttctcc atcttctg 48

<210> SEQ ID NO 426
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 426
ctacacgacg ctcttccgat ctnncctctg gcgccttctc catcttctg 49

<210> SEQ ID NO 427
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 427
ctacacgacg ctcttccgat ctnccattgt ggccttctcc atcttctg 48

<210> SEQ ID NO 428
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 428
ctacacgacg ctcttccgat ctnnactacg gtgccttctc catcttctg 49

<210> SEQ ID NO 429
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 429
ctacacgacg ctcttccgat ctnnnaagtg ctagccttct ccatcttctg 50

<210> SEQ ID NO 430
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 430
ctacacgacg ctcttccgat ctnnnngccg aacggccttc tccatcttct g 51

<210> SEQ ID NO 431
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 431
ctacacgacg ctcttccgat ctntgtccac ggccttctcc atcttctg 48

<210> SEQ ID NO 432
<211> LENGTH: 49
<212> TYPE: DNA
<213> ORGANISM: Artificial Sequence
<220> FEATURE:
<223> OTHER INFORMATION: primer
<220> FEATURE:

<221> NAME/KEY: misc_feature
<222> LOCATION: (23)..(24)
<223> OTHER INFORMATION: n is a, c, g, or t

<400> SEQUENCE: 432
ctacacgacg ctcttccgat ctnngacaca ctgccttctc catcttctg 49

<210> SEQ ID NO 433
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 433
ctacacgacg ctcttccgat ctnnnaatat gctgccttct ccatcttctg 50

<210> SEQ ID NO 434
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 434
ctacacgacg ctcttccgat ctnnnnttct catagccttc tccatcttct g 51

<210> SEQ ID NO 435
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 435
ctacacgacg ctcttccgat ctntctgtga tgccttctcc atcttctg 48

<210> SEQ ID NO 436
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 436
ctacacgacg ctcttccgat ctnnccgaac ttgccttctc catcttctg 49

<210> SEQ ID NO 437
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 437
ctacacgacg ctcttccgat ctnnngtcta acagccttct ccatcttctg 50

<210> SEQ ID NO 438
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 438
ctacacgacg ctcttccgat ctnnnngacg ccatgccttc tccatcttct g 51

<210> SEQ ID NO 439
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 439
ctacacgacg ctcttccgat ctngccaatg tgccttctcc atcttctg 48

<210> SEQ ID NO 440
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 440
ctacacgacg ctcttccgat ctnnccaacg tcgccttctc catcttctg 49

<210> SEQ ID NO 441
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 441
ctacacgacg ctcttccgat ctnnngtaga taagccttct ccatcttctg 50

<210> SEQ ID NO 442
<211> LENGTH: 51
<212> TYPE: DNA
<213> ORGANISM: Artificial Sequence
<220> FEATURE:

<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 442
ctacacgacg ctcttccgat ctnnnnctta cggcgccttc tccatcttct g 51

<210> SEQ ID NO 443
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 443
ctacacgacg ctcttccgat ctnccaagtg cgccttctcc atcttctg 48

<210> SEQ ID NO 444
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 444
ctacacgacg ctcttccgat ctnnctaact cagccttctc catcttctg 49

<210> SEQ ID NO 445
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 445
ctacacgacg ctcttccgat ctnnnaatat ctggccttct ccatcttctg 50

<210> SEQ ID NO 446
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 446
ctacacgacg ctcttccgat ctnnnnttat atcagccttc tccatcttct g 51

<210> SEQ ID NO 447
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 447
ctacacgacg ctcttccgat ctnctgcgga tgccttctcc atcttctg 48

<210> SEQ ID NO 448
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 448
ctacacgacg ctcttccgat ctnngcggct tggccttctc catcttctg 49

<210> SEQ ID NO 449
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 449
ctacacgacg ctcttccgat ctnnngagtt gatgccttct ccatcttctg 50

<210> SEQ ID NO 450
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 450
ctacacgacg ctcttccgat ctnnnngcac tgaggccttc tccatcttct g 51

<210> SEQ ID NO 451
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 451
ctacacgacg ctcttccgat ctngaccacc tgccttctcc atcttctg 48

<210> SEQ ID NO 452
<211> LENGTH: 48
<212> TYPE: DNA

<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 452
ctacacgacg ctcttccgat ctnaatagca agccttctcc atcttctg 48

<210> SEQ ID NO 453
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 453
ctacacgacg ctcttccgat ctncctaccg ggccttctcc atcttctg 48

<210> SEQ ID NO 454
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 454
ctacacgacg ctcttccgat ctnnggagga tggccttctc catcttctg 49

<210> SEQ ID NO 455
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 455
ctacacgacg ctcttccgat ctnnncgctg aatgccttct ccatcttctg 50

<210> SEQ ID NO 456
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 456
ctacacgacg ctcttccgat ctnnnntgtg acgagccttc tccatcttct g 51

<210> SEQ ID NO 457
<211> LENGTH: 48

<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 457
ctacacgacg ctcttccgat ctnaatagat tgccttctcc atcttctg 48

<210> SEQ ID NO 458
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 458
ctacacgacg ctcttccgat ctnnttagcg cagccttctc catcttctg 49

<210> SEQ ID NO 459
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 459
ctacacgacg ctcttccgat ctnnngcggc cgtgccttct ccatcttctg 50

<210> SEQ ID NO 460
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 460
ctacacgacg ctcttccgat ctnnnncagt aaccgccttc tccatcttct g 51

<210> SEQ ID NO 461
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 461
ctacacgacg ctcttccgat ctngcctagt agccttctcc atcttctg 48

<210> SEQ ID NO 462

<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 462
ctacacgacg ctcttccgat ctnncacggc gcgccttctc catcttctg 49

<210> SEQ ID NO 463
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 463
ctacacgacg ctcttccgat ctnnnggtgc agagccttct ccatcttctg 50

<210> SEQ ID NO 464
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 464
ctacacgacg ctcttccgat ctnnnntcgc tgacgccttc tccatcttct g 51

<210> SEQ ID NO 465
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 465
ctacacgacg ctcttccgat ctncagccag tgccttctcc atcttctg 48

<210> SEQ ID NO 466
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 466
ctacacgacg ctcttccgat ctnncgtcaa ccgccttctc catcttctg 49

<210> SEQ ID NO 467
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 467
ctacacgacg ctcttccgat ctngccggcg agccttctcc atcttctg 48

<210> SEQ ID NO 468
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 468
ctacacgacg ctcttccgat ctnngcctcc gggccttctc catcttctg 49

<210> SEQ ID NO 469
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 469
ctacacgacg ctcttccgat ctnnnaatag tccgccttct ccatcttctg 50

<210> SEQ ID NO 470
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 470
ctacacgacg ctcttccgat ctnnnnttag acgtgccttc tccatcttct g 51

<210> SEQ ID NO 471
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 471
ctacacgacg ctcttccgat ctngtggact agccttctcc atcttctg 48

<210> SEQ ID NO 472
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 472
ctacacgacg ctcttccgat ctnncacgga cggccttctc catcttctg 49

<210> SEQ ID NO 473
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 473
ctacacgacg ctcttccgat ctnnncacta gaggccttct ccatcttctg 50

<210> SEQ ID NO 474
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 474
ctacacgacg ctcttccgat ctnnnngcag atgggccttc tccatcttct g 51

<210> SEQ ID NO 475
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 475
ctacacgacg ctcttccgat ctnctctcac ggccttctcc atcttctg 48

<210> SEQ ID NO 476
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 476
ctacacgacg ctcttccgat ctnnggaatc acgccttctc catcttctg 49

<210> SEQ ID NO 477
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 477
ctacacgacg ctcttccgat ctnnncgttg acggccttct ccatcttctg 50

<210> SEQ ID NO 478
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 478
ctacacgacg ctcttccgat ctnnnncatc aggtgccttc tccatcttct g 51

<210> SEQ ID NO 479
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 479
ctacacgacg ctcttccgat ctncgttgta agccttctcc atcttctg 48

<210> SEQ ID NO 480
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 480
ctacacgacg ctcttccgat ctnnggcacg gtgccttctc catcttctg 49

<210> SEQ ID NO 481
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 481
ctacacgacg ctcttccgat ctnaattaat gtcctccggc ccctgaat 48

<210> SEQ ID NO 482
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 482
ctacacgacg ctcttccgat ctnnttaatt cctcctccgg cccctgaat 49

<210> SEQ ID NO 483
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 483
ctacacgacg ctcttccgat ctnccaatac ttcctccggc ccctgaat 48

<210> SEQ ID NO 484
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 484
ctacacgacg ctcttccgat ctnntcgcgc attcctccgg cccctgaat 49

<210> SEQ ID NO 485
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 485
ctacacgacg ctcttccgat ctnnngtgtg aactcctccg gcccctgaat 50

<210> SEQ ID NO 486
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 486
ctacacgacg ctcttccgat ctnnnnggtg gcactcctcc ggcccctgaa t 51

<210> SEQ ID NO 487
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 487
ctacacgacg ctcttccgat ctntaggtgc ttcctccggc ccctgaat 48

<210> SEQ ID NO 488
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 488
ctacacgacg ctcttccgat ctnngagcgg tttcctccgg cccctgaat 49

<210> SEQ ID NO 489
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 489
ctacacgacg ctcttccgat ctnnnaggat tagtcctccg gcccctgaat 50

<210> SEQ ID NO 490
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 490
ctacacgacg ctcttccgat ctnnnngtga gccatcctcc ggcccctgaa t 51

<210> SEQ ID NO 491
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 491
ctacacgacg ctcttccgat ctnaattatg ctcctccggc ccctgaat 48

<210> SEQ ID NO 492
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 492
ctacacgacg ctcttccgat ctnnttacgc cgtcctccgg cccctgaat 49

<210> SEQ ID NO 493
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(25)
<223> OTHER INFORMATION: n is a, c, g, or t

<400> SEQUENCE: 493
ctacacgacg ctcttccgat ctnnngtagt gattcctccg gcccctgaat 50

<210> SEQ ID NO 494
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(26)
<223> OTHER INFORMATION: n is a, c, g, or t

<400> SEQUENCE: 494
ctacacgacg ctcttccgat ctnnnntggt tgcatcctcc ggcccctgaa t 51

<210> SEQ ID NO 495
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 23
<223> OTHER INFORMATION: n is a, c, g, or t

<400> SEQUENCE: 495
ctacacgacg ctcttccgat ctngtccgac ctcctccggc ccctgaat 48

<210> SEQ ID NO 496
<211> LENGTH: 66
<212> TYPE: DNA
<213> ORGANISM: Artificial Sequence
<220> FEATURE:
<223> OTHER INFORMATION: primer

<400> SEQUENCE: 496
gtgactggag ttcagacgtg tgctcttccg atctagcttg gttctggtta ctgccagttg 60
aatctg 66

<210> SEQ ID NO 497
<211> LENGTH: 66
<212> TYPE: DNA
<213> ORGANISM: Artificial Sequence
<220> FEATURE:
<223> OTHER INFORMATION: primer

<400> SEQUENCE: 497
gtgactggag ttcagacgtg tgctcttccg atctagctta tgtctggtta ctgccagttg 60
aatctg 66

<210> SEQ ID NO 498
<211> LENGTH: 66
<212> TYPE: DNA
<213> ORGANISM: Artificial Sequence
<220> FEATURE:
<223> OTHER INFORMATION: primer

<400> SEQUENCE: 498
gtgactggag ttcagacgtg tgctcttccg atctataacg actctggtta ctgccagttg 60
aatctg 66

<210> SEQ ID NO 499
<211> LENGTH: 66
<212> TYPE: DNA
<213> ORGANISM: Artificial Sequence
<220> FEATURE:
<223> OTHER INFORMATION: primer

<400> SEQUENCE: 499
gtgactggag ttcagacgtg tgctcttccg atctgatgga gttctggtta ctgccagttg 60
aatctg 66

<210> SEQ ID NO 500
<211> LENGTH: 66
<212> TYPE: DNA
<213> ORGANISM: Artificial Sequence
<220> FEATURE:
<223> OTHER INFORMATION: primer

<400> SEQUENCE: 500
gtgactggag ttcagacgtg tgctcttccg atcttgatct aatctggtta ctgccagttg 60
aatctg 66

<210> SEQ ID NO 501
<211> LENGTH: 66
<212> TYPE: DNA
<213> ORGANISM: Artificial Sequence
<220> FEATURE:
<223> OTHER INFORMATION: primer

<400> SEQUENCE: 501
gtgactggag ttcagacgtg tgctcttccg atctagctat attctggtta ctgccagttg 60
aatctg 66

<210> SEQ ID NO 502
<211> LENGTH: 66
<212> TYPE: DNA
<213> ORGANISM: Artificial Sequence
<220> FEATURE:

<223> OTHER INFORMATION: primer

<400> SEQUENCE: 502
gtgactggag ttcagacgtg tgctcttccg atctagcaga gatctggtta ctgccagttg 60
aatctg 66

<210> SEQ ID NO 503
<211> LENGTH: 66
<212> TYPE: DNA
<213> ORGANISM: Artificial Sequence
<220> FEATURE:
<223> OTHER INFORMATION: primer

<400> SEQUENCE: 503
gtgactggag ttcagacgtg tgctcttccg atctgacgta agtctggtta ctgccagttg 60
aatctg 66

<210> SEQ ID NO 504
<211> LENGTH: 66
<212> TYPE: DNA
<213> ORGANISM: Artificial Sequence
<220> FEATURE:
<223> OTHER INFORMATION: primer

<400> SEQUENCE: 504
gtgactggag ttcagacgtg tgctcttccg atctaggcct gatctggtta ctgccagttg 60
aatctg 66

<210> SEQ ID NO 505
<211> LENGTH: 66
<212> TYPE: DNA
<213> ORGANISM: Artificial Sequence
<220> FEATURE:
<223> OTHER INFORMATION: primer

<400> SEQUENCE: 505
gtgactggag ttcagacgtg tgctcttccg atcttaagat tatctggtta ctgccagttg 60
aatctg 66

<210> SEQ ID NO 506
<211> LENGTH: 66
<212> TYPE: DNA
<213> ORGANISM: Artificial Sequence
<220> FEATURE:
<223> OTHER INFORMATION: primer

<400> SEQUENCE: 506
gtgactggag ttcagacgtg tgctcttccg atctaggcga attctggtta ctgccagttg 60
aatctg 66

<210> SEQ ID NO 507
<211> LENGTH: 66
<212> TYPE: DNA
<213> ORGANISM: Artificial Sequence
<220> FEATURE:
<223> OTHER INFORMATION: primer

<400> SEQUENCE: 507
gtgactggag ttcagacgtg tgctcttccg atctttgttc tttctggtta ctgccagttg 60
aatctg 66

<210> SEQ ID NO 508
<211> LENGTH: 66
<212> TYPE: DNA
<213> ORGANISM: Artificial Sequence
<220> FEATURE:
<223> OTHER INFORMATION: primer

<400> SEQUENCE: 508
gtgactggag ttcagacgtg tgctcttccg atcttactcc tgtctggtta ctgccagttg 60
aatctg 66

<210> SEQ ID NO 509
<211> LENGTH: 66
<212> TYPE: DNA
<213> ORGANISM: Artificial Sequence
<220> FEATURE:
<223> OTHER INFORMATION: primer

<400> SEQUENCE: 509
gtgactggag ttcagacgtg tgctcttccg atctgactgg cgtctggtta ctgccagttg 60
aatctg 66

<210> SEQ ID NO 510
<211> LENGTH: 66
<212> TYPE: DNA
<213> ORGANISM: Artificial Sequence
<220> FEATURE:
<223> OTHER INFORMATION: primer

<400> SEQUENCE: 510
gtgactggag ttcagacgtg tgctcttccg atctatatat actctggtta ctgccagttg 60
aatctg 66

<210> SEQ ID NO 511
<211> LENGTH: 66
<212> TYPE: DNA
<213> ORGANISM: Artificial Sequence
<220> FEATURE:
<223> OTHER INFORMATION: primer

<400> SEQUENCE: 511
gtgactggag ttcagacgtg tgctcttccg atcttagatc ggtctggtta ctgccagttg 60
aatctg 66

<210> SEQ ID NO 512
<211> LENGTH: 66
<212> TYPE: DNA
<213> ORGANISM: Artificial Sequence
<220> FEATURE:
<223> OTHER INFORMATION: primer

<400> SEQUENCE: 512
gtgactggag ttcagacgtg tgctcttccg atctaggcaa gctctggtta ctgccagttg 60
aatctg 66

<210> SEQ ID NO 513
<211> LENGTH: 66
<212> TYPE: DNA
<213> ORGANISM: Artificial Sequence
<220> FEATURE:
<223> OTHER INFORMATION: primer

<400> SEQUENCE: 513
gtgactggag ttcagacgtg tgctcttccg atcttccagg tatctggtta ctgccagttg 60
aatctg 66

<210> SEQ ID NO 514
<211> LENGTH: 66
<212> TYPE: DNA
<213> ORGANISM: Artificial Sequence
<220> FEATURE:
<223> OTHER INFORMATION: primer

<400> SEQUENCE: 514
gtgactggag ttcagacgtg tgctcttccg atctaggtca agtctggtta ctgccagttg 60
aatctg 66

<210> SEQ ID NO 515
<211> LENGTH: 66
<212> TYPE: DNA
<213> ORGANISM: Artificial Sequence
<220> FEATURE:
<223> OTHER INFORMATION: primer

<400> SEQUENCE: 515
gtgactggag ttcagacgtg tgctcttccg atcttacact ggtctggtta ctgccagttg 60
aatctg 66

<210> SEQ ID NO 516
<211> LENGTH: 66
<212> TYPE: DNA
<213> ORGANISM: Artificial Sequence
<220> FEATURE:
<223> OTHER INFORMATION: primer

<400> SEQUENCE: 516
gtgactggag ttcagacgtg tgctcttccg atcttccttg cgtctggtta ctgccagttg 60
aatctg 66

<210> SEQ ID NO 517
<211> LENGTH: 66
<212> TYPE: DNA
<213> ORGANISM: Artificial Sequence
<220> FEATURE:
<223> OTHER INFORMATION: primer

<400> SEQUENCE: 517
gtgactggag ttcagacgtg tgctcttccg atctaggacc tctctggtta ctgccagttg 60
aatctg 66

<210> SEQ ID NO 518
<211> LENGTH: 66
<212> TYPE: DNA
<213> ORGANISM: Artificial Sequence
<220> FEATURE:
<223> OTHER INFORMATION: primer

<400> SEQUENCE: 518
gtgactggag ttcagacgtg tgctcttccg atcttaagca tttctggtta ctgccagttg 60
aatctg 66

<210> SEQ ID NO 519
<211> LENGTH: 66
<212> TYPE: DNA
<213> ORGANISM: Artificial Sequence
<220> FEATURE:
<223> OTHER INFORMATION: primer

<400> SEQUENCE: 519
gtgactggag ttcagacgtg tgctcttccg atctaggata tttctggtta ctgccagttg 60
aatctg 66

<210> SEQ ID NO 520
<211> LENGTH: 66
<212> TYPE: DNA
<213> ORGANISM: Artificial Sequence
<220> FEATURE:
<223> OTHER INFORMATION: primer

<400> SEQUENCE: 520
gtgactggag ttcagacgtg tgctcttccg atctaatcgt tatctggtta ctgccagttg 60
aatctg 66

<210> SEQ ID NO 521
<211> LENGTH: 66
<212> TYPE: DNA
<213> ORGANISM: Artificial Sequence
<220> FEATURE:
<223> OTHER INFORMATION: primer

<400> SEQUENCE: 521
gtgactggag ttcagacgtg tgctcttccg atctgtctac attctggtta ctgccagttg 60
aatctg 66

<210> SEQ ID NO 522
<211> LENGTH: 66
<212> TYPE: DNA
<213> ORGANISM: Artificial Sequence
<220> FEATURE:
<223> OTHER INFORMATION: primer

<400> SEQUENCE: 522
gtgactggag ttcagacgtg tgctcttccg atctcgctgc tctctggtta ctgccagttg 60
aatctg 66

<210> SEQ ID NO 523
<211> LENGTH: 66
<212> TYPE: DNA
<213> ORGANISM: Artificial Sequence
<220> FEATURE:
<223> OTHER INFORMATION: primer

<400> SEQUENCE: 523
gtgactggag ttcagacgtg tgctcttccg atctgatcaa catctggtta ctgccagttg 60
aatctg 66

<210> SEQ ID NO 524
<211> LENGTH: 66
<212> TYPE: DNA
<213> ORGANISM: Artificial Sequence
<220> FEATURE:
<223> OTHER INFORMATION: primer

<400> SEQUENCE: 524
gtgactggag ttcagacgtg tgctcttccg atctcgaagg actctggtta ctgccagttg 60
aatctg 66

<210> SEQ ID NO 525
<211> LENGTH: 66
<212> TYPE: DNA
<213> ORGANISM: Artificial Sequence
<220> FEATURE:
<223> OTHER INFORMATION: primer

<400> SEQUENCE: 525
gtgactggag ttcagacgtg tgctcttccg atctgatgcc ggtctggtta ctgccagttg 60
aatctg 66

<210> SEQ ID NO 526
<211> LENGTH: 66
<212> TYPE: DNA
<213> ORGANISM: Artificial Sequence
<220> FEATURE:
<223> OTHER INFORMATION: primer

<400> SEQUENCE: 526
gtgactggag ttcagacgtg tgctcttccg atctctacga agtctggtta ctgccagttg 60
aatctg 66

<210> SEQ ID NO 527
<211> LENGTH: 66
<212> TYPE: DNA
<213> ORGANISM: Artificial Sequence
<220> FEATURE:
<223> OTHER INFORMATION: primer

<400> SEQUENCE: 527
gtgactggag ttcagacgtg tgctcttccg atctgatgcg tctctggtta ctgccagttg 60
aatctg 66

<210> SEQ ID NO 528
<211> LENGTH: 66
<212> TYPE: DNA
<213> ORGANISM: Artificial Sequence
<220> FEATURE:
<223> OTHER INFORMATION: primer

<400> SEQUENCE: 528
gtgactggag ttcagacgtg tgctcttccg atctctacgg catctggtta ctgccagttg 60
aatctg 66

<210> SEQ ID NO 529
<211> LENGTH: 66
<212> TYPE: DNA
<213> ORGANISM: Artificial Sequence
<220> FEATURE:
<223> OTHER INFORMATION: primer

<400> SEQUENCE: 529
gtgactggag ttcagacgtg tgctcttccg atctgattcc tttctggtta ctgccagttg 60
aatctg 66

<210> SEQ ID NO 530
<211> LENGTH: 66
<212> TYPE: DNA
<213> ORGANISM: Artificial Sequence
<220> FEATURE:
<223> OTHER INFORMATION: primer

<400> SEQUENCE: 530
gtgactggag ttcagacgtg tgctcttccg atctctactc gatctggtta ctgccagttg 60
aatctg 66

<210> SEQ ID NO 531
<211> LENGTH: 66
<212> TYPE: DNA
<213> ORGANISM: Artificial Sequence
<220> FEATURE:
<223> OTHER INFORMATION: primer

<400> SEQUENCE: 531
gtgactggag ttcagacgtg tgctcttccg atctgattcg agtctggtta ctgccagttg 60
aatctg 66

<210> SEQ ID NO 532
<211> LENGTH: 66
<212> TYPE: DNA
<213> ORGANISM: Artificial Sequence
<220> FEATURE:
<223> OTHER INFORMATION: primer

<400> SEQUENCE: 532
gtgactggag ttcagacgtg tgctcttccg atctaatcgg cgtctggtta ctgccagttg 60
aatctg 66

<210> SEQ ID NO 533
<211> LENGTH: 66
<212> TYPE: DNA
<213> ORGANISM: Artificial Sequence
<220> FEATURE:
<223> OTHER INFORMATION: primer

<400> SEQUENCE: 533
gtgactggag ttcagacgtg tgctcttccg atctttcgcc gatctggtta ctgccagttg 60
aatctg 66

<210> SEQ ID NO 534
<211> LENGTH: 66
<212> TYPE: DNA
<213> ORGANISM: Artificial Sequence
<220> FEATURE:
<223> OTHER INFORMATION: primer

<400> SEQUENCE: 534
gtgactggag ttcagacgtg tgctcttccg atctctggcc tctctggtta ctgccagttg 60
aatctg 66

<210> SEQ ID NO 535
<211> LENGTH: 66
<212> TYPE: DNA
<213> ORGANISM: Artificial Sequence
<220> FEATURE:
<223> OTHER INFORMATION: primer

<400> SEQUENCE: 535
gtgactggag ttcagacgtg tgctcttccg atctgaactt attctggtta ctgccagttg 60
aatctg 66

<210> SEQ ID NO 536
<211> LENGTH: 66
<212> TYPE: DNA

<213> ORGANISM: Artificial Sequence
<220> FEATURE:
<223> OTHER INFORMATION: primer

<400> SEQUENCE: 536
gtgactggag ttcagacgtg tgctcttccg atctcgtatt ggtctggtta ctgccagttg 60
aatctg 66

<210> SEQ ID NO 537
<211> LENGTH: 66
<212> TYPE: DNA
<213> ORGANISM: Artificial Sequence
<220> FEATURE:
<223> OTHER INFORMATION: primer

<400> SEQUENCE: 537
gtgactggag ttcagacgtg tgctcttccg atctgaagca catctggtta ctgccagttg 60
aatctg 66

<210> SEQ ID NO 538
<211> LENGTH: 66
<212> TYPE: DNA
<213> ORGANISM: Artificial Sequence
<220> FEATURE:
<223> OTHER INFORMATION: primer

<400> SEQUENCE: 538
gtgactggag ttcagacgtg tgctcttccg atctcttaat actctggtta ctgccagttg 60
aatctg 66

<210> SEQ ID NO 539
<211> LENGTH: 66
<212> TYPE: DNA
<213> ORGANISM: Artificial Sequence
<220> FEATURE:
<223> OTHER INFORMATION: primer

<400> SEQUENCE: 539
gtgactggag ttcagacgtg tgctcttccg atctgaagtc tttctggtta ctgccagttg 60
aatctg 66

<210> SEQ ID NO 540
<211> LENGTH: 66
<212> TYPE: DNA
<213> ORGANISM: Artificial Sequence
<220> FEATURE:
<223> OTHER INFORMATION: primer

<400> SEQUENCE: 540
gtgactggag ttcagacgtg tgctcttccg atctgaagag gctctggtta ctgccagttg 60
aatctg 66

<210> SEQ ID NO 541
<211> LENGTH: 66
<212> TYPE: DNA
<213> ORGANISM: Artificial Sequence
<220> FEATURE:
<223> OTHER INFORMATION: primer

<400> SEQUENCE: 541
gtgactggag ttcagacgtg tgctcttccg atctcggata actctggtta ctgccagttg 60
aatctg 66

<210> SEQ ID NO 542
<211> LENGTH: 66
<212> TYPE: DNA
<213> ORGANISM: Artificial Sequence
<220> FEATURE:
<223> OTHER INFORMATION: primer

<400> SEQUENCE: 542
gtgactggag ttcagacgtg tgctcttccg atctgaatct ggtctggtta ctgccagttg 60
aatctg 66

<210> SEQ ID NO 543
<211> LENGTH: 66
<212> TYPE: DNA
<213> ORGANISM: Artificial Sequence
<220> FEATURE:
<223> OTHER INFORMATION: primer

<400> SEQUENCE: 543
gtgactggag ttcagacgtg tgctcttccg atctctgatt gatctggtta ctgccagttg 60
aatctg 66

<210> SEQ ID NO 544
<211> LENGTH: 66
<212> TYPE: DNA
<213> ORGANISM: Artificial Sequence
<220> FEATURE:
<223> OTHER INFORMATION: primer

<400> SEQUENCE: 544
gtgactggag ttcagacgtg tgctcttccg atctaatccg tttctggtta ctgccagttg 60
aatctg 66

<210> SEQ ID NO 545
<211> LENGTH: 66
<212> TYPE: DNA
<213> ORGANISM: Artificial Sequence
<220> FEATURE:
<223> OTHER INFORMATION: primer

<400> SEQUENCE: 545
gtgactggag ttcagacgtg tgctcttccg atcttgcgta catctggtta ctgccagttg 60
aatctg 66

<210> SEQ ID NO 546
<211> LENGTH: 66
<212> TYPE: DNA
<213> ORGANISM: Artificial Sequence
<220> FEATURE:
<223> OTHER INFORMATION: primer

<400> SEQUENCE: 546
gtgactggag ttcagacgtg tgctcttccg atctgaatca attctggtta ctgccagttg 60
aatctg 66

<210> SEQ ID NO 547
<211> LENGTH: 66
<212> TYPE: DNA
<213> ORGANISM: Artificial Sequence
<220> FEATURE:
<223> OTHER INFORMATION: primer

<400> SEQUENCE: 547
gtgactggag ttcagacgtg tgctcttccg atcttgagtc agtctggtta ctgccagttg 60
aatctg 66

<210> SEQ ID NO 548
<211> LENGTH: 66
<212> TYPE: DNA
<213> ORGANISM: Artificial Sequence
<220> FEATURE:
<223> OTHER INFORMATION: primer

<400> SEQUENCE: 548
gtgactggag ttcagacgtg tgctcttccg atctgaatgc tctctggtta ctgccagttg 60
aatctg 66

<210> SEQ ID NO 549
<211> LENGTH: 66
<212> TYPE: DNA
<213> ORGANISM: Artificial Sequence
<220> FEATURE:
<223> OTHER INFORMATION: primer

<400> SEQUENCE: 549
gtgactggag ttcagacgtg tgctcttccg atctgaatat cctctggtta ctgccagttg 60
aatctg 66

<210> SEQ ID NO 550
<211> LENGTH: 66
<212> TYPE: DNA
<213> ORGANISM: Artificial Sequence
<220> FEATURE:
<223> OTHER INFORMATION: primer

<400> SEQUENCE: 550
gtgactggag ttcagacgtg tgctcttccg atctcttatg aatctggtta ctgccagttg 60
aatctg 66

<210> SEQ ID NO 551
<211> LENGTH: 66
<212> TYPE: DNA
<213> ORGANISM: Artificial Sequence
<220> FEATURE:
<223> OTHER INFORMATION: primer

<400> SEQUENCE: 551
gtgactggag ttcagacgtg tgctcttccg atcttcggca cctctggtta ctgccagttg 60
aatctg 66

<210> SEQ ID NO 552
<211> LENGTH: 66
<212> TYPE: DNA
<213> ORGANISM: Artificial Sequence
<220> FEATURE:
<223> OTHER INFORMATION: primer

<400> SEQUENCE: 552
gtgactggag ttcagacgtg tgctcttccg atctaagaag cgtctggtta ctgccagttg 60
aatctg 66

<210> SEQ ID NO 553
<211> LENGTH: 66

<212> TYPE: DNA
<213> ORGANISM: Artificial Sequence
<220> FEATURE:
<223> OTHER INFORMATION: primer

<400> SEQUENCE: 553
gtgactggag ttcagacgtg tgctcttccg atctctcacg attctggtta ctgccagttg 60
aatctg 66

<210> SEQ ID NO 554
<211> LENGTH: 66
<212> TYPE: DNA
<213> ORGANISM: Artificial Sequence
<220> FEATURE:
<223> OTHER INFORMATION: primer

<400> SEQUENCE: 554
gtgactggag ttcagacgtg tgctcttccg atcttcggtc gatctggtta ctgccagttg 60
aatctg 66

<210> SEQ ID NO 555
<211> LENGTH: 66
<212> TYPE: DNA
<213> ORGANISM: Artificial Sequence
<220> FEATURE:
<223> OTHER INFORMATION: primer

<400> SEQUENCE: 555
gtgactggag ttcagacgtg tgctcttccg atcttcggta agtctggtta ctgccagttg 60
aatctg 66

<210> SEQ ID NO 556
<211> LENGTH: 66
<212> TYPE: DNA
<213> ORGANISM: Artificial Sequence
<220> FEATURE:
<223> OTHER INFORMATION: primer

<400> SEQUENCE: 556
gtgactggag ttcagacgtg tgctcttccg atctaagata catctggtta ctgccagttg 60
aatctg 66

<210> SEQ ID NO 557
<211> LENGTH: 66
<212> TYPE: DNA
<213> ORGANISM: Artificial Sequence
<220> FEATURE:
<223> OTHER INFORMATION: primer

<400> SEQUENCE: 557
gtgactggag ttcagacgtg tgctcttccg atctgtcgct gttctggtta ctgccagttg 60
aatctg 66

<210> SEQ ID NO 558
<211> LENGTH: 66
<212> TYPE: DNA
<213> ORGANISM: Artificial Sequence
<220> FEATURE:
<223> OTHER INFORMATION: primer

<400> SEQUENCE: 558
gtgactggag ttcagacgtg tgctcttccg atcttcggat gttctggtta ctgccagttg 60
aatctg 66

<210> SEQ ID NO 559
<211> LENGTH: 66
<212> TYPE: DNA
<213> ORGANISM: Artificial Sequence
<220> FEATURE:
<223> OTHER INFORMATION: primer

<400> SEQUENCE: 559
gtgactggag ttcagacgtg tgctcttccg atctcgagcc ggtctggtta ctgccagttg 60
aatctg 66

<210> SEQ ID NO 560
<211> LENGTH: 66
<212> TYPE: DNA
<213> ORGANISM: Artificial Sequence
<220> FEATURE:
<223> OTHER INFORMATION: primer

<400> SEQUENCE: 560
gtgactggag ttcagacgtg tgctcttccg atctcgatta tctctggtta ctgccagttg 60
aatctg 66

<210> SEQ ID NO 561
<211> LENGTH: 66
<212> TYPE: DNA
<213> ORGANISM: Artificial Sequence
<220> FEATURE:
<223> OTHER INFORMATION: primer

<400> SEQUENCE: 561
gtgactggag ttcagacgtg tgctcttccg atcttcgaag cttctggtta ctgccagttg 60
aatctg 66

<210> SEQ ID NO 562
<211> LENGTH: 66
<212> TYPE: DNA
<213> ORGANISM: Artificial Sequence
<220> FEATURE:
<223> OTHER INFORMATION: primer

<400> SEQUENCE: 562
gtgactggag ttcagacgtg tgctcttccg atctctatca tttctggtta ctgccagttg 60
aatctg 66

<210> SEQ ID NO 563
<211> LENGTH: 66
<212> TYPE: DNA
<213> ORGANISM: Artificial Sequence
<220> FEATURE:
<223> OTHER INFORMATION: primer

<400> SEQUENCE: 563
gtgactggag ttcagacgtg tgctcttccg atctaagtta tctctggtta ctgccagttg 60
aatctg 66

<210> SEQ ID NO 564
<211> LENGTH: 66
<212> TYPE: DNA
<213> ORGANISM: Artificial Sequence
<220> FEATURE:
<223> OTHER INFORMATION: primer

<400> SEQUENCE: 564
gtgactggag ttcagacgtg tgctcttccg atctcgaacg gatctggtta ctgccagttg 60
aatctg 66

<210> SEQ ID NO 565
<211> LENGTH: 66
<212> TYPE: DNA
<213> ORGANISM: Artificial Sequence
<220> FEATURE:
<223> OTHER INFORMATION: primer

<400> SEQUENCE: 565
gtgactggag ttcagacgtg tgctcttccg atctctactg actctggtta ctgccagttg 60
aatctg 66

<210> SEQ ID NO 566
<211> LENGTH: 66
<212> TYPE: DNA
<213> ORGANISM: Artificial Sequence
<220> FEATURE:
<223> OTHER INFORMATION: primer

<400> SEQUENCE: 566
gtgactggag ttcagacgtg tgctcttccg atcttcttaa gttctggtta ctgccagttg 60
aatctg 66

<210> SEQ ID NO 567
<211> LENGTH: 66
<212> TYPE: DNA
<213> ORGANISM: Artificial Sequence
<220> FEATURE:
<223> OTHER INFORMATION: primer

<400> SEQUENCE: 567
gtgactggag ttcagacgtg tgctcttccg atctttagag tctctggtta ctgccagttg 60
aatctg 66

<210> SEQ ID NO 568
<211> LENGTH: 66
<212> TYPE: DNA
<213> ORGANISM: Artificial Sequence
<220> FEATURE:
<223> OTHER INFORMATION: primer

<400> SEQUENCE: 568
gtgactggag ttcagacgtg tgctcttccg atctaagacg aatctggtta ctgccagttg 60
aatctg 66

<210> SEQ ID NO 569
<211> LENGTH: 66
<212> TYPE: DNA
<213> ORGANISM: Artificial Sequence
<220> FEATURE:
<223> OTHER INFORMATION: primer

<400> SEQUENCE: 569
gtgactggag ttcagacgtg tgctcttccg atctttatta tgtctggtta ctgccagttg 60
aatctg 66

<210> SEQ ID NO 570

<211> LENGTH: 66
<212> TYPE: DNA
<213> ORGANISM: Artificial Sequence
<220> FEATURE:
<223> OTHER INFORMATION: primer

<400> SEQUENCE: 570
gtgactggag ttcagacgtg tgctcttccg atctcgctat tatctggtta ctgccagttg 60
aatctg 66

<210> SEQ ID NO 571
<211> LENGTH: 66
<212> TYPE: DNA
<213> ORGANISM: Artificial Sequence
<220> FEATURE:
<223> OTHER INFORMATION: primer

<400> SEQUENCE: 571
gtgactggag ttcagacgtg tgctcttccg atcttctatc agtctggtta ctgccagttg 60
aatctg 66

<210> SEQ ID NO 572
<211> LENGTH: 66
<212> TYPE: DNA
<213> ORGANISM: Artificial Sequence
<220> FEATURE:
<223> OTHER INFORMATION: primer

<400> SEQUENCE: 572
gtgactggag ttcagacgtg tgctcttccg atctcggtgg tatctggtta ctgccagttg 60
aatctg 66

<210> SEQ ID NO 573
<211> LENGTH: 66
<212> TYPE: DNA
<213> ORGANISM: Artificial Sequence
<220> FEATURE:
<223> OTHER INFORMATION: primer

<400> SEQUENCE: 573
gtgactggag ttcagacgtg tgctcttccg atcttcacca attctggtta ctgccagttg 60
aatctg 66

<210> SEQ ID NO 574
<211> LENGTH: 66
<212> TYPE: DNA
<213> ORGANISM: Artificial Sequence
<220> FEATURE:
<223> OTHER INFORMATION: primer

<400> SEQUENCE: 574
gtgactggag ttcagacgtg tgctcttccg atctctggaa gctctggtta ctgccagttg 60
aatctg 66

<210> SEQ ID NO 575
<211> LENGTH: 66
<212> TYPE: DNA
<213> ORGANISM: Artificial Sequence
<220> FEATURE:
<223> OTHER INFORMATION: primer

<400> SEQUENCE: 575
gtgactggag ttcagacgtg tgctcttccg atctcgtaag agtctggtta ctgccagttg 60
aatctg 66

<210> SEQ ID NO 576
<211> LENGTH: 66
<212> TYPE: DNA
<213> ORGANISM: Artificial Sequence
<220> FEATURE:
<223> OTHER INFORMATION: primer

<400> SEQUENCE: 576
gtgactggag ttcagacgtg tgctcttccg atctaagaga gctctggtta ctgccagttg 60
aatctg 66

<210> SEQ ID NO 577
<211> LENGTH: 66
<212> TYPE: DNA
<213> ORGANISM: Artificial Sequence
<220> FEATURE:
<223> OTHER INFORMATION: primer

<400> SEQUENCE: 577
gtgactggag ttcagacgtg tgctcttccg atcttcaacg agtctggtta ctgccagttg 60
aatctg 66

<210> SEQ ID NO 578
<211> LENGTH: 66
<212> TYPE: DNA
<213> ORGANISM: Artificial Sequence
<220> FEATURE:
<223> OTHER INFORMATION: primer

<400> SEQUENCE: 578
gtgactggag ttcagacgtg tgctcttccg atcttgcgag actctggtta ctgccagttg 60
aatctg 66

<210> SEQ ID NO 579
<211> LENGTH: 66
<212> TYPE: DNA
<213> ORGANISM: Artificial Sequence
<220> FEATURE:
<223> OTHER INFORMATION: primer

<400> SEQUENCE: 579
gtgactggag ttcagacgtg tgctcttccg atctcctggt gttctggtta ctgccagttg 60
aatctg 66

<210> SEQ ID NO 580
<211> LENGTH: 66
<212> TYPE: DNA
<213> ORGANISM: Artificial Sequence
<220> FEATURE:
<223> OTHER INFORMATION: primer

<400> SEQUENCE: 580
gtgactggag ttcagacgtg tgctcttccg atctaagtaa gttctggtta ctgccagttg 60
aatctg 66

<210> SEQ ID NO 581
<211> LENGTH: 66
<212> TYPE: DNA
<213> ORGANISM: Artificial Sequence
<220> FEATURE:

<223> OTHER INFORMATION: primer

<400> SEQUENCE: 581
gtgactggag ttcagacgtg tgctcttccg atcttgactg aatctggtta ctgccagttg 60
aatctg 66

<210> SEQ ID NO 582
<211> LENGTH: 66
<212> TYPE: DNA
<213> ORGANISM: Artificial Sequence
<220> FEATURE:
<223> OTHER INFORMATION: primer

<400> SEQUENCE: 582
gtgactggag ttcagacgtg tgctcttccg atctaagact gttctggtta ctgccagttg 60
aatctg 66

<210> SEQ ID NO 583
<211> LENGTH: 66
<212> TYPE: DNA
<213> ORGANISM: Artificial Sequence
<220> FEATURE:
<223> OTHER INFORMATION: primer

<400> SEQUENCE: 583
gtgactggag ttcagacgtg tgctcttccg atctcaatga tgtctggtta ctgccagttg 60
aatctg 66

<210> SEQ ID NO 584
<211> LENGTH: 66
<212> TYPE: DNA
<213> ORGANISM: Artificial Sequence
<220> FEATURE:
<223> OTHER INFORMATION: primer

<400> SEQUENCE: 584
gtgactggag ttcagacgtg tgctcttccg atctcacagt aatctggtta ctgccagttg 60
aatctg 66

<210> SEQ ID NO 585
<211> LENGTH: 66
<212> TYPE: DNA
<213> ORGANISM: Artificial Sequence
<220> FEATURE:
<223> OTHER INFORMATION: primer

<400> SEQUENCE: 585
gtgactggag ttcagacgtg tgctcttccg atcttggtca tttctggtta ctgccagttg 60
aatctg 66

<210> SEQ ID NO 586
<211> LENGTH: 66
<212> TYPE: DNA
<213> ORGANISM: Artificial Sequence
<220> FEATURE:
<223> OTHER INFORMATION: primer

<400> SEQUENCE: 586
gtgactggag ttcagacgtg tgctcttccg atctcaaccg tgtctggtta ctgccagttg 60
aatctg 66

<210> SEQ ID NO 587
<211> LENGTH: 66
<212> TYPE: DNA
<213> ORGANISM: Artificial Sequence
<220> FEATURE:
<223> OTHER INFORMATION: primer

<400> SEQUENCE: 587
gtgactggag ttcagacgtg tgctcttccg atcttggtgc actctggtta ctgccagttg 60
aatctg 66

<210> SEQ ID NO 588
<211> LENGTH: 66
<212> TYPE: DNA
<213> ORGANISM: Artificial Sequence
<220> FEATURE:
<223> OTHER INFORMATION: primer

<400> SEQUENCE: 588
gtgactggag ttcagacgtg tgctcttccg atctccacaa tgtctggtta ctgccagttg 60
aatctg 66

<210> SEQ ID NO 589
<211> LENGTH: 66
<212> TYPE: DNA
<213> ORGANISM: Artificial Sequence
<220> FEATURE:
<223> OTHER INFORMATION: primer

<400> SEQUENCE: 589
gtgactggag ttcagacgtg tgctcttccg atcttgtgtg cctctggtta ctgccagttg 60
aatctg 66

<210> SEQ ID NO 590
<211> LENGTH: 66
<212> TYPE: DNA
<213> ORGANISM: Artificial Sequence
<220> FEATURE:
<223> OTHER INFORMATION: primer

<400> SEQUENCE: 590
gtgactggag ttcagacgtg tgctcttccg atctcaccac ggtctggtta ctgccagttg 60
aatctg 66

<210> SEQ ID NO 591
<211> LENGTH: 66
<212> TYPE: DNA
<213> ORGANISM: Artificial Sequence
<220> FEATURE:
<223> OTHER INFORMATION: primer

<400> SEQUENCE: 591
gtgactggag ttcagacgtg tgctcttccg atcttgtgtt aatctggtta ctgccagttg 60
aatctg 66

<210> SEQ ID NO 592
<211> LENGTH: 63
<212> TYPE: DNA
<213> ORGANISM: Artificial Sequence
<220> FEATURE:
<223> OTHER INFORMATION: primer

<400> SEQUENCE: 592
gtgactggag ttcagacgtg tgctcttccg atctagcttg gttgtagcac gattgcagca 60
ttg 63

<210> SEQ ID NO 593
<211> LENGTH: 63
<212> TYPE: DNA
<213> ORGANISM: Artificial Sequence
<220> FEATURE:
<223> OTHER INFORMATION: primer

<400> SEQUENCE: 593
gtgactggag ttcagacgtg tgctcttccg atctagctta tgtgtagcac gattgcagca 60
ttg 63

<210> SEQ ID NO 594
<211> LENGTH: 63
<212> TYPE: DNA
<213> ORGANISM: Artificial Sequence
<220> FEATURE:
<223> OTHER INFORMATION: primer

<400> SEQUENCE: 594
gtgactggag ttcagacgtg tgctcttccg atctataacg actgtagcac gattgcagca 60
ttg 63

<210> SEQ ID NO 595
<211> LENGTH: 63
<212> TYPE: DNA
<213> ORGANISM: Artificial Sequence
<220> FEATURE:
<223> OTHER INFORMATION: primer

<400> SEQUENCE: 595
gtgactggag ttcagacgtg tgctcttccg atctgatgga gttgtagcac gattgcagca 60
ttg 63

<210> SEQ ID NO 596
<211> LENGTH: 63
<212> TYPE: DNA
<213> ORGANISM: Artificial Sequence
<220> FEATURE:
<223> OTHER INFORMATION: primer

<400> SEQUENCE: 596
gtgactggag ttcagacgtg tgctcttccg atcttgatct aatgtagcac gattgcagca 60
ttg 63

<210> SEQ ID NO 597
<211> LENGTH: 63
<212> TYPE: DNA
<213> ORGANISM: Artificial Sequence
<220> FEATURE:
<223> OTHER INFORMATION: primer

<400> SEQUENCE: 597
gtgactggag ttcagacgtg tgctcttccg atctagctat attgtagcac gattgcagca 60
ttg 63

<210> SEQ ID NO 598
<211> LENGTH: 63
<212> TYPE: DNA
<213> ORGANISM: Artificial Sequence
<220> FEATURE:
<223> OTHER INFORMATION: primer

<400> SEQUENCE: 598
gtgactggag ttcagacgtg tgctcttccg atctagcaga gatgtagcac gattgcagca 60
ttg 63

<210> SEQ ID NO 599
<211> LENGTH: 63
<212> TYPE: DNA
<213> ORGANISM: Artificial Sequence
<220> FEATURE:
<223> OTHER INFORMATION: primer

<400> SEQUENCE: 599
gtgactggag ttcagacgtg tgctcttccg atctgacgta agtgtagcac gattgcagca 60
ttg 63

<210> SEQ ID NO 600
<211> LENGTH: 63
<212> TYPE: DNA
<213> ORGANISM: Artificial Sequence
<220> FEATURE:
<223> OTHER INFORMATION: primer

<400> SEQUENCE: 600
gtgactggag ttcagacgtg tgctcttccg atctaggcct gatgtagcac gattgcagca 60
ttg 63

<210> SEQ ID NO 601
<211> LENGTH: 63
<212> TYPE: DNA
<213> ORGANISM: Artificial Sequence
<220> FEATURE:
<223> OTHER INFORMATION: primer

<400> SEQUENCE: 601
gtgactggag ttcagacgtg tgctcttccg atcttaagat tatgtagcac gattgcagca 60
ttg 63

<210> SEQ ID NO 602
<211> LENGTH: 63
<212> TYPE: DNA
<213> ORGANISM: Artificial Sequence
<220> FEATURE:
<223> OTHER INFORMATION: primer

<400> SEQUENCE: 602
gtgactggag ttcagacgtg tgctcttccg atctaggcga attgtagcac gattgcagca 60
ttg 63

<210> SEQ ID NO 603
<211> LENGTH: 63
<212> TYPE: DNA
<213> ORGANISM: Artificial Sequence
<220> FEATURE:
<223> OTHER INFORMATION: primer

<400> SEQUENCE: 603
gtgactggag ttcagacgtg tgctcttccg atctttgttc tttgtagcac gattgcagca 60
ttg 63

<210> SEQ ID NO 604
<211> LENGTH: 63
<212> TYPE: DNA
<213> ORGANISM: Artificial Sequence
<220> FEATURE:
<223> OTHER INFORMATION: primer

<400> SEQUENCE: 604
gtgactggag ttcagacgtg tgctcttccg atcttactcc tgtgtagcac gattgcagca 60
ttg 63

<210> SEQ ID NO 605
<211> LENGTH: 63
<212> TYPE: DNA
<213> ORGANISM: Artificial Sequence
<220> FEATURE:
<223> OTHER INFORMATION: primer

<400> SEQUENCE: 605
gtgactggag ttcagacgtg tgctcttccg atctgactgg cgtgtagcac gattgcagca 60
ttg 63

<210> SEQ ID NO 606
<211> LENGTH: 63
<212> TYPE: DNA
<213> ORGANISM: Artificial Sequence
<220> FEATURE:
<223> OTHER INFORMATION: primer

<400> SEQUENCE: 606
gtgactggag ttcagacgtg tgctcttccg atctatatat actgtagcac gattgcagca 60
ttg 63

<210> SEQ ID NO 607
<211> LENGTH: 63
<212> TYPE: DNA
<213> ORGANISM: Artificial Sequence
<220> FEATURE:
<223> OTHER INFORMATION: primer

<400> SEQUENCE: 607
gtgactggag ttcagacgtg tgctcttccg atcttagatc ggtgtagcac gattgcagca 60
ttg 63

<210> SEQ ID NO 608
<211> LENGTH: 63
<212> TYPE: DNA
<213> ORGANISM: Artificial Sequence
<220> FEATURE:
<223> OTHER INFORMATION: primer

<400> SEQUENCE: 608
gtgactggag ttcagacgtg tgctcttccg atctaggcaa gctgtagcac gattgcagca 60
ttg 63

<210> SEQ ID NO 609
<211> LENGTH: 63
<212> TYPE: DNA
<213> ORGANISM: Artificial Sequence
<220> FEATURE:
<223> OTHER INFORMATION: primer

<400> SEQUENCE: 609
gtgactggag ttcagacgtg tgctcttccg atcttccagg tatgtagcac gattgcagca 60
ttg 63

<210> SEQ ID NO 610
<211> LENGTH: 63
<212> TYPE: DNA
<213> ORGANISM: Artificial Sequence
<220> FEATURE:
<223> OTHER INFORMATION: primer

<400> SEQUENCE: 610
gtgactggag ttcagacgtg tgctcttccg atctaggtca agtgtagcac gattgcagca 60
ttg 63

<210> SEQ ID NO 611
<211> LENGTH: 63
<212> TYPE: DNA
<213> ORGANISM: Artificial Sequence
<220> FEATURE:
<223> OTHER INFORMATION: primer

<400> SEQUENCE: 611
gtgactggag ttcagacgtg tgctcttccg atcttacact ggtgtagcac gattgcagca 60
ttg 63

<210> SEQ ID NO 612
<211> LENGTH: 63
<212> TYPE: DNA
<213> ORGANISM: Artificial Sequence
<220> FEATURE:
<223> OTHER INFORMATION: primer

<400> SEQUENCE: 612
gtgactggag ttcagacgtg tgctcttccg atcttccttg cgtgtagcac gattgcagca 60
ttg 63

<210> SEQ ID NO 613
<211> LENGTH: 63
<212> TYPE: DNA
<213> ORGANISM: Artificial Sequence
<220> FEATURE:
<223> OTHER INFORMATION: primer

<400> SEQUENCE: 613
gtgactggag ttcagacgtg tgctcttccg atctaggacc tctgtagcac gattgcagca 60
ttg 63

<210> SEQ ID NO 614
<211> LENGTH: 63
<212> TYPE: DNA
<213> ORGANISM: Artificial Sequence
<220> FEATURE:
<223> OTHER INFORMATION: primer

<400> SEQUENCE: 614
gtgactggag ttcagacgtg tgctcttccg atcttaagca tttgtagcac gattgcagca 60
ttg 63

<210> SEQ ID NO 615
<211> LENGTH: 63
<212> TYPE: DNA

<213> ORGANISM: Artificial Sequence
<220> FEATURE:
<223> OTHER INFORMATION: primer

<400> SEQUENCE: 615
gtgactggag ttcagacgtg tgctcttccg atctaggata tttgtagcac gattgcagca 60
ttg 63

<210> SEQ ID NO 616
<211> LENGTH: 63
<212> TYPE: DNA
<213> ORGANISM: Artificial Sequence
<220> FEATURE:
<223> OTHER INFORMATION: primer

<400> SEQUENCE: 616
gtgactggag ttcagacgtg tgctcttccg atctaatcgt tatgtagcac gattgcagca 60
ttg 63

<210> SEQ ID NO 617
<211> LENGTH: 63
<212> TYPE: DNA
<213> ORGANISM: Artificial Sequence
<220> FEATURE:
<223> OTHER INFORMATION: primer

<400> SEQUENCE: 617
gtgactggag ttcagacgtg tgctcttccg atctgtctac attgtagcac gattgcagca 60
ttg 63

<210> SEQ ID NO 618
<211> LENGTH: 63
<212> TYPE: DNA
<213> ORGANISM: Artificial Sequence
<220> FEATURE:
<223> OTHER INFORMATION: primer

<400> SEQUENCE: 618
gtgactggag ttcagacgtg tgctcttccg atctcgctgc tctgtagcac gattgcagca 60
ttg 63

<210> SEQ ID NO 619
<211> LENGTH: 63
<212> TYPE: DNA
<213> ORGANISM: Artificial Sequence
<220> FEATURE:
<223> OTHER INFORMATION: primer

<400> SEQUENCE: 619
gtgactggag ttcagacgtg tgctcttccg atctgatcaa catgtagcac gattgcagca 60
ttg 63

<210> SEQ ID NO 620
<211> LENGTH: 63
<212> TYPE: DNA
<213> ORGANISM: Artificial Sequence
<220> FEATURE:
<223> OTHER INFORMATION: primer

<400> SEQUENCE: 620
gtgactggag ttcagacgtg tgctcttccg atctcgaagg actgtagcac gattgcagca 60
ttg 63

<210> SEQ ID NO 621
<211> LENGTH: 63
<212> TYPE: DNA
<213> ORGANISM: Artificial Sequence
<220> FEATURE:
<223> OTHER INFORMATION: primer

<400> SEQUENCE: 621
gtgactggag ttcagacgtg tgctcttccg atctgatgcc ggtgtagcac gattgcagca 60
ttg 63

<210> SEQ ID NO 622
<211> LENGTH: 63
<212> TYPE: DNA
<213> ORGANISM: Artificial Sequence
<220> FEATURE:
<223> OTHER INFORMATION: primer

<400> SEQUENCE: 622
gtgactggag ttcagacgtg tgctcttccg atctctacga agtgtagcac gattgcagca 60
ttg 63

<210> SEQ ID NO 623
<211> LENGTH: 63
<212> TYPE: DNA
<213> ORGANISM: Artificial Sequence
<220> FEATURE:
<223> OTHER INFORMATION: primer

<400> SEQUENCE: 623
gtgactggag ttcagacgtg tgctcttccg atctgatgcg tctgtagcac gattgcagca 60
ttg 63

<210> SEQ ID NO 624
<211> LENGTH: 63
<212> TYPE: DNA
<213> ORGANISM: Artificial Sequence
<220> FEATURE:
<223> OTHER INFORMATION: primer

<400> SEQUENCE: 624
gtgactggag ttcagacgtg tgctcttccg atctctacgg catgtagcac gattgcagca 60
ttg 63

<210> SEQ ID NO 625
<211> LENGTH: 63
<212> TYPE: DNA
<213> ORGANISM: Artificial Sequence
<220> FEATURE:
<223> OTHER INFORMATION: primer

<400> SEQUENCE: 625
gtgactggag ttcagacgtg tgctcttccg atctgattcc tttgtagcac gattgcagca 60
ttg 63

<210> SEQ ID NO 626
<211> LENGTH: 63
<212> TYPE: DNA
<213> ORGANISM: Artificial Sequence
<220> FEATURE:
<223> OTHER INFORMATION: primer

<400> SEQUENCE: 626
gtgactggag ttcagacgtg tgctcttccg atctctactc gatgtagcac gattgcagca 60
ttg 63

<210> SEQ ID NO 627
<211> LENGTH: 63
<212> TYPE: DNA
<213> ORGANISM: Artificial Sequence
<220> FEATURE:
<223> OTHER INFORMATION: primer

<400> SEQUENCE: 627
gtgactggag ttcagacgtg tgctcttccg atctgattcg agtgtagcac gattgcagca 60
ttg 63

<210> SEQ ID NO 628
<211> LENGTH: 63
<212> TYPE: DNA
<213> ORGANISM: Artificial Sequence
<220> FEATURE:
<223> OTHER INFORMATION: primer

<400> SEQUENCE: 628
gtgactggag ttcagacgtg tgctcttccg atctaatcgg cgtgtagcac gattgcagca 60
ttg 63

<210> SEQ ID NO 629
<211> LENGTH: 63
<212> TYPE: DNA
<213> ORGANISM: Artificial Sequence
<220> FEATURE:
<223> OTHER INFORMATION: primer

<400> SEQUENCE: 629
gtgactggag ttcagacgtg tgctcttccg atctttcgcc gatgtagcac gattgcagca 60
ttg 63

<210> SEQ ID NO 630
<211> LENGTH: 63
<212> TYPE: DNA
<213> ORGANISM: Artificial Sequence
<220> FEATURE:
<223> OTHER INFORMATION: primer

<400> SEQUENCE: 630
gtgactggag ttcagacgtg tgctcttccg atctctggcc tctgtagcac gattgcagca 60
ttg 63

<210> SEQ ID NO 631
<211> LENGTH: 63
<212> TYPE: DNA
<213> ORGANISM: Artificial Sequence
<220> FEATURE:
<223> OTHER INFORMATION: primer

<400> SEQUENCE: 631
gtgactggag ttcagacgtg tgctcttccg atctgaactt attgtagcac gattgcagca 60
ttg 63

<210> SEQ ID NO 632
<211> LENGTH: 63

<212> TYPE: DNA
<213> ORGANISM: Artificial Sequence
<220> FEATURE:
<223> OTHER INFORMATION: primer

<400> SEQUENCE: 632
gtgactggag ttcagacgtg tgctcttccg atctcgtatt ggtgtagcac gattgcagca 60
ttg 63

<210> SEQ ID NO 633
<211> LENGTH: 63
<212> TYPE: DNA
<213> ORGANISM: Artificial Sequence
<220> FEATURE:
<223> OTHER INFORMATION: primer

<400> SEQUENCE: 633
gtgactggag ttcagacgtg tgctcttccg atctgaagca catgtagcac gattgcagca 60
ttg 63

<210> SEQ ID NO 634
<211> LENGTH: 63
<212> TYPE: DNA
<213> ORGANISM: Artificial Sequence
<220> FEATURE:
<223> OTHER INFORMATION: primer

<400> SEQUENCE: 634
gtgactggag ttcagacgtg tgctcttccg atctcttaat actgtagcac gattgcagca 60
ttg 63

<210> SEQ ID NO 635
<211> LENGTH: 63
<212> TYPE: DNA
<213> ORGANISM: Artificial Sequence
<220> FEATURE:
<223> OTHER INFORMATION: primer

<400> SEQUENCE: 635
gtgactggag ttcagacgtg tgctcttccg atctgaagtc tttgtagcac gattgcagca 60
ttg 63

<210> SEQ ID NO 636
<211> LENGTH: 63
<212> TYPE: DNA
<213> ORGANISM: Artificial Sequence
<220> FEATURE:
<223> OTHER INFORMATION: primer

<400> SEQUENCE: 636
gtgactggag ttcagacgtg tgctcttccg atctgaagag gctgtagcac gattgcagca 60
ttg 63

<210> SEQ ID NO 637
<211> LENGTH: 63
<212> TYPE: DNA
<213> ORGANISM: Artificial Sequence
<220> FEATURE:
<223> OTHER INFORMATION: primer

<400> SEQUENCE: 637
gtgactggag ttcagacgtg tgctcttccg atctcggata actgtagcac gattgcagca 60
ttg 63

<210> SEQ ID NO 638
<211> LENGTH: 63
<212> TYPE: DNA
<213> ORGANISM: Artificial Sequence
<220> FEATURE:
<223> OTHER INFORMATION: primer

<400> SEQUENCE: 638
gtgactggag ttcagacgtg tgctcttccg atctgaatct ggtgtagcac gattgcagca 60
ttg 63

<210> SEQ ID NO 639
<211> LENGTH: 63
<212> TYPE: DNA
<213> ORGANISM: Artificial Sequence
<220> FEATURE:
<223> OTHER INFORMATION: primer

<400> SEQUENCE: 639
gtgactggag ttcagacgtg tgctcttccg atctctgatt gatgtagcac gattgcagca 60
ttg 63

<210> SEQ ID NO 640
<211> LENGTH: 63
<212> TYPE: DNA
<213> ORGANISM: Artificial Sequence
<220> FEATURE:
<223> OTHER INFORMATION: primer

<400> SEQUENCE: 640
gtgactggag ttcagacgtg tgctcttccg atctaatccg tttgtagcac gattgcagca 60
ttg 63

<210> SEQ ID NO 641
<211> LENGTH: 63
<212> TYPE: DNA
<213> ORGANISM: Artificial Sequence
<220> FEATURE:
<223> OTHER INFORMATION: primer

<400> SEQUENCE: 641
gtgactggag ttcagacgtg tgctcttccg atcttgcgta catgtagcac gattgcagca 60
ttg 63

<210> SEQ ID NO 642
<211> LENGTH: 63
<212> TYPE: DNA
<213> ORGANISM: Artificial Sequence
<220> FEATURE:
<223> OTHER INFORMATION: primer

<400> SEQUENCE: 642
gtgactggag ttcagacgtg tgctcttccg atctgaatca attgtagcac gattgcagca 60
ttg 63

<210> SEQ ID NO 643
<211> LENGTH: 63
<212> TYPE: DNA
<213> ORGANISM: Artificial Sequence
<220> FEATURE:
<223> OTHER INFORMATION: primer

<400> SEQUENCE: 643
gtgactggag ttcagacgtg tgctcttccg atcttgagtc agtgtagcac gattgcagca 60
ttg 63

<210> SEQ ID NO 644
<211> LENGTH: 63
<212> TYPE: DNA
<213> ORGANISM: Artificial Sequence
<220> FEATURE:
<223> OTHER INFORMATION: primer

<400> SEQUENCE: 644
gtgactggag ttcagacgtg tgctcttccg atctgaatgc tctgtagcac gattgcagca 60
ttg 63

<210> SEQ ID NO 645
<211> LENGTH: 63
<212> TYPE: DNA
<213> ORGANISM: Artificial Sequence
<220> FEATURE:
<223> OTHER INFORMATION: primer

<400> SEQUENCE: 645
gtgactggag ttcagacgtg tgctcttccg atctgaatat cctgtagcac gattgcagca 60
ttg 63

<210> SEQ ID NO 646
<211> LENGTH: 63
<212> TYPE: DNA
<213> ORGANISM: Artificial Sequence
<220> FEATURE:
<223> OTHER INFORMATION: primer

<400> SEQUENCE: 646
gtgactggag ttcagacgtg tgctcttccg atctcttatg aatgtagcac gattgcagca 60
ttg 63

<210> SEQ ID NO 647
<211> LENGTH: 63
<212> TYPE: DNA
<213> ORGANISM: Artificial Sequence
<220> FEATURE:
<223> OTHER INFORMATION: primer

<400> SEQUENCE: 647
gtgactggag ttcagacgtg tgctcttccg atcttcggca cctgtagcac gattgcagca 60
ttg 63

<210> SEQ ID NO 648
<211> LENGTH: 63
<212> TYPE: DNA
<213> ORGANISM: Artificial Sequence
<220> FEATURE:
<223> OTHER INFORMATION: primer

<400> SEQUENCE: 648
gtgactggag ttcagacgtg tgctcttccg atctaagaag cgtgtagcac gattgcagca 60
ttg 63

<210> SEQ ID NO 649

<211> LENGTH: 63
<212> TYPE: DNA
<213> ORGANISM: Artificial Sequence
<220> FEATURE:
<223> OTHER INFORMATION: primer

<400> SEQUENCE: 649
gtgactggag ttcagacgtg tgctcttccg atctctcacg attgtagcac gattgcagca 60
ttg 63

<210> SEQ ID NO 650
<211> LENGTH: 63
<212> TYPE: DNA
<213> ORGANISM: Artificial Sequence
<220> FEATURE:
<223> OTHER INFORMATION: primer

<400> SEQUENCE: 650
gtgactggag ttcagacgtg tgctcttccg atcttcggtc gatgtagcac gattgcagca 60
ttg 63

<210> SEQ ID NO 651
<211> LENGTH: 63
<212> TYPE: DNA
<213> ORGANISM: Artificial Sequence
<220> FEATURE:
<223> OTHER INFORMATION: primer

<400> SEQUENCE: 651
gtgactggag ttcagacgtg tgctcttccg atcttcggta agtgtagcac gattgcagca 60
ttg 63

<210> SEQ ID NO 652
<211> LENGTH: 63
<212> TYPE: DNA
<213> ORGANISM: Artificial Sequence
<220> FEATURE:
<223> OTHER INFORMATION: primer

<400> SEQUENCE: 652
gtgactggag ttcagacgtg tgctcttccg atctaagata catgtagcac gattgcagca 60
ttg 63

<210> SEQ ID NO 653
<211> LENGTH: 63
<212> TYPE: DNA
<213> ORGANISM: Artificial Sequence
<220> FEATURE:
<223> OTHER INFORMATION: primer

<400> SEQUENCE: 653
gtgactggag ttcagacgtg tgctcttccg atctgtcgct gttgtagcac gattgcagca 60
ttg 63

<210> SEQ ID NO 654
<211> LENGTH: 63
<212> TYPE: DNA
<213> ORGANISM: Artificial Sequence
<220> FEATURE:
<223> OTHER INFORMATION: primer

<400> SEQUENCE: 654
gtgactggag ttcagacgtg tgctcttccg atcttcggat gttgtagcac gattgcagca 60
ttg 63

<210> SEQ ID NO 655
<211> LENGTH: 63
<212> TYPE: DNA
<213> ORGANISM: Artificial Sequence
<220> FEATURE:
<223> OTHER INFORMATION: primer

<400> SEQUENCE: 655
gtgactggag ttcagacgtg tgctcttccg atctcgagcc ggtgtagcac gattgcagca 60
ttg 63

<210> SEQ ID NO 656
<211> LENGTH: 63
<212> TYPE: DNA
<213> ORGANISM: Artificial Sequence
<220> FEATURE:
<223> OTHER INFORMATION: primer

<400> SEQUENCE: 656
gtgactggag ttcagacgtg tgctcttccg atctcgatta tctgtagcac gattgcagca 60
ttg 63

<210> SEQ ID NO 657
<211> LENGTH: 63
<212> TYPE: DNA
<213> ORGANISM: Artificial Sequence
<220> FEATURE:
<223> OTHER INFORMATION: primer

<400> SEQUENCE: 657
gtgactggag ttcagacgtg tgctcttccg atcttcgaag cttgtagcac gattgcagca 60
ttg 63

<210> SEQ ID NO 658
<211> LENGTH: 63
<212> TYPE: DNA
<213> ORGANISM: Artificial Sequence
<220> FEATURE:
<223> OTHER INFORMATION: primer

<400> SEQUENCE: 658
gtgactggag ttcagacgtg tgctcttccg atctctatca tttgtagcac gattgcagca 60
ttg 63

<210> SEQ ID NO 659
<211> LENGTH: 63
<212> TYPE: DNA
<213> ORGANISM: Artificial Sequence
<220> FEATURE:
<223> OTHER INFORMATION: primer

<400> SEQUENCE: 659
gtgactggag ttcagacgtg tgctcttccg atctaagtta tctgtagcac gattgcagca 60
ttg 63

<210> SEQ ID NO 660
<211> LENGTH: 63
<212> TYPE: DNA
<213> ORGANISM: Artificial Sequence
<220> FEATURE:

<223> OTHER INFORMATION: primer

<400> SEQUENCE: 660
gtgactggag ttcagacgtg tgctcttccg atctcgaacg gatgtagcac gattgcagca 60
ttg 63

<210> SEQ ID NO 661
<211> LENGTH: 63
<212> TYPE: DNA
<213> ORGANISM: Artificial Sequence
<220> FEATURE:
<223> OTHER INFORMATION: primer

<400> SEQUENCE: 661
gtgactggag ttcagacgtg tgctcttccg atctctactg actgtagcac gattgcagca 60
ttg 63

<210> SEQ ID NO 662
<211> LENGTH: 63
<212> TYPE: DNA
<213> ORGANISM: Artificial Sequence
<220> FEATURE:
<223> OTHER INFORMATION: primer

<400> SEQUENCE: 662
gtgactggag ttcagacgtg tgctcttccg atcttcttaa gttgtagcac gattgcagca 60
ttg 63

<210> SEQ ID NO 663
<211> LENGTH: 63
<212> TYPE: DNA
<213> ORGANISM: Artificial Sequence
<220> FEATURE:
<223> OTHER INFORMATION: primer

<400> SEQUENCE: 663
gtgactggag ttcagacgtg tgctcttccg atctttagag tctgtagcac gattgcagca 60
ttg 63

<210> SEQ ID NO 664
<211> LENGTH: 63
<212> TYPE: DNA
<213> ORGANISM: Artificial Sequence
<220> FEATURE:
<223> OTHER INFORMATION: primer

<400> SEQUENCE: 664
gtgactggag ttcagacgtg tgctcttccg atctaagacg aatgtagcac gattgcagca 60
ttg 63

<210> SEQ ID NO 665
<211> LENGTH: 63
<212> TYPE: DNA
<213> ORGANISM: Artificial Sequence
<220> FEATURE:
<223> OTHER INFORMATION: primer

<400> SEQUENCE: 665
gtgactggag ttcagacgtg tgctcttccg atctttatta tgtgtagcac gattgcagca 60
ttg 63

<210> SEQ ID NO 666
<211> LENGTH: 63
<212> TYPE: DNA
<213> ORGANISM: Artificial Sequence
<220> FEATURE:
<223> OTHER INFORMATION: primer

<400> SEQUENCE: 666
gtgactggag ttcagacgtg tgctcttccg atctcgctat tatgtagcac gattgcagca 60
ttg 63

<210> SEQ ID NO 667
<211> LENGTH: 63
<212> TYPE: DNA
<213> ORGANISM: Artificial Sequence
<220> FEATURE:
<223> OTHER INFORMATION: primer

<400> SEQUENCE: 667
gtgactggag ttcagacgtg tgctcttccg atcttctatc agtgtagcac gattgcagca 60
ttg 63

<210> SEQ ID NO 668
<211> LENGTH: 63
<212> TYPE: DNA
<213> ORGANISM: Artificial Sequence
<220> FEATURE:
<223> OTHER INFORMATION: primer

<400> SEQUENCE: 668
gtgactggag ttcagacgtg tgctcttccg atctcggtgg tatgtagcac gattgcagca 60
ttg 63

<210> SEQ ID NO 669
<211> LENGTH: 63
<212> TYPE: DNA
<213> ORGANISM: Artificial Sequence
<220> FEATURE:
<223> OTHER INFORMATION: primer

<400> SEQUENCE: 669
gtgactggag ttcagacgtg tgctcttccg atcttcacca attgtagcac gattgcagca 60
ttg 63

<210> SEQ ID NO 670
<211> LENGTH: 63
<212> TYPE: DNA
<213> ORGANISM: Artificial Sequence
<220> FEATURE:
<223> OTHER INFORMATION: primer

<400> SEQUENCE: 670
gtgactggag ttcagacgtg tgctcttccg atctctggaa gctgtagcac gattgcagca 60
ttg 63

<210> SEQ ID NO 671
<211> LENGTH: 63
<212> TYPE: DNA
<213> ORGANISM: Artificial Sequence
<220> FEATURE:
<223> OTHER INFORMATION: primer

<400> SEQUENCE: 671
gtgactggag ttcagacgtg tgctcttccg atctcgtaag agtgtagcac gattgcagca 60
ttg 63

<210> SEQ ID NO 672
<211> LENGTH: 63
<212> TYPE: DNA
<213> ORGANISM: Artificial Sequence
<220> FEATURE:
<223> OTHER INFORMATION: primer

<400> SEQUENCE: 672
gtgactggag ttcagacgtg tgctcttccg atctaagaga gctgtagcac gattgcagca 60
ttg 63

<210> SEQ ID NO 673
<211> LENGTH: 63
<212> TYPE: DNA
<213> ORGANISM: Artificial Sequence
<220> FEATURE:
<223> OTHER INFORMATION: primer

<400> SEQUENCE: 673
gtgactggag ttcagacgtg tgctcttccg atcttcaacg agtgtagcac gattgcagca 60
ttg 63

<210> SEQ ID NO 674
<211> LENGTH: 63
<212> TYPE: DNA
<213> ORGANISM: Artificial Sequence
<220> FEATURE:
<223> OTHER INFORMATION: primer

<400> SEQUENCE: 674
gtgactggag ttcagacgtg tgctcttccg atcttgcgag actgtagcac gattgcagca 60
ttg 63

<210> SEQ ID NO 675
<211> LENGTH: 63
<212> TYPE: DNA
<213> ORGANISM: Artificial Sequence
<220> FEATURE:
<223> OTHER INFORMATION: primer

<400> SEQUENCE: 675
gtgactggag ttcagacgtg tgctcttccg atctcctggt gttgtagcac gattgcagca 60
ttg 63

<210> SEQ ID NO 676
<211> LENGTH: 63
<212> TYPE: DNA
<213> ORGANISM: Artificial Sequence
<220> FEATURE:
<223> OTHER INFORMATION: primer

<400> SEQUENCE: 676
gtgactggag ttcagacgtg tgctcttccg atctaagtaa gttgtagcac gattgcagca 60
ttg 63

<210> SEQ ID NO 677
<211> LENGTH: 63
<212> TYPE: DNA
<213> ORGANISM: Artificial Sequence
<220> FEATURE:
<223> OTHER INFORMATION: primer

<400> SEQUENCE: 677
gtgactggag ttcagacgtg tgctcttccg atcttgactg aatgtagcac gattgcagca 60
ttg 63

<210> SEQ ID NO 678
<211> LENGTH: 63
<212> TYPE: DNA
<213> ORGANISM: Artificial Sequence
<220> FEATURE:
<223> OTHER INFORMATION: primer

<400> SEQUENCE: 678
gtgactggag ttcagacgtg tgctcttccg atctaagact gttgtagcac gattgcagca 60
ttg 63

<210> SEQ ID NO 679
<211> LENGTH: 63
<212> TYPE: DNA
<213> ORGANISM: Artificial Sequence
<220> FEATURE:
<223> OTHER INFORMATION: primer

<400> SEQUENCE: 679
gtgactggag ttcagacgtg tgctcttccg atctcaatga tgtgtagcac gattgcagca 60
ttg 63

<210> SEQ ID NO 680
<211> LENGTH: 63
<212> TYPE: DNA
<213> ORGANISM: Artificial Sequence
<220> FEATURE:
<223> OTHER INFORMATION: primer

<400> SEQUENCE: 680
gtgactggag ttcagacgtg tgctcttccg atctcacagt aatgtagcac gattgcagca 60
ttg 63

<210> SEQ ID NO 681
<211> LENGTH: 63
<212> TYPE: DNA
<213> ORGANISM: Artificial Sequence
<220> FEATURE:
<223> OTHER INFORMATION: primer

<400> SEQUENCE: 681
gtgactggag ttcagacgtg tgctcttccg atcttggtca tttgtagcac gattgcagca 60
ttg 63

<210> SEQ ID NO 682
<211> LENGTH: 63
<212> TYPE: DNA
<213> ORGANISM: Artificial Sequence
<220> FEATURE:
<223> OTHER INFORMATION: primer

<400> SEQUENCE: 682
gtgactggag ttcagacgtg tgctcttccg atctcaaccg tgtgtagcac gattgcagca 60
ttg 63

<210> SEQ ID NO 683
<211> LENGTH: 63
<212> TYPE: DNA
<213> ORGANISM: Artificial Sequence
<220> FEATURE:
<223> OTHER INFORMATION: primer

<400> SEQUENCE: 683
gtgactggag ttcagacgtg tgctcttccg atcttggtgc actgtagcac gattgcagca 60
ttg 63

<210> SEQ ID NO 684
<211> LENGTH: 63
<212> TYPE: DNA
<213> ORGANISM: Artificial Sequence
<220> FEATURE:
<223> OTHER INFORMATION: primer

<400> SEQUENCE: 684
gtgactggag ttcagacgtg tgctcttccg atctccacaa tgtgtagcac gattgcagca 60
ttg 63

<210> SEQ ID NO 685
<211> LENGTH: 63
<212> TYPE: DNA
<213> ORGANISM: Artificial Sequence
<220> FEATURE:
<223> OTHER INFORMATION: primer

<400> SEQUENCE: 685
gtgactggag ttcagacgtg tgctcttccg atcttgtgtg cctgtagcac gattgcagca 60
ttg 63

<210> SEQ ID NO 686
<211> LENGTH: 63
<212> TYPE: DNA
<213> ORGANISM: Artificial Sequence
<220> FEATURE:
<223> OTHER INFORMATION: primer

<400> SEQUENCE: 686
gtgactggag ttcagacgtg tgctcttccg atctcaccac ggtgtagcac gattgcagca 60
ttg 63

<210> SEQ ID NO 687
<211> LENGTH: 63
<212> TYPE: DNA
<213> ORGANISM: Artificial Sequence
<220> FEATURE:
<223> OTHER INFORMATION: primer

<400> SEQUENCE: 687
gtgactggag ttcagacgtg tgctcttccg atcttgtgtt aatgtagcac gattgcagca 60
ttg 63

<210> SEQ ID NO 688
<211> LENGTH: 64
<212> TYPE: DNA
<213> ORGANISM: Artificial Sequence
<220> FEATURE:
<223> OTHER INFORMATION: primer

<400> SEQUENCE: 688
gtgactggag ttcagacgtg tgctcttccg atctagcttg gtggcaaatg ctttcgctct 60
ggtc 64

<210> SEQ ID NO 689
<211> LENGTH: 64
<212> TYPE: DNA
<213> ORGANISM: Artificial Sequence
<220> FEATURE:
<223> OTHER INFORMATION: primer

<400> SEQUENCE: 689
gtgactggag ttcagacgtg tgctcttccg atctagctta tgggcaaatg ctttcgctct 60
ggtc 64

<210> SEQ ID NO 690
<211> LENGTH: 64
<212> TYPE: DNA
<213> ORGANISM: Artificial Sequence
<220> FEATURE:
<223> OTHER INFORMATION: primer

<400> SEQUENCE: 690
gtgactggag ttcagacgtg tgctcttccg atctataacg acggcaaatg ctttcgctct 60
ggtc 64

<210> SEQ ID NO 691
<211> LENGTH: 64
<212> TYPE: DNA
<213> ORGANISM: Artificial Sequence
<220> FEATURE:
<223> OTHER INFORMATION: primer

<400> SEQUENCE: 691
gtgactggag ttcagacgtg tgctcttccg atctgatgga gtggcaaatg ctttcgctct 60
ggtc 64

<210> SEQ ID NO 692
<211> LENGTH: 64
<212> TYPE: DNA
<213> ORGANISM: Artificial Sequence
<220> FEATURE:
<223> OTHER INFORMATION: primer

<400> SEQUENCE: 692
gtgactggag ttcagacgtg tgctcttccg atcttgatct aaggcaaatg ctttcgctct 60
ggtc 64

<210> SEQ ID NO 693
<211> LENGTH: 64
<212> TYPE: DNA
<213> ORGANISM: Artificial Sequence
<220> FEATURE:
<223> OTHER INFORMATION: primer

<400> SEQUENCE: 693
gtgactggag ttcagacgtg tgctcttccg atctagctat atggcaaatg ctttcgctct 60
ggtc 64

<210> SEQ ID NO 694
<211> LENGTH: 64
<212> TYPE: DNA

<213> ORGANISM: Artificial Sequence
<220> FEATURE:
<223> OTHER INFORMATION: primer

<400> SEQUENCE: 694
gtgactggag ttcagacgtg tgctcttccg atctagcaga gaggcaaatg ctttcgctct 60
ggtc 64

<210> SEQ ID NO 695
<211> LENGTH: 64
<212> TYPE: DNA
<213> ORGANISM: Artificial Sequence
<220> FEATURE:
<223> OTHER INFORMATION: primer

<400> SEQUENCE: 695
gtgactggag ttcagacgtg tgctcttccg atctgacgta agggcaaatg ctttcgctct 60
ggtc 64

<210> SEQ ID NO 696
<211> LENGTH: 64
<212> TYPE: DNA
<213> ORGANISM: Artificial Sequence
<220> FEATURE:
<223> OTHER INFORMATION: primer

<400> SEQUENCE: 696
gtgactggag ttcagacgtg tgctcttccg atctaggcct gaggcaaatg ctttcgctct 60
ggtc 64

<210> SEQ ID NO 697
<211> LENGTH: 64
<212> TYPE: DNA
<213> ORGANISM: Artificial Sequence
<220> FEATURE:
<223> OTHER INFORMATION: primer

<400> SEQUENCE: 697
gtgactggag ttcagacgtg tgctcttccg atcttaagat taggcaaatg ctttcgctct 60
ggtc 64

<210> SEQ ID NO 698
<211> LENGTH: 64
<212> TYPE: DNA
<213> ORGANISM: Artificial Sequence
<220> FEATURE:
<223> OTHER INFORMATION: primer

<400> SEQUENCE: 698
gtgactggag ttcagacgtg tgctcttccg atctaggcga atggcaaatg ctttcgctct 60
ggtc 64

<210> SEQ ID NO 699
<211> LENGTH: 64
<212> TYPE: DNA
<213> ORGANISM: Artificial Sequence
<220> FEATURE:
<223> OTHER INFORMATION: primer

<400> SEQUENCE: 699
gtgactggag ttcagacgtg tgctcttccg atctttgttc ttggcaaatg ctttcgctct 60
ggtc 64

<210> SEQ ID NO 700
<211> LENGTH: 64
<212> TYPE: DNA
<213> ORGANISM: Artificial Sequence
<220> FEATURE:
<223> OTHER INFORMATION: primer

<400> SEQUENCE: 700
gtgactggag ttcagacgtg tgctcttccg atcttactcc tgggcaaatg ctttcgctct 60
ggtc 64

<210> SEQ ID NO 701
<211> LENGTH: 64
<212> TYPE: DNA
<213> ORGANISM: Artificial Sequence
<220> FEATURE:
<223> OTHER INFORMATION: primer

<400> SEQUENCE: 701
gtgactggag ttcagacgtg tgctcttccg atctgactgg cgggcaaatg ctttcgctct 60
ggtc 64

<210> SEQ ID NO 702
<211> LENGTH: 64
<212> TYPE: DNA
<213> ORGANISM: Artificial Sequence
<220> FEATURE:
<223> OTHER INFORMATION: primer

<400> SEQUENCE: 702
gtgactggag ttcagacgtg tgctcttccg atctatatat acggcaaatg ctttcgctct 60
ggtc 64

<210> SEQ ID NO 703
<211> LENGTH: 64
<212> TYPE: DNA
<213> ORGANISM: Artificial Sequence
<220> FEATURE:
<223> OTHER INFORMATION: primer

<400> SEQUENCE: 703
gtgactggag ttcagacgtg tgctcttccg atcttagatc ggggcaaatg ctttcgctct 60
ggtc 64

<210> SEQ ID NO 704
<211> LENGTH: 64
<212> TYPE: DNA
<213> ORGANISM: Artificial Sequence
<220> FEATURE:
<223> OTHER INFORMATION: primer

<400> SEQUENCE: 704
gtgactggag ttcagacgtg tgctcttccg atctaggcaa gcggcaaatg ctttcgctct 60
ggtc 64

<210> SEQ ID NO 705
<211> LENGTH: 64
<212> TYPE: DNA
<213> ORGANISM: Artificial Sequence
<220> FEATURE:
<223> OTHER INFORMATION: primer

<400> SEQUENCE: 705
gtgactggag ttcagacgtg tgctcttccg atcttccagg taggcaaatg ctttcgctct 60
ggtc 64

<210> SEQ ID NO 706
<211> LENGTH: 64
<212> TYPE: DNA
<213> ORGANISM: Artificial Sequence
<220> FEATURE:
<223> OTHER INFORMATION: primer

<400> SEQUENCE: 706
gtgactggag ttcagacgtg tgctcttccg atctaggtca agggcaaatg ctttcgctct 60
ggtc 64

<210> SEQ ID NO 707
<211> LENGTH: 64
<212> TYPE: DNA
<213> ORGANISM: Artificial Sequence
<220> FEATURE:
<223> OTHER INFORMATION: primer

<400> SEQUENCE: 707
gtgactggag ttcagacgtg tgctcttccg atcttacact ggggcaaatg ctttcgctct 60
ggtc 64

<210> SEQ ID NO 708
<211> LENGTH: 64
<212> TYPE: DNA
<213> ORGANISM: Artificial Sequence
<220> FEATURE:
<223> OTHER INFORMATION: primer

<400> SEQUENCE: 708
gtgactggag ttcagacgtg tgctcttccg atcttccttg cgggcaaatg ctttcgctct 60
ggtc 64

<210> SEQ ID NO 709
<211> LENGTH: 64
<212> TYPE: DNA
<213> ORGANISM: Artificial Sequence
<220> FEATURE:
<223> OTHER INFORMATION: primer

<400> SEQUENCE: 709
gtgactggag ttcagacgtg tgctcttccg atctaggacc tcggcaaatg ctttcgctct 60
ggtc 64

<210> SEQ ID NO 710
<211> LENGTH: 64
<212> TYPE: DNA
<213> ORGANISM: Artificial Sequence
<220> FEATURE:
<223> OTHER INFORMATION: primer

<400> SEQUENCE: 710
gtgactggag ttcagacgtg tgctcttccg atcttaagca ttggcaaatg ctttcgctct 60
ggtc 64

<210> SEQ ID NO 711
<211> LENGTH: 64

<212> TYPE: DNA
<213> ORGANISM: Artificial Sequence
<220> FEATURE:
<223> OTHER INFORMATION: primer

<400> SEQUENCE: 711
gtgactggag ttcagacgtg tgctcttccg atctaggata ttggcaaatg ctttcgctct 60
ggtc 64

<210> SEQ ID NO 712
<211> LENGTH: 64
<212> TYPE: DNA
<213> ORGANISM: Artificial Sequence
<220> FEATURE:
<223> OTHER INFORMATION: primer

<400> SEQUENCE: 712
gtgactggag ttcagacgtg tgctcttccg atctaatcgt taggcaaatg ctttcgctct 60
ggtc 64

<210> SEQ ID NO 713
<211> LENGTH: 64
<212> TYPE: DNA
<213> ORGANISM: Artificial Sequence
<220> FEATURE:
<223> OTHER INFORMATION: primer

<400> SEQUENCE: 713
gtgactggag ttcagacgtg tgctcttccg atctgtctac atggcaaatg ctttcgctct 60
ggtc 64

<210> SEQ ID NO 714
<211> LENGTH: 64
<212> TYPE: DNA
<213> ORGANISM: Artificial Sequence
<220> FEATURE:
<223> OTHER INFORMATION: primer

<400> SEQUENCE: 714
gtgactggag ttcagacgtg tgctcttccg atctcgctgc tcggcaaatg ctttcgctct 60
ggtc 64

<210> SEQ ID NO 715
<211> LENGTH: 64
<212> TYPE: DNA
<213> ORGANISM: Artificial Sequence
<220> FEATURE:
<223> OTHER INFORMATION: primer

<400> SEQUENCE: 715
gtgactggag ttcagacgtg tgctcttccg atctgatcaa caggcaaatg ctttcgctct 60
ggtc 64

<210> SEQ ID NO 716
<211> LENGTH: 64
<212> TYPE: DNA
<213> ORGANISM: Artificial Sequence
<220> FEATURE:
<223> OTHER INFORMATION: primer

<400> SEQUENCE: 716
gtgactggag ttcagacgtg tgctcttccg atctcgaagg acggcaaatg ctttcgctct 60
ggtc 64

<210> SEQ ID NO 717
<211> LENGTH: 64
<212> TYPE: DNA
<213> ORGANISM: Artificial Sequence
<220> FEATURE:
<223> OTHER INFORMATION: primer

<400> SEQUENCE: 717
gtgactggag ttcagacgtg tgctcttccg atctgatgcc ggggcaaatg ctttcgctct 60
ggtc 64

<210> SEQ ID NO 718
<211> LENGTH: 64
<212> TYPE: DNA
<213> ORGANISM: Artificial Sequence
<220> FEATURE:
<223> OTHER INFORMATION: primer

<400> SEQUENCE: 718
gtgactggag ttcagacgtg tgctcttccg atctctacga agggcaaatg ctttcgctct 60
ggtc 64

<210> SEQ ID NO 719
<211> LENGTH: 64
<212> TYPE: DNA
<213> ORGANISM: Artificial Sequence
<220> FEATURE:
<223> OTHER INFORMATION: primer

<400> SEQUENCE: 719
gtgactggag ttcagacgtg tgctcttccg atctgatgcg tcggcaaatg ctttcgctct 60
ggtc 64

<210> SEQ ID NO 720
<211> LENGTH: 64
<212> TYPE: DNA
<213> ORGANISM: Artificial Sequence
<220> FEATURE:
<223> OTHER INFORMATION: primer

<400> SEQUENCE: 720
gtgactggag ttcagacgtg tgctcttccg atctctacgg caggcaaatg ctttcgctct 60
ggtc 64

<210> SEQ ID NO 721
<211> LENGTH: 64
<212> TYPE: DNA
<213> ORGANISM: Artificial Sequence
<220> FEATURE:
<223> OTHER INFORMATION: primer

<400> SEQUENCE: 721
gtgactggag ttcagacgtg tgctcttccg atctgattcc ttggcaaatg ctttcgctct 60
ggtc 64

<210> SEQ ID NO 722
<211> LENGTH: 64
<212> TYPE: DNA
<213> ORGANISM: Artificial Sequence
<220> FEATURE:
<223> OTHER INFORMATION: primer

<400> SEQUENCE: 722
gtgactggag ttcagacgtg tgctcttccg atctctactc gaggcaaatg ctttcgctct 60
ggtc 64

<210> SEQ ID NO 723
<211> LENGTH: 64
<212> TYPE: DNA
<213> ORGANISM: Artificial Sequence
<220> FEATURE:
<223> OTHER INFORMATION: primer

<400> SEQUENCE: 723
gtgactggag ttcagacgtg tgctcttccg atctgattcg agggcaaatg ctttcgctct 60
ggtc 64

<210> SEQ ID NO 724
<211> LENGTH: 64
<212> TYPE: DNA
<213> ORGANISM: Artificial Sequence
<220> FEATURE:
<223> OTHER INFORMATION: primer

<400> SEQUENCE: 724
gtgactggag ttcagacgtg tgctcttccg atctaatcgg cgggcaaatg ctttcgctct 60
ggtc 64

<210> SEQ ID NO 725
<211> LENGTH: 64
<212> TYPE: DNA
<213> ORGANISM: Artificial Sequence
<220> FEATURE:
<223> OTHER INFORMATION: primer

<400> SEQUENCE: 725
gtgactggag ttcagacgtg tgctcttccg atctttcgcc gaggcaaatg ctttcgctct 60
ggtc 64

<210> SEQ ID NO 726
<211> LENGTH: 64
<212> TYPE: DNA
<213> ORGANISM: Artificial Sequence
<220> FEATURE:
<223> OTHER INFORMATION: primer

<400> SEQUENCE: 726
gtgactggag ttcagacgtg tgctcttccg atctctggcc tcggcaaatg ctttcgctct 60
ggtc 64

<210> SEQ ID NO 727
<211> LENGTH: 64
<212> TYPE: DNA
<213> ORGANISM: Artificial Sequence
<220> FEATURE:
<223> OTHER INFORMATION: primer

<400> SEQUENCE: 727
gtgactggag ttcagacgtg tgctcttccg atctgaactt atggcaaatg ctttcgctct 60
ggtc 64

<210> SEQ ID NO 728

<211> LENGTH: 64
<212> TYPE: DNA
<213> ORGANISM: Artificial Sequence
<220> FEATURE:
<223> OTHER INFORMATION: primer

<400> SEQUENCE: 728
gtgactggag ttcagacgtg tgctcttccg atctcgtatt ggggcaaatg ctttcgctct 60
ggtc 64

<210> SEQ ID NO 729
<211> LENGTH: 64
<212> TYPE: DNA
<213> ORGANISM: Artificial Sequence
<220> FEATURE:
<223> OTHER INFORMATION: primer

<400> SEQUENCE: 729
gtgactggag ttcagacgtg tgctcttccg atctgaagca caggcaaatg ctttcgctct 60
ggtc 64

<210> SEQ ID NO 730
<211> LENGTH: 64
<212> TYPE: DNA
<213> ORGANISM: Artificial Sequence
<220> FEATURE:
<223> OTHER INFORMATION: primer

<400> SEQUENCE: 730
gtgactggag ttcagacgtg tgctcttccg atctcttaat acggcaaatg ctttcgctct 60
ggtc 64

<210> SEQ ID NO 731
<211> LENGTH: 64
<212> TYPE: DNA
<213> ORGANISM: Artificial Sequence
<220> FEATURE:
<223> OTHER INFORMATION: primer

<400> SEQUENCE: 731
gtgactggag ttcagacgtg tgctcttccg atctgaagtc ttggcaaatg ctttcgctct 60
ggtc 64

<210> SEQ ID NO 732
<211> LENGTH: 64
<212> TYPE: DNA
<213> ORGANISM: Artificial Sequence
<220> FEATURE:
<223> OTHER INFORMATION: primer

<400> SEQUENCE: 732
gtgactggag ttcagacgtg tgctcttccg atctgaagag gcggcaaatg ctttcgctct 60
ggtc 64

<210> SEQ ID NO 733
<211> LENGTH: 64
<212> TYPE: DNA
<213> ORGANISM: Artificial Sequence
<220> FEATURE:
<223> OTHER INFORMATION: primer

<400> SEQUENCE: 733
gtgactggag ttcagacgtg tgctcttccg atctcggata acggcaaatg ctttcgctct 60
ggtc 64

<210> SEQ ID NO 734
<211> LENGTH: 64
<212> TYPE: DNA
<213> ORGANISM: Artificial Sequence
<220> FEATURE:
<223> OTHER INFORMATION: primer

<400> SEQUENCE: 734
gtgactggag ttcagacgtg tgctcttccg atctgaatct ggggcaaatg ctttcgctct 60
ggtc 64

<210> SEQ ID NO 735
<211> LENGTH: 64
<212> TYPE: DNA
<213> ORGANISM: Artificial Sequence
<220> FEATURE:
<223> OTHER INFORMATION: primer

<400> SEQUENCE: 735
gtgactggag ttcagacgtg tgctcttccg atctctgatt gaggcaaatg ctttcgctct 60
ggtc 64

<210> SEQ ID NO 736
<211> LENGTH: 64
<212> TYPE: DNA
<213> ORGANISM: Artificial Sequence
<220> FEATURE:
<223> OTHER INFORMATION: primer

<400> SEQUENCE: 736
gtgactggag ttcagacgtg tgctcttccg atctaatccg ttggcaaatg ctttcgctct 60
ggtc 64

<210> SEQ ID NO 737
<211> LENGTH: 64
<212> TYPE: DNA
<213> ORGANISM: Artificial Sequence
<220> FEATURE:
<223> OTHER INFORMATION: primer

<400> SEQUENCE: 737
gtgactggag ttcagacgtg tgctcttccg atcttgcgta caggcaaatg ctttcgctct 60
ggtc 64

<210> SEQ ID NO 738
<211> LENGTH: 64
<212> TYPE: DNA
<213> ORGANISM: Artificial Sequence
<220> FEATURE:
<223> OTHER INFORMATION: primer

<400> SEQUENCE: 738
gtgactggag ttcagacgtg tgctcttccg atctgaatca atggcaaatg ctttcgctct 60
ggtc 64

<210> SEQ ID NO 739
<211> LENGTH: 64
<212> TYPE: DNA
<213> ORGANISM: Artificial Sequence
<220> FEATURE:

<223> OTHER INFORMATION: primer

<400> SEQUENCE: 739
gtgactggag ttcagacgtg tgctcttccg atcttgagtc agggcaaatg ctttcgctct 60
ggtc 64

<210> SEQ ID NO 740
<211> LENGTH: 64
<212> TYPE: DNA
<213> ORGANISM: Artificial Sequence
<220> FEATURE:
<223> OTHER INFORMATION: primer

<400> SEQUENCE: 740
gtgactggag ttcagacgtg tgctcttccg atctgaatgc tcggcaaatg ctttcgctct 60
ggtc 64

<210> SEQ ID NO 741
<211> LENGTH: 64
<212> TYPE: DNA
<213> ORGANISM: Artificial Sequence
<220> FEATURE:
<223> OTHER INFORMATION: primer

<400> SEQUENCE: 741
gtgactggag ttcagacgtg tgctcttccg atctgaatat ccggcaaatg ctttcgctct 60
ggtc 64

<210> SEQ ID NO 742
<211> LENGTH: 64
<212> TYPE: DNA
<213> ORGANISM: Artificial Sequence
<220> FEATURE:
<223> OTHER INFORMATION: primer

<400> SEQUENCE: 742
gtgactggag ttcagacgtg tgctcttccg atctcttatg aaggcaaatg ctttcgctct 60
ggtc 64

<210> SEQ ID NO 743
<211> LENGTH: 64
<212> TYPE: DNA
<213> ORGANISM: Artificial Sequence
<220> FEATURE:
<223> OTHER INFORMATION: primer

<400> SEQUENCE: 743
gtgactggag ttcagacgtg tgctcttccg atcttcggca ccggcaaatg ctttcgctct 60
ggtc 64

<210> SEQ ID NO 744
<211> LENGTH: 64
<212> TYPE: DNA
<213> ORGANISM: Artificial Sequence
<220> FEATURE:
<223> OTHER INFORMATION: primer

<400> SEQUENCE: 744
gtgactggag ttcagacgtg tgctcttccg atctaagaag cgggcaaatg ctttcgctct 60
ggtc 64

<210> SEQ ID NO 745
<211> LENGTH: 64
<212> TYPE: DNA
<213> ORGANISM: Artificial Sequence
<220> FEATURE:
<223> OTHER INFORMATION: primer

<400> SEQUENCE: 745
gtgactggag ttcagacgtg tgctcttccg atctctcacg atggcaaatg ctttcgctct 60
ggtc 64

<210> SEQ ID NO 746
<211> LENGTH: 64
<212> TYPE: DNA
<213> ORGANISM: Artificial Sequence
<220> FEATURE:
<223> OTHER INFORMATION: primer

<400> SEQUENCE: 746
gtgactggag ttcagacgtg tgctcttccg atcttcggtc gaggcaaatg ctttcgctct 60
ggtc 64

<210> SEQ ID NO 747
<211> LENGTH: 64
<212> TYPE: DNA
<213> ORGANISM: Artificial Sequence
<220> FEATURE:
<223> OTHER INFORMATION: primer

<400> SEQUENCE: 747
gtgactggag ttcagacgtg tgctcttccg atcttcggta agggcaaatg ctttcgctct 60
ggtc 64

<210> SEQ ID NO 748
<211> LENGTH: 64
<212> TYPE: DNA
<213> ORGANISM: Artificial Sequence
<220> FEATURE:
<223> OTHER INFORMATION: primer

<400> SEQUENCE: 748
gtgactggag ttcagacgtg tgctcttccg atctaagata caggcaaatg ctttcgctct 60
ggtc 64

<210> SEQ ID NO 749
<211> LENGTH: 64
<212> TYPE: DNA
<213> ORGANISM: Artificial Sequence
<220> FEATURE:
<223> OTHER INFORMATION: primer

<400> SEQUENCE: 749
gtgactggag ttcagacgtg tgctcttccg atctgtcgct gtggcaaatg ctttcgctct 60
ggtc 64

<210> SEQ ID NO 750
<211> LENGTH: 64
<212> TYPE: DNA
<213> ORGANISM: Artificial Sequence
<220> FEATURE:
<223> OTHER INFORMATION: primer

<400> SEQUENCE: 750
gtgactggag ttcagacgtg tgctcttccg atcttcggat gtggcaaatg ctttcgctct 60
ggtc 64

<210> SEQ ID NO 751
<211> LENGTH: 64
<212> TYPE: DNA
<213> ORGANISM: Artificial Sequence
<220> FEATURE:
<223> OTHER INFORMATION: primer

<400> SEQUENCE: 751
gtgactggag ttcagacgtg tgctcttccg atctcgagcc ggggcaaatg ctttcgctct 60
ggtc 64

<210> SEQ ID NO 752
<211> LENGTH: 64
<212> TYPE: DNA
<213> ORGANISM: Artificial Sequence
<220> FEATURE:
<223> OTHER INFORMATION: primer

<400> SEQUENCE: 752
gtgactggag ttcagacgtg tgctcttccg atctcgatta tcggcaaatg ctttcgctct 60
ggtc 64

<210> SEQ ID NO 753
<211> LENGTH: 64
<212> TYPE: DNA
<213> ORGANISM: Artificial Sequence
<220> FEATURE:
<223> OTHER INFORMATION: primer

<400> SEQUENCE: 753
gtgactggag ttcagacgtg tgctcttccg atcttcgaag ctggcaaatg ctttcgctct 60
ggtc 64

<210> SEQ ID NO 754
<211> LENGTH: 64
<212> TYPE: DNA
<213> ORGANISM: Artificial Sequence
<220> FEATURE:
<223> OTHER INFORMATION: primer

<400> SEQUENCE: 754
gtgactggag ttcagacgtg tgctcttccg atctctatca ttggcaaatg ctttcgctct 60
ggtc 64

<210> SEQ ID NO 755
<211> LENGTH: 64
<212> TYPE: DNA
<213> ORGANISM: Artificial Sequence
<220> FEATURE:
<223> OTHER INFORMATION: primer

<400> SEQUENCE: 755
gtgactggag ttcagacgtg tgctcttccg atctaagtta tcggcaaatg ctttcgctct 60
ggtc 64

<210> SEQ ID NO 756
<211> LENGTH: 64
<212> TYPE: DNA
<213> ORGANISM: Artificial Sequence
<220> FEATURE:
<223> OTHER INFORMATION: primer

<400> SEQUENCE: 756
gtgactggag ttcagacgtg tgctcttccg atctcgaacg gaggcaaatg ctttcgctct 60
ggtc 64

<210> SEQ ID NO 757
<211> LENGTH: 64
<212> TYPE: DNA
<213> ORGANISM: Artificial Sequence
<220> FEATURE:
<223> OTHER INFORMATION: primer

<400> SEQUENCE: 757
gtgactggag ttcagacgtg tgctcttccg atctctactg acggcaaatg ctttcgctct 60
ggtc 64

<210> SEQ ID NO 758
<211> LENGTH: 64
<212> TYPE: DNA
<213> ORGANISM: Artificial Sequence
<220> FEATURE:
<223> OTHER INFORMATION: primer

<400> SEQUENCE: 758
gtgactggag ttcagacgtg tgctcttccg atcttcttaa gtggcaaatg ctttcgctct 60
ggtc 64

<210> SEQ ID NO 759
<211> LENGTH: 64
<212> TYPE: DNA
<213> ORGANISM: Artificial Sequence
<220> FEATURE:
<223> OTHER INFORMATION: primer

<400> SEQUENCE: 759
gtgactggag ttcagacgtg tgctcttccg atctttagag tcggcaaatg ctttcgctct 60
ggtc 64

<210> SEQ ID NO 760
<211> LENGTH: 64
<212> TYPE: DNA
<213> ORGANISM: Artificial Sequence
<220> FEATURE:
<223> OTHER INFORMATION: primer

<400> SEQUENCE: 760
gtgactggag ttcagacgtg tgctcttccg atctaagacg aaggcaaatg ctttcgctct 60
ggtc 64

<210> SEQ ID NO 761
<211> LENGTH: 64
<212> TYPE: DNA
<213> ORGANISM: Artificial Sequence
<220> FEATURE:
<223> OTHER INFORMATION: primer

<400> SEQUENCE: 761
gtgactggag ttcagacgtg tgctcttccg atctttatta tgggcaaatg ctttcgctct 60
ggtc 64

<210> SEQ ID NO 762
<211> LENGTH: 64
<212> TYPE: DNA
<213> ORGANISM: Artificial Sequence
<220> FEATURE:
<223> OTHER INFORMATION: primer

<400> SEQUENCE: 762
gtgactggag ttcagacgtg tgctcttccg atctcgctat taggcaaatg ctttcgctct 60
ggtc 64

<210> SEQ ID NO 763
<211> LENGTH: 64
<212> TYPE: DNA
<213> ORGANISM: Artificial Sequence
<220> FEATURE:
<223> OTHER INFORMATION: primer

<400> SEQUENCE: 763
gtgactggag ttcagacgtg tgctcttccg atcttctatc agggcaaatg ctttcgctct 60
ggtc 64

<210> SEQ ID NO 764
<211> LENGTH: 64
<212> TYPE: DNA
<213> ORGANISM: Artificial Sequence
<220> FEATURE:
<223> OTHER INFORMATION: primer

<400> SEQUENCE: 764
gtgactggag ttcagacgtg tgctcttccg atctcggtgg taggcaaatg ctttcgctct 60
ggtc 64

<210> SEQ ID NO 765
<211> LENGTH: 64
<212> TYPE: DNA
<213> ORGANISM: Artificial Sequence
<220> FEATURE:
<223> OTHER INFORMATION: primer

<400> SEQUENCE: 765
gtgactggag ttcagacgtg tgctcttccg atcttcacca atggcaaatg ctttcgctct 60
ggtc 64

<210> SEQ ID NO 766
<211> LENGTH: 64
<212> TYPE: DNA
<213> ORGANISM: Artificial Sequence
<220> FEATURE:
<223> OTHER INFORMATION: primer

<400> SEQUENCE: 766
gtgactggag ttcagacgtg tgctcttccg atctctggaa gcggcaaatg ctttcgctct 60
ggtc 64

<210> SEQ ID NO 767
<211> LENGTH: 64
<212> TYPE: DNA
<213> ORGANISM: Artificial Sequence
<220> FEATURE:
<223> OTHER INFORMATION: primer

<400> SEQUENCE: 767
gtgactggag ttcagacgtg tgctcttccg atctcgtaag agggcaaatg ctttcgctct 60
ggtc 64

<210> SEQ ID NO 768
<211> LENGTH: 64
<212> TYPE: DNA
<213> ORGANISM: Artificial Sequence
<220> FEATURE:
<223> OTHER INFORMATION: primer

<400> SEQUENCE: 768
gtgactggag ttcagacgtg tgctcttccg atctaagaga gcggcaaatg ctttcgctct 60
ggtc 64

<210> SEQ ID NO 769
<211> LENGTH: 64
<212> TYPE: DNA
<213> ORGANISM: Artificial Sequence
<220> FEATURE:
<223> OTHER INFORMATION: primer

<400> SEQUENCE: 769
gtgactggag ttcagacgtg tgctcttccg atcttcaacg agggcaaatg ctttcgctct 60
ggtc 64

<210> SEQ ID NO 770
<211> LENGTH: 64
<212> TYPE: DNA
<213> ORGANISM: Artificial Sequence
<220> FEATURE:
<223> OTHER INFORMATION: primer

<400> SEQUENCE: 770
gtgactggag ttcagacgtg tgctcttccg atcttgcgag acggcaaatg ctttcgctct 60
ggtc 64

<210> SEQ ID NO 771
<211> LENGTH: 64
<212> TYPE: DNA
<213> ORGANISM: Artificial Sequence
<220> FEATURE:
<223> OTHER INFORMATION: primer

<400> SEQUENCE: 771
gtgactggag ttcagacgtg tgctcttccg atctcctggt gtggcaaatg ctttcgctct 60
ggtc 64

<210> SEQ ID NO 772
<211> LENGTH: 64
<212> TYPE: DNA
<213> ORGANISM: Artificial Sequence
<220> FEATURE:
<223> OTHER INFORMATION: primer

<400> SEQUENCE: 772
gtgactggag ttcagacgtg tgctcttccg atctaagtaa gtggcaaatg ctttcgctct 60
ggtc 64

<210> SEQ ID NO 773
<211> LENGTH: 64
<212> TYPE: DNA

<213> ORGANISM: Artificial Sequence
<220> FEATURE:
<223> OTHER INFORMATION: primer

<400> SEQUENCE: 773
gtgactggag ttcagacgtg tgctcttccg atcttgactg aaggcaaatg ctttcgctct 60
ggtc 64

<210> SEQ ID NO 774
<211> LENGTH: 64
<212> TYPE: DNA
<213> ORGANISM: Artificial Sequence
<220> FEATURE:
<223> OTHER INFORMATION: primer

<400> SEQUENCE: 774
gtgactggag ttcagacgtg tgctcttccg atctaagact gtggcaaatg ctttcgctct 60
ggtc 64

<210> SEQ ID NO 775
<211> LENGTH: 64
<212> TYPE: DNA
<213> ORGANISM: Artificial Sequence
<220> FEATURE:
<223> OTHER INFORMATION: primer

<400> SEQUENCE: 775
gtgactggag ttcagacgtg tgctcttccg atctcaatga tgggcaaatg ctttcgctct 60
ggtc 64

<210> SEQ ID NO 776
<211> LENGTH: 64
<212> TYPE: DNA
<213> ORGANISM: Artificial Sequence
<220> FEATURE:
<223> OTHER INFORMATION: primer

<400> SEQUENCE: 776
gtgactggag ttcagacgtg tgctcttccg atctcacagt aaggcaaatg ctttcgctct 60
ggtc 64

<210> SEQ ID NO 777
<211> LENGTH: 64
<212> TYPE: DNA
<213> ORGANISM: Artificial Sequence
<220> FEATURE:
<223> OTHER INFORMATION: primer

<400> SEQUENCE: 777
gtgactggag ttcagacgtg tgctcttccg atcttggtca ttggcaaatg ctttcgctct 60
ggtc 64

<210> SEQ ID NO 778
<211> LENGTH: 64
<212> TYPE: DNA
<213> ORGANISM: Artificial Sequence
<220> FEATURE:
<223> OTHER INFORMATION: primer

<400> SEQUENCE: 778
gtgactggag ttcagacgtg tgctcttccg atctcaaccg tgggcaaatg ctttcgctct 60
ggtc 64

<210> SEQ ID NO 779
<211> LENGTH: 64
<212> TYPE: DNA
<213> ORGANISM: Artificial Sequence
<220> FEATURE:
<223> OTHER INFORMATION: primer

<400> SEQUENCE: 779
gtgactggag ttcagacgtg tgctcttccg atcttggtgc acggcaaatg ctttcgctct 60
ggtc 64

<210> SEQ ID NO 780
<211> LENGTH: 64
<212> TYPE: DNA
<213> ORGANISM: Artificial Sequence
<220> FEATURE:
<223> OTHER INFORMATION: primer

<400> SEQUENCE: 780
gtgactggag ttcagacgtg tgctcttccg atctccacaa tgggcaaatg ctttcgctct 60
ggtc 64

<210> SEQ ID NO 781
<211> LENGTH: 64
<212> TYPE: DNA
<213> ORGANISM: Artificial Sequence
<220> FEATURE:
<223> OTHER INFORMATION: primer

<400> SEQUENCE: 781
gtgactggag ttcagacgtg tgctcttccg atcttgtgtg ccggcaaatg ctttcgctct 60
ggtc 64

<210> SEQ ID NO 782
<211> LENGTH: 64
<212> TYPE: DNA
<213> ORGANISM: Artificial Sequence
<220> FEATURE:
<223> OTHER INFORMATION: primer

<400> SEQUENCE: 782
gtgactggag ttcagacgtg tgctcttccg atctcaccac ggggcaaatg ctttcgctct 60
ggtc 64

<210> SEQ ID NO 783
<211> LENGTH: 64
<212> TYPE: DNA
<213> ORGANISM: Artificial Sequence
<220> FEATURE:
<223> OTHER INFORMATION: primer

<400> SEQUENCE: 783
gtgactggag ttcagacgtg tgctcttccg atcttgtgtt aaggcaaatg ctttcgctct 60
ggtc 64

<210> SEQ ID NO 784
<211> LENGTH: 65
<212> TYPE: DNA
<213> ORGANISM: Artificial Sequence
<220> FEATURE:
<223> OTHER INFORMATION: primer
<220> FEATURE:

<221> NAME/KEY: misc_feature
<222> LOCATION: 51
<223> OTHER INFORMATION: n is a, c, g, or t

<400> SEQUENCE: 784
gtgactggag ttcagacgtg tgctcttccg atctagcttg gttggacaaa ncgtctacgc 60
tgcag 65

<210> SEQ ID NO 785
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 785
gtgactggag ttcagacgtg tgctcttccg atctagctta tgtggacaaa ncgtctacgc 60
tgcag 65

<210> SEQ ID NO 786
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 786
gtgactggag ttcagacgtg tgctcttccg atctataacg actggacaaa ncgtctacgc 60
tgcag 65

<210> SEQ ID NO 787
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 787
gtgactggag ttcagacgtg tgctcttccg atctgatgga gttggacaaa ncgtctacgc 60
tgcag 65

<210> SEQ ID NO 788
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 788
gtgactggag ttcagacgtg tgctcttccg atcttgatct aatggacaaa ncgtctacgc 60
tgcag 65

<210> SEQ ID NO 789
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 789
gtgactggag ttcagacgtg tgctcttccg atctagctat attggacaaa ncgtctacgc 60
tgcag 65

<210> SEQ ID NO 790
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 790
gtgactggag ttcagacgtg tgctcttccg atctagcaga gatggacaaa ncgtctacgc 60
tgcag 65

<210> SEQ ID NO 791
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 791
gtgactggag ttcagacgtg tgctcttccg atctgacgta agtggacaaa ncgtctacgc 60
tgcag 65

<210> SEQ ID NO 792
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 792
gtgactggag ttcagacgtg tgctcttccg atctaggcct gatggacaaa ncgtctacgc 60
tgcag 65

<210> SEQ ID NO 793
<211> LENGTH: 65
<212> TYPE: DNA

<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 793
gtgactggag ttcagacgtg tgctcttccg atcttaagat tatggacaaa ncgtctacgc 60
tgcag 65

<210> SEQ ID NO 794
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 794
gtgactggag ttcagacgtg tgctcttccg atctaggcga attggacaaa ncgtctacgc 60
tgcag 65

<210> SEQ ID NO 795
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 795
gtgactggag ttcagacgtg tgctcttccg atctttgttc tttggacaaa ncgtctacgc 60
tgcag 65

<210> SEQ ID NO 796
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 796
gtgactggag ttcagacgtg tgctcttccg atcttactcc tgtggacaaa ncgtctacgc 60
tgcag 65

<210> SEQ ID NO 797
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 797
gtgactggag ttcagacgtg tgctcttccg atctgactgg cgtggacaaa ncgtctacgc 60
tgcag 65

<210> SEQ ID NO 798
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 798
gtgactggag ttcagacgtg tgctcttccg atctatatat actggacaaa ncgtctacgc 60
tgcag 65

<210> SEQ ID NO 799
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 799
gtgactggag ttcagacgtg tgctcttccg atcttagatc ggtggacaaa ncgtctacgc 60
tgcag 65

<210> SEQ ID NO 800
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 800
gtgactggag ttcagacgtg tgctcttccg atctaggcaa gctggacaaa ncgtctacgc 60
tgcag 65

<210> SEQ ID NO 801
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 801
gtgactggag ttcagacgtg tgctcttccg atcttccagg tatggacaaa ncgtctacgc 60
tgcag 65

<210> SEQ ID NO 802
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 802
gtgactggag ttcagacgtg tgctcttccg atctaggtca agtggacaaa ncgtctacgc 60
tgcag 65

<210> SEQ ID NO 803
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 803
gtgactggag ttcagacgtg tgctcttccg atcttacact ggtggacaaa ncgtctacgc 60
tgcag 65

<210> SEQ ID NO 804
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 804
gtgactggag ttcagacgtg tgctcttccg atcttccttg cgtggacaaa ncgtctacgc 60
tgcag 65

<210> SEQ ID NO 805
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 805
gtgactggag ttcagacgtg tgctcttccg atctaggacc tctggacaaa ncgtctacgc 60
tgcag 65

<210> SEQ ID NO 806
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 806
gtgactggag ttcagacgtg tgctcttccg atcttaagca tttggacaaa ncgtctacgc 60
tgcag 65

<210> SEQ ID NO 807
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 807
gtgactggag ttcagacgtg tgctcttccg atctaggata tttggacaaa ncgtctacgc 60
tgcag 65

<210> SEQ ID NO 808
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 808
gtgactggag ttcagacgtg tgctcttccg atctaatcgt tatggacaaa ncgtctacgc 60
tgcag 65

<210> SEQ ID NO 809
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 809
gtgactggag ttcagacgtg tgctcttccg atctgtctac attggacaaa ncgtctacgc 60
tgcag 65

<210> SEQ ID NO 810
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 810
gtgactggag ttcagacgtg tgctcttccg atctcgctgc tctggacaaa ncgtctacgc 60
tgcag 65

<210> SEQ ID NO 811
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 811
gtgactggag ttcagacgtg tgctcttccg atctgatcaa catggacaaa ncgtctacgc 60
tgcag 65

<210> SEQ ID NO 812
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 812
gtgactggag ttcagacgtg tgctcttccg atctcgaagg actggacaaa ncgtctacgc 60
tgcag 65

<210> SEQ ID NO 813
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 813
gtgactggag ttcagacgtg tgctcttccg atctgatgcc ggtggacaaa ncgtctacgc 60
tgcag 65

<210> SEQ ID NO 814
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 814
gtgactggag ttcagacgtg tgctcttccg atctctacga agtggacaaa ncgtctacgc 60
tgcag 65

<210> SEQ ID NO 815
<211> LENGTH: 65

<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 815
gtgactggag ttcagacgtg tgctcttccg atctgatgcg tctggacaaa ncgtctacgc 60
tgcag 65

<210> SEQ ID NO 816
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 816
gtgactggag ttcagacgtg tgctcttccg atctctacgg catggacaaa ncgtctacgc 60
tgcag 65

<210> SEQ ID NO 817
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 817
gtgactggag ttcagacgtg tgctcttccg atctgattcc tttggacaaa ncgtctacgc 60
tgcag 65

<210> SEQ ID NO 818
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 818
gtgactggag ttcagacgtg tgctcttccg atctctactc gatggacaaa ncgtctacgc 60
tgcag 65

<210> SEQ ID NO 819
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51

<223> OTHER INFORMATION: n is a, c, g, or t

<400> SEQUENCE: 819
gtgactggag ttcagacgtg tgctcttccg atctgattcg agtggacaaa ncgtctacgc 60
tgcag 65

<210> SEQ ID NO 820
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 820
gtgactggag ttcagacgtg tgctcttccg atctaatcgg cgtggacaaa ncgtctacgc 60
tgcag 65

<210> SEQ ID NO 821
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 821
gtgactggag ttcagacgtg tgctcttccg atctttcgcc gatggacaaa ncgtctacgc 60
tgcag 65

<210> SEQ ID NO 822
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 822
gtgactggag ttcagacgtg tgctcttccg atctctggcc tctggacaaa ncgtctacgc 60
tgcag 65

<210> SEQ ID NO 823
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 823
gtgactggag ttcagacgtg tgctcttccg atctgaactt attggacaaa ncgtctacgc 60
tgcag 65

<210> SEQ ID NO 824
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 824
gtgactggag ttcagacgtg tgctcttccg atctcgtatt ggtggacaaa ncgtctacgc 60
tgcag 65

<210> SEQ ID NO 825
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 825
gtgactggag ttcagacgtg tgctcttccg atctgaagca catggacaaa ncgtctacgc 60
tgcag 65

<210> SEQ ID NO 826
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 826
gtgactggag ttcagacgtg tgctcttccg atctcttaat actggacaaa ncgtctacgc 60
tgcag 65

<210> SEQ ID NO 827
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 827
gtgactggag ttcagacgtg tgctcttccg atctgaagtc tttggacaaa ncgtctacgc 60
tgcag 65

<210> SEQ ID NO 828
<211> LENGTH: 65
<212> TYPE: DNA
<213> ORGANISM: Artificial Sequence
<220> FEATURE:

<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 828
gtgactggag ttcagacgtg tgctcttccg atctgaagag gctggacaaa ncgtctacgc 60
tgcag 65

<210> SEQ ID NO 829
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 829
gtgactggag ttcagacgtg tgctcttccg atctcggata actggacaaa ncgtctacgc 60
tgcag 65

<210> SEQ ID NO 830
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 830
gtgactggag ttcagacgtg tgctcttccg atctgaatct ggtggacaaa ncgtctacgc 60
tgcag 65

<210> SEQ ID NO 831
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 831
gtgactggag ttcagacgtg tgctcttccg atctctgatt gatggacaaa ncgtctacgc 60
tgcag 65

<210> SEQ ID NO 832
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 832
gtgactggag ttcagacgtg tgctcttccg atctaatccg tttggacaaa ncgtctacgc 60
tgcag 65

<210> SEQ ID NO 833
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 833
gtgactggag ttcagacgtg tgctcttccg atcttgcgta catggacaaa ncgtctacgc 60
tgcag 65

<210> SEQ ID NO 834
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 834
gtgactggag ttcagacgtg tgctcttccg atctgaatca attggacaaa ncgtctacgc 60
tgcag 65

<210> SEQ ID NO 835
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 835
gtgactggag ttcagacgtg tgctcttccg atcttgagtc agtggacaaa ncgtctacgc 60
tgcag 65

<210> SEQ ID NO 836
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 836
gtgactggag ttcagacgtg tgctcttccg atctgaatgc tctggacaaa ncgtctacgc 60
tgcag 65

<210> SEQ ID NO 837

<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 837
gtgactggag ttcagacgtg tgctcttccg atctgaatat cctggacaaa ncgtctacgc 60
tgcag 65

<210> SEQ ID NO 838
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 838
gtgactggag ttcagacgtg tgctcttccg atctcttatg aatggacaaa ncgtctacgc 60
tgcag 65

<210> SEQ ID NO 839
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 839
gtgactggag ttcagacgtg tgctcttccg atcttcggca cctggacaaa ncgtctacgc 60
tgcag 65

<210> SEQ ID NO 840
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 840
gtgactggag ttcagacgtg tgctcttccg atctaagaag cgtggacaaa ncgtctacgc 60
tgcag 65

<210> SEQ ID NO 841
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 841
gtgactggag ttcagacgtg tgctcttccg atctctcacg attggacaaa ncgtctacgc 60
tgcag 65

<210> SEQ ID NO 842
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 842
gtgactggag ttcagacgtg tgctcttccg atcttcggtc gatggacaaa ncgtctacgc 60
tgcag 65

<210> SEQ ID NO 843
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 843
gtgactggag ttcagacgtg tgctcttccg atcttcggta agtggacaaa ncgtctacgc 60
tgcag 65

<210> SEQ ID NO 844
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 844
gtgactggag ttcagacgtg tgctcttccg atctaagata catggacaaa ncgtctacgc 60
tgcag 65

<210> SEQ ID NO 845
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 845
gtgactggag ttcagacgtg tgctcttccg atctgtcgct gttggacaaa ncgtctacgc 60
tgcag 65

<210> SEQ ID NO 846
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 846
gtgactggag ttcagacgtg tgctcttccg atcttcggat gttggacaaa ncgtctacgc 60
tgcag 65

<210> SEQ ID NO 847
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 847
gtgactggag ttcagacgtg tgctcttccg atctcgagcc ggtggacaaa ncgtctacgc 60
tgcag 65

<210> SEQ ID NO 848
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 848
gtgactggag ttcagacgtg tgctcttccg atctcgatta tctggacaaa ncgtctacgc 60
tgcag 65

<210> SEQ ID NO 849
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 849
gtgactggag ttcagacgtg tgctcttccg atcttcgaag cttggacaaa ncgtctacgc 60
tgcag 65

<210> SEQ ID NO 850
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 850
gtgactggag ttcagacgtg tgctcttccg atctctatca tttggacaaa ncgtctacgc 60
tgcag 65

<210> SEQ ID NO 851
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 851
gtgactggag ttcagacgtg tgctcttccg atctaagtta tctggacaaa ncgtctacgc 60
tgcag 65

<210> SEQ ID NO 852
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 852
gtgactggag ttcagacgtg tgctcttccg atctcgaacg gatggacaaa ncgtctacgc 60
tgcag 65

<210> SEQ ID NO 853
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 853
gtgactggag ttcagacgtg tgctcttccg atctctactg actggacaaa ncgtctacgc 60
tgcag 65

<210> SEQ ID NO 854
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 854
gtgactggag ttcagacgtg tgctcttccg atcttcttaa gttggacaaa ncgtctacgc 60
tgcag 65

<210> SEQ ID NO 855
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 855
gtgactggag ttcagacgtg tgctcttccg atctttagag tctggacaaa ncgtctacgc 60
tgcag 65

<210> SEQ ID NO 856
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 856
gtgactggag ttcagacgtg tgctcttccg atctaagacg aatggacaaa ncgtctacgc 60
tgcag 65

<210> SEQ ID NO 857
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 857
gtgactggag ttcagacgtg tgctcttccg atctttatta tgtggacaaa ncgtctacgc 60
tgcag 65

<210> SEQ ID NO 858
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 858
gtgactggag ttcagacgtg tgctcttccg atctcgctat tatggacaaa ncgtctacgc 60
tgcag 65

<210> SEQ ID NO 859
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 859
gtgactggag ttcagacgtg tgctcttccg atcttctatc agtggacaaa ncgtctacgc 60
tgcag 65

<210> SEQ ID NO 860
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 860
gtgactggag ttcagacgtg tgctcttccg atctcggtgg tatggacaaa ncgtctacgc 60
tgcag 65

<210> SEQ ID NO 861
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 861
gtgactggag ttcagacgtg tgctcttccg atcttcacca attggacaaa ncgtctacgc 60
tgcag 65

<210> SEQ ID NO 862
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 862
gtgactggag ttcagacgtg tgctcttccg atctctggaa gctggacaaa ncgtctacgc 60
tgcag 65

<210> SEQ ID NO 863
<211> LENGTH: 65
<212> TYPE: DNA
<213> ORGANISM: Artificial Sequence
<220> FEATURE:
<223> OTHER INFORMATION: primer
<220> FEATURE:

<221> NAME/KEY: misc_feature
<222> LOCATION: 51
<223> OTHER INFORMATION: n is a, c, g, or t

<400> SEQUENCE: 863
gtgactggag ttcagacgtg tgctcttccg atctcgtaag agtggacaaa ncgtctacgc 60
tgcag 65

<210> SEQ ID NO 864
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 864
gtgactggag ttcagacgtg tgctcttccg atctaagaga gctggacaaa ncgtctacgc 60
tgcag 65

<210> SEQ ID NO 865
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 865
gtgactggag ttcagacgtg tgctcttccg atcttcaacg agtggacaaa ncgtctacgc 60
tgcag 65

<210> SEQ ID NO 866
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 866
gtgactggag ttcagacgtg tgctcttccg atcttgcgag actggacaaa ncgtctacgc 60
tgcag 65

<210> SEQ ID NO 867
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 867
gtgactggag ttcagacgtg tgctcttccg atctcctggt gttggacaaa ncgtctacgc 60
tgcag 65

<210> SEQ ID NO 868
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 868
gtgactggag ttcagacgtg tgctcttccg atctaagtaa gttggacaaa ncgtctacgc 60
tgcag 65

<210> SEQ ID NO 869
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 869
gtgactggag ttcagacgtg tgctcttccg atcttgactg aatggacaaa ncgtctacgc 60
tgcag 65

<210> SEQ ID NO 870
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 870
gtgactggag ttcagacgtg tgctcttccg atctaagact gttggacaaa ncgtctacgc 60
tgcag 65

<210> SEQ ID NO 871
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 871
gtgactggag ttcagacgtg tgctcttccg atctcaatga tgtggacaaa ncgtctacgc 60
tgcag 65

<210> SEQ ID NO 872
<211> LENGTH: 65
<212> TYPE: DNA

<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 872
gtgactggag ttcagacgtg tgctcttccg atctcacagt aatggacaaa ncgtctacgc 60
tgcag 65

<210> SEQ ID NO 873
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 873
gtgactggag ttcagacgtg tgctcttccg atcttggtca tttggacaaa ncgtctacgc 60
tgcag 65

<210> SEQ ID NO 874
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 874
gtgactggag ttcagacgtg tgctcttccg atctcaaccg tgtggacaaa ncgtctacgc 60
tgcag 65

<210> SEQ ID NO 875
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 875
gtgactggag ttcagacgtg tgctcttccg atcttggtgc actggacaaa ncgtctacgc 60
tgcag 65

<210> SEQ ID NO 876
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 876
gtgactggag ttcagacgtg tgctcttccg atctccacaa tgtggacaaa ncgtctacgc 60
tgcag 65

<210> SEQ ID NO 877
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 877
gtgactggag ttcagacgtg tgctcttccg atcttgtgtg cctggacaaa ncgtctacgc 60
tgcag 65

<210> SEQ ID NO 878
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 878
gtgactggag ttcagacgtg tgctcttccg atctcaccac ggtggacaaa ncgtctacgc 60
tgcag 65

<210> SEQ ID NO 879
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n is a, c, g, or t

<400> SEQUENCE: 879
gtgactggag ttcagacgtg tgctcttccg atcttgtgtt aatggacaaa ncgtctacgc 60
tgcag 65

<210> SEQ ID NO 880
<211> LENGTH: 60
<212> TYPE: DNA
<213> ORGANISM: Artificial Sequence
<220> FEATURE:
<223> OTHER INFORMATION: primer

<400> SEQUENCE: 880
gtgactggag ttcagacgtg tgctcttccg atctagcttg gtgtcgctgt ttggagacac 60

<210> SEQ ID NO 881
<211> LENGTH: 60
<212> TYPE: DNA
<213> ORGANISM: Artificial Sequence
<220> FEATURE:

<223> OTHER INFORMATION: primer

<400> SEQUENCE: 881
gtgactggag ttcagacgtg tgctcttccg atctagctta tggtcgctgt ttggagacac 60

<210> SEQ ID NO 882
<211> LENGTH: 60
<212> TYPE: DNA
<213> ORGANISM: Artificial Sequence
<220> FEATURE:
<223> OTHER INFORMATION: primer

<400> SEQUENCE: 882
gtgactggag ttcagacgtg tgctcttccg atctataacg acgtcgctgt ttggagacac 60

<210> SEQ ID NO 883
<211> LENGTH: 60
<212> TYPE: DNA
<213> ORGANISM: Artificial Sequence
<220> FEATURE:
<223> OTHER INFORMATION: primer

<400> SEQUENCE: 883
gtgactggag ttcagacgtg tgctcttccg atctgatgga gtgtcgctgt ttggagacac 60

<210> SEQ ID NO 884
<211> LENGTH: 60
<212> TYPE: DNA
<213> ORGANISM: Artificial Sequence
<220> FEATURE:
<223> OTHER INFORMATION: primer

<400> SEQUENCE: 884
gtgactggag ttcagacgtg tgctcttccg atcttgatct aagtcgctgt ttggagacac 60

<210> SEQ ID NO 885
<211> LENGTH: 60
<212> TYPE: DNA
<213> ORGANISM: Artificial Sequence
<220> FEATURE:
<223> OTHER INFORMATION: primer

<400> SEQUENCE: 885
gtgactggag ttcagacgtg tgctcttccg atctagctat atgtcgctgt ttggagacac 60

<210> SEQ ID NO 886
<211> LENGTH: 60
<212> TYPE: DNA
<213> ORGANISM: Artificial Sequence
<220> FEATURE:
<223> OTHER INFORMATION: primer

<400> SEQUENCE: 886
gtgactggag ttcagacgtg tgctcttccg atctagcaga gagtcgctgt ttggagacac 60

<210> SEQ ID NO 887
<211> LENGTH: 60
<212> TYPE: DNA
<213> ORGANISM: Artificial Sequence
<220> FEATURE:
<223> OTHER INFORMATION: primer

<400> SEQUENCE: 887
gtgactggag ttcagacgtg tgctcttccg atctgacgta aggtcgctgt ttggagacac 60

<210> SEQ ID NO 888
<211> LENGTH: 60
<212> TYPE: DNA
<213> ORGANISM: Artificial Sequence
<220> FEATURE:
<223> OTHER INFORMATION: primer

<400> SEQUENCE: 888
gtgactggag ttcagacgtg tgctcttccg atctaggcct gagtcgctgt ttggagacac 60

<210> SEQ ID NO 889
<211> LENGTH: 60
<212> TYPE: DNA
<213> ORGANISM: Artificial Sequence
<220> FEATURE:
<223> OTHER INFORMATION: primer

<400> SEQUENCE: 889
gtgactggag ttcagacgtg tgctcttccg atcttaagat tagtcgctgt ttggagacac 60

<210> SEQ ID NO 890
<211> LENGTH: 60
<212> TYPE: DNA
<213> ORGANISM: Artificial Sequence
<220> FEATURE:
<223> OTHER INFORMATION: primer

<400> SEQUENCE: 890
gtgactggag ttcagacgtg tgctcttccg atctaggcga atgtcgctgt ttggagacac 60

<210> SEQ ID NO 891
<211> LENGTH: 60
<212> TYPE: DNA
<213> ORGANISM: Artificial Sequence
<220> FEATURE:
<223> OTHER INFORMATION: primer

<400> SEQUENCE: 891
gtgactggag ttcagacgtg tgctcttccg atctttgttc ttgtcgctgt ttggagacac 60

<210> SEQ ID NO 892
<211> LENGTH: 60
<212> TYPE: DNA
<213> ORGANISM: Artificial Sequence
<220> FEATURE:
<223> OTHER INFORMATION: primer

<400> SEQUENCE: 892
gtgactggag ttcagacgtg tgctcttccg atcttactcc tggtcgctgt ttggagacac 60

<210> SEQ ID NO 893
<211> LENGTH: 60
<212> TYPE: DNA
<213> ORGANISM: Artificial Sequence
<220> FEATURE:
<223> OTHER INFORMATION: primer

<400> SEQUENCE: 893
gtgactggag ttcagacgtg tgctcttccg atctgactgg cggtcgctgt ttggagacac 60

<210> SEQ ID NO 894
<211> LENGTH: 60
<212> TYPE: DNA
<213> ORGANISM: Artificial Sequence
<220> FEATURE:
<223> OTHER INFORMATION: primer

<400> SEQUENCE: 894
gtgactggag ttcagacgtg tgctcttccg atctatatat acgtcgctgt ttggagacac 60

<210> SEQ ID NO 895
<211> LENGTH: 60
<212> TYPE: DNA
<213> ORGANISM: Artificial Sequence
<220> FEATURE:
<223> OTHER INFORMATION: primer

<400> SEQUENCE: 895
gtgactggag ttcagacgtg tgctcttccg atcttagatc gggtcgctgt ttggagacac 60

<210> SEQ ID NO 896
<211> LENGTH: 60
<212> TYPE: DNA
<213> ORGANISM: Artificial Sequence
<220> FEATURE:
<223> OTHER INFORMATION: primer

<400> SEQUENCE: 896
gtgactggag ttcagacgtg tgctcttccg atctaggcaa gcgtcgctgt ttggagacac 60

<210> SEQ ID NO 897
<211> LENGTH: 60
<212> TYPE: DNA
<213> ORGANISM: Artificial Sequence
<220> FEATURE:
<223> OTHER INFORMATION: primer

<400> SEQUENCE: 897
gtgactggag ttcagacgtg tgctcttccg atcttccagg tagtcgctgt ttggagacac 60

<210> SEQ ID NO 898
<211> LENGTH: 60
<212> TYPE: DNA
<213> ORGANISM: Artificial Sequence
<220> FEATURE:
<223> OTHER INFORMATION: primer

<400> SEQUENCE: 898
gtgactggag ttcagacgtg tgctcttccg atctaggtca aggtcgctgt ttggagacac 60

<210> SEQ ID NO 899
<211> LENGTH: 60
<212> TYPE: DNA
<213> ORGANISM: Artificial Sequence
<220> FEATURE:
<223> OTHER INFORMATION: primer

<400> SEQUENCE: 899
gtgactggag ttcagacgtg tgctcttccg atcttacact gggtcgctgt ttggagacac 60

<210> SEQ ID NO 900
<211> LENGTH: 60
<212> TYPE: DNA
<213> ORGANISM: Artificial Sequence
<220> FEATURE:
<223> OTHER INFORMATION: primer

<400> SEQUENCE: 900
gtgactggag ttcagacgtg tgctcttccg atcttccttg cggtcgctgt ttggagacac 60

<210> SEQ ID NO 901
<211> LENGTH: 60

<212> TYPE: DNA
<213> ORGANISM: Artificial Sequence
<220> FEATURE:
<223> OTHER INFORMATION: primer

<400> SEQUENCE: 901
gtgactggag ttcagacgtg tgctcttccg atctaggacc tcgtcgctgt ttggagacac 60

<210> SEQ ID NO 902
<211> LENGTH: 60
<212> TYPE: DNA
<213> ORGANISM: Artificial Sequence
<220> FEATURE:
<223> OTHER INFORMATION: primer

<400> SEQUENCE: 902
gtgactggag ttcagacgtg tgctcttccg atcttaagca ttgtcgctgt ttggagacac 60

<210> SEQ ID NO 903
<211> LENGTH: 60
<212> TYPE: DNA
<213> ORGANISM: Artificial Sequence
<220> FEATURE:
<223> OTHER INFORMATION: primer

<400> SEQUENCE: 903
gtgactggag ttcagacgtg tgctcttccg atctaggata ttgtcgctgt ttggagacac 60

<210> SEQ ID NO 904
<211> LENGTH: 60
<212> TYPE: DNA
<213> ORGANISM: Artificial Sequence
<220> FEATURE:
<223> OTHER INFORMATION: primer

<400> SEQUENCE: 904
gtgactggag ttcagacgtg tgctcttccg atctaatcgt tagtcgctgt ttggagacac 60

<210> SEQ ID NO 905
<211> LENGTH: 60
<212> TYPE: DNA
<213> ORGANISM: Artificial Sequence
<220> FEATURE:
<223> OTHER INFORMATION: primer

<400> SEQUENCE: 905
gtgactggag ttcagacgtg tgctcttccg atctgtctac atgtcgctgt ttggagacac 60

<210> SEQ ID NO 906
<211> LENGTH: 60
<212> TYPE: DNA
<213> ORGANISM: Artificial Sequence
<220> FEATURE:
<223> OTHER INFORMATION: primer

<400> SEQUENCE: 906
gtgactggag ttcagacgtg tgctcttccg atctcgctgc tcgtcgctgt ttggagacac 60

<210> SEQ ID NO 907
<211> LENGTH: 60
<212> TYPE: DNA
<213> ORGANISM: Artificial Sequence
<220> FEATURE:
<223> OTHER INFORMATION: primer

<400> SEQUENCE: 907
gtgactggag ttcagacgtg tgctcttccg atctgatcaa cagtcgctgt ttggagacac 60

<210> SEQ ID NO 908
<211> LENGTH: 60
<212> TYPE: DNA
<213> ORGANISM: Artificial Sequence
<220> FEATURE:
<223> OTHER INFORMATION: primer

<400> SEQUENCE: 908
gtgactggag ttcagacgtg tgctcttccg atctcgaagg acgtcgctgt ttggagacac 60

<210> SEQ ID NO 909
<211> LENGTH: 60
<212> TYPE: DNA
<213> ORGANISM: Artificial Sequence
<220> FEATURE:
<223> OTHER INFORMATION: primer

<400> SEQUENCE: 909
gtgactggag ttcagacgtg tgctcttccg atctgatgcc gggtcgctgt ttggagacac 60

<210> SEQ ID NO 910
<211> LENGTH: 60
<212> TYPE: DNA
<213> ORGANISM: Artificial Sequence
<220> FEATURE:
<223> OTHER INFORMATION: primer

<400> SEQUENCE: 910
gtgactggag ttcagacgtg tgctcttccg atctctacga aggtcgctgt ttggagacac 60

<210> SEQ ID NO 911
<211> LENGTH: 60
<212> TYPE: DNA
<213> ORGANISM: Artificial Sequence
<220> FEATURE:
<223> OTHER INFORMATION: primer

<400> SEQUENCE: 911
gtgactggag ttcagacgtg tgctcttccg atctgatgcg tcgtcgctgt ttggagacac 60

<210> SEQ ID NO 912
<211> LENGTH: 60
<212> TYPE: DNA
<213> ORGANISM: Artificial Sequence
<220> FEATURE:
<223> OTHER INFORMATION: primer

<400> SEQUENCE: 912
gtgactggag ttcagacgtg tgctcttccg atctctacgg cagtcgctgt ttggagacac 60

<210> SEQ ID NO 913
<211> LENGTH: 60
<212> TYPE: DNA
<213> ORGANISM: Artificial Sequence
<220> FEATURE:
<223> OTHER INFORMATION: primer

<400> SEQUENCE: 913
gtgactggag ttcagacgtg tgctcttccg atctgattcc ttgtcgctgt ttggagacac 60

<210> SEQ ID NO 914
<211> LENGTH: 60
<212> TYPE: DNA
<213> ORGANISM: Artificial Sequence
<220> FEATURE:
<223> OTHER INFORMATION: primer

<400> SEQUENCE: 914
gtgactggag ttcagacgtg tgctcttccg atctctactc gagtcgctgt ttggagacac 60

<210> SEQ ID NO 915
<211> LENGTH: 60
<212> TYPE: DNA
<213> ORGANISM: Artificial Sequence
<220> FEATURE:
<223> OTHER INFORMATION: primer

<400> SEQUENCE: 915
gtgactggag ttcagacgtg tgctcttccg atctgattcg aggtcgctgt ttggagacac 60

<210> SEQ ID NO 916
<211> LENGTH: 60
<212> TYPE: DNA
<213> ORGANISM: Artificial Sequence
<220> FEATURE:
<223> OTHER INFORMATION: primer

<400> SEQUENCE: 916
gtgactggag ttcagacgtg tgctcttccg atctaatcgg cggtcgctgt ttggagacac 60

<210> SEQ ID NO 917
<211> LENGTH: 60
<212> TYPE: DNA
<213> ORGANISM: Artificial Sequence
<220> FEATURE:
<223> OTHER INFORMATION: primer

<400> SEQUENCE: 917
gtgactggag ttcagacgtg tgctcttccg atctttcgcc gagtcgctgt ttggagacac 60

<210> SEQ ID NO 918
<211> LENGTH: 60
<212> TYPE: DNA
<213> ORGANISM: Artificial Sequence
<220> FEATURE:
<223> OTHER INFORMATION: primer

<400> SEQUENCE: 918
gtgactggag ttcagacgtg tgctcttccg atctctggcc tcgtcgctgt ttggagacac 60

<210> SEQ ID NO 919
<211> LENGTH: 60
<212> TYPE: DNA
<213> ORGANISM: Artificial Sequence
<220> FEATURE:
<223> OTHER INFORMATION: primer

<400> SEQUENCE: 919
gtgactggag ttcagacgtg tgctcttccg atctgaactt atgtcgctgt ttggagacac 60

<210> SEQ ID NO 920
<211> LENGTH: 60
<212> TYPE: DNA
<213> ORGANISM: Artificial Sequence
<220> FEATURE:
<223> OTHER INFORMATION: primer

<400> SEQUENCE: 920
gtgactggag ttcagacgtg tgctcttccg atctcgtatt gggtcgctgt ttggagacac 60

<210> SEQ ID NO 921
<211> LENGTH: 60
<212> TYPE: DNA
<213> ORGANISM: Artificial Sequence
<220> FEATURE:
<223> OTHER INFORMATION: primer

<400> SEQUENCE: 921
gtgactggag ttcagacgtg tgctcttccg atctgaagca cagtcgctgt ttggagacac 60

<210> SEQ ID NO 922
<211> LENGTH: 60
<212> TYPE: DNA
<213> ORGANISM: Artificial Sequence
<220> FEATURE:
<223> OTHER INFORMATION: primer

<400> SEQUENCE: 922
gtgactggag ttcagacgtg tgctcttccg atctcttaat acgtcgctgt ttggagacac 60

<210> SEQ ID NO 923
<211> LENGTH: 60
<212> TYPE: DNA
<213> ORGANISM: Artificial Sequence
<220> FEATURE:
<223> OTHER INFORMATION: primer

<400> SEQUENCE: 923
gtgactggag ttcagacgtg tgctcttccg atctgaagtc ttgtcgctgt ttggagacac 60

<210> SEQ ID NO 924
<211> LENGTH: 60
<212> TYPE: DNA
<213> ORGANISM: Artificial Sequence
<220> FEATURE:
<223> OTHER INFORMATION: primer

<400> SEQUENCE: 924
gtgactggag ttcagacgtg tgctcttccg atctgaagag gcgtcgctgt ttggagacac 60

<210> SEQ ID NO 925
<211> LENGTH: 60
<212> TYPE: DNA
<213> ORGANISM: Artificial Sequence
<220> FEATURE:
<223> OTHER INFORMATION: primer

<400> SEQUENCE: 925
gtgactggag ttcagacgtg tgctcttccg atctcggata acgtcgctgt ttggagacac 60

<210> SEQ ID NO 926
<211> LENGTH: 60
<212> TYPE: DNA
<213> ORGANISM: Artificial Sequence
<220> FEATURE:
<223> OTHER INFORMATION: primer

<400> SEQUENCE: 926
gtgactggag ttcagacgtg tgctcttccg atctgaatct gggtcgctgt ttggagacac 60

<210> SEQ ID NO 927
<211> LENGTH: 60
<212> TYPE: DNA
<213> ORGANISM: Artificial Sequence
<220> FEATURE:
<223> OTHER INFORMATION: primer

<400> SEQUENCE: 927
gtgactggag ttcagacgtg tgctcttccg atctctgatt gagtcgctgt ttggagacac 60

<210> SEQ ID NO 928
<211> LENGTH: 60
<212> TYPE: DNA
<213> ORGANISM: Artificial Sequence
<220> FEATURE:
<223> OTHER INFORMATION: primer

<400> SEQUENCE: 928
gtgactggag ttcagacgtg tgctcttccg atctaatccg ttgtcgctgt ttggagacac 60

<210> SEQ ID NO 929
<211> LENGTH: 60
<212> TYPE: DNA
<213> ORGANISM: Artificial Sequence
<220> FEATURE:
<223> OTHER INFORMATION: primer

<400> SEQUENCE: 929
gtgactggag ttcagacgtg tgctcttccg atcttgcgta cagtcgctgt ttggagacac 60

<210> SEQ ID NO 930
<211> LENGTH: 60
<212> TYPE: DNA
<213> ORGANISM: Artificial Sequence
<220> FEATURE:
<223> OTHER INFORMATION: primer

<400> SEQUENCE: 930
gtgactggag ttcagacgtg tgctcttccg atctgaatca atgtcgctgt ttggagacac 60

<210> SEQ ID NO 931
<211> LENGTH: 60
<212> TYPE: DNA
<213> ORGANISM: Artificial Sequence
<220> FEATURE:
<223> OTHER INFORMATION: primer

<400> SEQUENCE: 931
gtgactggag ttcagacgtg tgctcttccg atcttgagtc aggtcgctgt ttggagacac 60

<210> SEQ ID NO 932
<211> LENGTH: 60
<212> TYPE: DNA
<213> ORGANISM: Artificial Sequence
<220> FEATURE:
<223> OTHER INFORMATION: primer

<400> SEQUENCE: 932
gtgactggag ttcagacgtg tgctcttccg atctgaatgc tcgtcgctgt ttggagacac 60

<210> SEQ ID NO 933
<211> LENGTH: 60
<212> TYPE: DNA
<213> ORGANISM: Artificial Sequence
<220> FEATURE:
<223> OTHER INFORMATION: primer

<400> SEQUENCE: 933
gtgactggag ttcagacgtg tgctcttccg atctgaatat ccgtcgctgt ttggagacac 60

<210> SEQ ID NO 934

<211> LENGTH: 60
<212> TYPE: DNA
<213> ORGANISM: Artificial Sequence
<220> FEATURE:
<223> OTHER INFORMATION: primer

<400> SEQUENCE: 934
gtgactggag ttcagacgtg tgctcttccg atctcttatg aagtcgctgt ttggagacac 60

<210> SEQ ID NO 935
<211> LENGTH: 60
<212> TYPE: DNA
<213> ORGANISM: Artificial Sequence
<220> FEATURE:
<223> OTHER INFORMATION: primer

<400> SEQUENCE: 935
gtgactggag ttcagacgtg tgctcttccg atcttcggca ccgtcgctgt ttggagacac 60

<210> SEQ ID NO 936
<211> LENGTH: 60
<212> TYPE: DNA
<213> ORGANISM: Artificial Sequence
<220> FEATURE:
<223> OTHER INFORMATION: primer

<400> SEQUENCE: 936
gtgactggag ttcagacgtg tgctcttccg atctaagaag cggtcgctgt ttggagacac 60

<210> SEQ ID NO 937
<211> LENGTH: 60
<212> TYPE: DNA
<213> ORGANISM: Artificial Sequence
<220> FEATURE:
<223> OTHER INFORMATION: primer

<400> SEQUENCE: 937
gtgactggag ttcagacgtg tgctcttccg atctctcacg atgtcgctgt ttggagacac 60

<210> SEQ ID NO 938
<211> LENGTH: 60
<212> TYPE: DNA
<213> ORGANISM: Artificial Sequence
<220> FEATURE:
<223> OTHER INFORMATION: primer

<400> SEQUENCE: 938
gtgactggag ttcagacgtg tgctcttccg atcttcggtc gagtcgctgt ttggagacac 60

<210> SEQ ID NO 939
<211> LENGTH: 60
<212> TYPE: DNA
<213> ORGANISM: Artificial Sequence
<220> FEATURE:
<223> OTHER INFORMATION: primer

<400> SEQUENCE: 939
gtgactggag ttcagacgtg tgctcttccg atcttcggta aggtcgctgt ttggagacac 60

<210> SEQ ID NO 940
<211> LENGTH: 60
<212> TYPE: DNA
<213> ORGANISM: Artificial Sequence
<220> FEATURE:
<223> OTHER INFORMATION: primer

<400> SEQUENCE: 940
gtgactggag ttcagacgtg tgctcttccg atctaagata cagtcgctgt ttggagacac 60

<210> SEQ ID NO 941
<211> LENGTH: 60
<212> TYPE: DNA
<213> ORGANISM: Artificial Sequence
<220> FEATURE:
<223> OTHER INFORMATION: primer

<400> SEQUENCE: 941
gtgactggag ttcagacgtg tgctcttccg atctgtcgct gtgtcgctgt ttggagacac 60

<210> SEQ ID NO 942
<211> LENGTH: 60
<212> TYPE: DNA
<213> ORGANISM: Artificial Sequence
<220> FEATURE:
<223> OTHER INFORMATION: primer

<400> SEQUENCE: 942
gtgactggag ttcagacgtg tgctcttccg atcttcggat gtgtcgctgt ttggagacac 60

<210> SEQ ID NO 943
<211> LENGTH: 60
<212> TYPE: DNA
<213> ORGANISM: Artificial Sequence
<220> FEATURE:
<223> OTHER INFORMATION: primer

<400> SEQUENCE: 943
gtgactggag ttcagacgtg tgctcttccg atctcgagcc gggtcgctgt ttggagacac 60

<210> SEQ ID NO 944
<211> LENGTH: 60
<212> TYPE: DNA
<213> ORGANISM: Artificial Sequence
<220> FEATURE:
<223> OTHER INFORMATION: primer

<400> SEQUENCE: 944
gtgactggag ttcagacgtg tgctcttccg atctcgatta tcgtcgctgt ttggagacac 60

<210> SEQ ID NO 945
<211> LENGTH: 60
<212> TYPE: DNA
<213> ORGANISM: Artificial Sequence
<220> FEATURE:
<223> OTHER INFORMATION: primer

<400> SEQUENCE: 945
gtgactggag ttcagacgtg tgctcttccg atcttcgaag ctgtcgctgt ttggagacac 60

<210> SEQ ID NO 946
<211> LENGTH: 60
<212> TYPE: DNA
<213> ORGANISM: Artificial Sequence
<220> FEATURE:
<223> OTHER INFORMATION: primer

<400> SEQUENCE: 946
gtgactggag ttcagacgtg tgctcttccg atctctatca ttgtcgctgt ttggagacac 60

<210> SEQ ID NO 947
<211> LENGTH: 60
<212> TYPE: DNA

<213> ORGANISM: Artificial Sequence
<220> FEATURE:
<223> OTHER INFORMATION: primer

<400> SEQUENCE: 947
gtgactggag ttcagacgtg tgctcttccg atctaagtta tcgtcgctgt ttggagacac 60

<210> SEQ ID NO 948
<211> LENGTH: 60
<212> TYPE: DNA
<213> ORGANISM: Artificial Sequence
<220> FEATURE:
<223> OTHER INFORMATION: primer

<400> SEQUENCE: 948
gtgactggag ttcagacgtg tgctcttccg atctcgaacg gagtcgctgt ttggagacac 60

<210> SEQ ID NO 949
<211> LENGTH: 60
<212> TYPE: DNA
<213> ORGANISM: Artificial Sequence
<220> FEATURE:
<223> OTHER INFORMATION: primer

<400> SEQUENCE: 949
gtgactggag ttcagacgtg tgctcttccg atctctactg acgtcgctgt ttggagacac 60

<210> SEQ ID NO 950
<211> LENGTH: 60
<212> TYPE: DNA
<213> ORGANISM: Artificial Sequence
<220> FEATURE:
<223> OTHER INFORMATION: primer

<400> SEQUENCE: 950
gtgactggag ttcagacgtg tgctcttccg atcttcttaa gtgtcgctgt ttggagacac 60

<210> SEQ ID NO 951
<211> LENGTH: 60
<212> TYPE: DNA
<213> ORGANISM: Artificial Sequence
<220> FEATURE:
<223> OTHER INFORMATION: primer

<400> SEQUENCE: 951
gtgactggag ttcagacgtg tgctcttccg atctttagag tcgtcgctgt ttggagacac 60

<210> SEQ ID NO 952
<211> LENGTH: 60
<212> TYPE: DNA
<213> ORGANISM: Artificial Sequence
<220> FEATURE:
<223> OTHER INFORMATION: primer

<400> SEQUENCE: 952
gtgactggag ttcagacgtg tgctcttccg atctaagacg aagtcgctgt ttggagacac 60

<210> SEQ ID NO 953
<211> LENGTH: 60
<212> TYPE: DNA
<213> ORGANISM: Artificial Sequence
<220> FEATURE:
<223> OTHER INFORMATION: primer

<400> SEQUENCE: 953
gtgactggag ttcagacgtg tgctcttccg atctttatta tggtcgctgt ttggagacac 60

<210> SEQ ID NO 954
<211> LENGTH: 60
<212> TYPE: DNA
<213> ORGANISM: Artificial Sequence
<220> FEATURE:
<223> OTHER INFORMATION: primer

<400> SEQUENCE: 954
gtgactggag ttcagacgtg tgctcttccg atctcgctat tagtcgctgt ttggagacac 60

<210> SEQ ID NO 955
<211> LENGTH: 60
<212> TYPE: DNA
<213> ORGANISM: Artificial Sequence
<220> FEATURE:
<223> OTHER INFORMATION: primer

<400> SEQUENCE: 955
gtgactggag ttcagacgtg tgctcttccg atcttctatc aggtcgctgt ttggagacac 60

<210> SEQ ID NO 956
<211> LENGTH: 60
<212> TYPE: DNA
<213> ORGANISM: Artificial Sequence
<220> FEATURE:
<223> OTHER INFORMATION: primer

<400> SEQUENCE: 956
gtgactggag ttcagacgtg tgctcttccg atctcggtgg tagtcgctgt ttggagacac 60

<210> SEQ ID NO 957
<211> LENGTH: 60
<212> TYPE: DNA
<213> ORGANISM: Artificial Sequence
<220> FEATURE:
<223> OTHER INFORMATION: primer

<400> SEQUENCE: 957
gtgactggag ttcagacgtg tgctcttccg atcttcacca atgtcgctgt ttggagacac 60

<210> SEQ ID NO 958
<211> LENGTH: 60
<212> TYPE: DNA
<213> ORGANISM: Artificial Sequence
<220> FEATURE:
<223> OTHER INFORMATION: primer

<400> SEQUENCE: 958
gtgactggag ttcagacgtg tgctcttccg atctctggaa gcgtcgctgt ttggagacac 60

<210> SEQ ID NO 959
<211> LENGTH: 60
<212> TYPE: DNA
<213> ORGANISM: Artificial Sequence
<220> FEATURE:
<223> OTHER INFORMATION: primer

<400> SEQUENCE: 959
gtgactggag ttcagacgtg tgctcttccg atctcgtaag aggtcgctgt ttggagacac 60

<210> SEQ ID NO 960
<211> LENGTH: 60
<212> TYPE: DNA
<213> ORGANISM: Artificial Sequence
<220> FEATURE:

<223> OTHER INFORMATION: primer

<400> SEQUENCE: 960
gtgactggag ttcagacgtg tgctcttccg atctaagaga gcgtcgctgt ttggagacac 60

<210> SEQ ID NO 961
<211> LENGTH: 60
<212> TYPE: DNA
<213> ORGANISM: Artificial Sequence
<220> FEATURE:
<223> OTHER INFORMATION: primer

<400> SEQUENCE: 961
gtgactggag ttcagacgtg tgctcttccg atcttcaacg aggtcgctgt ttggagacac 60

<210> SEQ ID NO 962
<211> LENGTH: 60
<212> TYPE: DNA
<213> ORGANISM: Artificial Sequence
<220> FEATURE:
<223> OTHER INFORMATION: primer

<400> SEQUENCE: 962
gtgactggag ttcagacgtg tgctcttccg atcttgcgag acgtcgctgt ttggagacac 60

<210> SEQ ID NO 963
<211> LENGTH: 60
<212> TYPE: DNA
<213> ORGANISM: Artificial Sequence
<220> FEATURE:
<223> OTHER INFORMATION: primer

<400> SEQUENCE: 963
gtgactggag ttcagacgtg tgctcttccg atctcctggt gtgtcgctgt ttggagacac 60

<210> SEQ ID NO 964
<211> LENGTH: 60
<212> TYPE: DNA
<213> ORGANISM: Artificial Sequence
<220> FEATURE:
<223> OTHER INFORMATION: primer

<400> SEQUENCE: 964
gtgactggag ttcagacgtg tgctcttccg atctaagtaa gtgtcgctgt ttggagacac 60

<210> SEQ ID NO 965
<211> LENGTH: 60
<212> TYPE: DNA
<213> ORGANISM: Artificial Sequence
<220> FEATURE:
<223> OTHER INFORMATION: primer

<400> SEQUENCE: 965
gtgactggag ttcagacgtg tgctcttccg atcttgactg aagtcgctgt ttggagacac 60

<210> SEQ ID NO 966
<211> LENGTH: 60
<212> TYPE: DNA
<213> ORGANISM: Artificial Sequence
<220> FEATURE:
<223> OTHER INFORMATION: primer

<400> SEQUENCE: 966
gtgactggag ttcagacgtg tgctcttccg atctaagact gtgtcgctgt ttggagacac 60

<210> SEQ ID NO 967
<211> LENGTH: 60
<212> TYPE: DNA
<213> ORGANISM: Artificial Sequence
<220> FEATURE:
<223> OTHER INFORMATION: primer

<400> SEQUENCE: 967
gtgactggag ttcagacgtg tgctcttccg atctcaatga tggtcgctgt ttggagacac 60

<210> SEQ ID NO 968
<211> LENGTH: 60
<212> TYPE: DNA
<213> ORGANISM: Artificial Sequence
<220> FEATURE:
<223> OTHER INFORMATION: primer

<400> SEQUENCE: 968
gtgactggag ttcagacgtg tgctcttccg atctcacagt aagtcgctgt ttggagacac 60

<210> SEQ ID NO 969
<211> LENGTH: 60
<212> TYPE: DNA
<213> ORGANISM: Artificial Sequence
<220> FEATURE:
<223> OTHER INFORMATION: primer

<400> SEQUENCE: 969
gtgactggag ttcagacgtg tgctcttccg atcttggtca ttgtcgctgt ttggagacac 60

<210> SEQ ID NO 970
<211> LENGTH: 60
<212> TYPE: DNA
<213> ORGANISM: Artificial Sequence
<220> FEATURE:
<223> OTHER INFORMATION: primer

<400> SEQUENCE: 970
gtgactggag ttcagacgtg tgctcttccg atctcaaccg tggtcgctgt ttggagacac 60

<210> SEQ ID NO 971
<211> LENGTH: 60
<212> TYPE: DNA
<213> ORGANISM: Artificial Sequence
<220> FEATURE:
<223> OTHER INFORMATION: primer

<400> SEQUENCE: 971
gtgactggag ttcagacgtg tgctcttccg atcttggtgc acgtcgctgt ttggagacac 60

<210> SEQ ID NO 972
<211> LENGTH: 60
<212> TYPE: DNA
<213> ORGANISM: Artificial Sequence
<220> FEATURE:
<223> OTHER INFORMATION: primer

<400> SEQUENCE: 972
gtgactggag ttcagacgtg tgctcttccg atctccacaa tggtcgctgt ttggagacac 60

<210> SEQ ID NO 973
<211> LENGTH: 60
<212> TYPE: DNA
<213> ORGANISM: Artificial Sequence
<220> FEATURE:
<223> OTHER INFORMATION: primer

<400> SEQUENCE: 973
gtgactggag ttcagacgtg tgctcttccg atcttgtgtg ccgtcgctgt ttggagacac 60

<210> SEQ ID NO 974
<211> LENGTH: 60
<212> TYPE: DNA
<213> ORGANISM: Artificial Sequence
<220> FEATURE:
<223> OTHER INFORMATION: primer

<400> SEQUENCE: 974
gtgactggag ttcagacgtg tgctcttccg atctcaccac gggtcgctgt ttggagacac 60

<210> SEQ ID NO 975
<211> LENGTH: 60
<212> TYPE: DNA
<213> ORGANISM: Artificial Sequence
<220> FEATURE:
<223> OTHER INFORMATION: primer

<400> SEQUENCE: 975
gtgactggag ttcagacgtg tgctcttccg atcttgtgtt aagtcgctgt ttggagacac 60

<210> SEQ ID NO 976
<211> LENGTH: 65
<212> TYPE: DNA
<213> ORGANISM: Artificial Sequence
<220> FEATURE:
<223> OTHER INFORMATION: primer

<400> SEQUENCE: 976
gtgactggag ttcagacgtg tgctcttccg atctagcgct cggaaacacg gacacccaaa 60
gtagt 65

<210> SEQ ID NO 977
<211> LENGTH: 65
<212> TYPE: DNA
<213> ORGANISM: Artificial Sequence
<220> FEATURE:
<223> OTHER INFORMATION: primer

<400> SEQUENCE: 977
gtgactggag ttcagacgtg tgctcttccg atcttgcgct tcgaaacacg gacacccaaa 60
gtagt 65

<210> SEQ ID NO 978
<211> LENGTH: 65
<212> TYPE: DNA
<213> ORGANISM: Artificial Sequence
<220> FEATURE:
<223> OTHER INFORMATION: primer

<400> SEQUENCE: 978
gtgactggag ttcagacgtg tgctcttccg atctagcttg gtgaaacacg gacacccaaa 60
gtagt 65

<210> SEQ ID NO 979
<211> LENGTH: 65
<212> TYPE: DNA
<213> ORGANISM: Artificial Sequence
<220> FEATURE:
<223> OTHER INFORMATION: primer

<400> SEQUENCE: 979
gtgactggag ttcagacgtg tgctcttccg atctagctta tggaaacacg gacacccaaa 60
gtagt 65

<210> SEQ ID NO 980
<211> LENGTH: 65
<212> TYPE: DNA
<213> ORGANISM: Artificial Sequence
<220> FEATURE:
<223> OTHER INFORMATION: primer

<400> SEQUENCE: 980
gtgactggag ttcagacgtg tgctcttccg atctataacg acgaaacacg gacacccaaa 60
gtagt 65

<210> SEQ ID NO 981
<211> LENGTH: 65
<212> TYPE: DNA
<213> ORGANISM: Artificial Sequence
<220> FEATURE:
<223> OTHER INFORMATION: primer

<400> SEQUENCE: 981
gtgactggag ttcagacgtg tgctcttccg atctgatgga gtgaaacacg gacacccaaa 60
gtagt 65

<210> SEQ ID NO 982
<211> LENGTH: 65
<212> TYPE: DNA
<213> ORGANISM: Artificial Sequence
<220> FEATURE:
<223> OTHER INFORMATION: primer

<400> SEQUENCE: 982
gtgactggag ttcagacgtg tgctcttccg atcttgatct aagaaacacg gacacccaaa 60
gtagt 65

<210> SEQ ID NO 983
<211> LENGTH: 65
<212> TYPE: DNA
<213> ORGANISM: Artificial Sequence
<220> FEATURE:
<223> OTHER INFORMATION: primer

<400> SEQUENCE: 983
gtgactggag ttcagacgtg tgctcttccg atctagctat atgaaacacg gacacccaaa 60
gtagt 65

<210> SEQ ID NO 984
<211> LENGTH: 65
<212> TYPE: DNA
<213> ORGANISM: Artificial Sequence
<220> FEATURE:
<223> OTHER INFORMATION: primer

<400> SEQUENCE: 984
gtgactggag ttcagacgtg tgctcttccg atctagcaga gagaaacacg gacacccaaa 60
gtagt 65

<210> SEQ ID NO 985
<211> LENGTH: 65
<212> TYPE: DNA

<213> ORGANISM: Artificial Sequence
<220> FEATURE:
<223> OTHER INFORMATION: primer

<400> SEQUENCE: 985
gtgactggag ttcagacgtg tgctcttccg atctgacgta aggaaacacg gacacccaaa 60
gtagt 65

<210> SEQ ID NO 986
<211> LENGTH: 65
<212> TYPE: DNA
<213> ORGANISM: Artificial Sequence
<220> FEATURE:
<223> OTHER INFORMATION: primer

<400> SEQUENCE: 986
gtgactggag ttcagacgtg tgctcttccg atctaggcct gagaaacacg gacacccaaa 60
gtagt 65

<210> SEQ ID NO 987
<211> LENGTH: 65
<212> TYPE: DNA
<213> ORGANISM: Artificial Sequence
<220> FEATURE:
<223> OTHER INFORMATION: primer

<400> SEQUENCE: 987
gtgactggag ttcagacgtg tgctcttccg atcttaagat tagaaacacg gacacccaaa 60
gtagt 65

<210> SEQ ID NO 988
<211> LENGTH: 65
<212> TYPE: DNA
<213> ORGANISM: Artificial Sequence
<220> FEATURE:
<223> OTHER INFORMATION: primer

<400> SEQUENCE: 988
gtgactggag ttcagacgtg tgctcttccg atctaggcga atgaaacacg gacacccaaa 60
gtagt 65

<210> SEQ ID NO 989
<211> LENGTH: 65
<212> TYPE: DNA
<213> ORGANISM: Artificial Sequence
<220> FEATURE:
<223> OTHER INFORMATION: primer

<400> SEQUENCE: 989
gtgactggag ttcagacgtg tgctcttccg atctttgttc ttgaaacacg gacacccaaa 60
gtagt 65

<210> SEQ ID NO 990
<211> LENGTH: 65
<212> TYPE: DNA
<213> ORGANISM: Artificial Sequence
<220> FEATURE:
<223> OTHER INFORMATION: primer

<400> SEQUENCE: 990
gtgactggag ttcagacgtg tgctcttccg atcttactcc tggaaacacg gacacccaaa 60
gtagt 65

<210> SEQ ID NO 991
<211> LENGTH: 22
<212> TYPE: DNA
<213> ORGANISM: Artificial Sequence
<220> FEATURE:
<223> OTHER INFORMATION: part of primer

<400> SEQUENCE: 991
ctacacgacg ctcttccgat ct 22

<210> SEQ ID NO 992
<211> LENGTH: 8
<212> TYPE: DNA
<213> ORGANISM: Artificial Sequence
<220> FEATURE:
<223> OTHER INFORMATION: part of primer

<400> SEQUENCE: 992 ccaatact 8

<210> SEQ ID NO 993
<211> LENGTH: 20
<212> TYPE: DNA
<213> ORGANISM: Artificial Sequence
<220> FEATURE:
<223> OTHER INFORMATION: part of primer

<400> SEQUENCE: 993
gaccccaaaa tcagcgaaat 20

<210> SEQ ID NO 994
<211> LENGTH: 22
<212> TYPE: DNA
<213> ORGANISM: Artificial Sequence
<220> FEATURE:
<223> OTHER INFORMATION: part of primer

<400> SEQUENCE: 994
gggagccttg aatacaccaa aa 22

<210> SEQ ID NO 995
<211> LENGTH: 21
<212> TYPE: DNA
<213> ORGANISM: Artificial Sequence
<220> FEATURE:
<223> OTHER INFORMATION: part of primer

<400> SEQUENCE: 995
ggcattcgta ttgcgccgct a 21

<210> SEQ ID NO 996
<211> LENGTH: 18
<212> TYPE: DNA
<213> ORGANISM: Artificial Sequence
<220> FEATURE:
<223> OTHER INFORMATION: part of primer

<400> SEQUENCE: 996
ctcatggart ggctaaag 18

<210> SEQ ID NO 997
<211> LENGTH: 17
<212> TYPE: DNA
<213> ORGANISM: Artificial Sequence
<220> FEATURE:

<223> OTHER INFORMATION: part of primer

<400> SEQUENCE: 997
gccttctcca tcttctg 17

<210> SEQ ID NO 998
<211> LENGTH: 17
<212> TYPE: DNA
<213> ORGANISM: Artificial Sequence
<220> FEATURE:
<223> OTHER INFORMATION: part of primer

<400> SEQUENCE: 998
tcctccggcc cctgaat 17

<210> SEQ ID NO 999
<211> LENGTH: 34
<212> TYPE: DNA
<213> ORGANISM: Artificial Sequence
<220> FEATURE:
<223> OTHER INFORMATION: part of primer

<400> SEQUENCE: 999
gtgactggag ttcagacgtg tgctcttccg atct 34

<210> SEQ ID NO 1000
<211> LENGTH: 8
<212> TYPE: DNA
<213> ORGANISM: Artificial Sequence
<220> FEATURE:
<223> OTHER INFORMATION: part of primer

<400> SEQUENCE: 1000 agcttggt 8

<210> SEQ ID NO 1001
<211> LENGTH: 24
<212> TYPE: DNA
<213> ORGANISM: Artificial Sequence
<220> FEATURE:
<223> OTHER INFORMATION: part of primer

<400> SEQUENCE: 1001
tctggttact gccagttgaa tctg 24

<210> SEQ ID NO 1002
<211> LENGTH: 21
<212> TYPE: DNA
<213> ORGANISM: Artificial Sequence
<220> FEATURE:
<223> OTHER INFORMATION: part of primer

<400> SEQUENCE: 1002
tgtagcacga ttgcagcatt g 21

<210> SEQ ID NO 1003
<211> LENGTH: 22
<212> TYPE: DNA
<213> ORGANISM: Artificial Sequence
<220> FEATURE:
<223> OTHER INFORMATION: part of primer

<400> SEQUENCE: 1003
ggcaaatgct ttcgctctgg tc 22

<210> SEQ ID NO 1004
<211> LENGTH: 23
<212> TYPE: DNA
<213> ORGANISM: Artificial Sequence
<220> FEATURE:
<223> OTHER INFORMATION: part of primer
<220> FEATURE:
<221> NAME/KEY: misc_feature
<222> LOCATION: (9)..(9)
<223> OTHER INFORMATION: n is a, c, g, or t

<400> SEQUENCE: 1004
tggacaaanc gtctacgctg cag 23

<210> SEQ ID NO 1005
<211> LENGTH: 18
<212> TYPE: DNA
<213> ORGANISM: Artificial Sequence
<220> FEATURE:
<223> OTHER INFORMATION: part of primer

<400> SEQUENCE: 1005
gtcgctgttt ggagacac 18

<210> SEQ ID NO 1006
<211> LENGTH: 23
<212> TYPE: DNA
<213> ORGANISM: Artificial Sequence
<220> FEATURE:
<223> OTHER INFORMATION: part of primer

<400> SEQUENCE: 1006
gaaacacgga cacccaaagt agt 23

<210> SEQ ID NO 1007
<211> LENGTH: 26
<212> TYPE: DNA
<213> ORGANISM: Artificial Sequence
<220> FEATURE:
<223> OTHER INFORMATION: primer part

<400> SEQUENCE: 1007
catgtatagc atggaaccaa gtaaca 26

<210> SEQ ID NO 1008
<211> LENGTH: 28
<212> TYPE: DNA
<213> ORGANISM: Artificial Sequence
<220> FEATURE:
<223> OTHER INFORMATION: primer part

<400> SEQUENCE: 1008
cgttattaac aataagtagg gactgggt 28

<210> SEQ ID NO 1009
<211> LENGTH: 32
<212> TYPE: DNA
<213> ORGANISM: Artificial Sequence
<220> FEATURE:
<223> OTHER INFORMATION: primer part

<400> SEQUENCE: 1009
ccatcaatat tcttaaacac aaattcccta ag 32

<210> SEQ ID NO 1010
<211> LENGTH: 21
<212> TYPE: DNA

<213> ORGANISM: Artificial Sequence
<220> FEATURE:
<223> OTHER INFORMATION: primer part

<400> SEQUENCE: 1010
cccacataat aagctgcagc a 21

<210> SEQ ID NO 1011
<211> LENGTH: 25
<212> TYPE: DNA
<213> ORGANISM: Artificial Sequence
<220> FEATURE:
<223> OTHER INFORMATION: primer part

<400> SEQUENCE: 1011
ctacagtgaa ggatttcaac gtaca 25

<210> SEQ ID NO 1012
<211> LENGTH: 27
<212> TYPE: DNA
<213> ORGANISM: Artificial Sequence
<220> FEATURE:
<223> OTHER INFORMATION: primer part

<400> SEQUENCE: 1012
gcatagacat tagtaaagca gagatca 27

<210> SEQ ID NO 1013
<211> LENGTH: 27
<212> TYPE: DNA
<213> ORGANISM: Artificial Sequence
<220> FEATURE:
<223> OTHER INFORMATION: primer part

<400> SEQUENCE: 1013
caggtaatta taattaccac caacctt 27

<210> SEQ ID NO 1014
<211> LENGTH: 28
<212> TYPE: DNA
<213> ORGANISM: Artificial Sequence
<220> FEATURE:
<223> OTHER INFORMATION: primer part

<400> SEQUENCE: 1014
agttcaaaag aaagtactac tactctgt 28

<210> SEQ ID NO 1015
<211> LENGTH: 24
<212> TYPE: DNA
<213> ORGANISM: Artificial Sequence
<220> FEATURE:
<223> OTHER INFORMATION: primer part

<400> SEQUENCE: 1015
ccaaattgtt ggaaaggcag aaac 24

<210> SEQ ID NO 1016
<211> LENGTH: 21
<212> TYPE: DNA
<213> ORGANISM: Artificial Sequence
<220> FEATURE:
<223> OTHER INFORMATION: primer part

<400> SEQUENCE: 1016
gcatgaatag caacagggac t 21

<210> SEQ ID NO 1017
<211> LENGTH: 25
<212> TYPE: DNA
<213> ORGANISM: Artificial Sequence
<220> FEATURE:
<223> OTHER INFORMATION: primer part

<400> SEQUENCE: 1017
gtctgataac tagcgcatat acctg 25

<210> SEQ ID NO 1018
<211> LENGTH: 25
<212> TYPE: DNA
<213> ORGANISM: Artificial Sequence
<220> FEATURE:
<223> OTHER INFORMATION: primer part

<400> SEQUENCE: 1018
gtacaatcta ctgatgtctt ggtca 25

<210> SEQ ID NO 1019
<211> LENGTH: 23
<212> TYPE: DNA
<213> ORGANISM: Artificial Sequence
<220> FEATURE:
<223> OTHER INFORMATION: primer part

<400> SEQUENCE: 1019
gtgcacaaat gaggtctcta gca 23

<210> SEQ ID NO 1020
<211> LENGTH: 32
<212> TYPE: DNA
<213> ORGANISM: Artificial Sequence
<220> FEATURE:
<223> OTHER INFORMATION: primer part

<400> SEQUENCE: 1020
gagattagac ttcctaaaca atctatacag gt 32

<210> SEQ ID NO 1021
<211> LENGTH: 28
<212> TYPE: DNA
<213> ORGANISM: Artificial Sequence
<220> FEATURE:
<223> OTHER INFORMATION: primer part

<400> SEQUENCE: 1021
ggggtactgc tgttatgtct ttaaaaga 28

<210> SEQ ID NO 1022
<211> LENGTH: 27
<212> TYPE: DNA
<213> ORGANISM: Artificial Sequence
<220> FEATURE:
<223> OTHER INFORMATION: primer part

<400> SEQUENCE: 1022
ctgaggatct gaaaactttg tcagggt 27

<210> SEQ ID NO 1023
<211> LENGTH: 27
<212> TYPE: DNA
<213> ORGANISM: Artificial Sequence
<220> FEATURE:

<223> OTHER INFORMATION: primer part

<400> SEQUENCE: 1023
cccctgcata cactaattct ttcacac 27

<210> SEQ ID NO 1024
<211> LENGTH: 28
<212> TYPE: DNA
<213> ORGANISM: Artificial Sequence
<220> FEATURE:
<223> OTHER INFORMATION: primer part

<400> SEQUENCE: 1024
ctgggtcttc gaatctaaag tagtacca 28

<210> SEQ ID NO 1025
<211> LENGTH: 32
<212> TYPE: DNA
<213> ORGANISM: Artificial Sequence
<220> FEATURE:
<223> OTHER INFORMATION: primer part

<400> SEQUENCE: 1025
gcttccactg agaagtctaa cataataaga gg 32

<210> SEQ ID NO 1026
<211> LENGTH: 22
<212> TYPE: DNA
<213> ORGANISM: Artificial Sequence
<220> FEATURE:
<223> OTHER INFORMATION: primer part

<400> SEQUENCE: 1026
ccctgttttc cttcaaggtc ca 22

<210> SEQ ID NO 1027
<211> LENGTH: 25
<212> TYPE: DNA
<213> ORGANISM: Artificial Sequence
<220> FEATURE:
<223> OTHER INFORMATION: primer part

<400> SEQUENCE: 1027
gttggatgga aagtgagttc agagt 25

<210> SEQ ID NO 1028
<211> LENGTH: 27
<212> TYPE: DNA
<213> ORGANISM: Artificial Sequence
<220> FEATURE:
<223> OTHER INFORMATION: primer part

<400> SEQUENCE: 1028
acctattggc aaatctacca atggttc 27

<210> SEQ ID NO 1029
<211> LENGTH: 21
<212> TYPE: DNA
<213> ORGANISM: Artificial Sequence
<220> FEATURE:
<223> OTHER INFORMATION: primer part

<400> SEQUENCE: 1029
gcgtgatctc cctcagggtt t 21

<210> SEQ ID NO 1030
<211> LENGTH: 26
<212> TYPE: DNA
<213> ORGANISM: Artificial Sequence
<220> FEATURE:
<223> OTHER INFORMATION: primer part

<400> SEQUENCE: 1030
cgtacacttt gtttctgaga gagggt 26

<210> SEQ ID NO 1031
<211> LENGTH: 23
<212> TYPE: DNA
<213> ORGANISM: Artificial Sequence
<220> FEATURE:
<223> OTHER INFORMATION: primer part

<400> SEQUENCE: 1031
cagatgctgt agactgtgca ctt 23

<210> SEQ ID NO 1032
<211> LENGTH: 27
<212> TYPE: DNA
<213> ORGANISM: Artificial Sequence
<220> FEATURE:
<223> OTHER INFORMATION: primer part

<400> SEQUENCE: 1032
cacttaaaag tggaaaatga tgcggaa 27

<210> SEQ ID NO 1033
<211> LENGTH: 25
<212> TYPE: DNA
<213> ORGANISM: Artificial Sequence
<220> FEATURE:
<223> OTHER INFORMATION: primer part

<400> SEQUENCE: 1033
ggaagagaat cagcaactgt gttgc 25

<210> SEQ ID NO 1034
<211> LENGTH: 33
<212> TYPE: DNA
<213> ORGANISM: Artificial Sequence
<220> FEATURE:
<223> OTHER INFORMATION: primer part

<400> SEQUENCE: 1034
caccaacctt agaatcaaga ttgttagaat tcc 33

<210> SEQ ID NO 1035
<211> LENGTH: 23
<212> TYPE: DNA
<213> ORGANISM: Artificial Sequence
<220> FEATURE:
<223> OTHER INFORMATION: primer part

<400> SEQUENCE: 1035
ccagatgatt ttacaggctg cgt 23

<210> SEQ ID NO 1036
<211> LENGTH: 31
<212> TYPE: DNA
<213> ORGANISM: Artificial Sequence
<220> FEATURE:
<223> OTHER INFORMATION: primer part

<400> SEQUENCE: 1036
gtactactac tctgtatggt tggtaaccaa c 31

<210> SEQ ID NO 1037
<211> LENGTH: 28
<212> TYPE: DNA
<213> ORGANISM: Artificial Sequence
<220> FEATURE:
<223> OTHER INFORMATION: primer part

<400> SEQUENCE: 1037
gtctaatctc aaacctttttg agagagat 28

<210> SEQ ID NO 1038
<211> LENGTH: 24
<212> TYPE: DNA
<213> ORGANISM: Artificial Sequence
<220> FEATURE:
<223> OTHER INFORMATION: primer part

<400> SEQUENCE: 1038
gaacacctgt gcctgttaaa ccat 24

<210> SEQ ID NO 1039
<211> LENGTH: 22
<212> TYPE: DNA
<213> ORGANISM: Artificial Sequence
<220> FEATURE:
<223> OTHER INFORMATION: primer part

<400> SEQUENCE: 1039
gcaccagcaa ctgtttgtgg ac 22

<210> SEQ ID NO 1040
<211> LENGTH: 28
<212> TYPE: DNA
<213> ORGANISM: Artificial Sequence
<220> FEATURE:
<223> OTHER INFORMATION: primer part

<400> SEQUENCE: 1040
cagcaacctg gttagaagta tttgttcc 28

<210> SEQ ID NO 1041
<211> LENGTH: 26
<212> TYPE: DNA
<213> ORGANISM: Artificial Sequence
<220> FEATURE:
<223> OTHER INFORMATION: primer part

<400> SEQUENCE: 1041
cgtgatccac agacacttga gattct 26

<210> SEQ ID NO 1042
<211> LENGTH: 23
<212> TYPE: DNA
<213> ORGANISM: Artificial Sequence
<220> FEATURE:
<223> OTHER INFORMATION: primer part

<400> SEQUENCE: 1042
cctgcaccaa tgggtatgtc aca 23

<210> SEQ ID NO 1043
<211> LENGTH: 22

```
<212> TYPE: DNA
<213> ORGANISM: Artificial Sequence
<220> FEATURE:
<223> OTHER INFORMATION: primer part

<400> SEQUENCE: 1043

gcaggctgtt taataggggc tg                                              22


<210> SEQ ID NO 1044
<211> LENGTH: 29
<212> TYPE: DNA
<213> ORGANISM: Artificial Sequence
<220> FEATURE:
<223> OTHER INFORMATION: primer part

<400> SEQUENCE: 1044

ggtcatagac actggtagaa tttctgtgg                                       29


<210> SEQ ID NO 1045
<211> LENGTH: 28
<212> TYPE: DNA
<213> ORGANISM: Artificial Sequence
<220> FEATURE:
<223> OTHER INFORMATION: primer part

<400> SEQUENCE: 1045

ggcagttttt gtacacaatt aaaccgtg                                        28


<210> SEQ ID NO 1046
<211> LENGTH: 24
<212> TYPE: DNA
<213> ORGANISM: Artificial Sequence
<220> FEATURE:
<223> OTHER INFORMATION: primer part

<400> SEQUENCE: 1046

tctagcagca atatcaccaa ggca                                            24
```